(12) United States Patent
Venkateshappa et al.

(10) Patent No.: US 11,529,341 B2
(45) Date of Patent: Dec. 20, 2022

(54) BICYCLIC COMPOUNDS AS INHIBITORS OF PD1/PD-L1 INTERACTION/ACTIVATION

(71) Applicant: JUBILANT PRODEL LLC, Yardley, PA (US)

(72) Inventors: Chandregowda Venkateshappa, Bangalore (IN); Jeyaraj D A, Bangalore (IN); Muralidhar Pendyala, Bangalore (IN); Dhanalakshmi Sivanandhan, Bangalore (IN); Sridharan Rajagopal, Bangalore (IN)

(*) Notice: Subject to any disclaimer, the term of this patent is extended or adjusted under 35 U.S.C. 154(b) by 0 days.

(21) Appl. No.: 16/980,284

(22) PCT Filed: Mar. 13, 2019

(86) PCT No.: PCT/IN2019/050203
§ 371 (c)(1),
(2) Date: Sep. 11, 2020

(87) PCT Pub. No.: WO2019/175897
PCT Pub. Date: Sep. 19, 2019

(65) Prior Publication Data
US 2021/0015810 A1    Jan. 21, 2021

(30) Foreign Application Priority Data

Mar. 13, 2018  (IN) .............. 201841009252

(51) Int. Cl.
| | |
|---|---|
| *A61K 31/4545* | (2006.01) |
| *A61K 31/165* | (2006.01) |
| *A61K 31/397* | (2006.01) |
| *A61K 31/40* | (2006.01) |
| *A61K 31/445* | (2006.01) |
| *A61K 31/454* | (2006.01) |
| *A61K 45/06* | (2006.01) |
| *C07C 233/36* | (2006.01) |
| *C07C 255/59* | (2006.01) |
| *C07D 207/16* | (2006.01) |
| *C07D 211/56* | (2006.01) |
| *C07D 211/60* | (2006.01) |
| *C07D 213/30* | (2006.01) |
| *C07D 295/096* | (2006.01) |
| *C07D 401/12* | (2006.01) |
| *C07D 401/14* | (2006.01) |
| *C07D 471/04* | (2006.01) |
| *C07D 491/107* | (2006.01) |

(52) U.S. Cl.
CPC ........ *A61K 31/4545* (2013.01); *A61K 31/165* (2013.01); *A61K 31/397* (2013.01); *A61K 31/40* (2013.01); *A61K 31/445* (2013.01); *A61K 31/454* (2013.01); *A61K 45/06* (2013.01); *C07C 233/36* (2013.01); *C07C 255/59* (2013.01); *C07D 207/16* (2013.01); *C07D 211/56* (2013.01); *C07D 211/60* (2013.01); *C07D 213/30* (2013.01); *C07D 295/096* (2013.01); *C07D 401/12* (2013.01); *C07D 401/14* (2013.01); *C07D 471/04* (2013.01); *C07D 491/107* (2013.01)

(58) Field of Classification Search
CPC ... C07C 233/36; C07C 255/59; C07D 207/16; C07D 211/56; C07D 211/60; C07D 213/30; C07D 295/096; C07D 401/12; C07D 401/14; C07D 471/04; C07D 491/107; A61K 31/4545; A61K 31/165; A61K 31/397; A61K 31/40; A61K 31/445; A61K 31/454; A61K 45/06
See application file for complete search history.

(56) References Cited

U.S. PATENT DOCUMENTS

| 3,565,896 A | 2/1971 | Ghielmetti et al. |
| 3,970,753 A | 7/1976 | Durant |

(Continued)

FOREIGN PATENT DOCUMENTS

| CN | 101838264 | 9/2010 |
| CN | 105461693 A | 4/2016 |

(Continued)

OTHER PUBLICATIONS

Chemical Abstracts STN Registry Database, Record for RN 1648388-87-7, Entered into STN Feb. 16, 2015. (Year: 2015).*

(Continued)

*Primary Examiner* — Daniel R Carcanague
(74) *Attorney, Agent, or Firm* — Knobbe, Martens, Olson & Bear LLP

(57) ABSTRACT

The compounds of Formula I is described herein along with their polymorphs, stereoisomers, tautomers, prodrugs, solvates, and pharmaceutically acceptable salts thereof. The compounds described herein, their polymorphs, stereoisomers, tautomers, prodrugs, solvates, and pharmaceutically acceptable salts thereof are bicyclic compounds that are inhibitors of PD-1/PD-L1 interaction/activation.

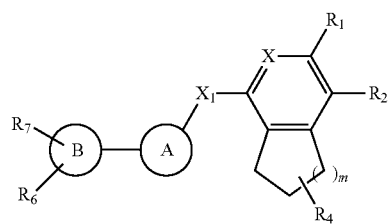

Formula (I)

15 Claims, No Drawings

(56) References Cited

U.S. PATENT DOCUMENTS

| | | |
|---|---|---|
| 3,985,881 A | 10/1976 | Mehrhof et al. |
| 4,246,274 A | 1/1981 | Regel et al. |
| 4,315,855 A | 2/1982 | Schefczik |
| 4,495,191 A | 1/1985 | Ehrhardt et al. |
| 4,703,056 A | 10/1987 | Hideg et al. |
| 4,757,081 A | 7/1988 | Yonekura et al. |
| 4,871,735 A | 10/1989 | Heider et al. |
| 4,871,751 A | 10/1989 | Yonekura et al. |
| 4,962,113 A | 10/1990 | Tsushima et al. |
| 5,001,132 A | 3/1991 | Manoury et al. |
| 5,010,094 A | 4/1991 | Schade et al. |
| 5,047,411 A | 9/1991 | Takasugi et al. |
| 5,100,890 A | 3/1992 | Siegal et al. |
| 5,179,125 A | 1/1993 | Mimura et al. |
| 5,210,266 A | 5/1993 | Mimura et al. |
| 5,229,516 A | 7/1993 | Messer et al. |
| 5,244,908 A | 9/1993 | Takatani et al. |
| 5,273,980 A | 12/1993 | Frenette et al. |
| 5,330,989 A | 7/1994 | Soll et al. |
| 5,420,289 A | 5/1995 | Musser et al. |
| 5,541,033 A | 7/1996 | Blakeney et al. |
| 5,547,814 A | 8/1996 | Blakeney et al. |
| 5,550,162 A | 8/1996 | Frost et al. |
| 5,554,621 A | 9/1996 | Poindexter et al. |
| 5,663,183 A | 9/1997 | Frost et al. |
| 6,844,445 B2 | 1/2005 | Wierzbicki et al. |
| 6,887,868 B2 | 5/2005 | Fu |
| 8,148,408 B2 | 4/2012 | Bunnelle et al. |
| 8,642,660 B2 | 2/2014 | Goldfarb |
| 9,067,898 B1 | 6/2015 | Illig |
| 9,732,066 B2 | 8/2017 | Otsu |
| 11,230,526 B1* | 1/2022 | Lanter .................. C07C 57/38 |
| 2002/0094989 A1 | 7/2002 | Hale et al. |
| 2002/0173531 A1 | 11/2002 | Wierzbicki et al. |
| 2003/0018025 A1 | 1/2003 | Thurkauf et al. |
| 2004/0158067 A1* | 8/2004 | Hutchison .............. A61P 29/00 |
| | | 546/256 |
| 2004/0229160 A1 | 11/2004 | Naiini et al. |
| 2005/0096336 A1* | 5/2005 | Ackermann .............. A61P 7/02 |
| | | 549/470 |
| 2005/0159334 A1 | 7/2005 | Gluck et al. |
| 2005/0228014 A1 | 10/2005 | Marquess et al. |
| 2006/0270686 A1 | 11/2006 | Kelly et al. |
| 2007/0191371 A1 | 8/2007 | Bennett et al. |
| 2007/0219218 A1 | 9/2007 | Yu et al. |
| 2008/0280891 A1 | 11/2008 | Kelly et al. |
| 2009/0069373 A1 | 3/2009 | Wrobel |
| 2009/0264433 A1 | 10/2009 | Russell |
| 2010/0249127 A1 | 9/2010 | Namdev et al. |
| 2016/0194307 A1* | 7/2016 | Chupak ................ C07D 211/34 |
| | | 514/330 |
| 2016/0229816 A1* | 8/2016 | Sato .................... C07D 413/14 |
| 2017/0105971 A1 | 4/2017 | Catrina et al. |
| 2017/0174672 A1 | 6/2017 | Amberg et al. |
| 2021/0179580 A1* | 6/2021 | Venkateshappa .... C07D 401/14 |
| 2021/0371431 A1 | 12/2021 | Vadivelu et al. |

FOREIGN PATENT DOCUMENTS

| | | |
|---|---|---|
| CN | 107056630 A | 8/2017 |
| CN | 107163044 A | 9/2017 |
| CN | 108358917 A | 8/2018 |
| CN | 110105299 A | 8/2019 |
| CN | 110963997 A | 9/2019 |
| CN | 107056630 B | 1/2020 |
| CN | 111606904 A | 9/2020 |
| DE | 1961595 A | 6/1970 |
| DE | 2832677 A1 | 2/1980 |
| DE | 3210570 A1 | 10/1983 |
| DE | 3628545 A1 | 4/1987 |
| DE | 3901723 A1 | 7/1990 |
| DE | 4227522 A1 | 2/1994 |
| DE | 19717371 A1 | 10/1998 |
| DE | 19834751 | 2/2000 |
| EP | 0090269 A1 | 10/1983 |
| EP | 0218118 A1 | 4/1987 |
| EP | 0239391 A2 | 9/1987 |
| EP | 0259793 A1 | 3/1988 |
| EP | 0301751 A1 | 2/1989 |
| EP | 0370852 A1 | 5/1990 |
| EP | 0218118 B1 | 9/1991 |
| EP | 0471236 A1 | 2/1992 |
| EP | 0259793 B1 | 7/1992 |
| EP | 0301751 B1 | 3/1993 |
| EP | 0533056 A2 | 3/1993 |
| EP | 0535924 A1 | 4/1993 |
| EP | 0533056 A3 | 6/1993 |
| EP | 0666250 A1 | 8/1995 |
| EP | 0747378 A1 | 12/1996 |
| EP | 0764640 A1 | 3/1997 |
| EP | 0819977 A1 | 1/1998 |
| EP | 0666250 B1 | 2/1998 |
| EP | 1245565 A1 | 10/2002 |
| EP | 1245565 B1 | 9/2003 |
| EP | 1388342 A1 | 2/2004 |
| EP | 2194035 A2 | 6/2010 |
| EP | 2194035 A3 | 6/2010 |
| EP | 2194035 B1 | 11/2011 |
| EP | 3 112 362 A1 | 1/2017 |
| FR | 2102082 A2 | 4/1972 |
| FR | 2102082 B2 | 10/1974 |
| FR | 2706895 A1 | 12/1994 |
| FR | 2706895 B1 | 8/1995 |
| GB | 1230663 A | 5/1971 |
| GB | 1356789 A | 6/1974 |
| JP | 62187452 A | 8/1987 |
| JP | H 02215809 A | 8/1990 |
| JP | 06184076 | 12/1992 |
| JP | 07304770 | 5/1994 |
| JP | 11119379 A1 | 4/1999 |
| JP | 2001233712 A | 8/2001 |
| JP | 2005060247 A | 3/2005 |
| JP | 2008280344 A | 11/2008 |
| JP | 2009209090 A | 9/2009 |
| JP | 2009274984 | 11/2009 |
| JP | 2011063589 A | 3/2011 |
| JP | 2011207765 | 10/2011 |
| JP | 2019156770 A | 9/2019 |
| JP | 2021054909 | 4/2021 |
| RU | 2371444 C1 | 10/2009 |
| RU | 2632908 C2 | 10/2017 |
| WO | WO 86/05519 | 9/1986 |
| WO | WO 9106537 A2 | 5/1991 |
| WO | WO 9106537 A3 | 10/1991 |
| WO | WO 9301157 A1 | 1/1993 |
| WO | WO 9312094 A1 | 6/1993 |
| WO | WO 9320099 A2 | 10/1993 |
| WO | WO 9320099 A3 | 11/1993 |
| WO | WO 9401407 A2 | 1/1994 |
| WO | WO 9401407 A3 | 3/1994 |
| WO | WO 9422829 A2 | 10/1994 |
| WO | WO 9422834 A1 | 10/1994 |
| WO | WO 9427971 A1 | 12/1994 |
| WO | WO 9422829 A3 | 1/1995 |
| WO | WO 9509843 A1 | 4/1995 |
| WO | WO 9511226 A1 | 4/1995 |
| WO | WO 9521164 A1 | 8/1995 |
| WO | WO 9521832 A1 | 8/1995 |
| WO | WO 9610012 A1 | 4/1996 |
| WO | WO 9616040 A1 | 5/1996 |
| WO | WO 9709066 A1 | 3/1997 |
| WO | WO 9724119 A1 | 7/1997 |
| WO | WO 9740051 A1 | 10/1997 |
| WO | WO 9817648 A1 | 4/1998 |
| WO | WO 9824766 A1 | 6/1998 |
| WO | WO 9834609 A1 | 8/1998 |
| WO | WO 9836749 A1 | 8/1998 |
| WO | WO 9838156 A1 | 9/1998 |
| WO | WO 9906387 A2 | 2/1999 |
| WO | WO 9906387 A3 | 4/1999 |
| WO | WO 9932447 A2 | 7/1999 |
| WO | WO 9932447 A3 | 10/1999 |
| WO | WO 2000007978 A1 | 2/2000 |

(56) References Cited

FOREIGN PATENT DOCUMENTS

| | | |
|---|---|---|
| WO | WO 2000023420 A1 | 4/2000 |
| WO | WO 2000026203 A1 | 5/2000 |
| WO | WO2001032178 * | 5/2001 |
| WO | WO 2001070731 A1 | 9/2001 |
| WO | WO 2001077075 A2 | 10/2001 |
| WO | WO 2001087293 A1 | 11/2001 |
| WO | WO 2002002518 A2 | 1/2002 |
| WO | WO 2002002520 A2 | 1/2002 |
| WO | WO 2002083673 A1 | 1/2002 |
| WO | WO 2001077075 A3 | 3/2002 |
| WO | WO 2002002518 A3 | 8/2002 |
| WO | WO 2002002520 A3 | 8/2002 |
| WO | WO 2002066478 A1 | 8/2002 |
| WO | WO 2002070510 A2 | 9/2002 |
| WO | WO 2002076964 A1 | 10/2002 |
| WO | WO 2002076979 A1 | 10/2002 |
| WO | WO 2002088089 A1 | 11/2002 |
| WO | WO 2002098869 A2 | 12/2002 |
| WO | WO 2002100813 A2 | 12/2002 |
| WO | WO 2002070510 A3 | 1/2003 |
| WO | WO 2008000408 A1 | 1/2003 |
| WO | WO 2003035076 A1 | 5/2003 |
| WO | WO 2003037887 A1 | 5/2003 |
| WO | WO 2003044016 A1 | 5/2003 |
| WO | WO 2003044017 A1 | 5/2003 |
| WO | WO 2003066613 A1 | 8/2003 |
| WO | WO 2003084916 A2 | 10/2003 |
| WO | WO 2002100813 A3 | 11/2003 |
| WO | WO 2003084916 A3 | 12/2003 |
| WO | WO 2002098869 A3 | 2/2004 |
| WO | WO 2004011430 A1 | 2/2004 |
| WO | WO 2004014372 A1 | 2/2004 |
| WO | WO 2004022558 A2 | 3/2004 |
| WO | WO 2004035579 A1 | 4/2004 |
| WO | WO 2004022558 A3 | 5/2004 |
| WO | WO 2004/052846 A1 | 6/2004 |
| WO | WO 2004048363 A1 | 6/2004 |
| WO | WO 2004052846 A1 | 6/2004 |
| WO | WO 2004058679 A2 | 7/2004 |
| WO | WO 2004058679 A3 | 8/2004 |
| WO | WO 2004078731 A1 | 9/2004 |
| WO | WO 2004109400 A2 | 12/2004 |
| WO | WO 2002034716 A2 | 5/2005 |
| WO | WO 2005058823 A1 | 6/2005 |
| WO | WO 2005092899 A1 | 10/2005 |
| WO | WO 2005100350 A1 | 10/2005 |
| WO | WO 2005105805 A1 | 11/2005 |
| WO | WO 2005105805 A9 | 1/2006 |
| WO | WO 2006048330 A1 | 5/2006 |
| WO | WO 2006062224 A1 | 6/2006 |
| WO | WO 2006069125 A1 | 6/2006 |
| WO | WO 2006102588 A1 | 9/2006 |
| WO | WO 2006105971 A1 | 10/2006 |
| WO | WO 2004109400 A3 | 11/2006 |
| WO | WO 2006125119 A1 | 11/2006 |
| WO | WO 2006130707 A2 | 12/2006 |
| WO | WO 2006133104 A2 | 12/2006 |
| WO | WO 2006130707 A3 | 1/2007 |
| WO | WO 2006133104 A3 | 4/2007 |
| WO | WO 2007073503 A2 | 6/2007 |
| WO | WO 2007087548 A2 | 8/2007 |
| WO | WO 2007105989 A2 | 9/2007 |
| WO | WO 2007106469 A2 | 9/2007 |
| WO | WO 2007073503 A3 | 11/2007 |
| WO | WO 2007105989 A3 | 11/2007 |
| WO | WO 2007133108 A1 | 11/2007 |
| WO | WO 2007106469 A3 | 12/2007 |
| WO | WO 2008008059 A1 | 1/2008 |
| WO | WO 20082022945 A1 | 2/2008 |
| WO | WO 2008/051757 A1 | 5/2008 |
| WO | WO 2008064320 A2 | 5/2008 |
| WO | WO 2008065500 A2 | 6/2008 |
| WO | WO 2008065500 A3 | 6/2008 |
| WO | WO 2008066789 A2 | 6/2008 |
| WO | WO 2008079988 A2 | 7/2008 |
| WO | WO 2008104077 A1 | 9/2008 |
| WO | WO 2008112715 A2 | 9/2008 |
| WO | WO 2008064320 A3 | 10/2008 |
| WO | WO 2008121687 A2 | 10/2008 |
| WO | WO 2008123582 A1 | 10/2008 |
| WO | WO 2008112715 A3 | 11/2008 |
| WO | WO 2008135526 A1 | 11/2008 |
| WO | WO 2008156142 A1 | 12/2008 |
| WO | WO 2009010925 A2 | 1/2009 |
| WO | WO 2009023179 A2 | 2/2009 |
| WO | WO 2009038842 A2 | 3/2009 |
| WO | WO 2009048152 A2 | 4/2009 |
| WO | WO 2009054914 A1 | 4/2009 |
| WO | WO 2009010925 A3 | 7/2009 |
| WO | WO 2009080351 A1 | 7/2009 |
| WO | WO 2009104819 A1 | 8/2009 |
| WO | WO 2009048152 A3 | 9/2009 |
| WO | WO 2009112651 A1 | 9/2009 |
| WO | WO 2009137309 A2 | 11/2009 |
| WO | WO 2009140101 A2 | 11/2009 |
| WO | WO 2005123703 A2 | 12/2009 |
| WO | WO 2009038842 A3 | 12/2009 |
| WO | WO 2009153313 A1 | 12/2009 |
| WO | WO 2010/048207 A2 | 4/2010 |
| WO | WO 2010075973 A1 | 7/2010 |
| WO | WO 2010077680 A2 | 7/2010 |
| WO | WO 2010091409 A1 | 8/2010 |
| WO | WO 2010098495 A1 | 9/2010 |
| WO | WO 2010151799 A2 | 12/2010 |
| WO | WO 2011023989 A1 | 3/2011 |
| WO | WO 2011086178 A1 | 7/2011 |
| WO | WO 2011100380 A1 | 8/2011 |
| WO | WO 2011123751 A2 | 10/2011 |
| WO | WO 2012006202 A1 | 1/2012 |
| WO | WO 2012006203 A1 | 1/2012 |
| WO | WO 2012022265 A1 | 2/2012 |
| WO | WO 2021028810 A1 | 2/2012 |
| WO | WO 20122022045 A1 | 2/2012 |
| WO | WO 2012058133 A1 | 5/2012 |
| WO | WO 2012087833 A1 | 6/2012 |
| WO | WO 2013000994 A1 | 1/2013 |
| WO | WO 2013002879 A1 | 1/2013 |
| WO | WO 2013002880 A1 | 1/2013 |
| WO | WO 2013018371 A1 | 2/2013 |
| WO | WO 2013025733 A1 | 2/2013 |
| WO | WO 2013068470 A1 | 5/2013 |
| WO | WO 2013096049 A1 | 6/2013 |
| WO | WO 2013096055 A1 | 6/2013 |
| WO | WO 2013096059 A1 | 6/2013 |
| WO | WO 2013096060 A1 | 6/2013 |
| WO | WO 2013096681 A1 | 6/2013 |
| WO | WO 2013120464 A1 | 8/2013 |
| WO | WO 2013127729 A1 | 9/2013 |
| WO | WO 2010077680 A3 | 10/2013 |
| WO | WO 2013174895 A1 | 11/2013 |
| WO | WO 2013178810 A1 | 12/2013 |
| WO | WO 2013192430 A2 | 12/2013 |
| WO | WO 2014013182 A1 | 1/2014 |
| WO | WO 2014015905 A1 | 1/2014 |
| WO | WO 2014031872 A2 | 2/2014 |
| WO | WO 2014031986 A1 | 2/2014 |
| WO | WO 2014031872 A3 | 4/2014 |
| WO | WO 2014077321 A1 | 5/2014 |
| WO | WO 2014100719 A2 | 6/2014 |
| WO | WO 2014100764 A2 | 6/2014 |
| WO | WO 2014100764 A3 | 9/2014 |
| WO | WO 2014152018 A1 | 9/2014 |
| WO | WO 2015011397 A1 | 1/2015 |
| WO | WO 2015/034820 A1 | 3/2015 |
| WO | WO 2015031295 A1 | 3/2015 |
| WO | WO 2015086512 A1 | 6/2015 |
| WO | WO 2015086527 A1 | 6/2015 |
| WO | WO 2015108038 A1 | 7/2015 |
| WO | WO 2015140051 A1 | 9/2015 |
| WO | WO 2015197028 A1 | 12/2015 |
| WO | WO 2016008433 A1 | 1/2016 |
| WO | WO 2016031815 A1 | 3/2016 |
| WO | WO 2016034675 A1 | 3/2016 |
| WO | WO 2016036636 A1 | 3/2016 |

(56) References Cited

FOREIGN PATENT DOCUMENTS

| | | |
|---|---|---|
| WO | WO 2016051306 A2 | 4/2016 |
| WO | WO 2016102727 A1 | 6/2016 |
| WO | WO 2006126939 A1 | 11/2016 |
| WO | WO 2016185279 A1 | 11/2016 |
| WO | WO 2017024180 A1 | 2/2017 |
| WO | WO 2017025510 A1 | 2/2017 |
| WO | WO 2017/042182 | 3/2017 |
| WO | WO 2017068412 A1 | 4/2017 |
| WO | WO 2017/106634 A1 | 6/2017 |
| WO | WO 2017109095 A1 | 6/2017 |
| WO | WO 2017/118762 | 7/2017 |
| WO | WO 2017/147102 | 8/2017 |
| WO | WO 2017216281 A1 | 12/2017 |
| WO | WO 2018002848 A1 | 1/2018 |
| WO | WO 2018/026971 A1 | 2/2018 |
| WO | WO 2018019204 A1 | 2/2018 |
| WO | WO 2018112843 A1 | 6/2018 |
| WO | WO 2018119036 A1 | 6/2018 |
| WO | WO 2018121610 A1 | 7/2018 |
| WO | WO 2018183411 A1 | 10/2018 |
| WO | WO 2018208985 A2 | 11/2018 |
| WO | WO 2018234342 A1 | 12/2018 |
| WO | WO 2019007696 A1 | 1/2019 |
| WO | WO 2019/058393 A1 | 3/2019 |
| WO | WO 2019/077631 A1 | 4/2019 |
| WO | WO 2019079783 A1 | 4/2019 |
| WO | WO 2019/087214 A1 | 5/2019 |
| WO | WO 2019/102494 A1 | 5/2019 |
| WO | WO 2019126081 A1 | 6/2019 |
| WO | WO 2019154047 A1 | 8/2019 |
| WO | WO 2019160014 A1 | 8/2019 |
| WO | WO 2019175897 A1 | 9/2019 |
| WO | WO 2019205147 A1 | 10/2019 |
| WO | WO 2019213234 A1 | 11/2019 |
| WO | WO 2020028723 A1 | 2/2020 |
| WO | WO 2020029980 A1 | 2/2020 |
| WO | WO 2020045216 A1 | 3/2020 |
| WO | WO 2020083971 A2 | 4/2020 |
| WO | WO 2020092394 A1 | 5/2020 |
| WO | WO 2020201773 A1 | 10/2020 |
| WO | WO 2020246910 A1 | 12/2020 |
| WO | WO 2021014949 A1 | 1/2021 |
| WO | WO 2021018858 A1 | 2/2021 |
| WO | WO 2021060432 A1 | 4/2021 |
| WO | WO 2021096238 A1 | 5/2021 |
| WO | WO 2021096241 A1 | 5/2021 |

OTHER PUBLICATIONS

STN Chemical Abstracts Registry Database, record for RN 1349491-87-7: 2-(4-Bromophenyl)-6-[[(2,3-dihydro-1H-inden-4-yl)oxy]methyl]-4-(1,1-dimethylethyl)-2-morpholinol. Entered STN Dec. 6, 2011. (Year: 2011).*
Mahoney; Nat Rev Drug Discov 2015, 14, 561-584. doi: 10.1038/nrd4591. (Year: 2015).*
Zak; Oncotarget 2016, 7, 30323-30335. https://doi.org/10.18632/oncotarget.8730 (Year: 2016).*
Acharya et al., "Neuronal PAD4 expression and protein citrullination: Possible role in production of autoantibodies associated with neurodegenerative disease", J. Autoimmun., vol. 38, pp. 369-380, 2012.
Arisan, et al., "Putative Roles for Peptidylarginine Deiminases in COVID-19", International Journal of Molecular Sciences, vol. 21, No. 13, in 29 pages, 2020.
Barnes, et al., "Targeting potential drivers of COVID-19: Neutrophil extracellular traps", Journal of Experimental Medicine, vol. 217, No. 6, in 7 pages, 2020.
Bertini, et al., "Carbazole-containing arylcarboxamides as BACE1 inhibitors," Bioorganic & Medicinal Chemistry Letters (2011), 21 (22), 6657-6661.
Borregaard, "Neutrophils, from Marrow to Microbes", Immunity, vol. 33, No. 5, pp. 657-670, 2010.
Brinkmann, et al., "Neutrophil Extracellular Traps Kill Bacteria", Science, vol. 303, No. 5663, pp. 1532-1535, 2004.
Candi et al., "The Cornified Envelope: A Model of Cell Death in the Skin", Nat. Rev. Mol. Cell Biol., vol. 6, pp. 328-340, 2005.
Cedervall et al., NETosis in Cancer, Oncoscience, vol. 2, No. 11, pp. 900-901, 2015.
Chang et al., "Increased PADI4 expression in blood and tissues of patients with malignant tumors", BMC Cancer, vol. 9, pp. 40, 2009.
Chiummiento, et a;., "New indolic non-peptidic HIV protease inhibitors from (S)-glycidol: synthesis and preliminary biological activity," Tetrahedron (2009), 65(31), 5984-5989.
Christophorou et al., Citrullination regulated pluripotency and histone H1 binding to chromatin, Nature, vol. 507, pp. 104-108, 2014.
Chumanevich et al., "Suppression of colitis in mice by C1-amidine: a novel peptidylarginine deiminase inhibitor", Am. J. Physiol. Gastrointest. Liver Physiol., vol. 300, No. 6, pp. G929-G938, 2011.
First Examination Report dated Sep. 8, 2021 received in Indian Patent Application No. 201741033768.
Fuhrmann, Jakob, et al., "Chemical Biology of Protein Arginine Modifications in Epigenetic Regulation," Chemical Reviews, 2015, 115, 5413-5461.
Guo, et al., "Development of Benzophenone-Alkyne Bifunctional Sigma Receptor Ligands," ChemBioChem (2012), 13(15), 2277-2289.
Gyorgy et al., "Citrullination: A posttranslational modification in health and disease", Int. J. Biochem. Cell Biol., vol. 38, pp. 1662-1677, 2006.
Hankovsky, et al., "New antiarrhythmic agents. 2,2,5,5-Tetramethyl-3-pyrroline-3-carboxamides and 2,2,5,5 tetramethylpyrrolidine-3-carboxamides," Journal of Medicinal Chemistry (1986), 29(7), 1138-52.
International Search Report and Written Opinion dated Nov. 12, 2018 for PCT/IN2018/050614.
International Search Report & written opinion, dated Feb. 14, 2019, in International Application No. PCT/IN2018/050671.
International Search Report & Written Opinion, dated Feb. 20, 2019, in International Application No. PCT/IN2018/050671.
Ireland et al., "Autophagy in antigen-presenting cells results in presentation of citrullinated peptides to CD4 T cells", J. Exp. Med., vol. 208, pp. 2625-2632, 2011.
Jones et al., "Protein arginine deiminase 4 (PAD4): current understanding and future therapeutic potential", Curr. Opin. Drug Discov. Devel., vol. 12, pp. 616-627, 2009.
Knight et al., "Peptidylarginine Deiminase Inhibition Reduces Vascular Damage and Modulates Innate Immune Responses in Murine Models of Atherosclerosis", Circ. Res., vol. 114, No. 6, pp. 947-956, 2014.
Kochi et al., "PADI4 polymorphism predisposes male smokers to rheumatoid arthritis", Ann. Rheum. Dis., vol. 70, pp. 512-515, 2011.
Labrie, et al., "In vitro activity of novel dual action MDR anthranilamide modulators with inhibitory activity at CYP450," Bioorganic & Medicinal Chemistry (2006), 14(23), 7972-7987.
Lakshmann, et al.,"Synthesis and evaluation of novel N-substituted-6 methoxynaphthalene-2-carboxamides as potential chemosensitizing agents for cancer," Chemical & Pharmaceutical Bulletin (2008), 56(7), 894-896.
Lange et al., "Protein deiminases: New players in the developmentally regulated loss of neural regenerative ability", Dev. Biol., vol. 355, No. 2, pp. 205-214, 2011.
"Letter to the Editors-in-Chief", Thrombosis Research 191, pp. 26-27, 2020.
Lewis et al, "Inhibition of PAD4 activity is sufficient to disrupt mouse and human NET formation", Nature Chemical Biology 11(3), 189-191. 10.1038/nchembio.1735, 2015.
Li et al., "Regulation of p53 Target Gene Expression by Peptidylarginine Deiminase 4", Mol. Cell Biol., vol. 28, pp. 4745-4758, 2008.
Liu, G.-Y, et al., "Overexpression of peptidylarginine deiminase IV features in apoptosis of haematopoietic cells", Apoptosis, vol. 11, pp. 183-196, 2006.
Loos et al., "Citrullination of CXCL10 and CXCL11 by peptidylarginine deiminase: a naturally occurring posttranslational modification of chemokines and new dimension of immunoregulation", Blood, vol. 112, pp. 2648-2656, 2008.

(56) References Cited

OTHER PUBLICATIONS

Makrygiannakis et al., "Citrullination is an inflammation-dependent process", Ann. Rheum. Dis., vol. 65, pp. 1219-1222, 2006.
Mastronardi et al., "Increased Citrullination of Histone H3 in Multiple Sclerosis Brain and Animal Models of Demyelination: A Role for Tumor Necrosis Factor-Induced Peptidylarginine Deiminase 4 Translocation", The Journal of Neurosciences, vol. 26, pp. 11387-11396, 2006.
Mohanan, Sunish, et al., "Potential Role of Peptidylarginine Deiminase Enzymes and Protein Citrullination in Cancer Pathogenesis," Biochemistry Research International, vol. 2012, article ID 895343.
Nakashima et al., "Molecular Characterization of Peptidylarginine Deiminase in HL-60 Cells Induced by Retinoic Acid and 1α,25-Dihydroxyvitamin D3", J. Biol. Chem., vol. 274, pp. 27786-27792, 1999.
Nathan, "Neutrophils and COVID-19: Nots, NETs, and knots", The Journal of Experimental Medicine, vol. 217, No. 9, in 3 pages, 2020.
Neeli et al., "Histone Deimination as a Response to Inflammatory Stimuli in Neutrophils", J. Immunol., vol. 180, pp. 1895-1902, 2008.
Omran, et al., "Synthesis and biological evaluation of new Donepezil-like Thiaindanones as AChE inhibitors," Journal of Enzyme Inhibition and Medicinal Chemistry (2008), 23(5), 696-703.
Schönrich, et al., "Neutrophil Extracellular Traps Go Viral", Frontiers in Immunology, vol. 7, No. 366 in 7 pages, 2016.
Slack et al., "Protein arginine deiminase 4: a target for an epigenetic cancer therapy", Cellular and Molecular Life Sciences, vol. 68, No. 4, pp. 709-720, 2011.
Wang et al., "Histone hypercitrullination mediates chromatin decondensation and neutrophil extracellular trap formation", J. Cell Biol., vol. 184, pp. 205-213, 2009.
Wang, Shu, et al., "Peptidylarginine deiminases in citrullination, gene regulation, health and pathogenesis," Biochim Biophys Acta, Oct. 2013; 1829 (10): 1126-1135.
Wei, Lianhu, et al., "Novel Inhibitors of Protein Arginine Deiminase with Potential Activity in Multiple Sclerosis Animal Model," Journal of Medicinal Chemistry, 2013, 56, 1715-1722.
Willis et al., N-α-Benzoyl-N5-(2-Chloro-1-Iminoethyl)-1-Ornithine Amine, a Protein Arginine Deiminase Inhibitor, Reduces the Severity of Murine Collagen-Induced Arthritis, J. Immunol., vol. 186, No. 7, pp. 4396-4404, 2011.
Zawrotniak, et al., "Neutrophil extracellular traps (NETs)—formation and implications", ACTA Biochimica Polonica, vol. 60, No. 3, pp. 277-284, 2013.
Zhuravel, et al, "Solution-phase synthesis of a combinatorial library of 3-[4-(Coumarin-3-yl)-1,3-thiazol-2-ylcarbamoyl]propanoic acid amides," Molecules (2005), 10(2), 444-456.
Zou, et al., "Neutrophil extracellular traps in COVID-19", JCI Insight, vol. 5, No. 11, pp. 1-11, 2020.
Dimauro et al., Discovery of Aminoquinazolines as Potent, Orally Bioavailable Inhibitor of Lck: Synthesis, SAR, and in Vivo Anti-inflammatory Activity, Journal of Medical Chemistry, vol. 49, No. 19, pp. 5671-5686, 2006.
International Search Report dated May 20, 2019 in International Application No. PCT/IN2019/050203.
Written Opinion dated May 20, 2019 in International Application No. PCT/IN2019/050203.
Cromwell, et al., "Amino ketones. III. B-Tetrahydroisoquinolino ketones and derivatives. Reaction with Grignard reagents," Journal of the American Chemical Society (1944), 66, 872-3.
Evans, et al. "Phenoxyacetic acids as PPAR☐ partial agonists: Synthesis, optimization, and in vivo efficacy," Bioorganic & Medicinal Chemistry Letters (2011), 21(8), 2345-2350.
Fukagawa, Tomokichi, "The biuret reaction. VII. Primary-quaternary bases which give the biuret reaction," Z. physiol. Chem. (1931), 201, 40-6.
Goi, et al., "Synthesis and pharmacological properties of pyridinecarbonyl derivatives of 7-substituted theophyllines," Chimica Therapeutica (1973), 8(6), 634-7.

Hwang, et al., "Synthesis and evaluation of methylsulfonylnitrobenzamides (MSNBAs) as inhibitors of the thyroid hormone receptor-coactivator interaction," Bioorganic & Medicinal Chemistry Letters (2013), 23(6), 1891-1895.
Ivaschenko, et al., "Synthesis, biological evaluation and in silico modeling of novel integrase strand transfer inhibitors (INSTIs)," European Journal of Medicinal Chemistry (2020), 189, 112064.
Nicolaou, et al., "Synthesis of imides, N-acyl vinylogous carbamates and ureas, and nitriles by oxidation of amides and amines with Dess-Martin periodinane," Angewandte Chemie, International Edition (2005), 44(37), 5992-5997.
Piper, et al., "Synthesis of potential inhibitors of hypoxanthine-guanine phosphoribosyltransferase for testing as antiprotozoal agents. 1. 7-Substituted 6-oxopurines," Journal of Medicinal Chemistry (1980), 23(4), 357-64.
Spassova, et al., "Synthesis of N-(3-azido-2 hydroxypropyl), N-(3-phthalimido-2-hydroxypropyl) and N-(3-amino-2 hydroxypropyl) derivatives of heterocyclic bases," Collection of Czechoslovak Chemical Communications (1994), 59(5), 1153-74.
Uenishi, et al, "Structural effects of diazonaphthoquinone-photoactivecompound backbone on resist lithographic properties," Proceedings of SPIE—The International Society for Optical Engineering (1991), 1466(Adv. Resist Technol. Process. 8), 102-16.
Vooturi, et al., "Solution-phase parallel synthesis of novel membrane-targeted antibiotics," Journal of Combinatorial Chemistry (2010), 12(1), 151-160.
Zajdel, et al, "Solid-phase synthesis of aryl-alkylamine derivatives using protected aminoalcohol building blocks on SynPhase lanterns," QSAR & Combinatorial Science (2007), 26(2), 215-219.
Search Report dated Sep. 2, 2021 in Russian Application No. 2020132944.
Barber, et al., "Restoring function in exhausted CD8 T cells during chronic viral infection", Nature, vol. 439, No. 7077, pp. 682-687, 2005.
Bardhan, et al., "The PD1:PD-L1/2 Pathway from Discovery to Clinical Implementation", Frontiers in Immunology, vol. 7, No. 550, pp. 1-17, 2016.
Chen, et al., "Anti-PD-1/PD-L1 therapy of human cancer: past, present, and future", Journal of Clinical Investigation, vol. 125, No. 9, pp. 3384-3391, 2015.
Curiel, et al., "Blockade of B7-H1 improves myeloid dendritic cell-mediated antitumor or immunity", Nature Medicine, vol. 9, No. 5, pp. 562-567, 2003.
Dong, et al., "Tumor-associated B7-H1 promotes T-cell apoptosis: A potential mechanism of immune evasion", Nature Medicine, vol. 8, No. 8, pp. 793-800, 2002.
Dong, et al., "PD-1 and its ligands are important immune checkpoints in cancer", Oncotarget, vol. 8, No. 2, pp. 2171-2186, 2017.
Flies, et al., "The New B7S: Playing a Pivotal Rose in Tumor Immunity", Immunotherapy, vol. 30, No. 3, pp. 251-260, 2007.
Flies, et al., "Blockade of the B7-H1/PD-1 Pathway for Cancer Immunotherapy", Yale J. Biology Medicine, vol. 84, No. 4, pp. 409-421, 2011.
Francisco, et al., "PD-L1 regulates the development, maintenance, and function of induced regulatory T cells", Journal of Experimental Medicine, vol. 206, No. 13, pp. 3015-3029, 2009.
Hamanishi, et al., "PD-1/PD-L1 blockade in cancer treatment: perspectives and issues", Int. J. Clin. Oncol., vol. 21, pp. 462-473, 2016.
He, et al., "Development of PD-1/PD-L1 Pathway in Tumor Immune Microenvironment and Treatment for Non-Small Cell Lung Cancer", Scientific Reports, vol. 5, pp. 1-9, 2015.
Lai, et al., "A Novel PD-L1-targeting Antagonistic DNA Aptamer With Antitumor Effects", Mol. Therapy—Nucl. Acids, vol. 5, pp. e397, 2016.
Lee, et al., Interferon regulatory factor-1 is prerequisite to the constitutive expression and IFN-γ-induced upregulation of B7-H1 (CD274), FEBS Letters, vol. 580, pp. 755-762, 2006.
Leung, et al., "The CD28-B7 Family in Anti-Tumor Immunity: Emerging Concepts in Cancer Immunotherapy", Immune Network, vol. 14, No. 6, pp. 265-276, 2014.

(56) References Cited

OTHER PUBLICATIONS

Muenst, et al., "Expression of programmed death ligand 1 (PD-L1) is associated with poor prognosis in human breast cancer", Breast Cancer Res. Treat., vol. 146, No. 1, pp. 15-24, 2014.

Patsoukis, et al., "PD-1 inhibits T cell proliferation by upregulating p27 and p15 and suppressing Cdc25A", Cell Cycle, vol. 11, No. 23, pp. 4305-4309, 2012.

Sheppard, et al., "PD-1 inhibits T-cell receptor induced phosphorylation of the ZAP70/CD3 signalosome and downstream signaling to PKC0", FEBS Letters, vol. 574, pp. 37-41, 2004.

Smahel, Michal, "PD-1/PD-L1 Blockade Therapy for Tumors with Downregulated MHC Class I Expression", Int. J. Mol. Sci., vol. 18, No. 6, pp. 1331, 2017.

Topalian, et al., "Targeting the PD-1/B7-H1 (PD-L1) pathway to activate anti-tumor immunity", Curr. Opin. Immunol., vol. 24, No. 2, pp. 207-212, 2012.

Vinay, et al., "Immune evasion in cancer: Mechanistic basis and therapeutic strategies", Seminars in Cancer Biology, vol. 35, pp. S185-S198, 2015.

Wang, et al., "Prognostic significance of PD-L1 in solid tumor", Medicine Baltimore, vol. 96, No. 18, pp. e6369, 2017.

Wang, et al., "PD-LI expression in human cancers and its association with clinical outcomes", Oncotargets and Therapy, vol. 9, pp. 5023-5039, 2016.

Zamarron, et al., "Dual Roles of Immune Cells and Their Factors in Cancer Development and Progression", Intl. J. Biol. Sciences, vol. 7, No. 5, pp. 651-658, 2011.

Zou, et al., "PD-L1 (B7-H1) and PD-1 pathway blockade for cancer therapy: Mechanisms, response biomarkers, and combinations", Sci. Transl. Med., vol. 8, No. 328, pp. 328rv4, 2016.

\* cited by examiner

BICYCLIC COMPOUNDS AS INHIBITORS OF PD1/PD-L1 INTERACTION/ACTIVATION

PRIORITY AND CROSS REFERENCE TO RELATED APPLICATIONS

This application is the U.S. National Stage Application under 35 U.S.C. § 371 of International Application No. PCT/IN2019/050203, filed Mar. 13, 2019, designating the U.S. and published in English as WO 2019/175897 A1 on Sep. 19, 2019, which claims the benefit of Indian Patent Application No. IN 201841009252, filed Mar. 13, 2018. Any and all applications for which a foreign or a domestic priority is claimed is/are identified in the Application Data Sheet filed herewith and is/are hereby incorporated by reference in their entireties under 37 C.F.R. § 1.57.

TECHNICAL FIELD OF THE INVENTION

The present invention relates to substituted bicyclic compounds of Formula I along with their polymorphs, stereoisomers, tautomers, prodrugs, solvates, and pharmaceutically acceptable salts thereof which are inhibitors of PD1/PD-L1 interaction. The present invention also relates to method of synthesizing the compounds of Formula I.

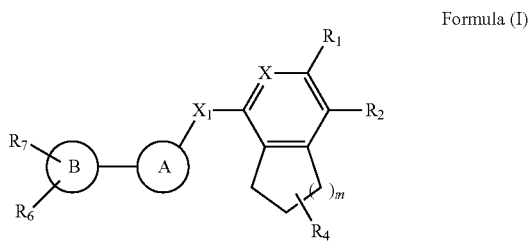

Formula (I)

The compounds described herein are inhibitors of PD1/PD-L1 activation and may be used in the treatment of cancer, and other diseases or conditions associated with activation of PD1/PD-L1.

BACKGROUND OF THE INVENTION

Tumour development and survival involves the interplay between cancer cells, normal stromal cells and host defence mechanisms (Vinay D. S. et al., Seminars in Cancer Biology, 2015, 35: S185-S198). Generally, CD8+ cytotoxic T cells (CTLs) and CD4+ helper T (Th1) cells curb cancer development via mechanisms commonly involving the production of interferon (IFN)-γ and cytotoxins (Zamarron B F et al., Intl. J. Biol. Sciences, 2011, 7(5):651-658). Tumours have, however evolved a number of mechanisms to escape immune eradications. The PD-1/PD-L1 molecular pathway is one such primary mechanism of cancer immune evasion.

PD-1 is a type 1 trans-membrane protein encoded by the PDCD1 gene. It is a member of the extended CD28/CTLA-4 immunoglobulin family and one of the most important inhibitory co-receptors expressed by T cells (He J. et al., Scientific Reports, 2015, 5:1-9). PD-1 is absent on resting T cells but is induced on activated T cells. It is also expressed on B cells, NK cells, dendritic cells (DCs) and macrophages. The programmed cell death protein (PD-1) down regulates the immune system and prevents it from killing cancerous cells present in the body. In cancer, high levels of PD-1 are detected in tumour infiltrating T cells and this expression has been associated with impaired CD8+ T cell function (Leung J et al., Immune Network, 2014, 14(6):265-276).

PD-1 has two ligands: PD-L1 (also named B7-H1; CD274) and PD-L2 (B7-DC; CD273), that are both co-inhibitory (Flies D. B. et al., Yale J. Biology Medicine, 2011, 84(4):409-421). PD-L1, expressed on almost all murine tumour cells, is the major ligand for PD-1 mediated immune suppression. It is constitutively expressed on APCs and can be broadly induced on cells in both lymphoid tissues and non-lymphoid peripheral tissues following cellular activation (Flies D. B. et al., Yale J. Biology Medicine, 2011, 84(4):409-421; Dong Y. et al., Oncotarget, 2017, 8(2):2171-2186). The cytokine IFN-γ is particularly effective in up-regulating PD-L1 expression due to IFN-γ response elements in the PD-L1 promoter region (Lee S. J. et al., FEBS Letters, 2006, 580:755-762; Flies D. B. et al., Immunotherapy, 2007, 30(3):251-260). The expression of B7-DC/PD-L2 is largely restricted to myeloid dendritic cells (DCs) and macrophages in lymphoid compartments and is not broadly expressed in peripheral tissues (Flies D. B. et al., Yale J. Biology Medicine, 2011, 84(4):409-421). In cancer, PD-L1 is expressed on the surface of tumour cells in various solid malignancies such as squamous cell carcinoma of the head and neck, melanoma, carcinomas of the brain, thyroid, thymus, esophagus, lung, breast, gastrointestinal tract, colorectum, liver, pancreas, kidney etc. (Topalian S. L. et al., Curr. Opin. Immunol., 2012, 24(2):207-212; Wang X. et al., Oncotargets and Therapy, 2016, 9:5023-5039). In hepatocellular carcinoma, melanoma and breast cancer, PD-L1 positivity was correlated with worse prognosis (Muenst S. et al., Breast Cancer Res. Treat., 2014, 146(1):15-24; Leung J. et al., Immune Network, 2014, 14(6):265-276; Wang Q. et al., Medicine (Baltimore), 2017, 96(18): e6369). In contrast, normal human tissues seldom express PD-L1 protein on their cell surface, indicating that PD-L1 can be a selective target for anti-tumour therapy (Chen L. et al., J. Clin. Invest., 2015, 125(9):3384-3391).

Cancer microenvironment manipulates the PD-1/PD-L1 pathway; induction of PD-L1 expression is associated with inhibition of immune responses against cancer, thus permitting cancer progression and metastasis (He J. et al., Scientific Reports, 2015, 5:1-9; Bardhan K. et al., Frontiers in Immunology, 2016, 7(550):1-17). Activation of PD-1/PD-L1 pathway induces apoptosis of activated T cells (Dong H. et al., Nature Medicine, 2002, 8(8):793-800; Curiel T. J. et al., Nature Medicine, 2003, 9(5):562-567), facilitates T cell anergy and exhaustion (Barber D. L. et al., Nature, 2005, 439(7077):682-687), enhances the function of regulatory T cells (Francisco L. M. et al., J. Exp. Med., 2009, 206(13): 3015-3029) and inhibits the proliferation of T cells (Sheppard K. A. et al., FEBS Letters, 2004, 574:37-41; Patsoukis N. et al., Cell Cycle, 2012, 11(23):4305-4309). Therefore, blocking this pathway restores the proliferation and cytotoxicity of CTLs, inhibiting the function of regulatory T cells (Tregs), and results in decrease T cell apoptosis.

Blockade of the PD-1/PD-L1 pathway by therapeutic antibodies has been shown to prevent inhibitory signalling from cancer cells and enabling CTLs to elicit an immune response against the target/cancer cells (Zou W. et al., Sci. Transl. Med., 2016, 8(328):328rv4; Smahel M., Int. J. Mol. Sci., 2017, 18(6):1331). A number of cancer immunotherapy agents targeting PD-1 have been developed till date and approved for a number of malignancies including melanoma, lung cancer, kidney cancer, Hodgkin's lymphoma, head and neck cancer and urothelial cancer. The first therapeutic anti-PD-L1 antibody was approved by the FDA in May 2016, for the treatment of patients with metastatic urothelial carcinoma and non-small cell lung cancer, with a number of additional therapies in the pipeline. Currently, there are at least 500 clinical studies on-going with PD-1/PD-L1 antibodies against 20 types of solid and haematological malignant tumours. However, there is still a need for potent and selective small molecule inhibitors of the PD-1/PD-L1 pathway.

Common drug-related adverse effects (AEs) of both anti-PD-1 and anti-PD-L antibodies include fatigue, rash, diarrhoea, pruritus, decrease appetite, arthralgia and nausea. Immune-related AEs (irAEs) such as dermatitis, colitis, hepatitis, vitiligo and thyroiditis have been reported and about 10% of patients develop grade 3 or 4 irAEs (Hamanishi J. et al., Int. J. Clin. Oncol., 2016, 21:462-473). The long residence time of the monoclonal antibodies (mAbs) could contribute to these AEs, which may be partially circumvented using a small molecule inhibitor. In addition, studies using smaller cell penetrating biologicals and DNA aptamers have shown to exert antibody-mimic functions and are advantageous over antibody for its chemically synthetic nature, low immunogenicity, and efficient tissue penetration (Lai W. Y. et al., Mol. Therapy-Nucl. Acids, 2016, 5: e397). Small molecule inhibitors, therefore, can provide increased oral bioavailability, increased bio-efficiency and shortened half-life activity for a more controllable treatment, particularly in the case of auto-immune or other adverse events.

As discussed, the PD-1/PD-L1 inhibitory compounds have vast utility in up-regulating the immune system for efficiently combating cancer. Therefore, the identification of a chemical moiety, especially small molecule inhibitors, that facilitates this inhibition is necessary. Therefore, the identification and development of new PD-1/PD-L1 inhibitor compounds treating cancer and other diseases or conditions associated with activation of PD-1/PD-L1 would open new opportunities in the realm of cancer treatment.

SUMMARY OF INVENTION

In an aspect of the present disclosure there is provided a compound of Formula I

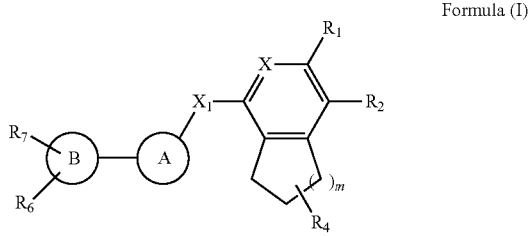

Formula (I)

their polymorphs, stereoisomers, tautomers, prodrugs, solvates, and pharmaceutically acceptable salts thereof, wherein $X_1$ is selected from —$CH_2O$—, —$OCH_2$—, —C(O)NH— or —NHC(O)—; $R_4$ is selected from hydrogen, hydroxyl, $C_{1-6}$ alkyl, amino, —C(O)O$R_{a1}$, C(O)N$R_{b1}R_{c1}$, $C_{5-6}$ aryl, or $C_{1-6}$ heteroaryl, wherein $C_{1-6}$ alkyl is optionally substituted with one or more of the groups selected from the group consisting of hydrogen, hydroxyl, amino, —C(O)O$R_{a1}$, C(O)N$R_{b1}R_{c1}$, $C_{5-6}$ aryl, and $C_{1-6}$ heteroaryl; $R_{a1}$, $R_{b1}$, and $R_{c1}$ are independently selected from hydrogen or $C_{1-6}$ alkyl; X is selected from $CR_3$ or N; $R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, C(O) $R^a$, C(O)N$R^aR^a$, C(O)O$R^a$, OC(O)$R^a$, OC(O)N$R^aR^a$, NH$R^a$, N$R^aR^a$, N$R^aC(O)R^a$, N$R^aC(O)OR^a$, N$R^aC(O)NR^aR^a$, C(=N$R^a$)$R^a$, C(=N$R^a$)N$R^aR^a$, N$R^aC(=NR^a)NR^aR^a$, N$R^aS(O)R^a$, N$R^aS(O)_2R^a$, N$R^aS(O)_2NR^aR^a$, S(O)$R^a$, S(O)N$R^aR^a$, S(O)$_2R^a$, or S(O)$_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents; $R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^c$, $OR^c$, $SR^c$, C(O)$R^c$, C(O)N$R^cR^c$, C(O)O$R^c$, OC(O)$R^c$, OC(O)N$R^cR^c$, C(=N$R^c$)N$R^cR^c$, N$R^cC(=NR^c)NR^cR^c$, NH$R^c$, N$R^cR^c$, N$R^cC(O)R^c$, N$R^cC(O)OR^c$, N$R^cC(O)NR^cR^c$, N$R^cS(O)R^c$, N$R^cS(O)_2R^c$, N$R^cS(O)_2NR^cR^c$, S(O)$R^c$, S(O)N$R^cR^c$, S(O)$_2R^c$ or S(O)$_2NR^cR^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents; $R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent; $R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^e$, $OR^e$, $SR^e$, C(O)$R^e$, C(O)N$R^eR^e$, C(O)O$R^e$, OC(O)$R^e$, OC(O)N$R^eR^e$, NH$R^e$, N$R^eR^e$, N$R^eC(O)R^e$, N$R^eC(O)NR^eR^e$, N$R^eC(O)OR^e$, C(=N$R^e$)N$R^eR^e$, N$R^eC(=NR^e)NR^eR^e$, N$R^eC(=NOH)NR^eR^e$, N$R^eC(=NCN)NR^eR^e$, S(O)$R^e$, S(O)N$R^eR^e$, S(O)$_2R^e$, N$R^eS(O)_2R^e$, N$R^eS(O)_2NR^eR^e$, or S(O)$_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents; $R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, or S(O)$_2$NR$^g$R$^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$haloalkyl are optionally substituted with 1, 2 or 3 $R^q$ substituents; $R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^r$, OR$^r$, SR$^r$, C(O)R$^r$, C(O)NR'R$^r$, C(O)OR$^r$, OC(O)R$^r$, OC(O)NR'R$^r$, NHR$^r$, NR'R$^r$, NR$^r$C(O)R$^r$, NR$^r$C(O)NR'R$^r$, NR$^r$C(O)OR$^r$, C(=NR$^r$)NR'R$^r$, NR$^r$C(=NR$^r$)NR'R$^r$, NR$^r$C(=NOH)NR'R$^r$, NR$^r$C(=NCN)NR'R$^r$, S(O)R$^r$, S(O)NR'R$^r$, S(O)$_2$R$^r$, NR'S(O)$_2$R$^r$, NR$^r$S(O)$_2$NR'R$^r$ or S(O)$_2$NR'R$^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, NHR$^8$, NR$^8$R$^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl; m is 1 or 2; Ring A is selected from substituted or unsubstituted $C_{5-10}$ aryl, substituted or unsubstituted $C_{3-6}$ cycloalkyl, and substituted or unsubstituted 5-10 membered monocyclic or bicyclic saturated or unsaturated heterocyclic ring with 1-3 heteroatoms selected from N, S or O; Ring B is selected from $C_{5-10}$ aryl, $C_{3-6}$ cycloalkyl, 5-10 membered monocyclic or bicyclic saturated or unsaturated heterocyclic ring with 1-3 heteroatoms selected from N, S or O.

In another aspect of the present disclosure there is provided a compound of Formula II Formula II

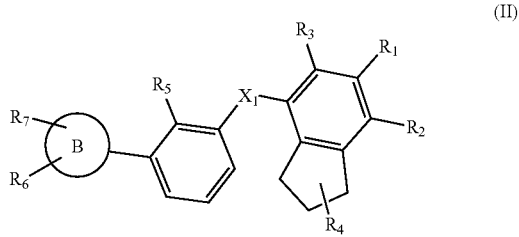

their polymorphs, stereoisomers, tautomers, prodrugs, solvates, and pharmaceutically acceptable salts thereof,
wherein $X_1$ is selected from —CH$_2$O—, —OCH$_2$—, —C(O)NH— or —NHC(O)—;
$R_4$ is selected from hydrogen, hydroxyl, $C_{1-6}$ alkyl, amino, —C(O)OR$_{a1}$, C(O)NR$_{b1}$R$_{c1}$, $C_{5-6}$ aryl, or $C_{1-6}$ heteroaryl, wherein $C_{1-6}$ alkyl is optionally substituted with one or more of the groups selected from the group consisting of hydrogen, hydroxyl, amino, —C(O)OR$_{a1}$, C(O)NR$_{b1}$R$_{c1}$, $C_{5-6}$ aryl, and $C_{1-6}$ heteroaryl;
$R_{a1}$, $R_{b1}$, and $R_{c1}$ are independently selected from hydrogen or $C_{1-6}$ alkyl;
$R_5$ is selected from $C_{1-4}$ alkyl, cyano, or $C_{1-4}$ haloalkyl;
$R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents;

$R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents;

$R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents;

$R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, or S(O)$_2$NR$^g$R$^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents; $R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$haloalkyl are optionally substituted with 1, 2 or 3 $R^q$ substituents;

$R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents;

$R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ or S(O)$_2$NR$^r$R$^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents;

$R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents;

$R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-6}$ cycloalkyl, 5-6 membered heteroaryl and 4-6 membered heterocycloalkyl;

$R^8$ is $C_{1-6}$ alkyl;

Ring B is selected from $C_{5-10}$ aryl, $C_{3-6}$ cycloalkyl, 5-10 membered monocyclic or bicyclic saturated or unsaturated heterocyclic ring with 1-3 heteroatoms selected from N, S or O.

In yet another aspect of the present disclosure there is provided a compound of Formula III

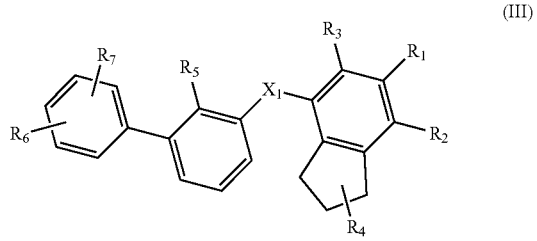

(III)

their polymorphs, stereoisomers, tautomers, prodrugs, solvates, and pharmaceutically acceptable salts thereof, wherein $X_1$ is selected from —$CH_2O$—, —$OCH_2$—, —C(O)NH— or —NHC(O)—;

$R_4$ is selected from hydrogen, hydroxyl, $C_{1-6}$ alkyl, amino, —C(O)OR$_{a1}$, C(O)NR$_{b1}$R$_{c1}$, $C_{5-6}$ aryl, or $C_{1-6}$ heteroaryl; wherein $C_{1-6}$ alkyl is optionally substituted with one or more of the groups selected from the group consisting of hydrogen, hydroxyl, amino, —C(O)OR$_{a1}$, C(O)NR$_{b1}$R$_{c1}$, $C_{5-6}$ aryl, and $C_{1-6}$ heteroaryl;

$R_{a1}$, $R_{b1}$, and $R_{c1}$ are independently selected from hydrogen or $C_{1-6}$ alkyl;

$R_5$ is selected from $C_{1-4}$ alkyl, cyano, or $C_{1-4}$ haloalkyl;

$R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, or $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents;

$R^a$ is selected from hydrogen, cyano, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents;

$R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)$ $NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents;

$R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^e$, $OR^e$, $SR^e$, $C(O)R^e$, $C(O)NR^eR^e$, $C(O)OR^e$, $OC(O)$ $R^e$, $OC(O)NR^eR^e$, $NHR^e$, $NR^eR^e$, $NR^eC(O)R^e$, $NR^eC(O)$ $NR^eR^e$, $NR^eC(O)OR^e$, $C(=NR^e)NR^eR^e$, $NR^eC(=NR^e)$ $NR^eR^e$, $NR^eC(=NOH)NR^eR^e$, $NR^eC(=NCN)NR^eR^e$, $S(O)$ $R^e$, $S(O)NR^eR^e$, $S(O)_2R^e$, $NR^eS(O)_2R^e$, $NR^eS(O)_2NR^eR^e$, or $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents;

$R^f$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^g$, $C(O)R^g$, $C(O)$ $NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)$ $NR^gR^g$, $NR^gC(=NR^g)NR^gR^g$, $S(O)R^g$, $S(O)NR^gR^g$, $S(O)_2$ $R^g$, $NR^gS(O)_2R^g$, $NR^gS(O)_2NR^gR^g$, or $S(O)_2NR^gR^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-C$_{1-4}$ alkyl-, and (4-10 membered heterocycloalkyl)-C$_{1-4}$ alkyl- are optionally substituted with 1, 2, 3, 4, or 5 R$^n$ substituents;

R$^n$ is selected from cyano, halo, C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl, C$_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl and C$_{1-4}$ haloalkyl are optionally substituted with 1, 2 or 3 R$^q$ substituents;

R$^g$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^p$ substituents;

R$^p$ is selected from halo, cyano, C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^r$, OR$^r$, SR$^r$, C(O)R$^r$, C(O)NR$'$R$'$, C(O)OR$^r$, OC(O)R$^r$, OC(O)NR$'$R$'$, NHR$^r$, NR$'$R$'$, NR$'$C(O)R$'$, NR$'$C(O)NR$'$R$'$, NR$'$C(O)OR$^r$, C(=NR$'$)NR$'$R$'$, NR$'$C(=NR$'$)NR$'$R$'$, NR$'$C(=NOH)NR$'$R$'$, NR$'$C(=NCN)NR$'$R$'$, S(O)R$'$, S(O)NR$'$R$'$, S(O)$_2$R$'$, NR$''$S(O)$_2$R$'$, NR$'$S(O)$_2$NR$'$R$'$ or S(O)$_2$NR$'$R$'$, wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2 or 3 R$^q$ substituents;

R$^e$, R$^i$, R$^k$, R$^o$ and R$^r$ are independently selected from hydrogen, C$_{1-4}$ alkyl, C$_{3-6}$ cycloalkyl, C$_{6-10}$ aryl, 5 or 6-membered heteroaryl, 4-6 membered heterocycloalkyl, C$_{1-4}$ haloalkyl, C$_{2-4}$ alkenyl, or C$_{2-4}$ alkynyl, wherein the C$_{1-4}$ alkyl, C$_{3-6}$ cycloalkyl, C$_{6-10}$ aryl, 5 or 6-membered heteroaryl, 4-6 membered heterocycloalkyl, C$_{2-4}$ alkenyl, and C$_{2-4}$ alkynyl are optionally substituted with 1, 2 or 3 R$^q$ substituents;

R$^q$ is selected from hydroxy, cyano, amino, halo, COOH, C$_{1-6}$ haloalkyl, C$_{1-6}$ alkyl, C$_{1-6}$ alkoxy, C$_{1-6}$ alkylthio, C$_{5-6}$ aryl, 5-6 membered heteroaryl, 4-6 membered heterocycloalkyl, C$_{3-6}$ cycloalkyl, NHR$^8$, NR$^8$R$^8$, and C$_{1-4}$ haloalkoxy, wherein the C$_{1-6}$ alkyl, C$_{5-6}$ aryl, C$_{3-6}$ cycloalkyl, 4-6 membered heterocycloalkyl, and 5-6 membered heteroaryl are optionally substituted with halo, hydroxy, cyano, COOH, amino, C$_{1-4}$ alkyl, C$_{1-4}$ alkoxy, C$_{1-4}$ haloalkyl, C$_{1-4}$ haloalkoxy, C$_{5-6}$ aryl, C$_{3-10}$ cycloalkyl, 5-6 membered heteroaryl and 4-6 membered heterocycloalkyl;

R$^8$ is C$_{1-6}$ alkyl.

In an aspect of the present disclosure there is provided a compound of Formula IV

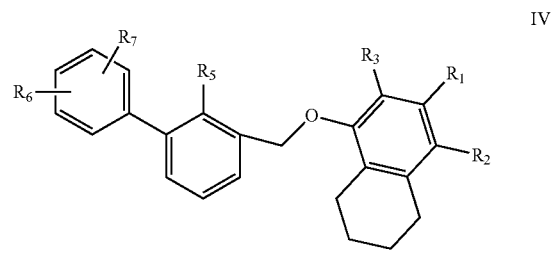

their polymorphs, stereoisomers, tautomers, prodrugs, solvates, and pharmaceutically acceptable salts thereof, wherein R$_5$ is selected from C$_{1-4}$ alkyl, cyano, or C$_{1-4}$ haloalkyl;

R$_1$, R$_2$, R$_3$, R$_6$, and R$_7$ are independently selected from hydrogen, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, (4-10 membered heterocycloalkyl)-C$_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl-, are independently optionally substituted with 1, 2, 3, or 4 R$^b$ substituents;

R$^a$ is selected from hydrogen, cyano, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are independently optionally substituted with 1, 2, 3, 4, or 5 R$^d$ substituents;

R$^b$ is selected from halo, hydroxy, cyano, amino, nitro, C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents;

$R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents;

$R^f$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, or S(O)$_2$NR$^g$R$^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R''$ substituents;

$R''$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$haloalkyl are optionally substituted with 1, 2 or 3 $R^q$ substituents;

$R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents;

$R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^r$, OR$^r$, SR$^r$, C(O)R$^r$, C(O)NR'R$^r$, C(O)OR$^r$, OC(O)R$^r$, OC(O)NR'R$^r$, NHR$^r$, NR'R$^r$, NR'C(O)R$^r$, NR'C(O)NR'R$^r$, NR'C(O)OR$^r$, C(=NR')NR'R$^r$, NR'C(=NR')NR'R$^r$, NR'C(=NOH)NR'R$^r$, NR'C(=NCN)NR'R$^r$, S(O)R$^r$, S(O)NR'R$^r$, S(O)$_2$R$^r$, NR'S(O)$_2$R$^r$, NR'S(O)$_2$NR'R$^r$ or S(O)$_2$NR'R$^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents;

$R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents;

$R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, NHR$^8$, NR$^8$R$^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl;

$R^8$ is $C_{1-6}$ alkyl.

In an aspect of the present disclosure there is provided a compound of Formula V

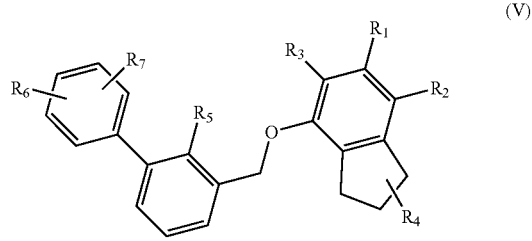

(V)

their polymorphs, stereoisomers, tautomers, prodrugs, solvates, and pharmaceutically acceptable salts thereof,
wherein $R_5$ is selected from $C_{1-4}$ alkyl, cyano, or $C_{1-4}$ haloalkyl;

$R_4$ is selected from hydrogen, hydroxyl, $C_{1-6}$ alkyl, amino, —C(O)OR$_{a1}$, C(O)NR$_{b1}$R$_{c1}$, $C_{5-6}$ aryl, or $C_{1-6}$ heteroaryl; wherein $C_{1-6}$ alkyl is optionally substituted with one or more of the groups selected from the group consisting of hydrogen, hydroxyl, amino, —C(O)OR$_{a1}$, C(O)NR$_{b1}$R$_{c1}$, $C_{5-6}$ aryl, and $C_{1-6}$ heteroaryl;

$R_{a1}$, $R_{b1}$, and $R_{c1}$ are independently selected from hydrogen or $C_{1-6}$ alkyl;

$R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 R$^b$ substituents;

$R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 R$^d$ substituents;

$R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 R$^d$ substituents;

$R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)R$^e$, NR$^e$S(O)$_2$NR$^e$R$^e$, or S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 R$^f$ substituents;

$R^f$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 R$^f$ substituent;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, or S(O)$_2$NR$^g$R$^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 R$^n$ substituents;

$R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$ haloalkyl are optionally substituted with 1, 2 or 3 R$^q$ substituents;

$R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 R$^p$ substituents;

$R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR′, OR′, SR′, C(O)R′, C(O)NR′R′, C(O)OR′, OC(O)R′, OC(O)NR′R′, NHR′, NR′R′, NR′C(O)R′, NR′C(O)NR′R′, NR′C(O)OR′, C(=NR)NR′R′, NR′C(=NR′)NR′R′, NR′C(=NOH)NR′R′, NR′C(=NCN)NR′R′, S(O)R′, S(O)NR′R′, S(O)$_2$R′, NR′S(O)$_2$R′, NR′S(O)$_2$NR′R′ or S(O)$_2$NR′R′, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents;

$R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents;

$R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, NHR$^8$, NR$^8$R$^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl;

$R^8$ is $C_{1-6}$ alkyl.

In an aspect of the present disclosure there is provided a compound of Formula VI

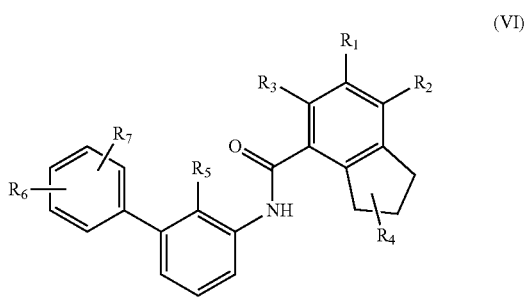

(VI)

their polymorphs, stereoisomers, tautomers, prodrugs, solvates, and pharmaceutically acceptable salts thereof, wherein $R_5$ is selected from $C_{1-4}$ alkyl, cyano, or $C_{1-4}$ haloalkyl;

$R_4$ is selected from hydrogen, hydroxyl, $C_{1-6}$ alkyl, amino, —C(O)OR$_{a1}$, C(O)NR$_{b1}$R$_{c1}$, $C_{5-6}$ aryl, or $C_{1-6}$ heteroaryl; wherein $C_{1-6}$ alkyl is optionally substituted with one or more of the groups selected from the group consisting of hydrogen, hydroxyl, amino, —C(O)OR$_{a1}$, C(O)NR$_{b1}$R$_{c1}$, $C_{5-6}$ aryl, and $C_{1-6}$ heteroaryl;

R$_{a1}$, R$_{b1}$, and R$_{c1}$ are independently selected from hydrogen or $C_{1-6}$ alkyl;

$R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents;

$R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents;

$R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents;

$R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents;

$R^e$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, or $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents;

$R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR)NR^oR^o$, $S(O)R^o$, $S(O)NR^oR^o$, $S(O)_2R^o$, $NR^oS(O)_2R^o$, $NR^oS(O)_2NR^oR^o$, or $S(O)_2NR^oR^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$ haloalkyl are optionally substituted with 1, 2 or 3 $R^q$ substituents;

$R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents;

$R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^r$, $OR^r$, $SR^r$, $C(O)R^r$, $C(O)NR'R^r$, $C(O)OR^r$, $OC(O)R^r$, $OC(O)NR'R^r$, $NHR^r$, $NR'R^r$, $NR'C(O)R^r$, $NR'C(O)NR'R^r$, $NR'C(O)OR^r$, $C(=NR')NR'R^r$, $NR'C(=NR')NR'R^r$, $NR'C(=NOH)NR'R^r$, $NR'C(=NCN)NR'R^r$, $S(O)R^r$, $S(O)NR'R^r$, $S(O)_2R^r$, $NR''S(O)_2R^r$, $NR''S(O)_2NR'R^r$ or $S(O)_2NR'R^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents;

$R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents;

$R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl;

$R^8$ is $C_{1-6}$ alkyl.

The present disclosure further describes the process of preparation of compounds of Formula I, Formula II, Formula III, Formula IV, Formula V, Formula VI, or their polymorphs, stereoisomers, tautomers, prodrugs, solvates, and pharmaceutically acceptable salts thereof.

The present disclosure also discloses the method for the treatment and/or prevention of various diseases, including cancer and infectious diseases, comprising administering to a subject suffering from the proliferative disorder or cancer a therapeutically effective amount of the compound of Formula I, Formula II, Formula III, Formula IV, Formula V, Formula VI, or the pharmaceutical composition comprising compound of Formula I, Formula II, Formula III, Formula IV, Formula V, or Formula VI, with other clinically relevant cytotoxic agents or non-cytotoxic agents to a subject in need thereof.

The present disclosure further discloses the use of the compounds of Formula I, Formula II, Formula III, Formula IV, Formula V, Formula VI, or the pharmaceutical composition comprising compounds of Formula I, Formula II, Formula III, Formula IV, Formula V, or Formula VI, for the treatment and/or prevention of various diseases including proliferative disorder or cancer; or treatment of cancer together with other clinically relevant cytotoxic agents or non-cytotoxic agents.

The present disclosure also discloses a method for the treatment of cancer, said method comprising administering a combination of the compounds of Formula I, Formula II, Formula III, Formula IV, Formula V, Formula VI, or the pharmaceutical composition comprising compounds of Formula I, Formula II, Formula III, Formula IV, Formula V, or Formula VI, with other clinically relevant cytotoxic agents or non-cytotoxic agents to a subject in need thereof.

The present disclosure further describes a method of treatment of cancer, said method comprising administering a combination of the compounds of Formula I, Formula II, Formula III, Formula IV, Formula V, Formula VI, or the pharmaceutical composition, with other clinically relevant immune modulators agents to a subject in need of thereof.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

Furthermore, the compound of Formula I, Formula II, Formula III, Formula IV, Formula V, Formula VI, can be its derivatives, analogs, stereoisomers, diastereomers, geometrical isomers, polymorphs, solvates, co-crystals, intermediates, metabolites, prodrugs or pharmaceutically acceptable salts and compositions.

The compounds of Formula I, Formula II, Formula III, Formula IV, Formula V, Formula VI, and their polymorphs, stereoisomers, prodrugs, solvates, co-crystals, intermediates, pharmaceutically acceptable salts, and metabolites thereof can also be referred as "compounds of the present disclosure".

The compounds according to Formula I, Formula II, Formula III, Formula IV, Formula V, Formula VI, may contain one or more asymmetric centers (also referred to as a chiral centers) and may, therefore, exist as individual enantiomers, diastereoisomers, or other stereoisomeric forms, or as mixtures thereof. Chiral centers, such as chiral carbon atoms, may also be present in a substituent such as an alkyl group. Where the stereochemistry of a chiral center present in Formula I, Formula II, Formula III, Formula IV, Formula V, Formula VI, or in any chemical structure illustrated herein, is not specified, the structure is intended to encompass any stereoisomer and all mixtures thereof. Thus, compounds according to Formula I-VI containing one or more chiral centers may be used as racemic modifications including racemic mixtures and racemates, enantiomerically-enriched mixtures, or as enantiomerically-pure individual stereoisomers.

Compounds disclosed herein include isotopes of hydrogen, carbon, oxygen, fluorine, chlorine, iodine and sulfur which can be incorporated into the compounds, such as not limited to $^2$H (D), $^3$H (T), c $^{11}$C, $^{13}$C, $^{14}$C, $^{15}$N, $^{18}$F, $^{35}$S, $^{36}$Cl and $^{125}$I. Compounds of this invention where in atoms were isotopically labeled for example radioisotopes such as $^3$H, $^{13}$C, $^{14}$C, and the like can be used in metabolic studies and kinetic studies. Compounds of the invention where hydrogen is replaced with deuterium may improve the metabolic stability and pharmacokinetics properties of the drug such as in vivo half life.

Individual stereoisomers of a compound according to Formula I-VI which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form.

Alternatively, specific stereoisomers may be synthesized by asymmetric synthesis using optically active reagents, substrates, catalysts or solvents, or by converting one enantiomer to the other by asymmetric transformation.

It is to be understood that the references herein to compounds of Formula I-VI and salts thereof covers the compounds of Formula I-VI as free bases, or as salts thereof, for example as pharmaceutically acceptable salts thereof. Thus, in one embodiment, the invention is directed to compounds of Formula I-VI as the free base. In another embodiment, the invention is directed to compounds of Formula I-VI and salts thereof. In a further embodiment, the invention is directed to compounds of Formula I-VI and pharmaceutically acceptable salts thereof.

It will be appreciated that pharmaceutically acceptable salts of the compounds according to Formula I, Formula II, Formula III, Formula IV, Formula V, or Formula VI, may be prepared. Indeed, in certain embodiments of the invention, pharmaceutically acceptable salts of the compounds according to Formula I-VI may be preferred over the respective free base because such salts impart greater stability or solubility to the molecule thereby facilitating formulation into a dosage form. Accordingly, the invention is further directed to compounds of Formula I-VI, and pharmaceutically acceptable salts thereof.

Included within the scope of the "compounds of the invention" are all solvates (including hydrates), complexes, polymorphs, prodrugs, radiolabelled derivatives, and stereoisomers of the compounds of Formula I-VI, and salts thereof.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, isopropyl alcohol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

The term "prodrugs" refers to the precursor of the compound of Formula Ia, and Formula I which on administration undergoes chemical conversion by metabolic processes before becoming active pharmacological substances. In general, such prodrugs will be functional derivatives of a compound of the invention, which are readily convertible in vivo into a compound of the invention.

The term "alkyl" refers to a saturated hydrocarbon chain having the specified number of carbon atoms. For example, which are not limited, $C_{1-6}$ alkyl refers to an alkyl group having from 1-6 carbon atoms, or 1-4 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, isobutyl, and t-butyl.

The term "alkoxy" refers to an alkyl group attached via an oxygen linkage to the rest of the molecule. For example, $C_{1-6}$ alkoxy refers to an alkyl group having from 1-6 carbon atoms, or 1-4 carbon atoms attached via an oxygen linkage to the rest of the molecule. Preferred alkoxy groups include, without limitation, —OCH$_3$ (methoxy), —OC$_2$H$_5$ (ethoxy) and the like.

The term "haloalkyl" refers to a halogen in an alkyl group as defined above attached via alkyl linkage to the rest of the molecule. For example, $C_{1-6}$ haloalkyl refers to an alkyl group having from 1-6 carbon atoms, or 1-4 carbon atoms wherein one or more hydrogen atoms are replaced by the same number of identical or different halogen atoms. Preferred haloalkyl groups include, without limitation, —CH2Cl, —CHCl2, trifluoromethyl, 2,2,2-trifluoroethyl, and the like.

The term "haloalkoxy" refers to a halogen in an alkoxy group as defined above further attached via oxygen linkage to the rest of the molecule. For example, $C_{1-6}$ haloalkoxy refers to an alkoxy group having from 1-6 carbon atoms, or 1-3 carbon atoms further attached via halo linkage. Preferred haloalkoxy groups include, without limitation, —OCH$_2$Cl, —OCHCl$_2$, and the like.

The term "halo" or "halogen" refers to a halogen radical, for example, fluoro, chloro, bromo, or iodo.

The term "cycloalkyl" refers to a saturated hydrocarbon ring having a specified number of carbon atoms, which may be monocyclic or polycyclic. For example, which are not limited, $C_{3-10}$ cycloalkyl refers to a cycloalkyl group having from 3 to 10 member atoms or 3 to 6 member atoms. The polycyclic ring denotes hydrocarbon systems containing two or more ring systems with one or more ring carbon atoms in common i.e. a spiro, fused or bridged structures. For example, which are not limited, $C_{3-6}$ cycloalkyl refers to a cycloalkyl group having from 3 to 6 membered atoms. Preferred cycloalkyl groups include, without limitation, cyclopropyl, cyclobutyl, cyclopentyl, cyclohexyl, cyclooctanyl, perhydronaphthyl, adamantyl, noradamantyl and norbornyl groups, bridged cyclic groups or spirobicyclic groups e.g spiro [4.4] non-2-yl, and the like.

The term "aryl" refers to aromatic ring having a specified number of carbon atoms. For example, $C_{5-6}$ aryl refers to an aryl group having 5 or 6 member atoms, or 6 member atoms. $C_{6-10}$ aryl refers to an aryl group having 6 to 10 member atoms. Preferred aryl groups include, without limitation, phenyl, and the like.

The term "heteroaryl" refers to aromatic rings containing from 1 to 3 heteroatoms in the ring. "Heteroaryl" groups may be substituted with one or one or more substituents if so defined herein. The "$C_{1-6}$ heteroaryl" rings having 1 or 6 carbon as member atoms. The term "5-14 membered heteroaryl" has 5 to 14 carbon as member atoms. The "heteroaryl" includes pyridinyl, tetrazolyl and pyrazolyl. "Heteroatom" refers to a nitrogen, sulfur, or oxygen atom, for example a nitrogen atom or an oxygen atom.

The term "heterocyclic" or refer to saturated or unsaturated monocyclic aliphatic rings containing 5, 6, or 7 ring members including 1-3 heteroatoms or to saturated or unsaturated bicyclic, tricyclic, tetracyclic aliphatic rings containing 5, 6 or 7 ring members including 1-3 heteroatoms, which may include spiro, fused, or bridged ring systems. In certain embodiments, "heterocyclic" groups are saturated. In other embodiments, "heterocyclic" groups are unsaturated. "heterocyclic" groups containing more than one heteroatom may contain different heteroatoms. "heterocyclic" groups may be substituted with one or more substituents as defined herein. "heterocyclic" includes piperidinyl, tetrahydropyranyl, azepinyl, oxazepinyl, azabicyclo[3.1.0] hexanyl.

The term "heterocycloalkyl-" refers to to a heterocyclic group as defined above further attached via alkyl linkage to the rest of the molecule. For example, 4-10 membered heterocycloalkyl refers to heterocyclic group as defined above further attached via alkyl linkage to the rest of the molecule.

The phrase "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid.

Salts and solvates having non-pharmaceutically acceptable counter-ions or associated solvents are within the scope of the present invention, for example, for use as intermediates in the preparation of other compounds of Formula I, Formula II, Formula III, Formula IV, Formula V, Formula VI, and their pharmaceutically acceptable salts.

Thus, one embodiment of the invention embraces compounds of Formula I, Formula II, Formula III, Formula IV, Formula V, Formula VI, and salts thereof. Compounds according to and Formula I, Formula II, Formula III, Formula IV, Formula V, Formula VI contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenyl acetate, propionate, butyrate, iso-butyrate, valerate, maleate, hydroxymaleate, acrylate, fumarate, malate, tartrate, citrate, salicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), aminobenzenesulfonate, p-toluenesulfonate (tosylate), and naphthalene-2-sulfonate.

The term "PD-1/PD-L1 inhibitor or inhibitory compounds" or "inhibitors of PD-1/PD-L1 activation" is used to identify a compound, which is capable of blocking PD-1/PD-L1 pathway to prevent inhibitory signalling from cancer cells and enabling CTLs to elicit an immune response against the target/cancer cells and thus treat cancer and other diseases or conditions associated with activation of PD1/PD-L1.

The term "cytotoxic agents" or "inhibitors" is used to identify any agents or drugs which are capable of killing cells including cancer cells. These agents or 10 inhibitors may stop cancer cells from growing and dividing and may cause tumors to shrink in size.

The term "non-cytotoxic agents" or "inhibitors" is used to identify any agents or inhibitors are which does not directly kill cells, but instead affects cellular transport and metabolic functions to ultimately produce cell death.

The term "immune checkpoint inhibitors agents" or "immune modulators agents" are used to identify any agents or inhibitors that blocks certain proteins made by some types of immune system cells, such as T cells, and some cancer cells. These proteins help keep immune responses in check and can keep T cells from killing cancer cells.

When these proteins are blocked, the "brakes" on the immune system are released 20 and T cells are able to kill cancer cells better. The immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1B), ICOS, A2AR, B7-H3, B7-H4, BTLA, CTLA-4, LAG3, TIM3, VISTA, PD-1, PD-L1 and PD-L2. The terms "immune modulators agents" and "immune checkpoint inhibitors" are used interchangeably throughout the present disclosure.

As discussed in the background section, the identification and development of new PD-1/PD-L1 inhibitor compounds treating cancer and other diseases or conditions associated with activation of PD-1/PD-L1 would open new opportunities in the realm of cancer treatment.

A term once described, the same meaning applies for it, throughout the disclosure.

In an embodiment of the present disclosure, there is provided a compound of Formula I

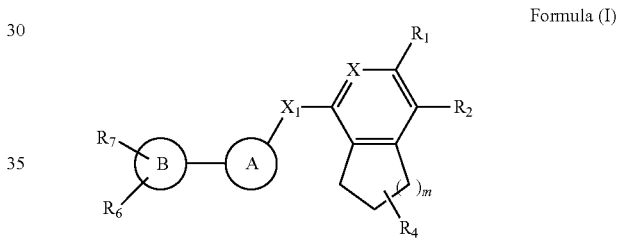

Formula (I)

their polymorphs, stereoisomers, tautomers, prodrugs, solvates, and pharmaceutically acceptable salts thereof, wherein $X_1$ is selected from —$CH_2O$—, —$OCH_2$—, —C(O)NH— or —NHC(O)—; $R_4$ is selected from hydrogen, hydroxyl, $C_{1-6}$ alkyl, amino, —C(O)OR$_{a1}$, C(O)NR$_{b1}$R$_{c1}$, $C_{5-6}$ aryl, or $C_{1-6}$ heteroaryl, wherein $C_{1-6}$ alkyl is optionally substituted with one or more of the groups selected from the group consisting of hydrogen, hydroxyl, amino, —C(O)OR$_{a1}$, C(O)NR$_{b1}$R$_{c1}$, $C_{5-6}$ aryl, and $C_{1-6}$ heteroaryl; R$_{a1}$, R$_{b1}$, and R$_{c1}$ are independently selected from hydrogen or $C_{1-6}$ alkyl; X is selected from CR$_3$ or N; $R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents; $R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents; $R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, or $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, or $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, or $S(O)_2NR^oR^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$ haloalkyl are optionally substituted with 1, 2 or 3 $R^q$ substituents; $R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$ or $S(O)_2NR^rR^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl; m is 1 or 2; Ring A is selected from substituted or unsubstituted $C_{5-10}$ aryl, substituted or unsubstituted $C_{3-6}$ cycloalkyl, and substituted or unsubstituted 5-10 membered monocyclic or bicyclic saturated or unsaturated heterocyclic ring with 1-3 heteroatoms selected from N, S or O; Ring B is selected from $C_{5-10}$ aryl, $C_{3-6}$ cycloalkyl, 5-10 membered monocyclic or bicyclic saturated or unsaturated heterocyclic ring with 1-3 heteroatoms selected from N, S or O.

In an embodiment of the present disclosure, there is provided a compound of Formula I, their polymorphs, stereoisomers, tautomers, prodrugs, solvates, and pharmaceutically acceptable salts thereof, wherein $X_1$ is selected from —$CH_2O$—, —$OCH_2$—, —C(O)NH— or —NHC(O)—; $R_4$ is selected from hydrogen, hydroxyl, $C_{1-6}$ alkyl, amino, —C(O)$OR_{a1}$, C(O)$NR_{b1}R_{c1}$, $C_{5-6}$ aryl, or $C_{1-6}$ heteroaryl, wherein $C_{1-6}$ alkyl is optionally substituted with one or more of the groups selected from the group consisting of hydrogen, hydroxyl, amino, —C(O)$OR_{a1}$, C(O)$NR_{b1}R_{c1}$, $C_{5-6}$ aryl, and $C_{1-6}$ heteroaryl; $R_{a1}$, $R_{b1}$, and $R_{c1}$ are independently selected from hydrogen or $C_{1-6}$ alkyl; X is $CR_3$; $R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHR^a$, C(O)$R^a$, C(O)$NR^aR^a$, C(O)$OR^a$, OC(O)$R^a$, OC(O)$NR^aR^a$, $NHR^a$, $NR^aR^a$, $NR^aC(O)R^a$, $NR^aC(O)OR^a$, $NR^aC(O)NR^aR^a$, C(=$NR^a$)$R^a$, C(=$NR^a$)$NR^aR^a$, $NR^aC$(=$NR^a$)$NR^aR^a$, $NR^aS(O)R^a$, $NR^aS(O)_2R^a$, $NR^aS(O)_2NR^aR^a$, S(O)$R^a$, S(O)$NR^aR^a$, S(O)$_2R^a$, or S(O)$_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents; $R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^c$, $OR^c$, $SR^c$, C(O)$R^c$, C(O)$NR^cR^c$, C(O)$OR^c$, OC(O)$R^c$, OC(O)$NR^cR^c$, C(=$NR^c$)$NR^cR^c$, $NR^cC$(=$NR^c$)$NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, S(O)$R^c$, S(O)$NR^cR^c$, S(O)$_2R^c$ or S(O)$_2NR^cR^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents; $R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^e$, $OR^e$, $SR^e$, C(O)$R^e$, C(O)$NR^eR^e$, C(O)$OR^e$, OC(O)$R^e$, OC(O)$NR^eR^e$, $NHR^e$, $NR^eR^e$, $NR^eC(O)R^e$, $NR^eC(O)NR^eR^e$, $NR^eC(O)OR^e$, C(=$NR^e$)$NR^eR^e$, $NR^eC$(=$NR^e$) $NR^eR^e$, $NR^eC$(=NOH)$NR^eR^e$, $NR^eC$(=NCN)$NR^eR^e$, S(O)$R^e$, S(O)$NR^eR^e$, S(O)$_2R^e$, $NR^eS(O)_2R^e$, $NR^eS(O)_2NR^eR^e$, or S(O)$_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents; $R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^g$, C(O)$R^g$, C(O)$NR^gR^g$, C(O)$OR^g$, OC(O)$R^g$, OC(O)$NR^gR^g$, $NHR^g$, $NR^gR^g$, $NR^gC(O)R^g$, $NR^gC(O)NR^gR^g$, $NR^gC(O)OR^g$, C(=$NR^g$) $NR^gR^g$, $NR^gC$(=$NR^g$)$NR^gR^g$, S(O)$R^g$, S(O)$NR^gR^g$, S(O)$_2R^g$, $NR^gS(O)_2R^g$, $NR^gS(O)_2NR^gR^g$, or S(O)$_2NR^gR^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, C(O)$R^o$, C(O)$NR^oR^o$, C(O)$OR^o$, OC(O)$R^o$, OC(O)$NR^oR^o$, $NHR^o$, $NR^oR^o$, $NR^oC(O)R^o$, $NR^oC(O)NR^oR^o$, $NR^oC(O)OR^o$, C(=NR)$NR^oR^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl and C$_{1-4}$haloalkyl are optionally substituted with 1, 2 or 3 R$^q$ substituents; R$^p$ is selected from halo, cyano, C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ or S(O)$_2$NR$^r$R$^r$, wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2 or 3 R$^q$ substituents; R$^e$, R$^i$, R$^k$, R$^o$ and R$^r$ are independently selected from hydrogen, C$_{1-4}$ alkyl, C$_{3-6}$ cycloalkyl, C$_{6-10}$ aryl, 5 or 6-membered heteroaryl, 4-6 membered heterocycloalkyl, C$_{1-4}$ haloalkyl, C$_{2-4}$ alkenyl, or C$_{2-4}$ alkynyl, wherein the C$_{1-4}$ alkyl, C$_{3-6}$ cycloalkyl, C$_{6-10}$ aryl, 5 or 6-membered heteroaryl, 4-6 membered heterocycloalkyl, C$_{2-4}$ alkenyl, and C$_{2-4}$ alkynyl are optionally substituted with 1, 2 or 3 R$^q$ substituents; R$^q$ is selected from hydroxy, cyano, amino, halo, COOH, C$_{1-6}$ haloalkyl, C$_{1-6}$ alkyl, C$_{1-6}$ alkoxy, C$_{1-6}$ alkylthio, C$_{5-6}$ aryl, 5-6 membered heteroaryl, 4-6 membered heterocycloalkyl, C$_{3-6}$ cycloalkyl, NHR$^8$, NR$^8$R$^8$, and C$_{1-4}$ haloalkoxy, wherein the C$_{1-6}$ alkyl, C$_{5-6}$ aryl, C$_{3-6}$ cycloalkyl, 4-6 membered heterocycloalkyl, and 5-6 membered heteroaryl are optionally substituted with halo, hydroxy, cyano, COOH, amino, C$_{1-4}$ alkyl, C$_{1-4}$ alkoxy, C$_{1-4}$ haloalkyl, C$_{1-4}$ haloalkoxy, C$_{5-6}$ aryl, C$_{3-10}$ cycloalkyl, 5-6 membered heteroaryl and 4-6 membered heterocycloalkyl; R$^8$ is C$_{1-6}$ alkyl; m is 1 or 2; Ring A is selected from substituted or unsubstituted C$_{5-10}$ aryl; Ring B is selected from C$_{5-10}$ aryl, C$_{3-6}$ cycloalkyl, 5-10 membered monocyclic or bicyclic saturated or unsaturated heterocyclic ring with 1-3 heteroatoms selected from N, S or O.

In an embodiment of the present disclosure, there is provided a compound of Formula II

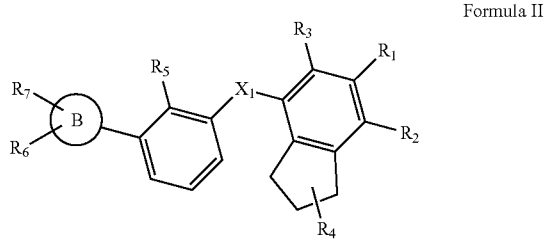

Formula II their polymorphs, stereoisomers, tautomers, prodrugs, solvates, and pharmaceutically acceptable salts thereof, wherein X$_1$ is selected from —CH$_2$O—, —OCH$_2$—, —C(O)NH— or —NHC(O)—; R$_4$ is selected from hydrogen, hydroxyl, C$_{1-6}$ alkyl, amino, —C(O)OR$_{a1}$, C(O)NR$_{b1}$R$_{c1}$, C$_{5-6}$ aryl, or C$_{1-6}$ heteroaryl, wherein C$_{1-6}$ alkyl is optionally substituted with one or more of the groups selected from the group consisting of hydrogen, hydroxyl, amino, —C(O)OR$_{a1}$, C(O)NR$_{b1}$R$_{c1}$, C$_{5-6}$ aryl, and C$_{1-6}$ heteroaryl; R$_{a1}$, R$_{b1}$, and R$_{c1}$ are independently selected from hydrogen or C$_{1-6}$ alkyl; R$_5$ is selected from C$_{1-4}$ alkyl, cyano, or C$_{1-4}$ haloalkyl; R$_1$, R$_2$, R$_3$, R$_6$, and R$_7$ are independently selected from hydrogen, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, (4-10 membered heterocycloalkyl)-C$_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl-, are independently optionally substituted with 1, 2, 3, or 4 R$^b$ substituents; R$^a$ is selected from hydrogen, cyano, C$_{1-6}$alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are independently optionally substituted with 1, 2, 3, 4, or 5 R$^d$ substituents; R$^b$ is selected from halo, hydroxy, cyano, amino, nitro, C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$) NR$^c$R$^c$, NHR$^c$, NR$^c$R$^c$, NR$^c$C(O)R$^c$, NR$^c$C(O)OR$^c$, NR$^c$C(O) NR$^c$R$^c$, NR$^c$S(O)R$^c$, NR$^c$S(O)$_2$R$^c$, NR$^c$S(O)$_2$NR$^c$R$^c$, S(O) R$^c$, S(O)NR$^c$R$^c$, S(O)$_2$R$^c$ or S(O)$_2$NR$^c$R$^c$; wherein the C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^d$ substituents; R$^d$ is selected from cyano, amino, C$_{1-6}$ alkyl, C$_{1-6}$ haloalkyl, halo, C$_{6-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^e$, OR$^e$, SR$^e$, C(O)R$^e$, C(O) NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$) NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the C$_{1-6}$ alkyl, C$_{1-6}$ haloalkyl, C$_{6-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents; $R^e$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, or $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R''$ substituents; $R''$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, or $S(O)_2NR^oR^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$haloalkyl are optionally substituted with 1, 2 or 3 $R^q$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)$ $NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$ or $S(O)_2NR^rR^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl; Ring B is selected from $C_{5-10}$ aryl, $C_{3-6}$ cycloalkyl, 5-10 membered monocyclic or bicyclic saturated or unsaturated heterocyclic ring with 1-3 heteroatoms selected from N, S or O.

In an embodiment of the present disclosure, there is provided a compound of Formula II, their polymorphs, stereoisomers, tautomers, prodrugs, solvates, and pharmaceutically acceptable salts thereof, wherein $X_1$ is selected from —$CH_2O$—, —$OCH_2$—, —C(O)NH— or —NHC(O)—; $R_4$ is selected from hydrogen, hydroxyl, $C_{1-6}$ alkyl, amino, —$C(O)OR_{a1}$, $C(O)NR_{b1}R_{c1}$, $C_{5-6}$ aryl, or $C_{1-6}$ heteroaryl, wherein $C_{1-6}$ alkyl is optionally substituted with one or more of the groups selected from the group consisting of hydrogen, hydroxyl, amino, —$C(O)OR_{a1}$, $C(O)NR_{b1}R_{c1}$, $C_{5-6}$ aryl, and $C_{1-6}$ heteroaryl; $R_{a1}$, $R_{b1}$, and $R_{c1}$ are independently selected from hydrogen or $C_{1-6}$ alkyl; $R_5$ is selected from $C_{1-4}$ alkyl, cyano, or $C_{1-4}$ haloalkyl; $R_3$ is independently selected from hydrogen, halo, $C(O)OR^a$, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, or $C_{3-10}$ cycloalkyl; $R_1$, $R_2$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2 R^a$, or $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents; $R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^c(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents; $R^d$ is selected from cyano, amino, $C_{1-6}$ alkyl, $C_{1-6}$haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, or $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents; $R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent;

$R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, or $S(O)_2NR^gR^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents;

$R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, or $S(O)_2NR^oR^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$haloalkyl are optionally substituted with 1, 2 or 3 $R^q$ substituents; $R^g$ is selected from hydrogen, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR)NR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$ or $S(O)_2NR^rR^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl; Ring B is selected from $C_{5-10}$ aryl, $C_{3-6}$ cycloalkyl, 5-10 membered monocyclic or bicyclic saturated or unsaturated heterocyclic ring with 1-3 heteroatoms selected from N, S or O.

In an embodiment of the present disclosure, there is provided a compound of Formula III

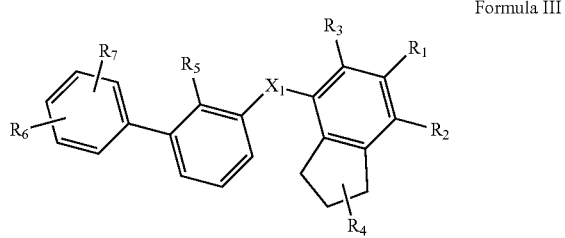

Formula III their polymorphs, stereoisomers, tautomers, prodrugs, solvates, and pharmaceutically acceptable salts thereof, wherein $X_1$ is selected from —CH$_2$O—, —OCH$_2$—, —C(O)NH— or —NHC(O)—; $R_4$ is selected from hydrogen, hydroxyl, $C_{1-6}$ alkyl, amino, —C(O)OR$_{a1}$, C(O)NR$_{b1}$R$_{c1}$, $C_{5-6}$ aryl, or $C_{1-6}$ heteroaryl; wherein $C_{1-6}$ alkyl is optionally substituted with one or more of the groups selected from the group consisting of hydrogen, hydroxyl, amino, —C(O)OR$_{a1}$, C(O)NR$_{b1}$R$_{c1}$, $C_{5-6}$ aryl, and $C_{1-6}$ heteroaryl; $R_{a1}$, $R_{b1}$, and $R_{c1}$ are independently selected from hydrogen or $C_{1-6}$ alkyl; $R_5$ is selected from $C_{1-4}$ alkyl, cyano, or $C_{1-4}$ haloalkyl; $R_1$, $R_2$, $R_3$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 R$^b$ substituents; R$^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 R$^d$ substituents; R$^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$) NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 R$^d$ substituents; R$^d$ is selected from cyano, amino, $C_{1-6}$ alkyl, $C_{1-6}$haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 R$^f$ substituents; R$^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 R$^f$ substituent; R$^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, NHOR$^g$, OR$^g$, SR$^g$, C(O)R$^g$, C(O)NR$^g$R$^g$, C(O) OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, or S(O)$_2$NR$^g$R$^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 R$^n$ substituents; R$^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, R$^o$, NHOR$^o$, OR$^o$, SR$^o$, C(O) R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O) OR$^o$, C(=NR$^o$)NR$^o$R$^o$, NR$^o$C(=NR$^o$)NR$^o$R$^o$, S(O)R$^o$, S(O) NR$^o$R$^o$, S(O)$_2$R$^o$, NR$^o$S(O)$_2$R$^o$, NR$^o$S(O)$_2$NR$^o$R$^o$, or S(O)$_2$ NR$^o$R$^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$ haloalkyl are optionally substituted with 1, 2 or 3 $R^q$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ or S(O)$_2$NR$^r$R$^r$, wherein the $C_{1-6}$ alkyl, $C_{1-6}$haloalkyl, $C_{1-6}$haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, NHR$^8$, NR$^8$R$^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl.

In an embodiment of the present disclosure, there is provided a compound of Formula III, their polymorphs, stereoisomers, tautomers, prodrugs, solvates, and pharmaceutically acceptable salts thereof, wherein $X_1$ is selected from —CH$_2$O—, —OCH$_2$—, or —C(O)NH—; $R_4$ is selected from hydrogen, hydroxyl, $C_{1-6}$ alkyl, amino, —C(O)OR$_{a1}$, C(O)NR$_{b1}$R$_{c1}$, $C_{5-6}$ aryl, or $C_{1-6}$ heteroaryl; wherein $C_{1-6}$ alkyl is optionally substituted with one or more of the groups selected from the group consisting of hydrogen, hydroxyl, amino, —C(O)OR$_{a1}$, C(O)NR$_{b1}$R$_{c1}$, $C_{5-6}$ aryl, and $C_{1-6}$ heteroaryl; $R_{a1}$, $R_{b1}$, and $R_{c1}$ are independently selected from hydrogen or $C_{1-6}$ alkyl; $R_5$ is selected from $C_{1-4}$ alkyl, cyano, or $C_{1-4}$ haloalkyl; $R_3$ is independently selected from hydrogen, halo, C(O)OR$^a$, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, or $C_{3-10}$ cycloalkyl; $R_1$, $R_2$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents; $R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents; $R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents; $R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, 3, 4, or 5 R$^f$ substituent; R$^f$ is selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, or S(O)$_2$NR$^g$R$^g$; wherein the C$_{1-4}$ alkyl, C$_{1-4}$haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are optionally substituted with 1, 2, 3, 4, or 5 R$^n$ substituents; R$^n$ is selected from cyano, halo, C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl, C$_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl and C$_{1-4}$ haloalkyl are optionally substituted with 1, 2 or 3 R$^q$ substituents; R$^g$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^p$ substituents; R$^p$ is selected from halo, cyano, C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^r$, OR$^r$, SR$^r$, C(O)R$^r$, C(O)NR$'$R$^r$, C(O)OR$^r$, OC(O)R$^r$, OC(O)NR$'$R$^r$, NHR$^r$, NR$'$R$^r$, NR$'$C(O)R$^r$, NR$'$C(O)NR$'$R$^r$, NR$'$C(O)OR$^r$, C(=NR$^r$)NR$'$R$^r$, NR$'$C(=NR$^r$)NR$'$R$^r$, NR$'$C(=NOH)NR$'$R$^r$, NR$'$C(=NCN)NR$'$R$^r$, S(O)R$^r$, S(O)NR$'$R$^r$, S(O)$_2$R$^r$, NR$'$S(O)$_2$R$^r$, NR$'$S(O)$_2$NR$'$R$^r$ or S(O)$_2$NR$'$R$^r$, wherein the C$_{1-6}$ alkyl, C$_{1-6}$haloalkyl, C$_{1-6}$haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2 or 3 R$^q$ substituents; R$^e$, R$^i$, R$^k$, R$^o$ and R$^r$ are independently selected from hydrogen, C$_{1-4}$ alkyl, C$_{3-6}$ cycloalkyl, C$_{6-10}$ aryl, 5 or 6-membered heteroaryl, 4-6 membered heterocycloalkyl, C$_{1-4}$ haloalkyl, C$_{2-4}$ alkenyl, or C$_{2-4}$ alkynyl, wherein the C$_{1-4}$ alkyl, C$_{3-6}$ cycloalkyl, C$_{6-10}$ aryl, 5 or 6-membered heteroaryl, 4-6 membered heterocycloalkyl, C$_{2-4}$ alkenyl, and C$_{2-4}$ alkynyl are optionally substituted with 1, 2 or 3 R$^q$ substituents; R$^q$ is selected from hydroxy, cyano, amino, halo, COOH, C$_{1-6}$ haloalkyl, C$_{1-6}$ alkyl, C$_{1-6}$ alkoxy, C$_{1-6}$ alkylthio, C$_{5-6}$ aryl, 5-6 membered heteroaryl, 4-6 membered heterocycloalkyl, C$_{3-6}$ cycloalkyl, NHR$^8$, NR$^8$R$^8$, and C$_{1-4}$ haloalkoxy, wherein the C$_{1-6}$ alkyl, C$_{5-6}$ aryl, C$_{3-6}$ cycloalkyl, 4-6 membered heterocycloalkyl, and 5-6 membered heteroaryl are optionally substituted with halo, hydroxy, cyano, COOH, amino, C$_{1-4}$ alkyl, C$_{1-4}$ alkoxy, C$_{1-4}$ haloalkyl, C$_{1-4}$ haloalkoxy, C$_{5-6}$ aryl, C$_{3-10}$ cycloalkyl, 5-6 membered heteroaryl and 4-6 membered heterocycloalkyl; R$^8$ is C$_{1-6}$ alkyl.

In an embodiment of the present disclosure, there is provided a compound of Formula IV

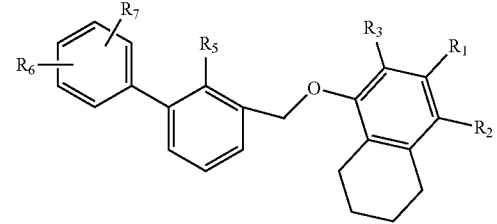

Formula IV their polymorphs, stereoisomers, tautomers, prodrugs, solvates, and pharmaceutically acceptable salts thereof, wherein R$_5$ is selected from C$_{1-4}$ alkyl, cyano, or C$_{1-4}$ haloalkyl; R$_1$, R$_2$, R$_3$, R$_6$, and R$_7$ are independently selected from hydrogen, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, (4-10 membered heterocycloalkyl)-C$_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$alkyl-, (5-14 membered heteroaryl)-C$_{1-4}$ alkyl-, and (4-10 membered heterocycloalkyl)-C$_{1-4}$ alkyl-, are independently optionally substituted with 1, 2, 3, or 4 R$^b$ substituents; R$^a$ is selected from hydrogen, cyano, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are independently optionally substituted with 1, 2, 3, 4, or 5 R$^d$ substituents; R$^b$ is selected from halo, hydroxy, cyano, amino, nitro, C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 R$^d$ substituents;

R$^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^e$, OR$^e$, SR$^e$, C(O)R$^e$, C(O)NR$^e$R$^e$, C(O)OR$^e$, OC(O) R$^e$, OC(O)NR$^e$R$^e$, NHR$^e$, NR$^e$R$^e$, NR$^e$C(O)R$^e$, NR$^e$C(O) NR$^e$R$^e$, NR$^e$C(O)OR$^e$, C(=NR$^e$)NR$^e$R$^e$, NR$^e$C(=NR$^e$) NR$^e$R$^e$, NR$^e$C(=NOH)NR$^e$R$^e$, NR$^e$C(=NCN)NR$^e$R$^e$, S(O) R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 R$^f$ substituents; R$^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 R$^f$ substituent; R$^f$ is selected from $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$ R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$ NR$^g$ R$^g$, or S(O)$_2$NR$^g$R$^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 R$^n$ substituents; R$^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C (O)R$^o$, NR$^o$C(O)NR$^o$R$^o$, NR$^o$C(O)OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$haloalkoxy, $C_{2-6}$ alkenyl, $C_{2-6}$ alkynyl and $C_{1-4}$haloalkyl are optionally substituted with 1, 2 or 3 R$^q$ substituents; R$^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 R$^p$ substituents; R$^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, NHOR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O) R$^r$, NR$^r$C(O)NR$^r$R$^r$, NR$^r$C(O)OR$^r$, C(=NR$^r$)NR$^r$R$^r$, NR$^r$C (=NR)NR$^r$R$^r$, NR$^r$C(=NOH)NR$^r$R$^r$, NR$^r$C(=NCN) NR$^r$R$^r$, S(O)R$^r$, S(O)NR$^r$R$^r$, S(O)$_2$R$^r$, NR$^r$S(O)$_2$R$^r$, NR$^r$S (O)$_2$NR$^r$R$^r$ or S(O)$_2$NR$^r$R$^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 R$^q$ substituents; R$^e$, R$^i$, R$^k$, R$^o$ and R$^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 R$^q$ substituents; R$^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, NHR$^8$, NR$^8$R$^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; R$^8$ is $C_{1-6}$ alkyl.

In an embodiment of the present disclosure, there is provided a compound of Formula IV, their polymorphs, stereoisomers, tautomers, prodrugs, solvates, and pharmaceutically acceptable salts thereof, wherein R$_5$ is selected from $C_{1-4}$ alkyl, cyano, or $C_{1-4}$ haloalkyl; R$_3$ is independently selected from hydrogen, halo, C(O)OR$^a$, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, or $C_{3-10}$ cycloalkyl; R$_1$, R$_2$, R$_6$, and R$_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, or S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl-, are independently optionally substituted with 1, 2, 3, or 4 R$^b$ substituents; R$^a$ is selected from hydrogen, cyano, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are independently optionally substituted with 1, 2, 3, 4, or 5 R$^d$ substituents; R$^b$ is selected from halo, hydroxy, cyano, amino, nitro, C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^d$ substituents; R$^d$ is selected from cyano, amino, C$_{1-6}$ alkyl, C$_{1-6}$haloalkyl, halo, C$_{1-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the C$_{1-6}$ alkyl, C$_{1-6}$ haloalkyl, C$_{6-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are optionally substituted with 1, 2, or 3 R$^f$ substituents; R$^c$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, 3, 4, or 5 R$^f$ substituent; R$^f$ is selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, or S(O)$_2$NR$^g$R$^g$; wherein the C$_{1-4}$ alkyl, C$_{1-4}$haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are optionally substituted with 1, 2, 3, 4, or 5 R$^n$ substituents; R$^n$ is selected from cyano, halo, C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl, C$_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl and C$_{1-4}$haloalkyl are optionally substituted with 1, 2 or 3 R$^q$ substituents; R$^g$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^p$ substituents; R$^p$ is selected from halo, cyano, C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ or S(O)$_2$NR$^r$R$^r$, wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2 or 3 R$^q$ substituents; R$^e$, R$^i$, R$^k$, R$^o$ and R are independently selected from hydrogen, C$_{1-4}$ alkyl, C$_{3-6}$ cycloalkyl, C$_{6-10}$ aryl, 5 or 6-membered heteroaryl, 4-6 membered heterocycloalkyl, C$_{1-4}$ haloalkyl, C$_{2-4}$ alkenyl, or C$_{2-4}$ alkynyl, wherein the C$_{1-4}$ alkyl, C$_{3-6}$ cycloalkyl, C$_{6-10}$ aryl, 5 or 6-membered heteroaryl, 4-6 membered heterocycloalkyl, C$_{2-4}$ alkenyl, and C$_{2-4}$ alkynyl are optionally substituted with 1, 2 or 3 R$^q$ substituents; R$^q$ is selected from hydroxy, cyano, amino, halo, COOH, C$_{1-6}$ haloalkyl, C$_{1-6}$ alkyl, C$_{1-6}$ alkoxy, C$_{1-6}$ alkylthio, C$_{5-6}$ aryl, 5-6 membered heteroaryl, 4-6 membered heterocycloalkyl, C$_{3-6}$ cycloalkyl, NHR$^8$, NR$^8$R$^8$, and C$_{1-4}$ haloalkoxy, wherein the C$_{1-6}$ alkyl, C$_{5-6}$ aryl, C$_{3-6}$ cycloalkyl, 4-6 membered heterocycloalkyl, and 5-6 membered heteroaryl are optionally substituted with halo, hydroxy, cyano, COOH, amino, C$_{1-4}$ alkyl, C$_{1-4}$ alkoxy, C$_{1-4}$ haloalkyl, C$_{1-4}$ haloalkoxy, C$_{5-6}$ aryl, C$_{3-10}$ cycloalkyl, 5-6 membered heteroaryl and 4-6 membered heterocycloalkyl; R$^8$ is C$_{1-6}$ alkyl.

In an embodiment of the present disclosure, there is provided A compound of Formula V

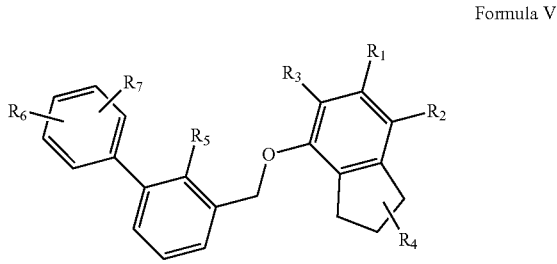

Formula V their polymorphs, stereoisomers, tautomers, prodrugs, solvates, and pharmaceutically acceptable salts thereof, wherein R$_5$ is selected from C$_{1-4}$ alkyl, cyano, or C$_{1-4}$ haloalkyl; R$_4$ is selected from hydrogen, hydroxyl, C$_{1-6}$ alkyl, amino, —C(O)OR$_{a1}$, C(O)NR$_{b1}$R$_{c1}$, C$_{5-6}$ aryl, or C$_{1-6}$ heteroaryl; wherein C$_{1-6}$ alkyl is optionally substituted with one or more of the groups selected from the group consisting of hydrogen, hydroxyl, amino, —C(O)OR$_{a1}$, C(O)NR$_{b1}$R$_{c1}$, C$_{5-6}$ aryl, and C$_{1-6}$ heteroaryl; R$_{a1}$, R$_{b1}$, and R$_{c1}$ are independently selected from hydrogen or C$_{1-6}$ alkyl; R$_1$, R$_2$, R$_3$, R$_6$, and R$_7$ are independently selected from hydrogen, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, (4-10 membered heterocycloalkyl)-C$_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$ R$^a$, or S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl-, are independently optionally substituted with 1, 2, 3, or 4 R$^b$ substituents; R$^a$ is selected from hydrogen, cyano, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are independently optionally substituted with 1, 2, 3, 4, or 5 R$^d$ substituents; R$^b$ is selected from halo, hydroxy, cyano, amino, nitro, C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$ R$^c$ or S(O)$_2$NR$^c$R$^c$; wherein the C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^d$ substituents; R$^d$ is selected from cyano, amino, C$_{1-6}$ alkyl, C$_{1-6}$ haloalkyl, halo, C$_{6-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the C$_{1-6}$ alkyl, C$_{1-6}$ haloalkyl, C$_{6-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are optionally substituted with 1, 2, or 3 R$^f$ substituents; R$^c$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, 3, 4, or 5 R$^f$ substituent; R$^f$ is selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$ R$^g$, or S(O)$_2$NR$^g$R$^g$; wherein the C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are optionally substituted with 1, 2, 3, 4, or 5 R$^h$ substituents; R$^h$ is selected from cyano, halo, C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl, C$_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$ NR$^o$R$^o$, wherein the C$_{1-4}$ alkyl, C$_{3-10}$ cycloalkyl, 4-7 membered heterocycloalkyl, C$_{6-10}$ aryl, 5-6 membered heteroaryl, C$_{6-10}$ aryl-C$_{1-4}$ alkyl-, C$_{3-10}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, C$_{1-6}$ haloalkoxy, C$_{2-6}$ alkenyl, C$_{2-6}$ alkynyl and C$_{1-4}$haloalkyl are optionally substituted with 1, 2 or 3 R$^q$ substituents; R$^g$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^p$ substituents; R$^p$ is selected from halo, cyano, C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ or S(O)$_2$NR$^r$R$^r$, wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2 or 3 R$^q$ substituents; R$^e$, R$^i$, R$^k$, R$^o$ and R$^r$ are independently selected from hydrogen, C$_{1-4}$ alkyl, C$_{3-6}$ cycloalkyl, C$_{6-10}$ aryl, 5 or 6-membered heteroaryl, 4-6 membered heterocycloalkyl, C$_{1-4}$ haloalkyl, C$_{2-4}$ alkenyl, or C$_{2-4}$ alkynyl, wherein the C$_{1-4}$ alkyl, C$_{3-6}$ cycloalkyl, C$_{6-10}$ aryl, 5 or 6-membered heteroaryl, 4-6 membered heterocycloalkyl, C$_{2-4}$ alkenyl, and C$_{2-4}$ alkynyl are optionally substituted with 1, 2 or 3 R$^q$ substituents; R$^q$ is selected from hydroxy, cyano, amino, halo, COOH, C$_{1-6}$ haloalkyl, C$_{1-6}$ alkyl, C$_{1-6}$ alkoxy, C$_{1-6}$ alkylthio, C$_{5-6}$ aryl, 5-6 membered heteroaryl, 4-6 membered heterocycloalkyl, C$_{3-6}$ cycloalkyl, NHR$^8$, NR$^8$R$^8$, and C$_{1-4}$ haloalkoxy, wherein the C$_{1-6}$ alkyl, C$_{5-6}$ aryl, C$_{3-6}$ cycloalkyl, 4-6 membered heterocycloalkyl, and 5-6 membered heteroaryl are optionally substituted with halo, hydroxy, cyano, COOH, amino, C$_{1-4}$ alkyl, C$_{1-4}$ alkoxy, C$_{1-4}$ haloalkyl, C$_{1-4}$ haloalkoxy, C$_{5-6}$ aryl, C$_{3-10}$ cycloalkyl, 5-6 membered heteroaryl and 4-6 membered heterocycloalkyl; R$^8$ is C$_{1-6}$ alkyl.

In an embodiment of the present disclosure, there is provided a compound of Formula V, their polymorphs, stereoisomers, tautomers, prodrugs, solvates, and pharmaceutically acceptable salts thereof, wherein R$_5$ is selected from C$_{1-4}$ alkyl, cyano, or C$_{1-4}$ haloalkyl; R$_4$ is selected from hydrogen, hydroxyl, C$_{1-6}$ alkyl, amino; R$_{a1}$, R$_{b1}$, and R$_{c1}$ are independently selected from hydrogen or C$_{1-6}$ alkyl; R$_3$ is independently selected from halo, C(O)OR$^a$, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, or C$_{3-10}$ cycloalkyl; R$_1$, R$_2$, R$_6$, and R$_7$ are independently selected from hydrogen, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-10 membered heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$ NR$^a$R$^a$, S(O)R$^a$, S(O)NR$^a$R$^a$, S(O)$_2$R$^a$, or S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-14 membered heteroaryl, 4-10 membered heterocycloalkyl, are independently optionally substituted with 1, 2, 3, or 4 R$^b$ substituents; R$^a$ is selected from hydrogen, cyano, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, or 4-10 membered heterocycloalkyl, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl are independently optionally substituted with 1, 2, 3, 4, or 5 R$^d$ substituents; R$^b$ is selected from halo, hydroxy, cyano, amino, nitro, C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, or 4-10 membered heterocycloalkyl are optionally substituted with 1, 2, or 3 R$^d$ substituents; R$^d$ is selected from cyano, amino, C$_{1-6}$ alkyl, C$_{1-6}$haloalkyl, halo, C$_{6-10}$ aryl, 5-10 membered heteroaryl, C$_{3-10}$ cycloalkyl, 4-10 membered heterocycloalkyl, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the C$_{1-6}$ alkyl, C$_{1-6}$ haloalkyl, C$_{6-10}$ aryl, 5-10 membered heteroaryl, C$_{3-10}$ cycloalkyl, or 4-10 membered heterocycloalkyl are optionally substituted with 1, 2, or 3 R$^f$ substituents; R$^c$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, are optionally substituted with 1, 2, 3, 4, or 5 R$^f$ substituent; R$^f$ is selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, halogen, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$ R$^g$, or S(O)$_2$NR$^g$R$^g$; wherein the C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, or 4-10 membered heterocycloalkyl are optionally substituted with 1, 2, 3, 4, or 5 R$^h$ substituents; R$^h$ is selected from cyano, halo, C$_{1-4}$ alkyl, C$_{3-10}$ cycloalkyl, 4-7 membered heterocycloalkyl, C$_{6-10}$ aryl, 5-6 membered heteroaryl, C$_{1-6}$ haloalkoxy, C$_{2-6}$ alkenyl, C$_{2-6}$ alkynyl, C$_{1-4}$ haloalkyl, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)

OR$^o$, C(=NR)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, or S(O)$_2$NR$^o$R$^o$, wherein the C$_{1-4}$ alkyl, C$_{3-10}$ cycloalkyl, 4-7 membered heterocycloalkyl, C$_{6-10}$ aryl, 5-6 membered heteroaryl, C$_{1-6}$ haloalkoxy, C$_{2-6}$ alkenyl, C$_{2-6}$ alkynyl and C$_{1-4}$ haloalkyl are optionally substituted with 1, 2 or 3 R$^q$ substituents; R$^g$ is selected from hydrogen, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl are optionally substituted with 1, 2, or 3 R$^p$ substituents; R$^p$ is selected from halo, cyano, C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR)NR$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ or S(O)$_2$NR$^r$R$^r$, wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, are optionally substituted with 1, 2 or 3 R$^q$ substituents; R$^e$, R$^i$, R$^k$, R$^o$ and R$^r$ are independently selected from hydrogen, C$_{1-4}$ alkyl, C$_{3-6}$ cycloalkyl, C$_{6-10}$ aryl, 5 or 6-membered heteroaryl, 4-6 membered heterocycloalkyl, C$_{1-4}$ haloalkyl, C$_{2-4}$ alkenyl, or C$_{2-4}$ alkynyl, wherein the C$_{1-4}$ alkyl, C$_{3-6}$ cycloalkyl, C$_{6-10}$ aryl, 5 or 6-membered heteroaryl, 4-6 membered heterocycloalkyl, C$_{2-4}$ alkenyl, and C$_{2-4}$ alkynyl are optionally substituted with 1, 2 or 3 R$^q$ substituents; R$^q$ is selected from hydroxy, cyano, amino, halo, COOH, C$_{1-6}$ haloalkyl, C$_{1-6}$ alkyl, C$_{1-6}$ alkoxy, C$_{1-6}$ alkylthio, C$_{5-6}$ aryl, 5-6 membered heteroaryl, 4-6 membered heterocycloalkyl, C$_{3-6}$ cycloalkyl, NHR$^8$, NR$^8$R$^8$, and C$_{1-4}$ haloalkoxy, wherein the C$_{1-6}$ alkyl, C$_{5-6}$ aryl, C$_{3-6}$ cycloalkyl, 4-6 membered heterocycloalkyl, and 5-6 membered heteroaryl are optionally substituted with halo, hydroxy, cyano, COOH, amino, C$_{1-4}$ alkyl, C$_{1-4}$ alkoxy, C$_{1-4}$ haloalkyl, C$_{1-4}$ haloalkoxy, C$_{5-6}$ aryl, C$_{3-10}$ cycloalkyl, 5-6 membered heteroaryl and 4-6 membered heterocycloalkyl; R$^8$ is C$_{1-6}$ alkyl.

In an embodiment of the present disclosure, there is provided a compound of Formula VI

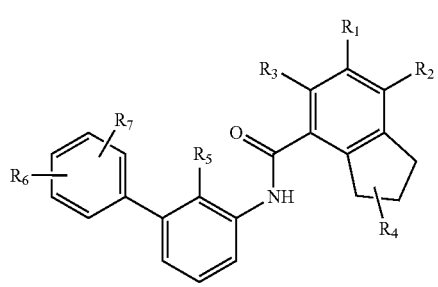

Formula V their polymorphs, stereoisomers, tautomers, prodrugs, solvates, and pharmaceutically acceptable salts thereof, wherein R$_5$ is selected from C$_{1-4}$ alkyl, cyano, or C$_{1-4}$ haloalkyl; R$_4$ is selected from hydrogen, hydroxyl, C$_{1-6}$ alkyl, amino, —C(O)OR$_{a1}$, C(O)NR$_{b1}$R$_{c1}$, C$_{5-6}$ aryl, or C$_{1-6}$ heteroaryl; wherein C$_{1-6}$ alkyl is optionally substituted with one or more of the groups selected from the group consisting of hydrogen, hydroxyl, amino, —C(O)OR$_{a1}$, C(O)NR$_{b1}$R$_{c1}$, C$_{5-6}$ aryl, and C$_{1-6}$ heteroaryl; R$_{a1}$, R$_{b1}$, and R$_{c1}$ are independently selected from hydrogen or C$_{1-6}$ alkyl; R$_1$, R$_2$, R$_3$, R$_6$, and R$_7$ are independently selected from hydrogen, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, (4-10 membered heterocycloalkyl)-C$_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$ R$^a$, or S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-14 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl-, are independently optionally substituted with 1, 2, 3, or 4 R$^b$ substituents; R$^a$ is selected from hydrogen, cyano, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are independently optionally substituted with 1, 2, 3, 4, or 5 R$^d$ substituents; R$^b$ is selected from halo, hydroxy, cyano, amino, nitro, C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the C$_{1-4}$ alkyl, C$_{2-4}$ alkenyl, C$_{2-4}$ alkynyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are optionally substituted with 1, 2, or 3 R$^d$ substituents; R$^d$ is selected from cyano, amino, C$_{1-6}$ alkyl, C$_{1-6}$ haloalkyl, halo, C$_{6-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, or S(O)$_2$NR$^e$R$^e$, wherein the C$_{1-6}$ alkyl, C$_{1-6}$ haloalkyl, C$_{6-10}$ aryl, 5-10 membered heteroaryl, C$_{3-10}$ cycloalkyl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are optionally substituted with 1, 2 or 3 R$^f$ substituents; R$^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent; $R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^f$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^g R^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^g R^g$, or $S(O)_2NR^gR^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents; $R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, or $S(O)_2NR^oR^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$haloalkyl are optionally substituted with 1, 2 or 3 $R^q$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$ or $S(O)_2NR^rR^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl.

In an embodiment of the present disclosure, there is provided a compound of Formula VI, their polymorphs, stereoisomers, tautomers, prodrugs, solvates, and pharmaceutically acceptable salts thereof, wherein $R_5$ is selected from $C_{1-4}$ alkyl, cyano, or $C_{1-4}$ haloalkyl; $R^4$ is selected from hydrogen, hydroxyl, $C_{1-6}$ alkyl, amino; $R_{a1}$, $R_{b1}$, and $R_{c1}$ are independently selected from hydrogen or $C_{1-6}$ alkyl; $R_3$ is independently selected from hydrogen, halo, $C(O)OR^a$, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, or $C_{3-10}$ cycloalkyl; $R_1$, $R_2$, $R_6$, and $R_7$ are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2 NR^aR^a$, $S(O)R^a$, $S(O)NR^aR^a$, $S(O)_2R^a$, or $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, or 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl are independently optionally substituted with 1, 2, 3, 4, or 5 $R^d$ substituents; $R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^c R^c$, $NR^cC(=NR^c)NR^cR^c$, $NHR^c$, $NR^cR^c$, $NR^cC(O)R^c$, $NR^c C(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2 NR^cR^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, or 4-10 membered heterocycloalkyl are optionally substituted with 1, 2, or 3 $R^d$ substituents; $R^d$ is selected from cyano, amino, $C_{1-6}$ alkyl, $C_{1-6}$haloalkyl, halo, $C_{6-10}$ aryl, 5-10 membered heteroaryl, $C_{3-10}$ cycloalkyl, 4-10 membered heterocycloalkyl, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, or $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, or 4-10 membered heterocycloalkyl are optionally substituted with 1, 2, or 3 $R^f$ substituents; $R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, are optionally substituted with 1, 2, 3, 4, or 5 $R^f$ substituent; $R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, halogen, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, or $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, or 4-10 membered heterocycloalkyl are optionally substituted with 1, 2, 3, 4, or 5 $R^n$ substituents; $R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, or $S(O)_2NR^oR^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{1-6}$ haloalkoxy, $C_{2-6}$ alkenyl, $C_{2-6}$ alkynyl and $C_{1-4}$ haloalkyl are optionally substituted with 1, 2 or 3 $R^q$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl are optionally substituted with 1, 2, or 3 $R^p$ substituents; $R^p$ is selected from halo, cyano, $C_{1-6}$alkyl, $C_{1-6}$ haloalkyl, $C_{1-6}$ haloalkoxy, $C_{2-6}$alkenyl, $C_{2-6}$alkynyl, $C_{6-10}$ aryl, $C_{3-10}$ cycloalkyl, 5-10 membered heteroaryl, 4-10 membered heterocycloalkyl, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$ or $S(O)_2NR^rR^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl In an embodiment, the present disclosure relates to compounds of Formula I, Formula II, Formula III, Formula IV, Formula V, Formula VI, or its polymorphs, stereoisomers, tautomers, prodrugs, solvates, and pharmaceutically acceptable salts thereof, which is selected from a group consisting of:

(S)-1-((7-((2-methyl-[1,1'-biphenyl]-3-yl)methoxy)-2,3-dihydro-1H-inden-4-yl)methyl) piperidine-2-carboxylic acid (1), N-(2-(((5-methoxy-7-((2-methyl-[1,1'-biphenyl]-3-yl)methoxy)-2,3-dihydro-1H-inden-4-yl) methyl)amino) ethyl)acetamide (2), (S)-1-((7-((3-(1-(3-(3,3-difluoropyrrolidin-1-yl)propyl)-1H-indol-4-yl)-2-methylbenzyl)oxy)-2,3-dihydro-1H-inden-4-yl)methyl)piperidine-2-carboxylic acid (3), (S)-1-((6-methyl-7-((2-methyl-[1,1'-biphenyl]-3-yl)methoxy)-2,3-dihydro-1H-inden-4-yl)methyl)piperidine-2-carboxylic acid (4), (S)-1-((6-chloro-7-((2-methyl-[1,1'-biphenyl]-3-yl)methoxy)-2,3-dihydro-1H-inden-4-yl)methyl)piperidine-2-carboxylic acid (5), Methyl 7-(((2-acetamidoethyl)amino)methyl)-4-((2-methyl-[1,1'-biphenyl]-3-yl)methoxy)-2,3-dihydro-1H-indene-5-carboxylate (6), (S)-1-((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)piperidine-2-carboxylic acid (7), (S)-1-((5-((3-cyanobenzyl)oxy)-7-((2-methyl-[1,1'-biphenyl]-3-yl)methoxy)-2,3-dihydro-1H-inden-4-yl)methyl) piperidine-2-carboxylic acid (8), (S)-1-((5-((5-fluoropyridin-3-yl)methoxy)-7-((2-methyl-[1,1'-biphenyl]-3-yl)methoxy)-2,3-dihydro-1H-inden-4-yl) methyl)piperidine-2-carboxylic acid (9)

N-(2-(((5-((5-fluoropyridin-3-yl)methoxy)-7-((2-methyl-[1,1'-biphenyl]-3-yl)methoxy)-2,3-dihydro-1H-inden-4-yl) methyl)amino)ethyl)acetamide (10)

(S)-5-((5-methoxy-7-((2-methyl-[1,1'-biphenyl]-3-yl)methoxy)-2,3-dihydro-1H-inden-4-yl)methyl)-5-azaspiro [2.4]heptane-6-carboxylic acid (11)

(S)-1-((7-((2-methyl-[1,1'-biphenyl]-3-yl)methoxy)-5-(2,2,2-trifluoroethoxy)-2,3-dihydro-1H-inden-4-yl)methyl)piperidine-2-carboxylic acid (12)

N-(2-(((5-((3-cyanobenzyl)oxy)-7-((2-methyl-[1,1'-biphenyl]-3-yl)methoxy)-2,3-dihydro-1H-inden-4-yl)methyl) amino)ethyl)-N-methylacetamide (13)

N-(2-(((5-(1-(3-cyanophenyl)ethoxy)-7-((2-methyl-[1,1'-biphenyl]-3-yl)methoxy)-2,3-dihydro-1H-inden-4-yl) methyl)amino)ethyl)acetamide (14)

N-(1-((5-((3-cyanobenzyl)oxy)-7-((2-methyl-[1,1'-biphenyl]-3-yl)methoxy)-2,3-dihydro-1H-inden-4-yl)methyl) piperidin-3-yl)acetamide (15)

N-(2-(((7-((2-methyl-[1,1'-biphenyl]-3-yl)methoxy)-2,3-dihydro-1H-inden-4-yl)methyl)amino)ethyl)acetamide (16)

6-((7-((2-methyl-[1,1'-biphenyl]-3-yl)methoxy)-2,3-dihydro-1H-inden-4-yl)methyl)-2-oxa-6-azaspiro[3.3]heptane (17)

2-(hydroxymethyl)-2-(((7-((2-methyl-[1,1'-biphenyl]-3-yl)methoxy)-2,3-dihydro-1H-inden-4-yl)methyl)amino)propane-1,3-diol (18)

1-(((7-((2-methyl-[1,1'-biphenyl]-3-yl)methoxy)-2,3-dihydro-1H-inden-4-yl)methyl)amino)cyclopropane-1-carboxylic acid (19)

((7-((2-methyl-[1,1'-biphenyl]-3-yl)methoxy)-2,3-dihydro-1H-inden-4-yl)methyl)glycine (20)

3-(((7-((2-methyl-[1,1'-biphenyl]-3-yl)methoxy)-2,3-dihydro-1H-inden-4-yl)methyl)amino)propanoic acid (21)

N-methyl-N-((7-((2-methyl-[1,1'-biphenyl]-3-yl)methoxy)-2,3-dihydro-1H-inden-4-yl)methyl)glycine (22)

3-(((7-((2-methyl-[1,1'-biphenyl]-3-yl)methoxy)-2,3-dihydro-1H-inden-4-yl)methyl)amino)butanoic acid (23)

((7-((2-methyl-[1,1'-biphenyl]-3-yl)methoxy)-2,3-dihydro-1H-inden-4-yl)methyl)alanine (24)

(2S,4R)-4-hydroxy-1-((5-methoxy-7-((2-methyl-[1,1'-biphenyl]-3-yl)methoxy)-2,3-dihydro-1H-inden-4-yl)methyl)pyrrolidine-2-carboxylic acid (25)

(S)-1-((5-methoxy-7-((2-methyl-[1,1'-biphenyl]-3-yl)methoxy)-2,3-dihydro-1H-inden-4-yl)methyl)piperidine-2-carboxylic acid (26)

1-((4-((2-methyl-[1,1'-biphenyl]-3-yl)methoxy)-5,6,7,8-tetrahydronaphthalen-1-yl)methyl)piperidine-2-carboxylic acid (27)

N-(2-(((6-methyl-7-((2-methyl-[1,1'-biphenyl]-3-yl)methoxy)-2,3-dihydro-1H-inden-4-yl)methyl)amino)ethyl)acetamide (28)

(2S,4R)-4-hydroxy-1-((6-methyl-7-((2-methyl-[1,1'-biphenyl]-3-yl)methoxy)-2,3-dihydro-1H-inden-4-yl)methyl)pyrrolidine-2-carboxylic acid (29)

N-(2-(((6-chloro-7-((2-methyl-[1,1'-biphenyl]-3-yl)methoxy)-2,3-dihydro-1H-inden-4-yl)methyl)amino)ethyl)acetamide (30)

(2S,4R)-1-((6-chloro-7-((2-methyl-[1,1'-biphenyl]-3-yl)methoxy)-2,3-dihydro-1H-inden-4-yl)methyl)-4-hydroxypyrrolidine-2-carboxylic acid (31)

N-(2-(((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)amino)ethyl)acetamide (32)

(2S,4R)-1-((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)-4-hydroxypyrrolidine-2-carboxylic acid (33)

N-(2-(((5-((3-cyanobenzyl)oxy)-7-((2-methyl-[1,1'-biphenyl]-3-yl)methoxy)-2,3-dihydro-1H-inden-4-yl)methyl)amino)ethyl)acetamide (34)

(2S,4R)-1-((5-((3-cyanobenzyl)oxy)-7-((2-methyl-[1,1'-biphenyl]-3-yl)methoxy)-2,3-dihydro-1H-inden-4-yl)methyl)-4-hydroxypyrrolidine-2-carboxylic acid (35)

(S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxylic acid (36)

(S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxamide (37)

3-(((4-(((1,3-dihydroxy-2-(hydroxymethyl)propan-2-yl)amino)methyl)-7-((2-methyl-[1,1'-biphenyl]-3-yl)methoxy)-2,3-dihydro-1H-inden-5-yl)oxy)methyl)benzonitrile (38)

3-(((4-((2-oxa-6-azaspiro[3.3]heptan-6-yl)methyl)-7-((2-methyl-[1,1'-biphenyl]-3-yl)methoxy)-2,3-dihydro-1H-inden-5-yl)oxy)methyl)benzonitrile (39)

3-(((4-((3-hydroxypiperidin-1-yl)methyl)-7-((2-methyl-[1,1'-biphenyl]-3-yl)methoxy)-2,3-dihydro-1H-inden-5-yl)oxy)methyl)benzonitrile (40)

((5-((3-cyanobenzyl)oxy)-7-((2-methyl-[1,1'-biphenyl]-3-yl)methoxy)-2,3-dihydro-1H-inden-4-yl)methyl)glycine (41)

(S)-5-((5-((3-cyanobenzyl)oxy)-7-((2-methyl-[1,1'-biphenyl]-3-yl)methoxy)-2,3-dihydro-1H-inden-4-yl)methyl)-5-azaspiro[2.4]heptane-6-carboxylic acid (42)

rac-(1R,6S)-2-((5-((3-cyanobenzyl)oxy)-7-((2-methyl-[1,1'-biphenyl]-3-yl) methoxy)-2,3-dihydro-1H-inden-4-yl)methyl)-2-azabicyclo[4.1.0]heptane-1-carboxylic acid (cis, racemic) (43)

4-(((5-((3-cyanobenzyl)oxy)-7-((2-methyl-[1,1'-biphenyl]-3-yl) methoxy)-2,3-dihydro-1H-inden-4-yl)methyl)amino)butanoic acid (44)

(1R,6S)-2-((5-methoxy-7-((2-methyl-[1,1'-biphenyl]-3-yl)methoxy)-2,3-dihydro-1H-inden-4-yl) methyl)-2-azabicyclo[4.1.0]heptane-1-carboxylic acid (cis, racemic) (45)

(S)-1-((5-((5-cyanopyridin-3-yl)methoxy)-7-((2-methyl-[1,1'-biphenyl]-3-yl) methoxy)-2,3-dihydro-1H-inden-4-yl)methyl)piperidine-2-carboxylic acid (46)

(2S,4R)-1-((5-((5-cyanopyridin-3-yl)methoxy)-7-((2-methyl-[1,1'-biphenyl]-3-yl)methoxy)-2,3-dihydro-1H-inden-4-yl)methyl)-4-hydroxypyrrolidine-2-carboxylic acid (47)

N-(2-(((5-((5-cyanopyridin-3-yl)methoxy)-7-((2-methyl-[1,1'-biphenyl]-3-yl)methoxy)-2,3-dihydro-1H-inden-4-yl)methyl)amino)ethyl)acetamide (48)

5-(((4-(((1,3-dihydroxy-2-(hydroxymethyl)propan-2-yl)amino)methyl)-7-((2-methyl-[1,1'-biphenyl]-3-yl)methoxy)-2,3-dihydro-1H-inden-5-yl)oxy)methyl)nicotinonitrile (49)

(S)-4-((5-((5-cyanopyridin-3-yl)methoxy)-7-((2-methyl-[1,1'-biphenyl]-3-yl)methoxy)-2,3-dihydro-1H-inden-4-yl)methyl)morpholine-3-carboxylicacid (50)

rac-(1R,6S)-2-((5-((5-cyanopyridin-3-yl)methoxy)-7-((2-methyl-[1,1'-biphenyl]-3-yl)methoxy)-2,3-dihydro-1H-inden-4-yl)methyl)-2-azabicyclo[4.1.0]heptane-1-carboxylic acid (cis, racemic) (51)

(S)-5-((5-((5-cyanopyridin-3-yl)methoxy)-7-((2-methyl-[1,1'-biphenyl]-3-yl)methoxy)-2,3-dihydro-1H-inden-4-yl)methyl)-5-azaspiro[2.4]heptane-6-carboxylic acid (52)

N-(2-(((5-((3-cyanobenzyl)oxy)-7-((2-methyl-[1,1'-biphenyl]-3-yl)methoxy)-2,3-dihydro-1H-inden-4-yl)methyl)(methyl)amino)ethyl)acetamide (53)

N-(2-(((5-((4-cyanobenzyl)oxy)-7-((2-methyl-[1,1'-biphenyl]-3-yl)methoxy)-2,3-dihydro-1H-inden-4-yl)methyl)amino)ethyl)acetamide (54)

(S)-1-((7-((2-cyano-[1,1'-biphenyl]-3-yl)methoxy)-5-methoxy-2,3-dihydro-1H-inden-4-yl)methyl)piperidine-2-carboxylic acid (55)

N-(2-(((7-((2-cyano-[1,1'-biphenyl]-3-yl)methoxy)-5-methoxy-2,3-dihydro-1H-inden-4-yl)methyl)amino)ethyl)acetamide (56)

(2S,4R)-1-((7-((2-cyano-[1,1'-biphenyl]-3-yl)methoxy)-5-methoxy-2,3-dihydro-1H-inden-4-yl)methyl)-4-hydroxypyrrolidine-2-carboxylic acid (57)

3-(((7-(((1,3-dihydroxy-2-(hydroxymethyl)propan-2-yl)amino)methyl)-6-methoxy-2,3-dihydro-1H-inden-4-yl)oxy)methyl)-[1,1'-biphenyl]-2-carbonitrile (58)

(S)-4-((7-((2-cyano-[1,1'-biphenyl]-3-yl)methoxy)-5-methoxy-2,3-dihydro-1H-inden-4-yl)methyl)morpholine-3-carboxylic acid (59)

((7-((2-cyano-[1,1'-biphenyl]-3-yl)methoxy)-5-methoxy-2,3-dihydro-1H-inden-4-yl)methyl)glycine (60)

(S)-5-((7-((2-cyano-[1,1'-biphenyl]-3-yl)methoxy)-5-methoxy-2,3-dihydro-1H-inden-4-yl)methyl)-5-azaspiro[2.4]heptane-6-carboxylic acid (61)

rac-(1R,6S)-2-((7-((2-cyano-[1,1'-biphenyl]-3-yl)methoxy)-5-methoxy-2,3-dihydro-1H-inden-4-yl)methyl)-2-azabicyclo[4.1.0]heptane-1-carboxylic acid (cis, racemic) (62)

2-(1-((7-((2-cyano-[1,1'-biphenyl]-3-yl)methoxy)-5-methoxy-2,3-dihydro-1H-inden-4-yl)methyl)piperidin-2-yl)acetic acid (63)

N-(2-(((7-((2-cyano-[1,1'-biphenyl]-3-yl)methoxy)-5-methoxy-2,3-dihydro-1H-inden-4-yl)methyl)(methyl)amino)ethyl)-N-methylacetamide (64)

5-((4-(((2-acetamidoethyl)amino)methyl)-7-((2-methyl-[1,1'-biphenyl]-3-yl)methoxy)-2,3-dihydro-1H-inden-5-yl)oxy)pentanoic acid (65)

5-((4-(((2-acetamidoethyl)amino)methyl)-7-((2-methyl-[1,1'-biphenyl]-3-yl)methoxy)-2,3-dihydro-1H-inden-5-yl)oxy)pentanamide (66)

(S)-1-((5-(4-carboxybutoxy)-7-((2-methyl-[1,1'-biphenyl]-3-yl)methoxy)-2,3-dihydro-1H-inden-4-yl)methyl)piperidine-2-carboxylic acid (67)

(S)-1-((5-((5-amino-5-oxopentyl)oxy)-7-((2-methyl-[1,1'-biphenyl]-3-yl)methoxy)-2,3-dihydro-1H-inden-4-yl)methyl)piperidine-2-carboxylic acid (68)

(S)-1-((5-((5-cyanopyridin-3-yl)methoxy)-7-((2-methyl-[1,1'-biphenyl]-3-yl) methoxy)-2,3-dihydro-1H-inden-4-yl)methyl)piperidine-2-carboxylic acid (69)

(2S,4R)-1-((7-((2-cyano-[1,1'-biphenyl]-3-yl)methoxy)-5-((5-cyanopyridin-3-yl)methoxy)-2,3-dihydro-1H-inden-4-yl)methyl)-4-hydroxypyrrolidine-2-carboxylic acid (70)

(R)-1-((7-((2-cyano-[1,1'-biphenyl]-3-yl)methoxy)-5-((5-cyanopyridin-3-yl)methoxy)-2,3-dihydro-1H-inden-4-yl)methyl)piperidine-3-carboxylic acid (71)

rac-(1R,6S)-2-((7-((2-cyano-[1,1'-biphenyl]-3-yl)methoxy)-5-((5-cyanopyridin-3-yl)methoxy)-2,3-dihydro-1H-inden-4-yl)methyl)-2-azabicyclo[4.1.0]heptane-1-carboxylic acid (cis; racemic) (72)

methyl 4-(((5-((3-cyanobenzyl)oxy)-7-((2-methyl-[1,1'-biphenyl]-3-yl)methoxy)-2,3-dihydro-1H-inden-4-yl)methyl)amino)bicyclo[2.2.2]octane-1-carboxylate (73)

4-(((5-((3-cyanobenzyl)oxy)-7-((2-methyl-[1,1'-biphenyl]-3-yl)methoxy)-2,3-dihydro-1H-inden-4-yl)methyl)amino)bicyclo[2.2.2]octane-1-carboxylic acid (74)

(S)-1-((5-methoxy-7-((2-(trifluoromethyl)-[1,1'-biphenyl]-3-yl)methoxy)-2,3-dihydro-1H-inden-4-yl)methyl)piperidine-2-carboxylic acid (75)

(2S,4R)-4-hydroxy-1-((5-methoxy-7-((2-(trifluoromethyl)-[1,1'-biphenyl]-3-yl)methoxy)-2,3-dihydro-1H-inden-4-yl)methyl)pyrrolidine-2-carboxylic acid (76)

(2S)-1-((7-((2-methyl-[1,1'-biphenyl]-3-yl)methoxy)-5-((1-methylpiperidin-3-yl)methoxy)-2,3-dihydro-1H-inden-4-yl)methyl)piperidine-2-carboxylic acid (77)

(S)-1-((5-(4-carboxybutoxy)-7-((2-cyano-[1,1'-biphenyl]-3-yl)methoxy)-2,3-dihydro-1H-inden-4-yl)methyl)piperidine-2-carboxylic acid (78)

N-(2-(((5-(4-cyanobutoxy)-7-((2-methyl-[1,1'-biphenyl]-3-yl)methoxy)-2,3-dihydro-1H-inden-4-yl)methyl)amino)ethyl)acetamide (79)

(S)-1-((5-(4-cyanobutoxy)-7-((2-methyl-[1,1'-biphenyl]-3-yl)methoxy)-2,3-dihydro-1H-inden-4-yl)methyl)piperidine-2-carboxamide (80)

(2S,4R)-1-((5-(4-cyanobutoxy)-7-((2-methyl-[1,1'-biphenyl]-3-yl)methoxy)-2,3-dihydro-1H-inden-4-yl)methyl)-4-hydroxypyrrolidine-2-carboxylic acid (81)

(S)-1-((5-(((1S,2R)-2-carboxycyclopropyl)methoxy)-7-((2-methyl-[1,1'-biphenyl]-3-yl)methoxy)-2,3-dihydro-1H-inden-4-yl)methyl)piperidine-2-carboxylic acid (82)

(1R,2S)-2-(((4-(((2-acetamidoethyl)amino)methyl)-7-((2-methyl-[1,1'-biphenyl]-3-yl)methoxy)-2,3-dihydro-1H-inden-5-yl)oxy)methyl)cyclopropane-1-carboxylic acid (83)

(S)-1-((7-((3-(2,3-dihydrobenzo[b][1,4]dioxin-6-yl)-2-methylbenzyl)oxy)-5-methoxy-2,3-dihydro-1H-inden-4-yl)methyl)piperidine-2-carboxylic acid (84)

(2S,4R)-1-((7-((3-(2,3-dihydrobenzo[b][1,4]dioxin-6-yl)-2-methylbenzyl)oxy)-5-methoxy-2,3-dihydro-1H-inden-4-yl)methyl)-4-hydroxypyrrolidine-2-carboxylic acid (85)

N-(2-(((5-((3-cyanobenzyl)oxy)-7-((2,2'-dimethyl-[1,1'-biphenyl]-3-yl)methoxy)-2,3-dihydro-1H-inden-4-yl)methyl)amino)ethyl)acetamide (86)

N-(2-(((5-((3-cyanobenzyl)oxy)-7-((4'-fluoro-2-methyl-[1,1'-biphenyl]-3-yl)methoxy)-2,3-dihydro-1H-inden-4-yl)methyl)amino)ethyl)acetamide (87)

(S)-1-((5-((3-carbamoylbenzyl)oxy)-7-((2-methyl-[1,1'-biphenyl]-3-yl)methoxy)-2,3-dihydro-1H-inden-4-yl)methyl)piperidine-2-carboxylic acid (88)

3-(((4-(aminomethyl)-7-((2-methyl-[1,1'-biphenyl]-3-yl)methoxy)-2,3-dihydro-1H-inden-5-yl)oxy)methyl)benzonitrile (89)

N-((5-((3-cyanobenzyl)oxy)-7-((2-methyl-[1,1'-biphenyl]-3-yl) methoxy)-2,3-dihydro-1H-inden-4-yl)methyl)acetamide (90)

6-acetamido-N-((5-((3-cyanobenzyl)oxy)-7-((2-methyl-[1,1'-biphenyl]-3-yl)methoxy)-2,3-dihydro-1H-inden-4-yl)methyl)hexanamide (91)

3-(((4-((dimethylamino)methyl)-7-((2-methyl-[1,1'-biphenyl]-3-yl)methoxy)-2,3-dihydro-1H-inden-5-yl)oxy)methyl)benzonitrile (92)

5-(((4-(((2-acetamidoethyl)amino)methyl)-7-((2-methyl-[1,1'-biphenyl]-3-yl)methoxy)-2,3-dihydro-1H-inden-5-yl)oxy)methyl)nicotinic acid (93)

5-(((4-(((2-acetamidoethyl)amino)methyl)-7-((2-methyl-[1,1'-biphenyl]-3-yl)methoxy)-2,3-dihydro-1H-inden-5-yl)oxy)methyl)nicotinamide (94)

3-(((4-(((2-acetamidoethyl)amino)methyl)-7-((2-methyl-[1,1'-biphenyl]-3-yl)methoxy)-2,3-dihydro-1H-inden-5-yl)oxy)methyl)benzamide (95)

(S)-1-((3-methoxy-1-((2-methyl-[1,1'-biphenyl]-3-yl)methoxy)-6,7-dihydro-5H-cyclopenta[c]pyridin-4-yl)methyl)piperidine-2-carboxylic acid (96)

N-(2-(((3-methoxy-1-((2-methyl-[1,1'-biphenyl]-3-yl)methoxy)-6,7-dihydro-5H-cyclopenta[c]pyridin-4-yl)methyl)amino)ethyl)acetamide (97)

(S)-4-((5-methoxy-7-((2-methyl-[1,1'-biphenyl]-3-yl)methoxy)-2,3-dihydro-1H-inden-4-yl)methyl)morpholine-3-carboxylic acid (98)

5-((5-((3-cyanobenzyl)oxy)-7-((2-methyl-[1,1'-biphenyl]-3-yl)methoxy)-2,3-dihydro-1H-inden-4-yl)methyl)-4,5,6,7-tetrahydro-1H-pyrazolo[4,3-c]pyridine-3-carboxylic acid (99)

In an embodiment, the present disclosure relates to a process of preparation of compounds of Formula I, Formula II, Formula III, Formula IV, Formula V, and Formula VI as described herein, or its polymorphs, stereoisomers, tautomers, prodrugs, solvates, and pharmaceutically acceptable salts thereof.

In an embodiment, the present disclosure relates to a process of preparation of Formula I, comprising steps of: (a) reacting compounds of Formula I (a) with substituted amines to obtain compounds of Formula I

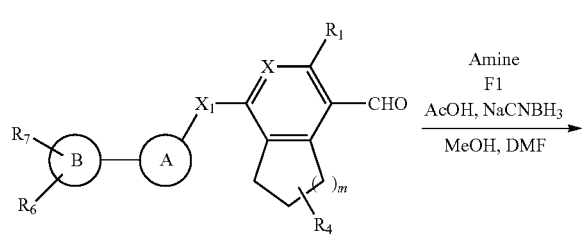

Formula (I) (a)

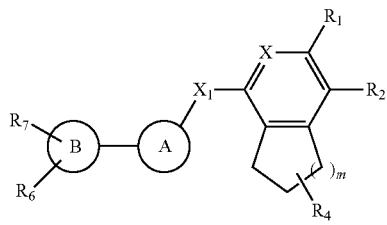

Formula (I)

In an embodiment, the present disclosure relates to a process of preparation of Formula I, comprising steps of: (a) reacting compounds of Formula I (a), wherein the $X_1$ of Formula I (a) and Formula I is selected from —$CH_2O$—, —$OCH_2$—, —C(O)NH— or —NHC(O)—; $R_4$ of Formula I (a) and Formula I is selected from hydrogen, hydroxyl, $C_{1-6}$ alkyl, amino, —C(O)O$R_{a1}$, C(O)N$R_{b1}R_{c1}$, $C_{5-6}$ aryl, or $C_{1-6}$ heteroaryl, wherein $C_{1-6}$ alkyl is optionally substituted with one or more of the groups selected from the group consisting of hydrogen, hydroxyl, amino, —C(O)O$R_{a1}$, C(O)N$R_{b1}R_{c1}$, $C_{5-6}$ aryl, and $C_{1-6}$ heteroaryl; $R_{a1}$, $R_{b1}$, and $R_{c1}$ are independently selected from hydrogen or $C_{1-6}$ alkyl; X of Formula I (a) and Formula I is selected from $CR_3$ or N; $R_1$, $R_2$, $R_6$, and $R_7$ of Formula I (a) and Formula I are independently selected from hydrogen, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^a$-$C(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, or $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl-, are independently optionally substituted with 1, 2, 3, or 4 $R^b$ substituents; $R^a$ is selected from hydrogen, cyano, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, 3, 4, or 5 $R^d$ substituents; $R^b$ is selected from halo, hydroxy, cyano, amino, nitro, $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein the $C_{1-4}$ alkyl, $C_{2-4}$ alkenyl, $C_{2-4}$ alkynyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^d$ substituents; $R^c$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, 3, 4, or 5 $R^f$ substituent; $R^d$ is selected from cyano, amino, $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)$ $NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, or $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, or 3 $R^f$ substituents; $R^f$ is selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halogen, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)$ $NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, or $S(O)_2NR^gR^g$; wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are optionally substituted with 1, 2, 3, 4, or 5 $R^n$ substituents; $R^g$ is selected from hydrogen, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2, or 3 $R^p$ substituents; $R^n$ is selected from cyano, halo, $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl, $C_{1-4}$ haloalkyl, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, or $S(O)_2NR^oR^o$, wherein the $C_{1-4}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkoxy, $C_{2-6}$ alkenyl, $C_{2-6}$ alkynyl and $C_{1-4}$ haloalkyl are optionally substituted with 1, 2 or 3 $R^q$ substituents; $R^p$ is selected from halo, cyano, $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $NHOR^r$, $OR^r$, $SR^r$, $C(O)R^r$, $C(O)NR'R^r$, $C(O)OR^r$, $OC(O)R^r$, $OC(O)NR'R^r$, $NHR^r$, $NR'R^r$, $NR'C(O)R^r$, $NR'C(O)NR'R^r$, $NR'C(O)OR^r$, $C(=NR')NR'R^r$, $NR'C(=NR')NR'R^r$, $NR'C(=NOH)NR'R^r$, $NR'C(=NCN)NR'R^r$, $S(O)R^r$, $S(O)NR'R^r$, $S(O)_2R^r$, $NR'S(O)_2R^r$, $NR'S(O)_2NR'R^r$ or $S(O)_2NR'R^r$, wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are optionally substituted with 1, 2 or 3 $R^q$ substituents; $R^e$, $R^i$, $R^k$, $R^o$ and $R^r$ are independently selected from hydrogen, $C_{1-4}$ alkyl, $C_{3-6}$ cycloalkyl, $C_{6-10}$ aryl, 5 or 6-membered heteroaryl, 4-6 membered heterocycloalkyl, $C_{1-4}$ haloalkyl, $C_{2-4}$ alkenyl, or $C_{2-4}$ alkynyl, wherein the $C_{1-4}$ alkyl, $C_{3-6}$ cycloalkyl, $C_{6-10}$ aryl, 5 or 6-membered heteroaryl, 4-6 membered heterocycloalkyl, $C_{2-4}$ alkenyl, and $C_{2-4}$ alkynyl are optionally substituted with 1, 2 or 3 $R^q$ substituents; $R^q$ is selected from hydroxy, cyano, amino, halo, COOH, $C_{1-6}$ haloalkyl, $C_{1-6}$ alkyl, $C_{1-6}$ alkoxy, $C_{1-6}$ alkylthio, $C_{5-6}$ aryl, 5-6 membered heteroaryl, 4-6 membered heterocycloalkyl, $C_{3-6}$ cycloalkyl, $NHR^8$, $NR^8R^8$, and $C_{1-4}$ haloalkoxy, wherein the $C_{1-6}$ alkyl, $C_{5-6}$ aryl, $C_{3-6}$ cycloalkyl, 4-6 membered heterocycloalkyl, and 5-6 membered heteroaryl are optionally substituted with halo, hydroxy, cyano, COOH, amino, $C_{1-4}$ alkyl, $C_{1-4}$ alkoxy, $C_{1-4}$ haloalkyl, $C_{1-4}$ haloalkoxy, $C_{5-6}$ aryl, $C_{3-10}$ cycloalkyl, 5-6 membered heteroaryl and 4-6 membered heterocycloalkyl; $R^8$ is $C_{1-6}$ alkyl; m is 1 or 2; Ring A is selected from substituted or unsubstituted $C_{5-10}$ aryl, substituted or unsubstituted $C_{3-6}$ cycloalkyl, and substituted or unsubstituted 5-10 membered monocyclic or bicyclic saturated or unsaturated heterocyclic ring with 1-3 heteroatoms selected from N, S or O; Ring B is selected from $C_{5-10}$ aryl, $C_{3-6}$ cycloalkyl, 5-10 membered monocyclic or bicyclic saturated or unsaturated heterocyclic ring with 1-3 heteroatoms selected from N, S or O, with substituted amines in the presence of solvents to obtain compounds of Formula I.

In an embodiment, the present disclosure relates to pharmaceutical composition comprising a compound of Formula I, or Formula II, or Formula III, or Formula IV, or Formula V, or Formula VI as described herein, or a pharmaceutically acceptable salt thereof together with a pharmaceutically acceptable carrier, optionally in combination with one or more other pharmaceutical compositions.

In another embodiment, the present disclosure relates to the pharmaceutical composition as described herein, wherein the composition is in the form selected from the group consisting of a tablet, capsule, powder, syrup, solution, aerosol and suspension.

In an embodiment of the present disclosure, there is provided compounds of Formula I, Formula II, Formula III, Formula IV, Formula V, and Formula VI or a pharmaceutically acceptable salt thereof as described herein, wherein the pharmaceutically acceptable salt selected derived from inorganic bases such as like Li, Na, K, Ca, Mg, Fe, Cu, Zn and Mn; salts of organic bases such as N, N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, ammonium, substituted ammonium salts, aluminum salts and the like. Salts also include amino acid salts such as glycine, alanine, cystine, cysteine, lysine, arginine, phenylalanine, and guanidine. Salts may include acid addition salts where appropriate which are sulfates, nitrates, phosphates, perchlorates, borates, hydrohalides, acetates, tartrates, maleates, citrates, succinates, palmoates, methanesulfonates, tosylates, benzoates, salicylates, hydroxynaphthoates, benzenesulfonates, ascorbates, glycerophosphates, ketoglutarates.

In an embodiment, the present disclosure relates to a method for the treatment and/or prevention of a proliferative disorder or cancer comprising administering to a subject suffering from the proliferative disorder or cancer a therapeutically effective amount of the compounds of Formula I, or Formula II, or Formula III, or Formula IV, or Formula V, or Formula VI or a pharmaceutically acceptable salt thereof together with a pharmaceutically acceptable carrier, with other clinically relevant cytotoxic agents or non-cytotoxic agents to a subject in need thereof.

In an embodiment, the present disclosure relates to the use of compounds of Formula I, or Formula II, or Formula III, or Formula IV, or Formula V, or Formula VI or a pharmaceutically acceptable salts thereof together with a pharmaceutically acceptable carrier, for the treatment and/or prevention of a proliferative disorder or cancer; or treatment of cancer together with other clinically relevant cytotoxic agents or non-cytotoxic agents.

In an embodiment, the present disclosure relates to the use of compounds of Formula I, or Formula II, or Formula III, or Formula IV, or Formula V, or Formula VI or pharmaceutically acceptable salts thereof together with a pharmaceutically acceptable carrier, for the treatment and/or prevention of various diseases including proliferative disorder or cancer; or treatment of cancer together with other clinically relevant cytotoxic agents or non-cytotoxic agents, wherein the other clinically relevant cytotoxic agents or non-cytotoxic agents are selected from the group consisting of carboplatin, bortezomib, carfilzomib, lenalidomide, pomalidomide, doxorubicin, daunorubicin, decitabine, denileukin, denileukin diftitox, dexrazoxane, docetaxel, doxorubicin, dromostanolone propionate cyclophosphamide, 5-fluorouracil, imatinib, methotrexate, irinotecan, toptecan, vinblastine, etoposide, vincristine, carmustine, paclitaxel, vorinostat, belinostat, panbinostat, romidepsin, chiadamide, entinostat, mocetinostat, afatinib, bosutinib, cetuximab, enterctinib, lapatinib, nilotinib, pazopanib, ruxlotinib, sorafenib, sunitinib, vermurafenib, axitinib, gefitinib, cobimetinib, carbozantinib, temozolomide, idarubicin, abarelix, aldesleukin, alemtuzumab, allopurinol, altretamine, anastrozole, asparaginase, bexarotene, baricitinib, bleomycin, busulfan, capecitabine, cladribine, clofarabine, cytarabine, dacarbazine, dactinomycin, sodium, dasatinib, letrozole, tamoxifen, oxaliplatin, procarbazine, zoleronate, and combinations thereof.

In an embodiment, the present disclosure relates to a method for the treatment of cancer as described herein, wherein said method comprising administering a combination of the compounds of Formula I, or Formula II, or Formula III, or Formula IV, or Formula V, or Formula VI or a pharmaceutically acceptable salts thereof together with a pharmaceutically acceptable carrier, with other clinically relevant cytotoxic agents or non-cytotoxic agents to a subject in need thereof.

In an aspect of the present disclosure there is provided a method of treatment and/or prevention of various diseases, including cancer and infectious diseases, comprising administering to a subject suffering from the viral infectious diseases such as HIV, Influenza, herpes virus, Hepatitis A, Hepatitis B, Hepatitis C, and Hepatitis D, a therapeutically effective amount of the compound of Formula I, Formula II, Formula III, Formula IV Formula V and Formula VI or the pharmaceutical composition, with other clinically relevant anti-viral drugs to a subject in need thereof.

In an embodiment, the present disclosure relates to a method of treatment of cancer as described herein, wherein said method comprising administering a combination of the compounds of Formula I, or Formula II, or Formula III, or Formula IV, or Formula V, or Formula VI or the pharmaceutical composition with other clinically relevant immune modulators agents to a subject in need of thereof.

EXAMPLES

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Abbreviations

Ac Acetyl;
Ac$_2$O Acetic anhydride;
ACN Acetonitrile;
AIBN Azobis(isobutyronitrile);
BINAP 2,2'-Bis(diphenylphosphino)-1,1'-binaphthyl;
BMS Borane-dimethyl sulfide complex;
Bn Benzyl;
Boc Tert-Butoxycarbonyl;
Boc$_2$O Di-tert-butyl dicarbonate;
BuLi Butyllithium;
CsF Cesium fluoride;
DCE 1,2-Dichloroethane;
DCM Dichloromethane;
DDQ 2,3-Dichloro-5,6-dicyano-1,4-benzoquinone;
DMS Dimethyl sufide;
ATP Adenosine triphosphate;
Bis-pinacolatodiboron 4,4,4',4',5,5,5',5'-Octamethyl-2,2'-bi-1,3,2-dioxaborolane;
BSA Bovine serum albumin;
C18 Refers to 18-carbon alkyl groups on silicon in HPLC stationary phase;
CH$_3$CN Acetonitrile;
Cy Cyclohexyl;
DIPEA Hünig's base, N-ethyl-N-(1-methylethyl)-2-propanamine;
Dioxane 1,4-Dioxane;
DMAP 4Ddimethylaminopyridine;
DME 1,2-Dimethoxyethane;
DMF N,N-Dimethylformamide;
DMSO Dimethylsulfoxide;
DPPA Diphenyl phosphoryl azide;
EtOAc Ethyl acetate;
EtOH Ethanol;
Et$_2$O Diethyl ether;
HOAc Acetic acid;
HPLC High pressure liquid chromatography;
HMDS Hexamethyldisilazide;
IPA Isopropylalcohol;
LAH Lithium aluminum hydride;
LDA Lithium diisopropylamide;
LHMDS Lithium hexamethyldisilazide;
MeOH Methanol;
MPLC Medium pressure liquid chromatography;
MTBE Methyl tert-butyl ether;
mCPBA m-Chloroperbezoic acid;
NaHMDS Sodium hexamethyldisilazide;
NBS N-bromosuccinimide;
NMR Nuclear magnetic resonance;
Pd$_2$(dba)$_3$ Tris(dibenzylideneacetone)dipalladium(0);
Pd(dppf)Cl$_2$.DCMComplex [1,1'-Bis(diphenylphosphino)ferrocene]dichloropalladium(II). dichloromethane complex;
RPHPLC Reverse phase high pressure liquid chromatography;
RT Room temperature;
Sat. Saturated;
SGC Silica gel chromatography;
SM Starting material;
TCL Thin layer chromatography;
TEA Triethylamine;
TFA Trifluoroacetic acid; and
THF Tetrahydrofuran.

The following examples provide the details about the synthesis, activities, and applications of the compounds of the present disclosure. It should be understood the following is representative only, and that the invention is not limited by the details set forth in these examples.

The compounds of the invention may be made by a variety of methods, including standard chemistry. Any previously defined variable will continue to have the previously defined meaning unless otherwise indicated. Illustrative general synthetic methods are set out in the following schemes and can be readily adapted to prepare other compounds of the invention.

There is also provided a process as shown in the following scheme 1, for the preparation of compounds of the Formula I, wherein all the groups are as defined earlier.

General Procedures for the Synthesis of Compounds Disclosed in Formula I:

Compounds of the invention (VI) were prepared generally according to Scheme-1

Scheme-1

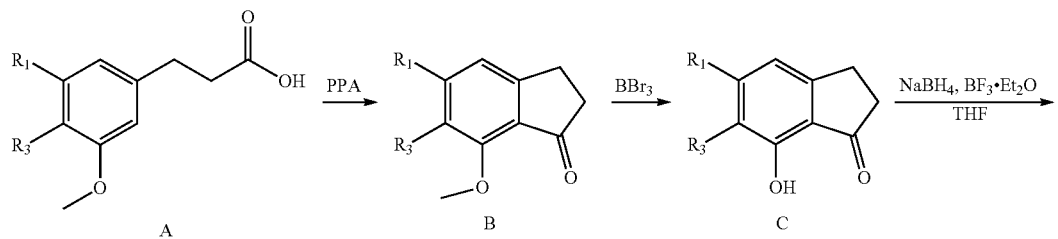

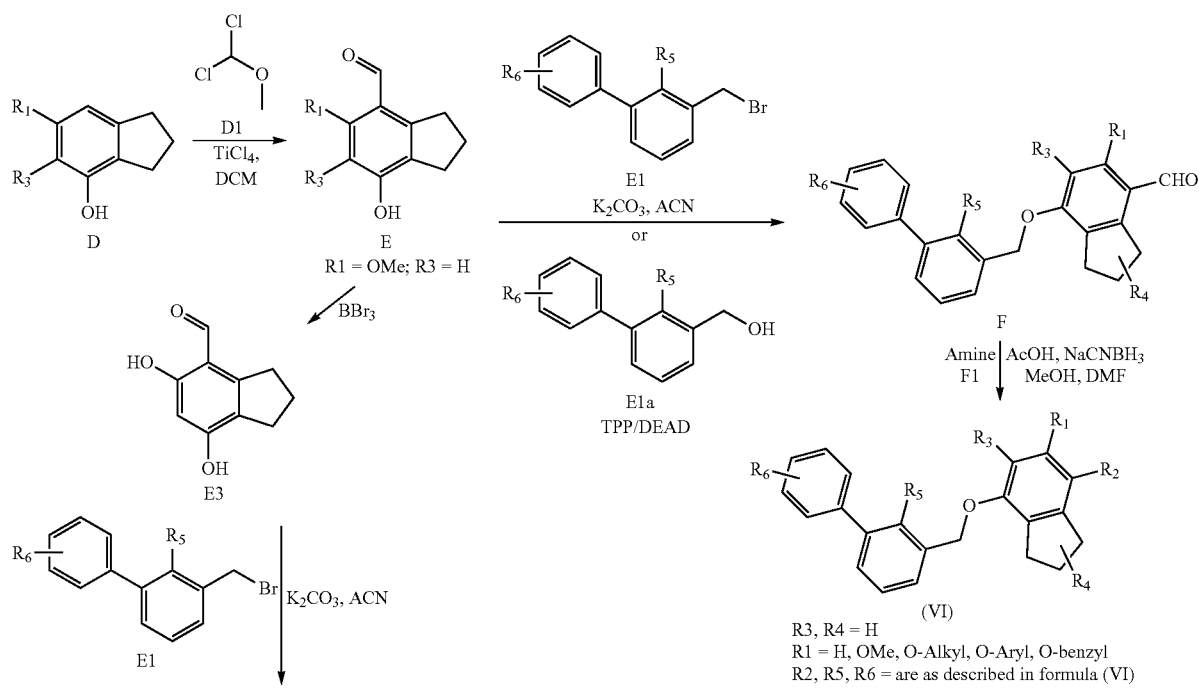

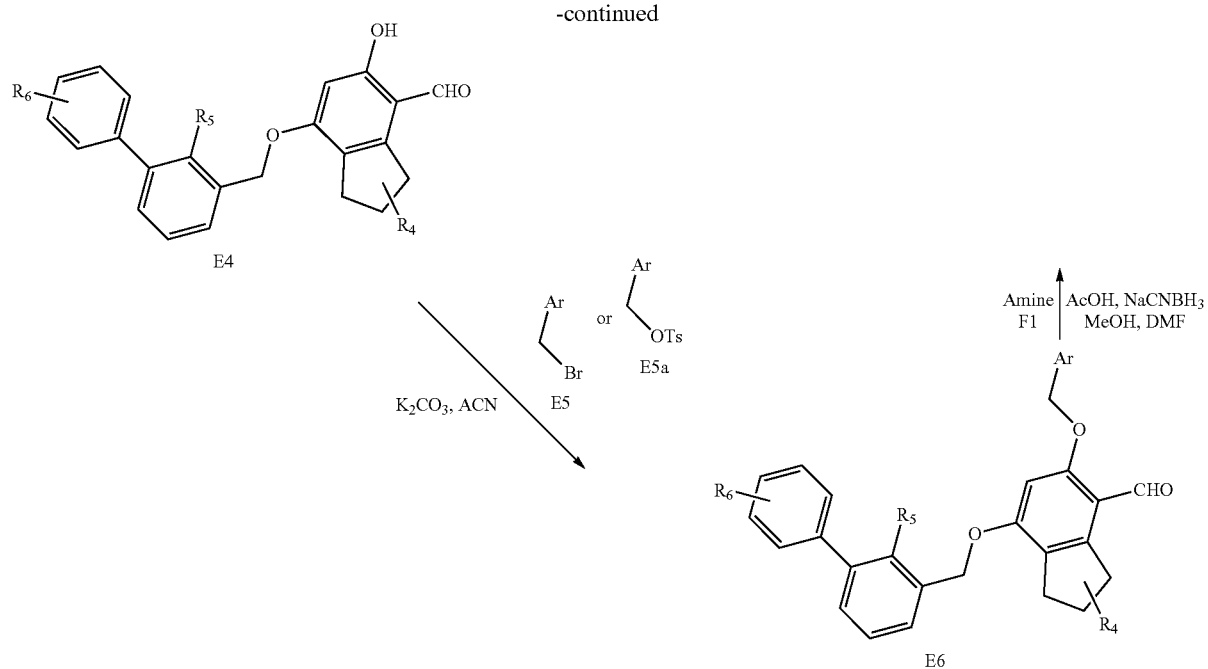

Compound B was prepared from dimethoxy phenyl propionic acid A, by reacting with polyphosphoric acid. Selective demethylation of compound B was performed using BBr₃ to obtain compound C. Upon decarbonylation of C using reducing agent compound D was obtained. Formylation of compound D using dichloro(methoxy)methane and titanium tetrachloride yielded compound E. O-alkylation of E using substituted biphenyl methyl bromides E1 gave compound F. In some cases of the present invention instead of biphenyl methyl bromide E1, biphenyl methyl alcohol E1a was used and followed by Mitsunobu reaction conditions to give intermediate F. Reductive amination of intermediate E with various substituted aliphatic, aromatic, heterocyclic and cyclic amines (E1) resulted compounds of general formula (VI) of the present invention. Alternatively, R₁ modifications such as O-benzyl substituted compounds of the general formula VI were prepared by demethylation of E to give 5,7-dihydroxy-2,3-dihydro-1H-indene-4-carbaldehyde. Selective benzylation of 7-hydroxy using E1 followed by second benzylation of 5-hydroxy using E5 or E5a resulted intermediate E6. Reductive amination of E6 with different amines resulted in compounds of the general formula (VI).

Alternatively, the unsubstituted indane core was prepared according to Scheme-2. Decarbonylation of G was performed using trifluoroacetic acid and triethylsilane to obtain intermediate H. Subsequent steps were performed following the procedure described in scheme-1 to obtain compounds of the general formula V and VI.

Scheme 2

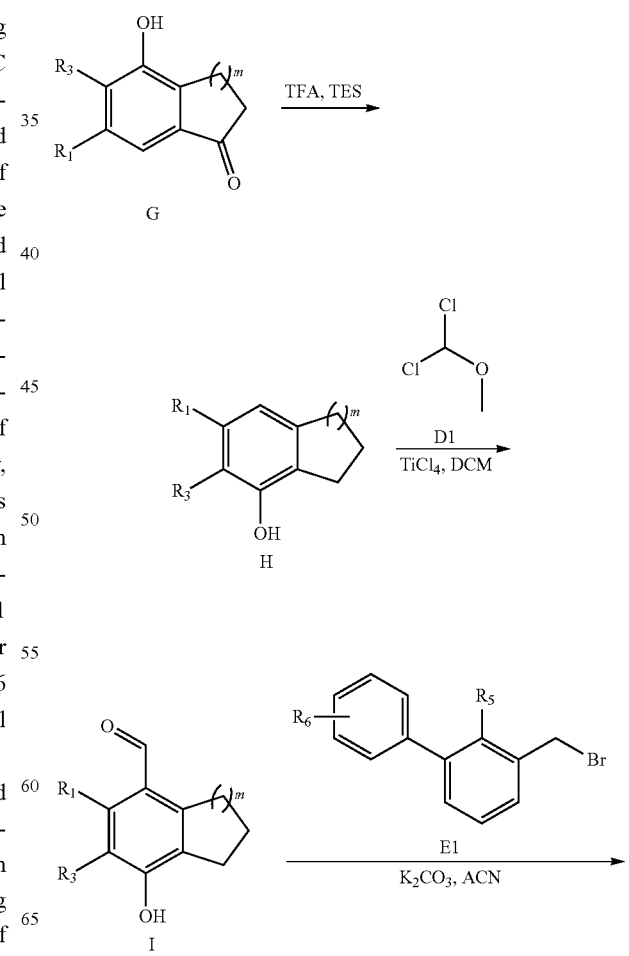

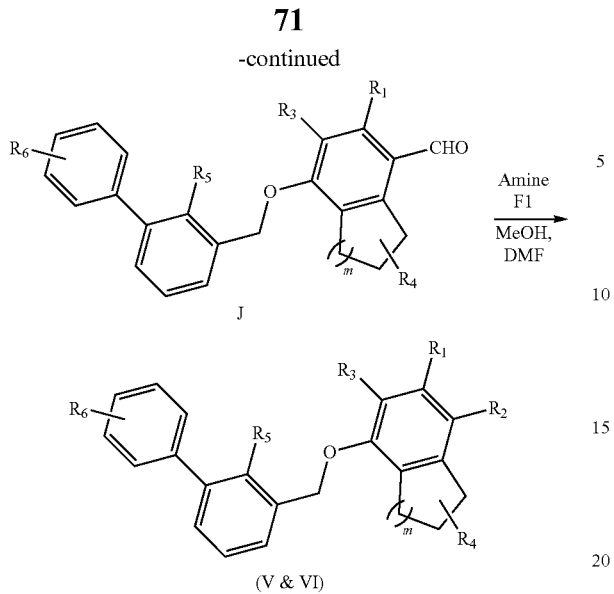

Alkyl-substituted indane derivatives were prepared according to Scheme 3. Formylation of o-cresol gave compound L. By reacting intermediate L with acetic anhydride compound M was obtained, which was hydrogenated to give 8-methylchroman-2-one N. Compound N was treated with aluminium chloride to give indenone derivative O. Decarbonylation of O followed by formylation gave intermediate Q. Subsequent steps were performed following the procedure described in scheme-1 to obtain compounds of the general formula VI.

Biphenyl methyl bromides (E1) or corresponding alcohols were prepared by following Suzuki coupling reaction using corresponding substituted phenyl boronic acid and substituted bromo benzene.

Scheme 3

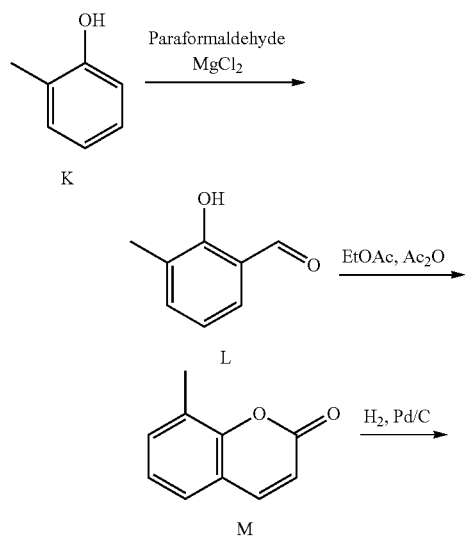

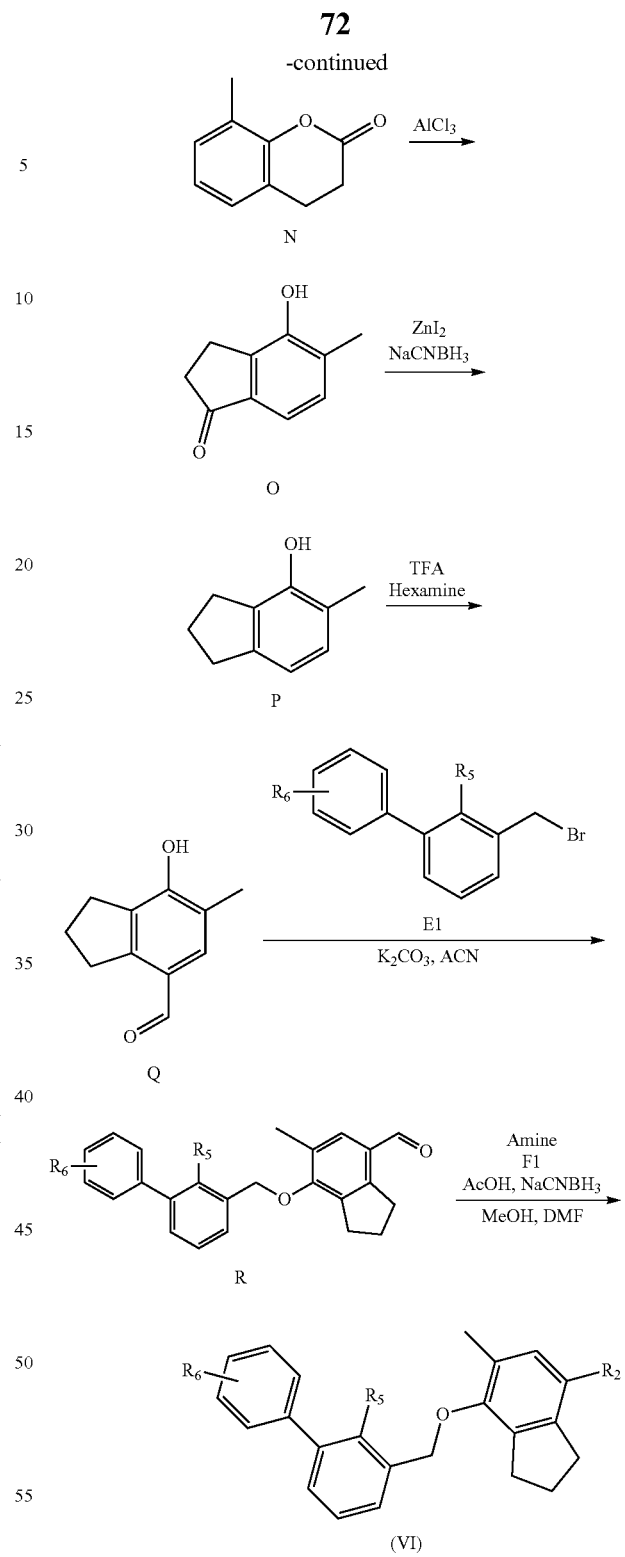

Halogen-substituted indane derivatives were prepared according to scheme-4. Decarbonylation of 4-hydroxy-2,3-dihydro-1H-inden-1-one S followed by chlorination gave 5-chloro-2,3-dihydro-1H-inden-4-ol U. Intermediate U was formylated to give 6-chloro-7-hydroxy-2,3-dihydro-1H-indene-4-carbaldehyde V. Subsequent steps were performed following the procedure described in Scheme-1 to obtain compounds of the general formula VI.

Scheme 4

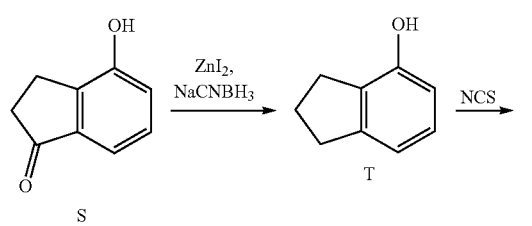

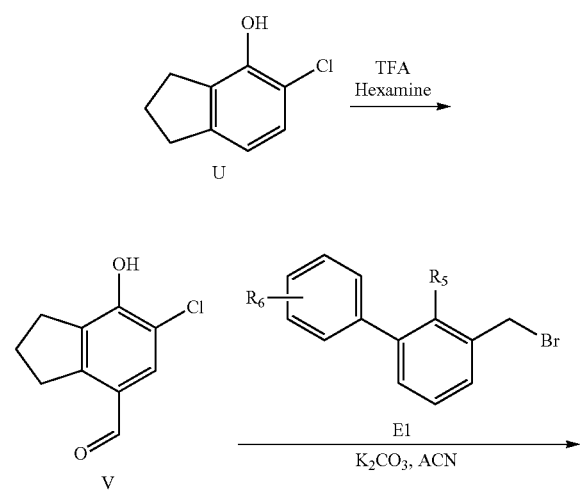

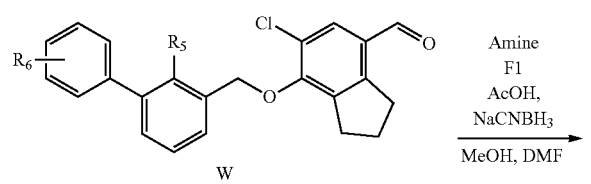

(VI)

Scheme 5

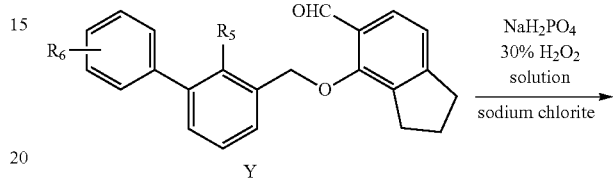

X

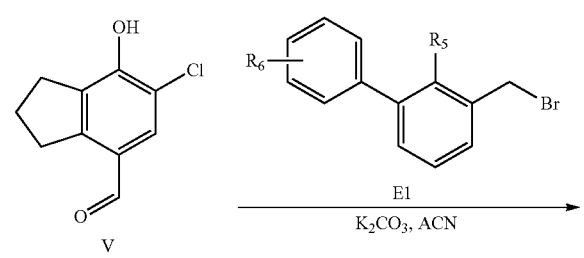

Y

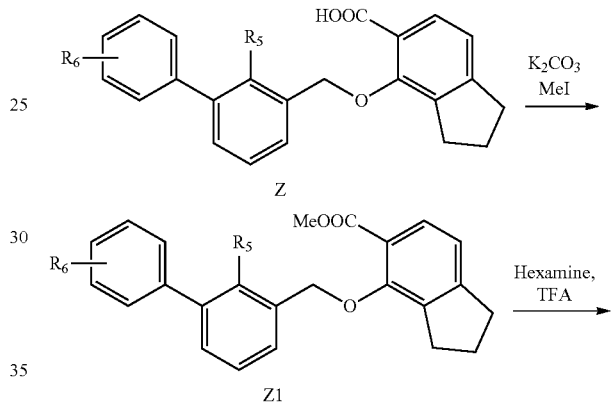

Z

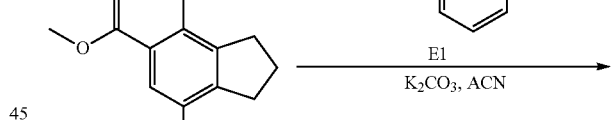

Z1

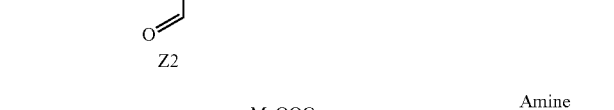

Z2

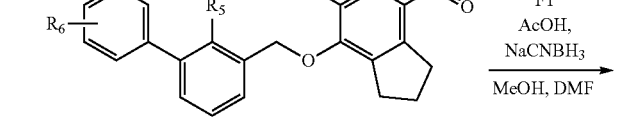

Z3

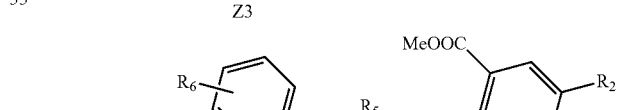

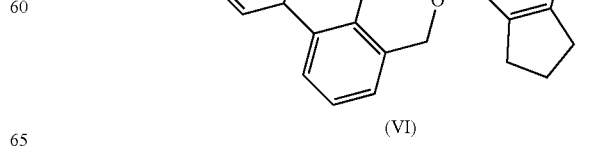

(VI)

Ester-substituted indane derivatives were prepared according to scheme-5. O-alkylation of 4-hydroxy-2,3-dihydro-1H-indene-5-carbaldehyde gave intermediate Y. Oxidation of aldehyde to acid using sodium dihydrogen phosphate and hydrogen peroxide gave intermediate Z. Intermediate Z was converted to corresponding ester Z1 using methyl iodide in presence of potassium carbonate. Intermediate Z1 was treated with TFA and hexamine to give benzyl de-protected aldehyde compound methyl 7-formyl-4-hydroxy-2,3-dihydro-1H-indene-5-carboxylate Z2. Subsequent steps were performed following the procedure described in Scheme-1 to obtain compounds of the general formula VI.

Compounds of the invention (VI) were prepared also prepared according to Scheme-6

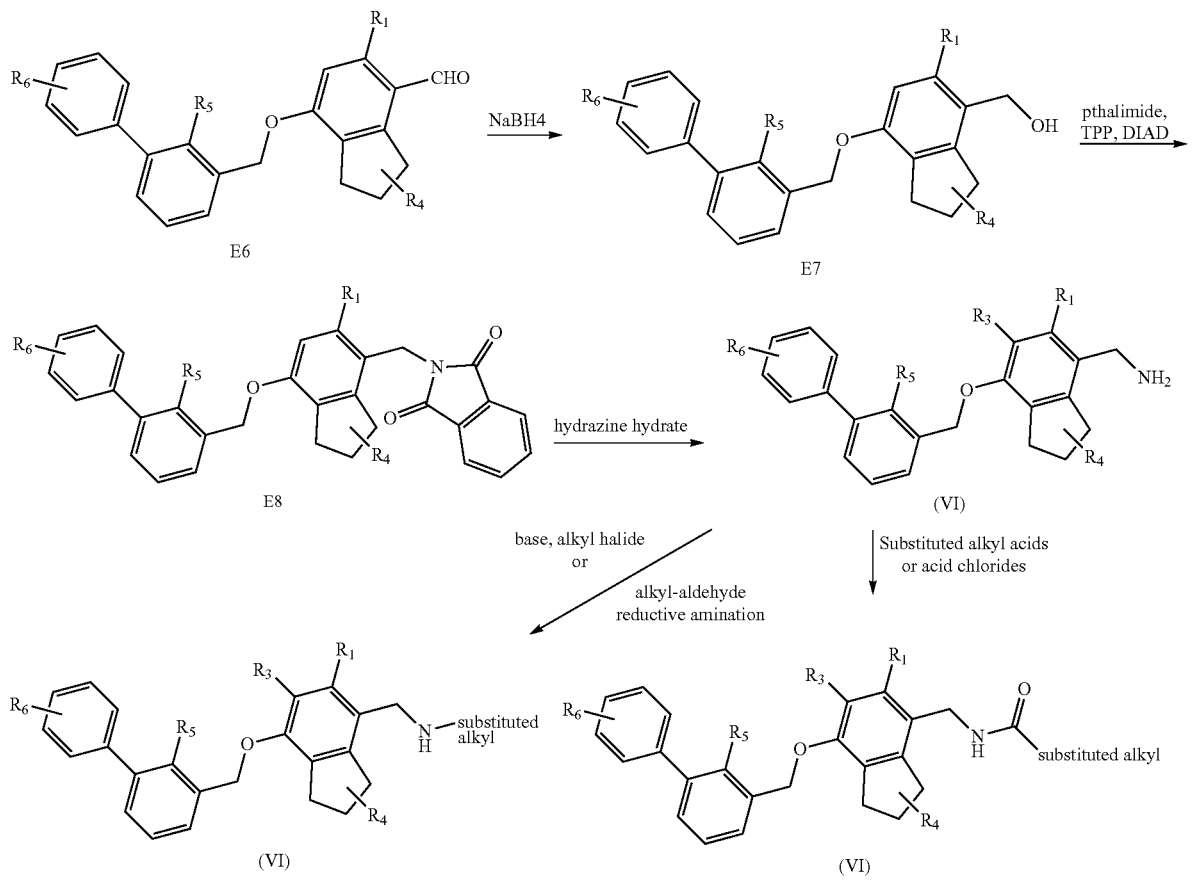

Compound E6 was reduced with sodium borohydride to give E7, which was reacted with pthalimide in presence of TPP and DIAD to obtain intermediate E8. Deprotection of pthalimide group gave free amine of the general formula (VI). Amine of general formula VI was reacted with alkyl halides in presence of base or reductive amination using aldehydes give alkyl amines of the general formula VI. Amides of the general formula VI were obtained by reaction amine with substituted acids or acid chlorides.

Nitrogen containing bicyclic heterocyclic compounds of the Formula I are prepared according to Scheme-7. Reacting cyclopentanone with malanonitrile and carbondisulphide gave bicyclic heterocycle intermediate E11. Hydrolysis and decarboxylation was performed using base to give E12. Methylation of thiol group using base and methyl iodide and O-alkylation using alkyl halide in presence of silveroxide or base gave intermediate E14. Bromination gave intermediate E15. Sulfoxidation of E15 gave intermediate E16. Nucleophilic displacement of E6 with E1a resulted with intermediate E17. Bromo to vinyl conversion was performed by Stille coupling, vinyl group was oxidized to aldehyde to give E19. Reductive amination of E19 with different amines resulted compounds of the general Formula I.

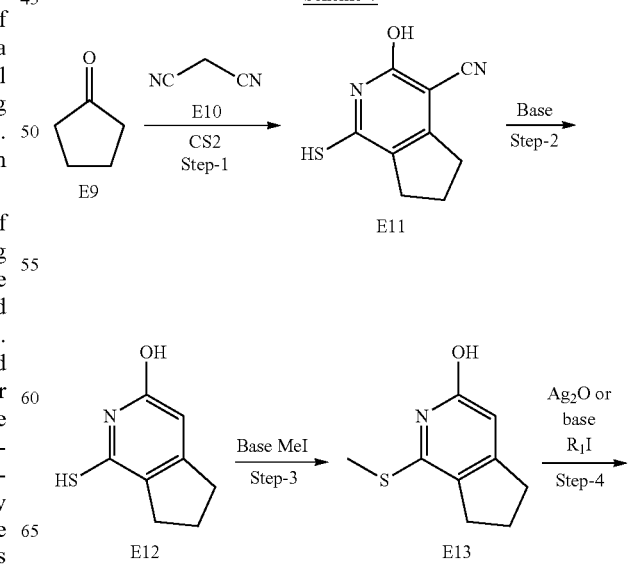

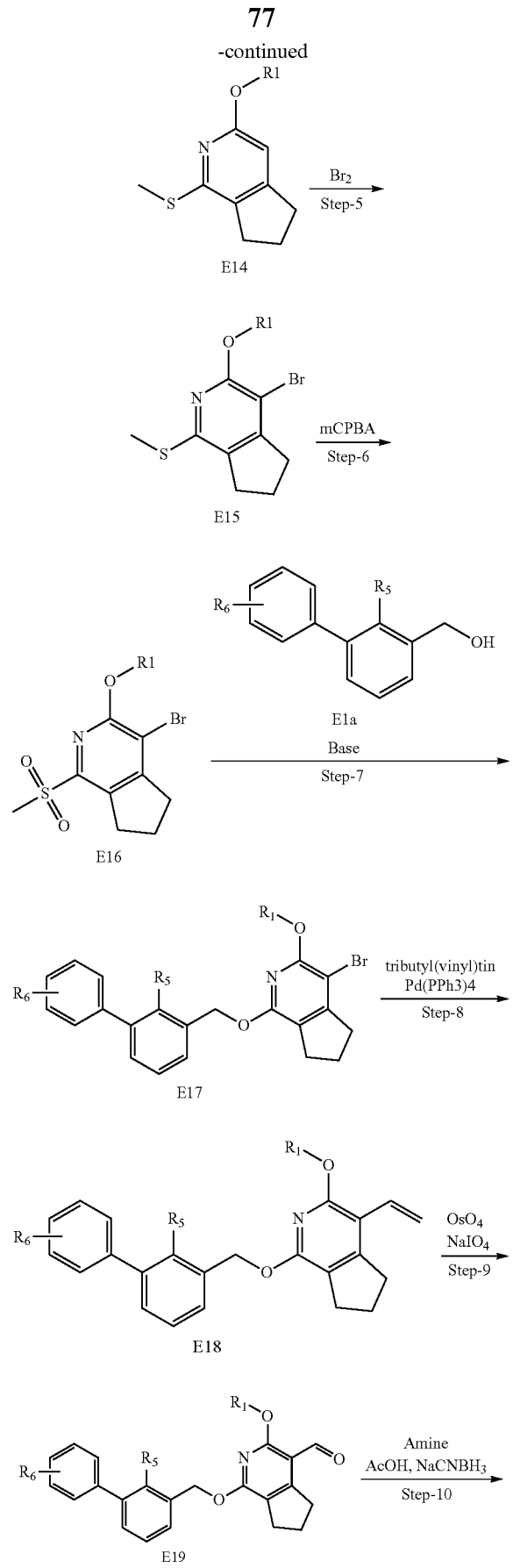

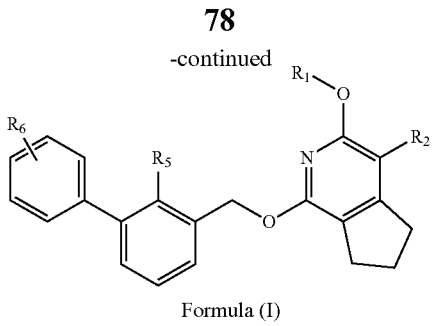

Formula (I)

R1 = H, OMe, O-Alkyl, O-Aryl, O-benzyl
R2, R5, R6 = are as described in formula (I)

Some of the intermediates used in present invention were prepared following procedure described in following schemes Scheme -8: Synthesis of 5-(chloromethyl)nicotinonitrile

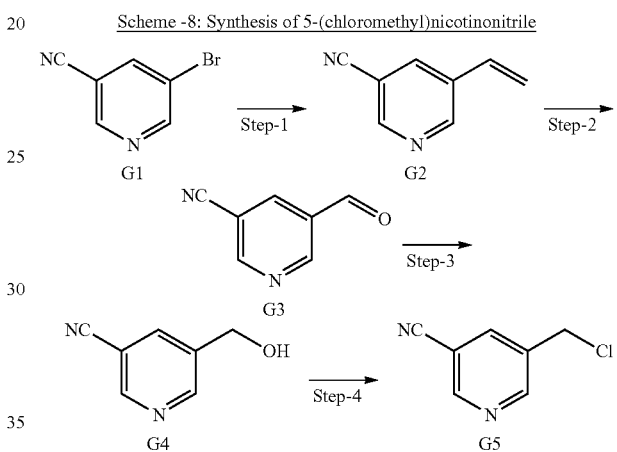

Step 1: A stirred solution of 5-bromonicotinonitrile (22 g, 0.120 mol) and tributyl vinyl tin (95.3 g, 0.300 mol) in DMF (200 mL) was purged with nitrogen for 10 min. To this mixture, Pd(PPh$_3$)$_4$ (13.84 g, 0.012 mol) was added and purged again with nitrogen for 20 min. Then the mixture was heated at 80° C. for 4 h. After completion, the reaction mixture was diluted with water (200 mL) and extracted with EtOAc (3×200 mL). The organic layer was washed with brine, dried over sodium sulfate, filtered and concentrated. The crude was purified by column chromatography (silica gel, 100-200 mesh) using 10% EtOAc in hexanes to obtain 5-vinylnicotinonitrile as off-white solid (Yield: 10.5 g, 67%). $^1$H NMR (400 MHz, DMSO-d$_6$, ppm): δ 5.55 (d, J=10.8 Hz, 1H), 6.17 (d, J=17.6 Hz, 1H), 6.80 (m, 1H), 8.52 (s, 1H), 8.90 (s, 1H), 9.03 (s, 1H).

Step-2: To a stirred solution of 5-vinylnicotinonitrile (10.5 g, 0.081 mol) in acetone (200 mL) and water (40 mL) at 0° C., OsO$_4$ (82 mL, 2.5 wt % solution in tert-butanol, 0.0081 mol) and N-Methylmorpholine N-oxide (29 g, 0.242 mol) were added and stirred for 3 h. To this mixture, NaIO$_4$ (60 g, 0.282 mol) was added and the reaction mixture was allowed to stir at room temperature for 12 h. After completion of the reaction, the reaction mixture was diluted with water (300 mL) and extracted with DCM (2×400 mL). The organic layer was dried over sodium sulfate, filtered and evaporated to give crude product. The crude product was purified on combiflash chromatography using 30% ethyl acetate in hexane as eluent to afford 5-formylnicotinonitrile (3) as yellow solid (Yield: 7.9 g, 74%). $^1$H NMR (400 MHz, DMSO-d$_6$, ppm): δ 8.77 (s, 1H), 9.29 (s, 1H), 9.31 (s, 1H), 10.12 (s, 1H).

Step-3: To a stirred solution of 5-formylnicotinonitrile (12 g, 0.091 mol) in methanol (100 mL) at 0° C., sodium borohydride (5.12 g, 0.136 mol) was added portion wise for 30 minutes and stirred the mixture at 0° C. for 2 h. The reaction mixture was concentrated and the residue was diluted with water (100 mL) and DCM (200 mL). The organic layer was dried over sodium sulfate and concentrated. The crude was purified by column chromatography (silica gel, 100-200 mesh) using 1% MeOH in DCM to obtain 5-(hydroxymethyl)nicotinonitrile as yellow solid (Yield: 7.4 g, 60.7%). $^1$H NMR (400 MHz, DMSO-d$_6$, ppm): δ, 8.91 (s, 1H), 8.80 (s, 1H), 8.19 (s, 1H), 5.54 (s, 2H), 4.50 (bs, 1H).

Step-4: To a stirred solution of 5-(hydroxymethyl)nicotinonitrile (3 g, 0.022 mol) in DCM (30 mL), 4M HCl in 1,4-dioxane (5 mL) was added and concentrated the mixture under vacuum. To the resulting residue, thionyl chloride (20 mL) was added and stirred the mixture at 60° C. for 3 h. After completion, the reaction was cooled to room temperature and diluted with toluene (150 mL) and filtered off the solid that precipitated out. The filtrate was diluted with DCM (200 mL) and washed with saturated sodium bicarbonate solution (200 mL). The organic layer was dried over sodium sulphate and concentrated to obtain 5-(chloromethyl)nicotinonitrile (Yield: 1.2 g, 35%) as yellow solid. $^1$H NMR (400 MHz, DMSO-d$_6$, ppm): δ 4.86 (s, 2H), 8.42 (s, 1H), 8.94 (d, J=2.0 Hz, 1H), 8.99 (d, J=2.0 Hz, 1H).

Scheme -9: Synthesis of 3-(hydroxymethyl)-[1,1'-biphenyl]-2-carbonitrile

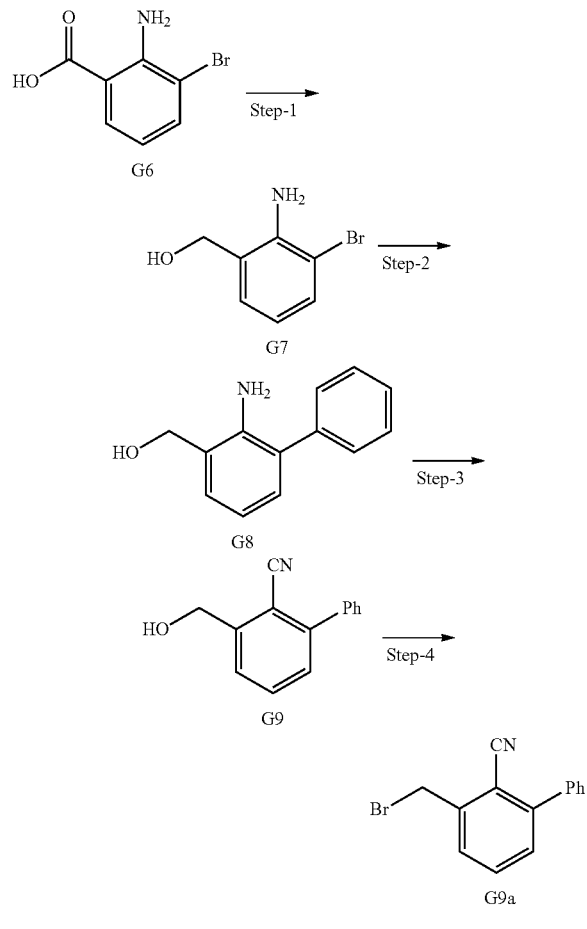

Step-1: A solution of 2-amino-3-bromobenzoic acid (10.0 g, 0.046 mol) in dry THF (100 mL) at 0° C., borane-DMS (118 mL, 1M in THF, 5 eq) was added and stirred the mixture at room temperature for 24 h. After completion, the reaction was quenched with methanol (20 mL) and concentrated under vacuum. The residue was diluted with EtOAc (500 mL) and was washed with water (300 mL), saturated sodium bicarbonate solution (300 mL), brine (200 mL) and concentrated to obtain (2-amino-3-bromophenyl)methanol (Yield: 7.3 g, 78%) as off-white solid. LCMS (ES) m/z=183.96 [M–H$_2$O+H]$^+$ & 185.93 [M+2-H$_2$O+H]$^+$; $^1$H NMR (400 MHz, DMSO-d$_6$, ppm) δ ppm: 4.43 (m, 2H), 5.05 (bs, 2H), 5.21 (m, 1H), 6.50 (t, J=7.6 Hz, 1H), 7.10 (d, J=7.2 Hz, 1H), 7.29 (d, J=7.6 Hz, 1H).

Step-2: A solution of (2-amino-3-bromophenyl)methanol (9.70 g, 0.048 mol) and phenyl boronic acid (7.65 g, 0.062 mol) in water (60 mL), toluene (60 mL) and methanol (70 mL) was degassed with nitrogen gas for 15 minutes. To this mixture, Pd(PPh$_3$)$_2$Cl$_2$ (3.37 g, 0.0048 mol) and sodium carbonate (13.4 g, 0.127 mol) were added and stirred the mixture at 80° C. for 8 h. After completion, the mixture was filtered over celite and washed with EtOAc (2×200 mL). The filtrate was washed with brine (20 mL) and concentrated. The resulting crude was purified by flash chromatography (silica gel, 12 g cartridge using 0-30% EtOAc in hexanes as eluent to obtain (2-amino-[1,1'-biphenyl]-3-yl)methanol (Yield: 8.2 g, 85%) as off-white solid. LCMS (ES) m/z=200.34 [M+H]$^+$; $^1$H NMR (400 MHz, DMSO-d$_6$, ppm) δ: 4.46 (m, 2H), 4.57 (bs, 2H), 5.14 (m, 1H), 6.67 (t, J=7.6 Hz, 1H), 6.93 (d, J=7.6 Hz, 1H), 7.05 (d, J=7.2 Hz, 1H), 7.34-7.39 (m, 3H), 7.47 (t, J=7.6 Hz, 2H).

Step-3: To a solution of (2-amino-[1,1'-biphenyl]-3-yl)methanol (2.5 g, 12.5 mmol) in water (15 mL) and toluene (15 mL), conc.HCl (6 mL) was added and cooled the mixture to 0° C. To this mixture, a solution of sodium nitrite (1.7 g, 18.8 mmol) in water (5 mL) was added slowly and continued stirring at 0° C. for 1.5 h. The pH of the solution was adjusted to 6.0 using sodium carbonate solution. This diazonium solution was added slowly to a solution of CuSO$_4$ (2.3 g, 15 mmol) and sodium cyanide (3.07 g, 62.5 mmol) in water (15 mL) and toluene (15 mL) at 60° C. After stirring at 60° C. for 2 h, the reaction mixture was cooled to room temperature and filtered and washed with EtOAc (100 mL). The organic layer of the filtrate was washed with brine (20 mL) and concentrated. The resulting crude was purified by flash chromatography (silica gel, 12 g, cartridge using 0-20% EtOAc in hexanes as eluent to obtain 3-(hydroxymethyl)-[1,1'-biphenyl]-2-carbonitrile (Yield: 450 mg, 17%) as brown liquid. LCMS (ES) m/z=210.36 [M+H]$^+$; $^1$H NMR (400 MHz, DMSO-d$_6$, ppm) δ: 4.73 (m, 2H), 5.63 (m, 1H), 7.47-7.56 (m, 6H), 7.67 (d, J=8.4 Hz, 1H), 7.77 (t, J=7.6 Hz, 1H).

Step-4: To a stirred solution of 3-(hydroxymethyl)-[1,1'-biphenyl]-2-carbonitrile (3.5 g, 16.7 mmol) in DCM (50 mL) at 0° C., triphenyl phosphine (6.5 g, 25.1 mmol) and carbon tetrabromide (8.31 g, 25.1 mmol) were added and allowed to stir at room temperature for 4 h. After completion, the reaction mixture was diluted with water (50 mL) and extracted with DCM (3×200 mL). The organic layer was dried over sodium sulfate and concentrated. The crude was purified by flash chromatography (silica gel, 12 g SNAP) using 0-20% EtOAc in hexanes to obtain 3-(bromomethyl)-[1,1'-biphenyl]-2-carbonitrile (Yield: 3.05 g, 66%) as brown solid. $^1$H NMR (400 MHz, DMSO-d$_6$, ppm) δ: 4.87 (s, 2H), 7.49-7.59 (m, 6H), 7.75-7.80 (m, 2H).

Scheme -10: Synthesis of 3-(chloromethyl)-5-fluoropyridine

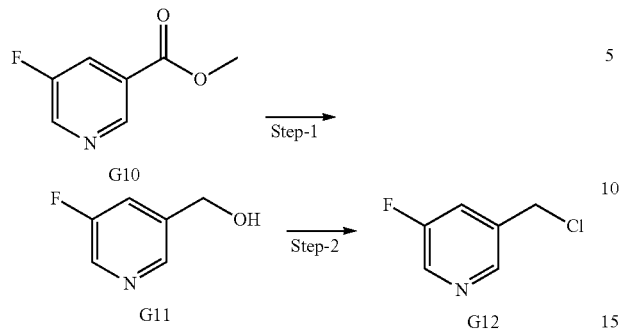

Step-1: To a stirred solution of methyl 5-fluoronicotinate (9.2 g, 59 mmol) in dry THF (40 mL) under nitrogen atmosphere at −78° C., a 2.5 M solution of LiAlH$_4$ in THF (31 mL, 77 mmol) was added drop wise and allowed the mixture to stir at same temperature for 40 minutes. After completion, the reaction was quenched at same temperature with saturated ammonium chloride (10 mL) and poured into ice cold water (100 mL). The mixture was extracted with EtOAc (3×100 mL) and the organic layer was dried over anhydrous sodium sulphate and concentrated to obtain (5-fluoropyridin-3-yl)methanol (Yield: 7.1 g, 95%) as red colored liquid. LCMS (ES) m/z=128.30[M+H]$^+$; $^1$H NMR (400 MHz, DMSO-d$_6$) δ ppm: 4.57 (m, 2H), 5.46 (t, J=5.6 Hz, 1H), 7.62 (d, J=10.0 Hz, 1H), 8.41 (s, 1H), 8.45 (d, J=2.8 Hz, 1H).

Step-2: To a solution of (5-fluoropyridin-3-yl)methanol (0.5 g, 3.93 mmol) in DCM (20 mL) at 0° C., triethylamine (1.63 mL, 11.80 mmol) and p-tosylchloride (2.24 g, 5.90 mmol) were added and then allowed the mixture to stir at room temperature for 6 h. The reaction mixture was diluted with water (25 mL) and extracted with DCM (3×40 mL). The organic layer was dried over anhydrous sodium sulphate and concentrated. The crude was purified by flash chromatography (silica gel, 12 g cartridge) using 20% EtOAc in hexanes as eluent to obtain 3-(chloromethyl)-5-fluoropyridine (Yield: 502 mg, 87%) as off-white solid. LCMS (ES) m/z=146.28[M+H]$^+$; $^1$H NMR (400 MHz, DMSO-d$_6$) δ ppm: 4.85 (s, 2H), 7.85 (d, J=9.2 Hz, 1H), 8.55 (s, 1H), 8.57 (d, J=2.4 Hz, 1H).

Scheme -11: Synthesis of N-(2-aminoethyl)-N-methylacetamide

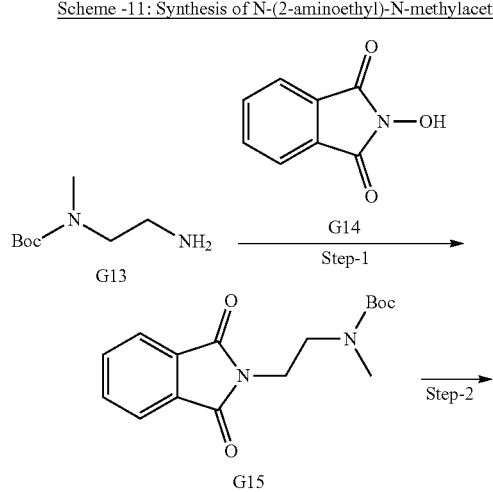

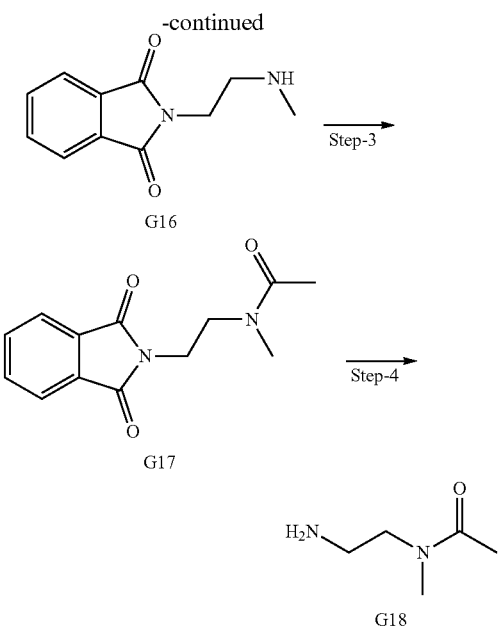

Step-1: To a solution of tert-butyl (2-aminoethyl)(methyl) carbamate (4.2 g, 25.7 mmol) in ethanol (60 mL), N-hydroxyphthalimide (4.50 g, 25.7 mmol) was added and stirred the mixture at 60° C. for 6 h. After completion, concentrated the mixture under vacuum. The residue was washed with diethyl ether (2×10 mL) to obtain tert-butyl (2-(1,3-dioxoisoindolin-2-yl)ethyl)(methyl)carbamate (Yield: 5.8 g, 74%) as white solid. LCMS (ES) m/z=305.42 [M+H]$^+$; $^1$H NMR (400 MHz, DMSO-d$_6$) δ ppm: 0.97 (s, 6H), 1.09 (s, 3H), 2.77 (s, 3H), 3.43 (m, 2H), 3.72 (t, J=5.2 Hz, 2H), 7.86 (m, 4H).

Step-2: To a solution of tert-butyl (2-(1,3-dioxoisoindolin-2-yl)ethyl)(methyl)carbamate (6 g, 19.7 mmol) in 1,4-dioxane (100 mL), 4M HCl in 1,4-dioxane (50 mL) was added and stirred the mixture at room temperature for 3 h. After completion, concentrated the mixture under vacuum. The resulting residue was washed with diethyl ether (2×10 mL) to obtain HCl salt of 2-(2-(methylamino)ethyl)isoindoline-1,3-dione (Yield: 4.0 g, 98%) as white solid. LCMS (ES) m/z=205.40 [M+H]$^+$; $^1$H NMR (400 MHz, DMSO-d$_6$) δ ppm: 2.56 (s, 3H), 3.18 (m, 2H), 3.89 (t, J=5.6 Hz, 2H), 7.88 (m, 4H), 8.83 (bs, 1H). Step-3: To a solution of 2-(2-(methylamino)ethyl)isoindoline-1,3-dione (3.5 g, 17.1 mmol) in DMF (40 mL), triethylamine (5.2 g, 51.3 mmol) and acetyl chloride (2 g, 25 mmol) were added and stirred for 2 h at room temperature. After completion, the reaction mixture was diluted with water (50 mL) and extracted with EtOAc (3×100 mL). The organic layer was dried over sodium sulfate and concentrated. The residue was washed with diethyl ether and pentane to obtain N-(2-(1,3-dioxoisoindolin-2-yl)ethyl)-N-methylacetamide (Yield: 2.5 g, 59%) as white solid. LCMS (ES) m/z=247.20 [M+H]$^+$.

Step-4: To a solution of N-(2-(1,3-dioxoisoindolin-2-yl) ethyl)-N-methylacetamide (2.2 g, 8.93 mmol) in ethanol (30 mL), hydrazine hydrate (0.58 g, 11.6 mmol) was added and stirred the mixture for 6 h at room temperature. After completion, the mixture was concentrated. The resulting residue was diluted with pentane (50 mL) and filtered. Concentration of the filtrate provided N-(2-aminoethyl)-N-methylacetamide (Yield: 106 mg, 10.2%) as an oil. $^1$H NMR (400 MHz, DMSO-d$_6$) δ ppm: 1.78 (s, 3H), 2.25 (s, 3H), 2.48 (m, 2H), 3.09 (m, 2H), 3.22 (m, 2H).

Scheme -12: Synthesis of N-(2-aminoethyl)-N-methylacetamide

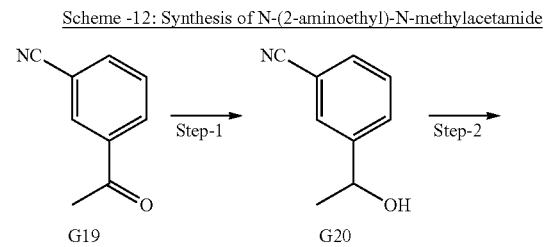

Step-1: To a stirred solution of 3-acetylbenzonitrile (2.0 g, 13.7 mmol) in methanol (30 mL), sodium borohydride (0.62 g, 15.5 mmol) was added and stirred at room temperature for 6 h. The reaction mixture was diluted with water (20 mL) and extracted with EtOAc (3×30 mL). The organic layer was dried and concentrated. The resulting crude was purified by flash chromatography (silica gel, 4 g cartridge) using 20% EtOAc in hexanes to obtain 3-(1-hydroxyethyl)benzonitrile (Yield: 1.8 mg, 91%) as colourless liquid. LCMS (ES) m/z=146.05 [M−H]$^+$; $^1$H NMR (400 MHz, DMSO-d$_6$) δ ppm: 1.32 (d, J=6.4 Hz, 3H), 4.77 (m, 1H), 5.39 (d, J=4.4 Hz, 1H), 7.53 (t, J=7.6 Hz, 1H), 7.69 (d, J=7.6 Hz, 2H), 7.76 (s, 1H).

Step-2: To a stirred solution of 3-(1-hydroxyethyl)benzonitrile (1.0 g, 6.8 mmol) in DCM (20 mL), carbon tetrabromide (2.67 g, 10 mmol) and triphenyl phosphine (3.37 g, 10 mmol) were added and stirred the mixture at room temperature for 4 h. After completion, the reaction mixture was diluted with water (10 mL) and separated the layers. The aqueous layer was further extracted with DCM (2×20 mL) and the combined organic layer was dried and concentrated. The resulting crude was purified by flash chromatography (silica gel, 4 g cartridge) using 20% EtOAc in hexanes to obtain 3-(1-bromoethyl)benzonitrile (Yield: 600 mg, 42%) as colourless liquid. LCMS (ES) m/z=146.05 [M−H]$^+$; $^1$H NMR (400 MHz, DMSO-d$_6$) δ ppm: 2.0 (d, J=6.8 Hz, 3H), 5.54 (m, 1H), 7.61 (t, J=7.6 Hz, 1H), 7.79 (d, J=7.6 Hz, 1H), 7.87 (d, J=7.6 Hz, 1H), 8.07 (s, 1H).

Scheme -13: Synthesis of N-(piperidin-3-yl)acetamide

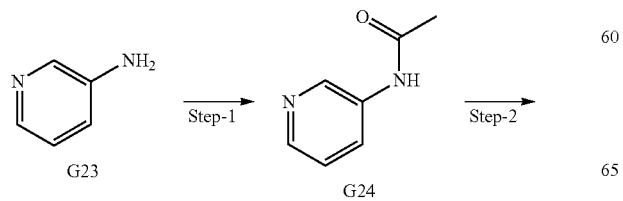

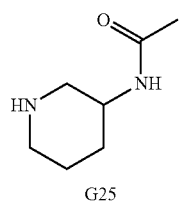

Step-1: To a stirred solution of 3-aminopyridine (3.0 g, 31.9 mmol) in THF (25 mL) at 0° C., acetic anhydride (3.70 g, 38 mmol) was added and stirred the mixture at room temperature for 8 h. After completion, the reaction mixture was diluted with water (25 mL) and extracted with EtOAc (3×50 mL). The combined organic layer was dried over sodium sulphate and concentrated to obtain N-(pyridin-3-yl)acetamide (Yield: 2.5 g, 58%) as white solid. $^1$H NMR (400 MHz, DMSO-d$_6$) δ ppm: 2.07 (s, 3H), 7.32 (m, 1H), 8.02 (m, 1H), 8.23 (m, 1H), 8.70 (s, 1H), 10.13 (s, 1H).

Step-2: To a solution of N-(pyridin-3-yl)acetamide (1.5 g, 11.0 mmol), HCl (3 mL) in ethanol (50 mL) was degassed with nitrogen gas for 10 min. To this mixture, PtO$_2$ (300 mg, 22 mmol) was added and the mixture was hydrogenated at 100 Psi pressure for 24 h. After completion, the mixture was filtered and the filtrate was concentrated under vacuum. The resulting residue was washed with EtOAc (10 mL) to obtain N-(piperidin-3-yl)acetamide (Yield: 1.0 g, 64%) as off-white solid. LCMS (ES) m/z=143.18 [M+H]$^+$.

Scheme -14: Synthesis of 3-(bromomethyl)-2-(trifluoromethyl)-1,1'-biphenyl

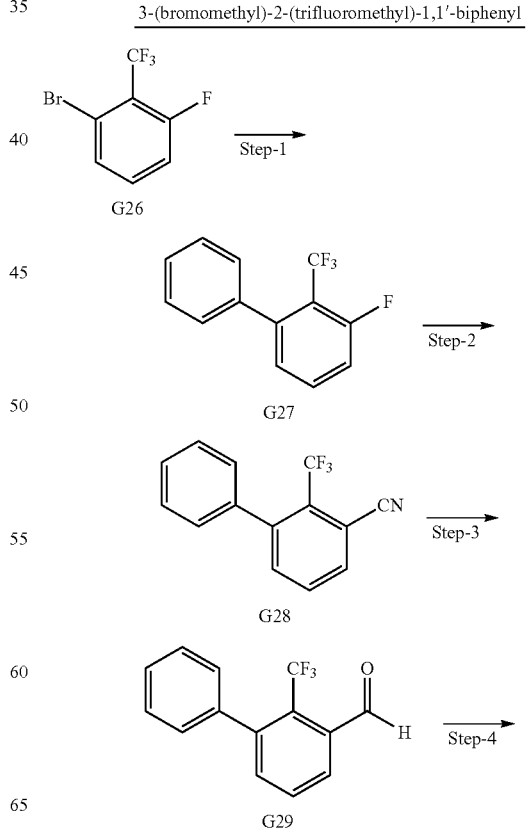

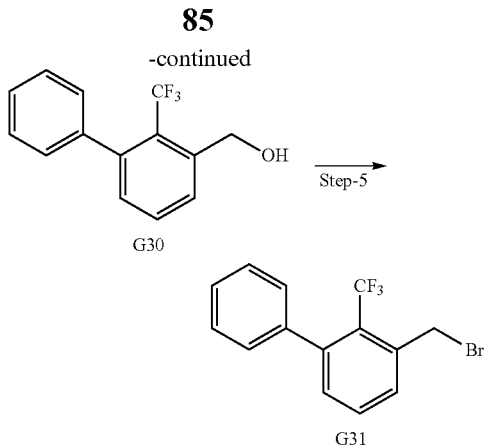

Step-1: A mixture of 1-bromo-3-fluoro-2-(trifluoromethyl)benzene (15 g, 62 mmol), phenyl boronic acid (22.7 g, 186 mmol), 2M sodium carbonate (150 mL), toluene (225 mL) and MeOH (75 mL) was degassed with nitrogen gas for 10 minutes. To this mixture, PdCl$_2$(dppf)DCM complex (5.75 g, 8.21 mmol) was added and degassed for another 5 minutes with nitrogen. After sealing the vessel, the mixture was heated at 90° C. for 12 h. After completion, the reaction was diluted with water (300 mL) and extracted with EtOAc (3×300 mL). The organic layer was dried over sodium sulphate and concentrated. The crude was purified by column chromatography (silica gel, 100-200 mesh) using 0-1% EtOAc in hexane to obtain 3-fluoro-2-(trifluoromethyl)-1,1'-biphenyl (Yield: 17 g, 39%) as colourless liquid. $^1$H NMR (400 MHz, DMSO-d$_6$) δ ppm: 7.21 (d, J=7.6 Hz, 1H) 7.31-7.34 (m, 2H), 7.44-7.50 (m, 3H), 7.65 (d, J=7.6 Hz, 1H), 7.72-7.78 (m, 1H).

Step-2: To a solution of 3-fluoro-2-(trifluoromethyl)-1,1'-biphenyl (17.0 g, 70.83 mmol) in DMSO (30 mL), KCN (4.6 g, 70.83 mmol) was added and stirred the mixture at 150° C. for 16 h. After completion, the reaction was diluted with water (100 mL) and extracted with EtOAc (3×100 mL). The organic layer was dried over sodium sulphate and concentrated. The crude was purified by column chromatography (silica gel, 100-200 mesh) using 0-5% EtOAc in hexanes to obtain 2-(trifluoromethyl)-[1,1'-biphenyl]-3-carbonitrile (Yield: 10.0 g, 58%) as yellow solid. $^1$H NMR (400 MHz, DMSO-d$_6$) δ ppm: 7.31-7.34 (m, 2H), 7.44-7.50 (m, 3H), 7.74 (d, J=6.4 Hz, 1H), 7.91 (t, J=8.0 Hz, 1H), 8.19 (d, J=7.6 Hz, 1H).

Step-3: To a solution of 2-(trifluoromethyl)-[1,1'-biphenyl]-3-carbonitrile (1.0 g, 4.0 mmol) in dry DCM (5 mL) at −65° C., DIBAl-H (1M solution in hexanes, 6.0 mL, 6.0 mmol) was added drop wise and stirred the mixture at −65° C. for 1 h. After completion, the reaction was quenched with cold water (20 mL) and extracted with DCM (3×25 mL). The organic layer was dried over sodium sulphate and concentrated. The crude was purified by flash chromatography (silica gel, 12 g cartridge) using 0-10% EtOAc in hexanes to obtain 2-(trifluoromethyl)-[1,1'-biphenyl]-3-carbaldehyde (Yield: 0.4 g, 39.5%) as colourless liquid. $^1$H NMR (400 MHz, DMSO-d$_6$) δ ppm: 7.35 (m, 2H), 7.47 (m, 3H), 7.67 (d, J=6.4 Hz, 1H), 7.89 (t, J=8.0 Hz, 1H), 7.99 (d, J=7.6 Hz, 1H), 10.37 (s, 1H).

Step-4: To a solution of 2-(trifluoromethyl)-[1,1'-biphenyl]-3-carbaldehyde (3.0 g, 12 mmol) in EtOH (30 mL) and THF (10 mL) at 0° C., sodium borohydride (0.90 g, 24 mmol) was added and allowed to stir at room temperature for 2 h. After completion of reaction, the reaction was quenched with water (50 mL) and extracted with EtOAc (3×100 mL). The organic layer was dried over sodium sulphate and concentrated to obtain (2-(trifluoromethyl)-[1,1'-biphenyl]-3-yl)methanol (Yield: 2.70 g, 90%) as yellow sticky liquid. $^1$H NMR (400 MHz, DMSO-d$_6$) δ ppm: 4.73 (s, 2H), 5.53 (m, 1H), 7.21 (d, J=7.6 Hz, 1H), 7.25 (d, J=6.8 Hz, 2H), 7.38-7.43 (m, 3H), 7.66 (t, J=8.0 Hz, 1H), 7.83 (d, J=7.6 Hz, 1H).

Step-5: To a solution of (2-(trifluoromethyl)-[1,1'-biphenyl]-3-yl)methanol (0.1 g, 0.39 mmol) in DCM (10 mL) at 0° C., triphenyl phosphine (0.25 g, 0.99 mmol) and carbon tetrabromide (0.33 g, 0.99 mmol) were added and allowed the mixture to stir at room temperature for 8 h. After completion of reaction, the reaction was diluted with water (10 mL) and extracted with DCM (3×20 mL). The organic layer was dried over sodium sulphate and concentrated to obtain 3-(bromomethyl)-2-(trifluoromethyl)-1,1'-biphenyl (Yield: 100 mg, 80%) as off-white solid. $^1$H NMR (400 MHz, DMSO-d$_6$) δ ppm: 4.87 (s, 1H), 4.95 (s, 1H), 7.26-7.28 (m, 2H), 7.30-7.36 (m, 1H), 7.42 (m, 3H), 7.68-7.76 (m, 2H).

Scheme -15: Synthesis of
methyl (1R,2S)-2-((tosyloxy)methyl)cyclopropane-1-carboxylate

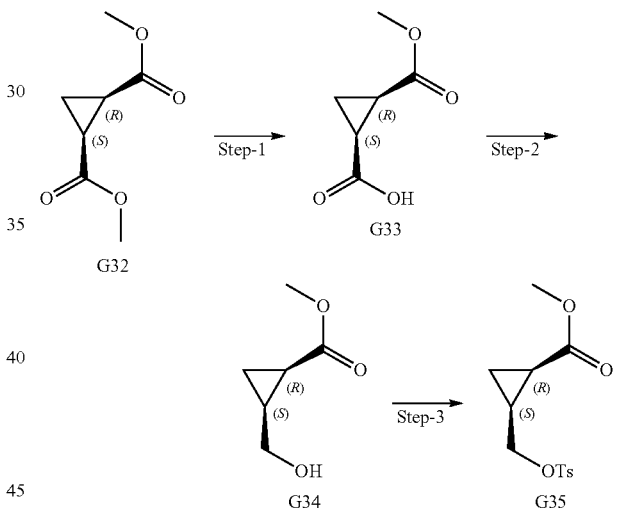

Step-1: To a stirred solution of dimethyl (1R,2S)-cyclopropane-1,2-dicarboxylate (2.0 g, 12.6 mmol) in THF (40 mL), a solution of lithium hydroxide monohydrate (0.53 g, 12.6 mmol) in water (40 mL) was added slowly and stirred for about 1 h. The reaction was cooled to 0° C. and pH was adjusted to 5-6. The aqueous mixture was extracted with 5% MeOH in DCM (3×50 mL) and the combined organic layer was dried over sodium sulphate and concentrated to obtain (1S,2R)-2-(methoxycarbonyl)cyclopropane-1-carboxylic acid (Yield: 0.80 g, 44%) as colourless liquid. LCMS (ES) m/z=143 [M−H]$^+$; $^1$H NMR (400 MHz, DMSO-d$_6$) δ ppm: 1.17 (m, 1H), 1.32 (m, 1H), 1.99-2.03 (m, 1H), 2.10-2.16 (m, 1H), 3.56 (s, 3H), 12.33 (s, 1H).

Step-2: To a solution of (1S,2R)-2-(methoxycarbonyl) cyclopropane-1-carboxylic acid (0.80 g, 5.5 mmol) in THF (15 mL) under nitrogen atmosphere at 0° C., borane-DMS (0.84 g, 11.1 mmol) was added and allowed the reaction mixture to stir at room temperature for 6 h. After completion, the reaction was quenched with MeOH (10 mL) at 0° C. and concentrated under vacuum. The resulting crude was purified by flash chromatography (silica gel, 4 g cartridge) using 5% MeOH in DCM as eluent to obtain methyl (1R,2S)-2-(hydroxymethyl)cyclopropane-1-carboxylate (Yield: 0.550 g, 76%) as colourless liquid. $^1$H NMR (400 MHz, DMSO-d$_6$) δ ppm: 0.82 (m, 1H), 1.05 (m, 1H), 1.50 (m, 1H), 1.72 (m, 1H), 3.38 (m, 1H), 3.58 (s, 3H), 3.62 (m, 1H), 4.51 (m, 1H).

Step-3: To a stirred solution of methyl (1R,2S)-2-(hydroxymethyl)cyclopropane-1-carboxylate (0.25 g, 1.9 mmol) in DCM (5 mL), triethylamine (0.58 g, 5.7 mmol), and DMAP (23 mg, 0.19 mmol) were added and stirred for 10 minutes. To this mixture, tosyl chloride (0.55 g, 2.8 mmol) was added and allowed the mixture to stir at room temperature for 6 h. After completion, the reaction mixture was diluted with water (10 mL) and extracted with DCM (3×15 mL). The organic layer was dried over sodium sulphate and concentrated. The resulting crude was purified by flash chromatography (silica gel, 4 g cartridge) using 5% MeOH in DCM as eluent to obtain methyl (1R,2S)-2-((tosyloxy)methyl)cyclopropane-1-carboxylate (Yield: 0.330 g, 60%) as colourless liquid.

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

TABLE 1

Prep-HPLC methods:

| Method | Column | Mobile phase | Compounds purified by prep HPLC |
|---|---|---|---|
| A | Xbridge Shield C-18, 19 × 250 mm, 10 u | 5 Mm Ammonium Acetate in water: Acetonitrile | 32, 12, 86 |
| B | Xselect CSH phenyl hexyl, 19 × 250 mm, 5 u | 5 Mm Ammonium Acetate in water: Acetonitrile | 46, 49, 85, 56, 93, 94 |
| C | Xselect CSH phenyl hexyl, 19 × 250 mm, 5 u | 0.1% TFA in water: Acetonitrile | 47 |
| D | Sunfire C18, 19 × 250 mm, 10µ | 5 mM Ammonium Acetate in water: Acetonitrile. | 76, 52, 81 |
| E | Sunfire C18, 19 × 250 mm, 10µ | 0.1% Formic Acid in water:Acetonitrile. | 79 |
| F | XTERRA C18, 19 × 250 mm, 10µ | 5 mM Ammonium Bicarbonate in water: Acetonitrile | 63 |

Example 1

(S)-1-((7-((2-methyl-[1,1'-biphenyl]-3-yl)methoxy)-2,3-dihydro-1H-inden-4-yl)methyl) piperidine-2-carboxylic acid (1)

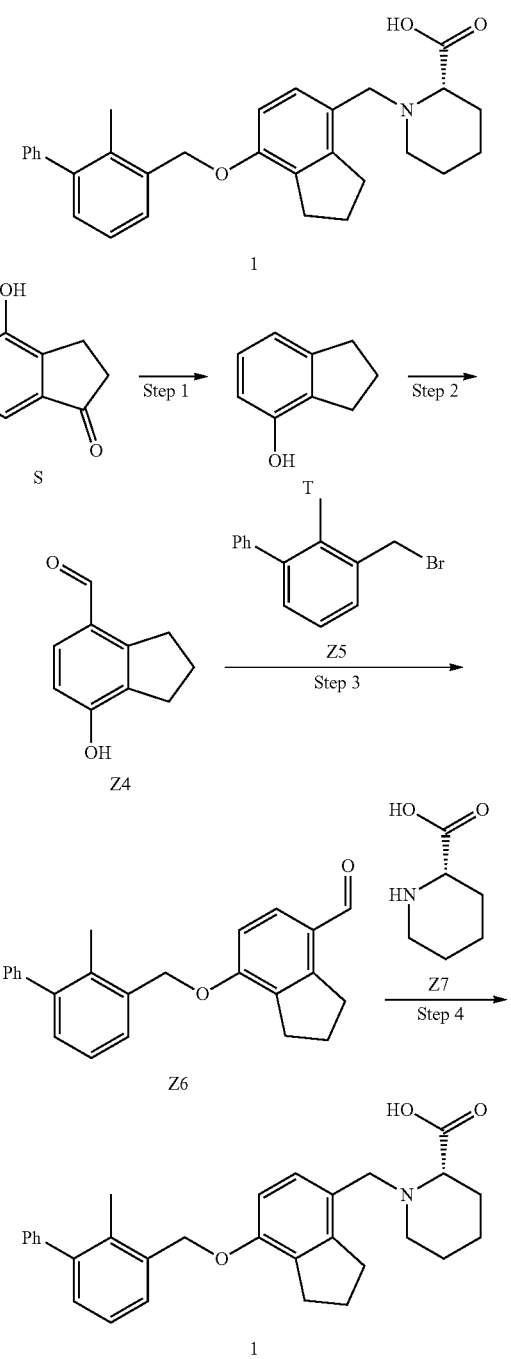

Step 1: To a solution of 4-hydroxy-2,3-dihydro-1H-inden-1-one (2.0 g, 13.5 mmol) in TFA (20 mL) at room temperature was added triethylsilane (5.3 mL, 33.72 mmol). The mixture was stirred at 100° C. for 16 h. The reaction mixture was cooled to room temperature and concentrated. The residue was quenched with sodium bicarbonate solution, extracted into ethyl acetate. The organic layer was dried over sodium sulphate and evaporated to obtain crude product, which was purified on combiflash MPLC using 10% EtOAc in Hexane as eluent to afford 2,3-dihydro-1H-inden-4-ol (1.8 g, crude) as pale brown liquid. $^1$H NMR (400 MHz, DMSO-$d_6$) δ ppm: 1.90-1.96 (m, 2H), 2.71 (t, J=7.4 Hz, 2H), 2.79 (t, J=7.6 Hz, 2H), 6.52 (d, J=8.0 Hz, 1H), 6.64 (d, J=7.6 Hz, 1H), 6.89 (t, J=7.8 Hz, 1H), 9.04 (s, 1H).

Step 2: To a mixture of 2,3-dihydro-1H-inden-4-ol (1.8 g, 13.43 mmol) in DCM (20 mL) was added $TiCl_4$ (2.7 mL, 24.17 mmol) at 0° C. and the reaction mixture was stirred for 15 min. Dichloro(methoxy)methane (1.3 mL, 14.77 mmol) was added to the reaction mixture at 0° C. The mixture was stirred at room temperature for 2 h. The reaction mixture was quenched with cold water and extracted with DCM. The combined organic layer was dried over sodium sulphate and evaporated to obtain crude which was purified on combiflash MPLC using 20% EtOAc in Hexane as eluent to afford 7-hydroxy-2,3-dihydro-1H-indene-4-carbaldehyde (0.31 g, crude) as white solid. LCMS (ES) m/z=163.1 [M+H.]$^+$. $^1$H NMR (400 MHz, DMSO-$d_6$) δ ppm: 2.00-2.04 (m, 2H), 2.73 (t, J=7.4 Hz, 2H), 3.16 (t, J=7.4 Hz, 2H), 6.75 (d, J=8.0 Hz, 1H), 7.52 (d, J=8.0 Hz, 1H), 9.86 (s, 1H), 10.34 (s, 1H).

Step 3: To a mixture of 7-hydroxy-2,3-dihydro-1H-indene-4-carbaldehyde (0.31 g, 1.91 mmol, 1 equiv) in ACN (10 mL) was added potassium carbonate (0.39 g, 2.87 mmol, 1.5 equiv). The reaction mixture was stirred at room temperature for 15 min. 3-(bromomethyl)-2-methyl-1,1'-biphenyl (0.5 g, 1.91 mmol, 1.0 equiv) was added to the reaction mixture and stirred at room temperature for 2 h. The reaction mixture was quenched with water and extracted with DCM. The combined organic layer was dried over sodium sulphate and evaporated to obtain crude product, which was purified on combiflash MPLC using 10% EtOAc in Hexane as eluent to afford 7-((2-methyl-[1,1'-biphenyl]-3-yl)methoxy)-2,3-dihydro-1H-indene-4-carbaldehyde (0.6 g, 92%) as white solid. LCMS (ES) m/z=343.2 [M+H.]$^+$. $^1$H NMR (400 MHz, DMSO-$d_6$) δ ppm: 2.02-2.09 (m, 2H), 2.19 (s, 3H), 2.81 (t, J=7.4 Hz, 2H), 3.20 (t, J=7.6 Hz, 2H), 5.28 (s, 2H), 7.18 (t, J=9.0 Hz, 2H), 7.25-7.31 (m, 3H), 7.34-7.38 (m, 1H), 7.42-7.46 (m, 3H), 7.72 (d, J=8.4 Hz, 1H), 9.95 (s, 1H).

Step 4: To a mixture of 7-((2-methyl-[1,1'-biphenyl]-3-yl)methoxy)-2,3-dihydro-1H-indene-4-carbaldehyde (0.1 g, 0.29 mmol) and (S)-piperidine-2-carboxylic acid (0.045 g, 0.35 mmol) in DMF:MeOH (10 mL) was added one drop of acetic acid at room temperature and the reaction mixture was stirred for 15 min. Sodium cyanoborohydride (0.054 g, 0.87 mmol) was added to the reaction mixture and the mixture was stirred at room temperature for 16 h. The reaction mixture was quenched with water and extracted with DCM. The combined organic layer was washed with sodium bicarbonate solution and dried over sodium sulphate and evaporated to obtain crude product, which was purified on combiflash MPLC using 20% MeOH in DCM as eluent to afford (S)-1-((7-((2-methyl-[1,1'-biphenyl]-3-yl)methoxy)-2,3-dihydro-1H-inden-4-yl)methyl)piperidine-2-carboxylic acid (15 mg, 11%) as white solid. LCMS (ES) m/z=456.2 [M+H. $^1$H NMR (400 MHz, DMSO-$d_6$) δ ppm: 1.35-1.46 (m, 3H), 1.71-1.73 (m, 2H), 1.95-1.99 (m, 2H), 2.18-2.25 (m, 4H), 2.78-3.05 (m, 6H), 3.41-3.71 (m, 2H), 3.81-4.45 (m, 2H), 5.12 (s, 2H), 6.87 (d, J=8.0 Hz, 1H), 7.08 (d, J=8.0 Hz, 1H), 7.17 (d, J=7.6 Hz, 1H), 7.24-7.31 (m, 3H), 7.34-7.37 (m, 1H), 7.42-7.45 (m, 3H).

Example 2

N-(2-(((5-methoxy-7-((2-methyl-[1,1'-biphenyl]-3-yl)methoxy)-2,3-dihydro-1H-inden-4-yl) methyl)amino)ethyl)acetamide (2)

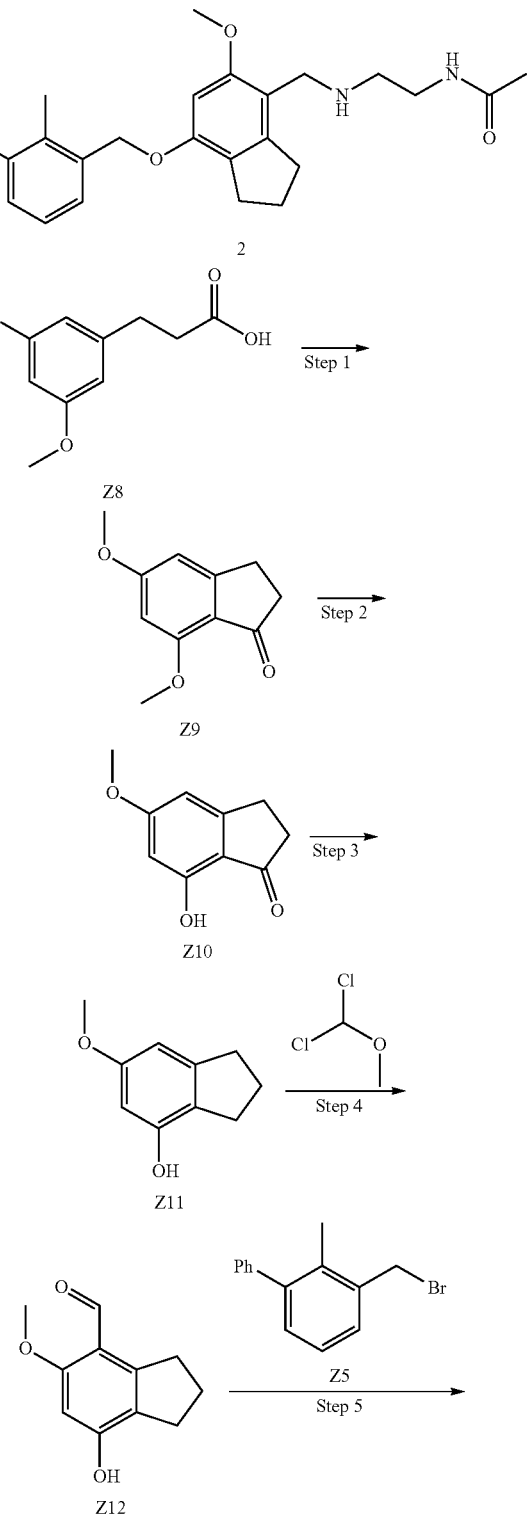

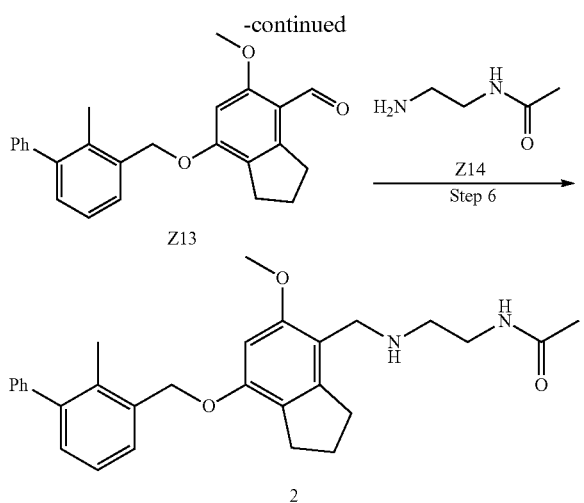

Step 1: A solution of 3-(3,5-dimethoxyphenyl)propanoic acid (10.0 g, 147.61 mmol) in polyphosphoric acid (100 mL) was stirred for 16 h at 80° C. The reaction mixture was cooled to room temperature and quenched with water, extracted using ethyl acetate. The organic layer was dried over sodium sulphate and evaporated to obtain crude product, which was purified on combiflash MPLC using 20% EtOAc in hexane as eluent to afford 5,7-dimethoxy-2,3-dihydro-1H-inden-1-one (4.0 g, 43%) as pale brown solid. LCMS (ES) m/z=193.1 [M+H]$^+$. $^1$H NMR (400 MHz, DMSO-d$_6$) δ ppm: 2.63-2.69 (m, 2H), 3.00-3.03 (m, 2H), 3.86 (s, 3H), 3.90 (s, 3H), 6.29 (s, 1H), 6.48 (s, 1H).

Step 2: To a solution of 5,7-dimethoxy-2,3-dihydro-1H-inden-1-one (3.5 g, 18.22 mmol) in DCM (50 mL) was added BBr$_3$ (1.71 mL, 17.18 mmol) drop wise over a period of 5 min at 0° C. and the reaction mixture was stirred at room temperature for 1 h. The reaction mixture was quenched with ice water and extracted with DCM. The organic layer was dried over sodium sulphate and evaporated to obtain crude which was purified on combiflash MPLC using 20% EtOAc in hexane as eluent to afford 7-hydroxy-5-methoxy-2,3-dihydro-1H-inden-1-one (3.5 g, crude) as pale brown solid. LCMS (ES) m/z=179.0 [M+H]$^+$. $^1$H NMR (400 MHz, DMSO-d$_6$) δ ppm: 2.48-2.52 (m, 2H), 2.92-2.95 (m, 2H), 3.77 (s, 3H), 6.24 (s, 1H), 6.51 (s, 1H), 9.85 (s, 1H).

Step 3: To a mixture of sodium borohydride (2.24 g, 58.98 mmol) in THF (50 mL) was added BF$_3$.Et$_2$O (24.2 mL, 196.66 mmol) drop wise over a period of 10 min at 0° C. After stirring at 0° C. for 1 h, 7-hydroxy-5-methoxy-2,3-dihydro-1H-inden-1-one (3.5 g, 19.66 mmol) in THF (20 mL) was added to the reaction mixture which was further stirred at room temperature for 16 h. The reaction mixture was quenched with ice water, extracted with DCM. The organic layer was dried over sodium sulphate and evaporated to obtain crude product, which was purified on combiflash MPLC using 20% EtOAc in hexane as eluent to afford 6-methoxy-2,3-dihydro-1H-inden-4-ol (2.5 g, crude) as pale brown solid. $^1$H NMR (400 MHz, DMSO-d$_6$) δ ppm: 1.89-1.96 (m, 2H), 2.61-2.65 (m, 2H), 2.72-2.76 (m, 2H), 3.62 (s, 3H), 6.12 (s, 1H), 6.25 (s, 1H), 9.08 (s, 1H).

Step 4: To a solution of 6-methoxy-2,3-dihydro-1H-inden-4-ol (2.5 g, 15.24 mmol) in DCM (50 mL) was added TiCl$_4$ (3.0 mL, 27.13 mmol) at 0° C. and stirred for 15 min. Dichloro(methoxy)methane (1.5 mL, 16.76 mmol) was added to the reaction mixture at 0° C. and stirred for additional 2 h at room temperature. The reaction mixture was quenched with cold water and extracted with DCM. The combined organic layer was dried over sodium sulphate and evaporated to obtain crude product, which was purified on combiflash MPLC using 20% EtOAc in hexane as eluent to afford 7-hydroxy-5-methoxy-2,3-dihydro-1H-indene-4-carbaldehyde (0.1 g, crude) as white solid. LCMS (ES) m/z=193.1 [M+H]$^+$. $^1$H NMR (400 MHz, DMSO-d$_6$) δ ppm: 1.91-1.97 (m, 2H), 2.60-2.64 (m, 2H), 3.04-3.08 (m, 2H), 3.78 (s, 3H), 6.34 (s, 1H), 10.22 (s, 1H), 10.41 (s, 1H).

Step 5: To a solution of 7-hydroxy-5-methoxy-2,3-dihydro-1H-indene-4-carbaldehyde (0.1 g, 0.52 mmol) in ACN (15 mL) was added potassium carbonate (0.10 g, 0.78 mmol) at room temperature. The mixture was stirred for 15 min and 3-(bromomethyl)-2-methyl-1,1'-biphenyl (0.13 g, 0.52 mmol) was added to the reaction mixture at room temperature. The reaction mixture was further stirred for 5 h. The reaction mixture was quenched with water and extracted with DCM. The combined organic layer was dried over sodium sulphate and evaporated to obtain crude product, which was purified on combiflash MPLC using 10% EtOAc in Hexane as eluent to afford 5-methoxy-7-((2-methyl-[1,1'-biphenyl]-3-yl)methoxy)-2,3-dihydro-1H-indene-4-carbaldehyde (0.1 g, crude) as white solid. LCMS (ES) m/z=373.2 [M+H]$^+$. $^1$H NMR (400 MHz, DMSO-d$_6$) δ ppm: 1.96-2.00 (m, 2H), 2.21 (s, 3H), 2.65-2.70 (m, 2H), 3.08-3.11 (m, 2H), 3.92 (s, 3H), 5.31 (s, 2H), 6.78 (s, 1H), 7.19-7.21 (m, 1H), 7.27-7.38 (m, 4H), 7.42-7.50 (m, 3H), 10.29 (s, 1H).

Step 6: To a mixture of 5-methoxy-7-((2-methyl-[1,1'-biphenyl]-3-yl)methoxy)-2,3-dihydro-1H-indene-4-carbaldehyde (0.05 g, 0.13 mmol) and N-(2-aminoethyl)acetamide (0.02 g, 0.20 mmol) in DMF:MeOH (10 mL) was added one drop acetic acid at room temperature. The mixture was stirred for 15 min and sodium cyanoborohydride (0.025 g, 0.40 mmol) was added to the reaction mixture. The reaction mixture was further allowed to stir at room temperature for 16 h. The reaction mixture was quenched with water and extracted with DCM. The combined organic layer was washed with sodium bicarbonate solution and dried over sodium sulphate and evaporated to obtain crude which was purified on combiflash MPLC using 20% MeOH in DCM as eluent to afford N-(2-(((5-methoxy-7-((2-methyl-[1,1'-biphenyl]-3-yl)methoxy)-2,3-dihydro-1H-inden-4-yl)methyl)amino)ethyl)acetamide (10 mg, 16%) as white solid. LCMS (ES) m/z=459.2 [M+H.]$^+$. HPLC purity 98.29%. $^1$H NMR (400 MHz, DMSO-d$_6$) δ ppm: 1.22 (bs, 2H), 1.75 (s, 3H), 1.94-1.97 (s, 2H), 2.20 (s, 3H), 2.71-2.75 (m, 2H), 2.82-2.86 (s, 2H), 3.08-3.09 (s, 2H), 3.57 (s, 2H), 3.77 (s, 3H), 5.15 (s, 2H), 6.61 (s, 1H), 7.16-7.38 (m, 5H), 7.42-7.47 (m, 3H), 7.73 (bs, 1H).

Example 3
(S)-1-((7-((3-(1-(3-(3,3-difluoropyrrolidin-1-yl)pro-
pyl)-1H-indol-4-yl)-2-methylbenzyl)oxy)-2,3-di-
hydro-1H-inden-4-yl)methyl)piperidine-2-carboxylic
acid (3
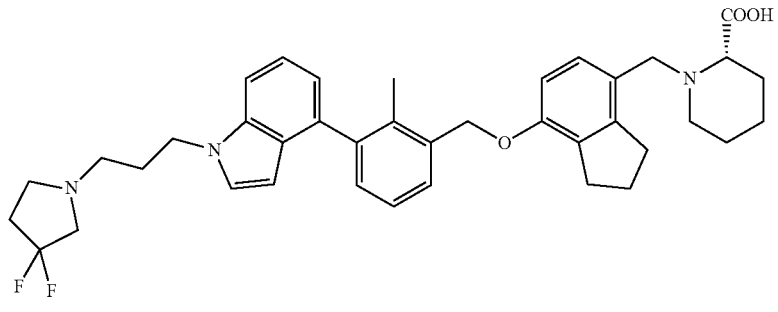
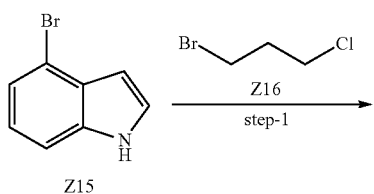
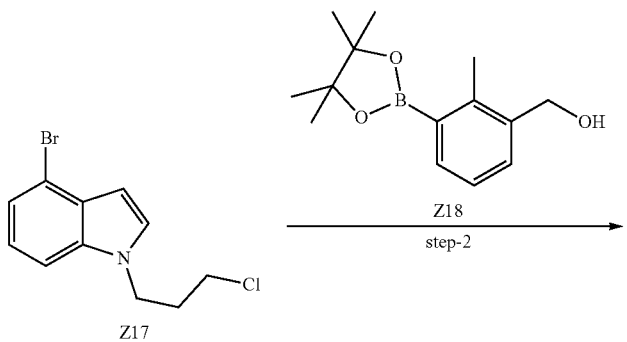
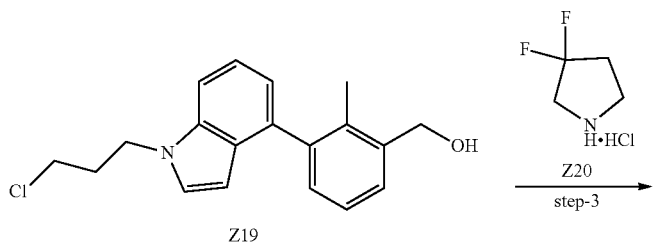
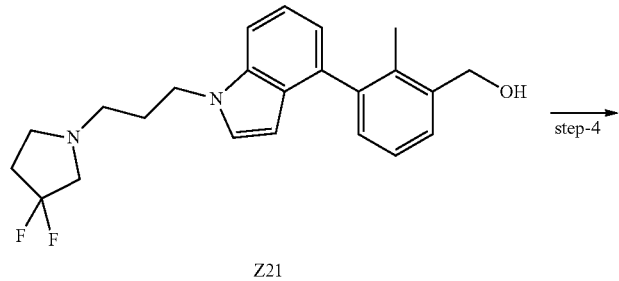

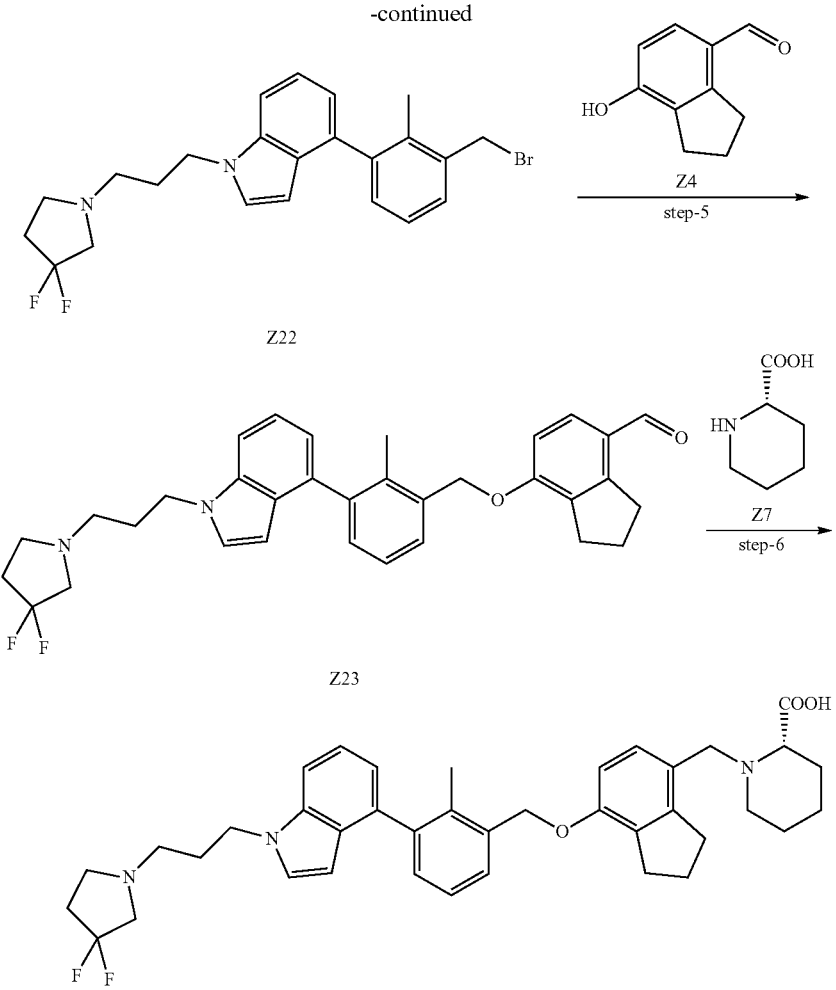

Step 1: To a solution of 5-bromo indole (1 g, 5.1 mmol) in DMF (60 mL) was added NaH (0.22 g, 5.6 mmol) at 0° C. The reaction mixture was stirred at room temperature for 30 min. Then 1-bromo-3-chloropropane (0.88 g, 5.6 mmol) was added to the reaction mixture at 0° C. and the reaction was stirred at room temperature for 6 h. The reaction mixture was quenched with water and extracted into ethyl acetate (2×100 mL). The combined organic layers were washed with brine, dried over sodium sulphate and evaporated to give the crude residue which was purified on combiflash MPLC using 9% ethyl acetate in Hexane to afford 4-bromo-1-(3-chloropropyl)-1H-indole as yellow viscous liquid (1.2 g, 86%). LCMS (ES) m/z=272.0 [M+H]$^+$; $^1$H NMR (400 MHz, DMSO-d$_6$) δ ppm: 2.18 (t, J=5.4 Hz, 2H), 3.53 (t, J=6.0 Hz, 2H), 4.31 (t, J=6.8 Hz, 2H)), 6.40 (bs, 1H), 7.07 (t, J=8.0 Hz, 1H), 7.23 (d, t, J=7.6 Hz, 1H), 7.49-7.54 (m, 2H).

Step 2: To a stirred solution of 4-bromo-1-(3-chloropropyl)-1H-indole (0.9 g, 3.3 mmol) and (2-methyl-3-(4,4,5,5-tetramethyl-1,3,2-dioxaborolan-2-yl)phenyl)methanol (0.98 g, 3.97 mmol) in dioxane:water (20 mL: 4 mL) were added Xphos (0.3 g, 0.33 mmol), CsF (1 g, 6.6 mmol), and Pd$_2$(dba)$_3$ (0.27 g, 0.33 mmol) simultaneously and the reaction mixture was purged with nitrogen for 15 min. The reaction mixture was then heated at 85° C. for 14 h in a sealed tube. The reaction mixture was filtered over celite, the filtrate was diluted with water and extracted into ethyl acetate (2×50 mL). The combined organic layers were washed with brine, dried over sodium sulphate and evaporated to get the crude residue which was purified on combiflash MPLC using 10% ethyl acetate in hexane to afford (3-(1-(3-chloropropyl)-1H-indol-4-yl)-2-methylphenyl) methanol as brown viscous liquid (0.8 g, 96%). LCMS (ES) m/z=314.1 [M+H]. $^1$H NMR (400 MHz, DMSO-d$_6$) δ ppm: 1.13-1.22 (m, 4H), 1.99 (s, 3H), 2.19-2.24 (m, 2H), 3.58 (t, J=6 Hz, 2H), 4.32 (bs, 2H), 4.54-4.55 (m, 2H), 5.07 (bs, 1H), 6.00 (s, 1H), 6.84 (d, J=7.2 Hz, 1H), 7.11 (d, J=7.6 Hz, 1H), 7.20 (q, J=8 Hz, 2H), 7.33-7.34 (m, 1H), 7.40 (d, J=7.6 Hz, 1H), 7.47 (d, J=8.4 Hz, 1H).

Step 3: To a solution of (3-(1-(3-chloropropyl)-1H-indol-4-yl)-2-methylphenyl)methanol (0.2 g, 0.6 mmol) in DMF (10 mL) were added 3,3-difluoropyrrolidine hydrochloride (0.133 g, 0.95 mmol), sodium iodide (0.143 g, 0.95 mmol) and K$_2$CO$_3$ (0.172 g, 1.27 mmol) simultaneously and the reaction mixture was heated at 80° C. for 16 h. The reaction mixture was cooled to room temperature, diluted with ice cooled water and extracted with ethyl acetate (2×50 mL). The combined organic layers were washed with brine, dried over sodium sulphate and evaporated to give the crude residue which was purified on combiflash MPLC using 15% ethyl acetate in hexane to afford (3-(1-(3-(3,3-difluoropyrrolidin-1-yl)propyl)-1H-indol-4-yl)-2-methylphenyl)methanol as brown viscous liquid (0.13 g, 43%). $^1$H NMR (400 MHz, DMSO-$d_6$) δ ppm: 1.90-1.97 (m, 2H), 2.00 (s, 3H), 2.12-2.18 (m, 2H), 2.37-2.48 (m, 2H), 2.62-2.64 (m, 2H), 2.81-2.87 (m, 2H), 4.18-4.25 (bs, 2H), 451-4.52 (m, 2H), 5.12-5.20 (m, 1H), 5.97 (s, 1H), 6.83 (d, J=7.2 Hz, 1H), 7.11 (d, J=7.6 Hz, 1H), 7.16-7.23 (m, 2H), 7.32 (bs, 1H), 7.39 (d, J=7.6 Hz, 2H), 7.45 (d, J=8.4 Hz, 1H).

Step 4: To a stirred solution (3-(1-(3-(3,3-difluoropyrrolidin-1-yl)propyl)-1H-indol-4-yl)-2-methylphenyl)methanol (0.3 g, 0.78 mmol) in DCM (20 mL) was added PBr$_3$ (0.42 g, 1.56 mmol) drop wise at 0° C. and the reaction mixture was stirred for 3 h at room temperature. The reaction mixture was quenched with a saturated sodium bicarbonate solution and extracted with ethyl acetate (2×50 mL). The combined organic layer was washed with brine, dried over sodium sulphate and evaporated to afford 4-(3-(bromomethyl)-2-methylphenyl)-1-(3-(3,3-difluoropyrrolidin-1-yl)propyl)-1H-indole as colorless viscous liquid (0.2 g, 59%). LCMS (ES) m/z=447, 449 [M, M+2H]$^+$.

Step 5: To a stirred solution of 7-hydroxy-2,3-dihydro-1H-indene-4-carbaldehyde (0.05 g, 0.13 mmol) and 4-(3-(bromomethyl)-2-methylphenyl)-1-(3-(3,3-difluoropyrrolidin-1-yl)propyl)-1H-indole (0.2, 0.34 mmol) in ACN (10 mL) was added K$_2$CO$_3$ (0.07 g, 0.41 mmol) and the reaction mixture was stirred for 14 h at room temperature. The reaction mixture was quenched with water, extracted into ethyl acetate (2×50 mL). The combined organic layer was washed with brine, dried over sodium sulphate and evaporated. The crude was purified on combiflash MPLC using 20%-ethyl acetate in hexane as eluent to afford 7-((3-(1-(3-(3,3-difluoropyrrolidin-1-yl)propyl)-1H-indol-4-yl)-2-methylbenzyl)oxy)-2,3-dihydro-1H-indene-4-carbaldehyde as colorless viscous oil (0.09 g, 36%). LCMS (ES) m/z=529.3, [M+H]$^+$; $^1$H NMR (400 MHz, DMSO-$d_6$) δ ppm: 1.14-1.18 (m, 3H), 1.91-1.94 (m, 2H), 1.97 (s, 2H), 2.05-2.10 (m, 5H), 2.19-2.26 (m, 2H), 2.81-2.88 (m, 4H), 4.23 (bs, 2H), 5.31 (s, 2H), 5.99 (s, 1H), 6.88 (d, J=7.2 Hz, 1H), 7.16-7.28 (m, 4H), 7.35-7.36 (m, 1H), 7.47 (d, J=8.0 Hz, 2H), 7.72-7.25 (m, 1H), 9.95 (s, 1H).

Step 6: To a solution of 7-((3-(1-(3-(3,3-difluoropyrrolidin-1-yl)propyl)-1H-indol-4-yl)-2-methylbenzyl)oxy)-2,3-dihydro-1H-indene-4-carbaldehyde (0.05 g, 0.09 mmol) in MeOH (2 mL) and DMF (2 mL) were added (S)-piperidine-2-carboxylic acid (0.037 g, 0.28 mmol) and acetic acid (0.05 mL) simultaneously and the reaction mixture was stirred at 50° C. for 2 h. The reaction mixture was then cooled to 0° C., NaCNBH$_3$ (0.030 g, 0.283 mmol) was added and the reaction mixture was stirred at r.t for 16 h. The reaction mixture was evaporated; the crude was taken in DCM (15 mL) and washed with water and brine. The organic layer was dried over sodium sulphate, concentrated to get the crude residue which was purified on combiflash MPLC using 5% methanol in dichloromethane as eluent to afford 1-((4-((2-methyl-[1,1'-biphenyl]-3-yl)methoxy)-5,6,7,8-tetrahydronaphthalen-1-yl)methyl)piperidine-2-carboxylic acid as white crystalline solid (0.006 g, 10%). LCMS (ES) m/z=642.3 [M+H]$^+$; $^1$H NMR (400 MHz, DMSO-$d_6$) δ ppm: 1.35-1.55 (m, 5H), 1.72 (bs, 2H), 1.92-1.99 (m, 5H), 2.09 (s, 3H), 2.21-2.26 (m, 3H), 2.31-2.37 (m, 4H), 2.81-2.91 (m, 7H), 3.81-3.84 (m, 1H), 4.22 (bs, 2H), 5.14 (s, 2H), 5.99 (s, 1H), 6.87 (d, J=7.2 Hz, 2H), 7.08 (d, J=7.6 Hz, 1H), 7.20-7.28 (m, 3H), 7.35 (s, 1H), 7.45-7.48 (m, 2H).

Example 4

(S)-1-((6-methyl-7-((2-methyl-[1,1'-biphenyl]-3-yl)methoxy)-2,3-dihydro-1H-inden-4-yl)methyl)piperidine-2-carboxylic acid (4)

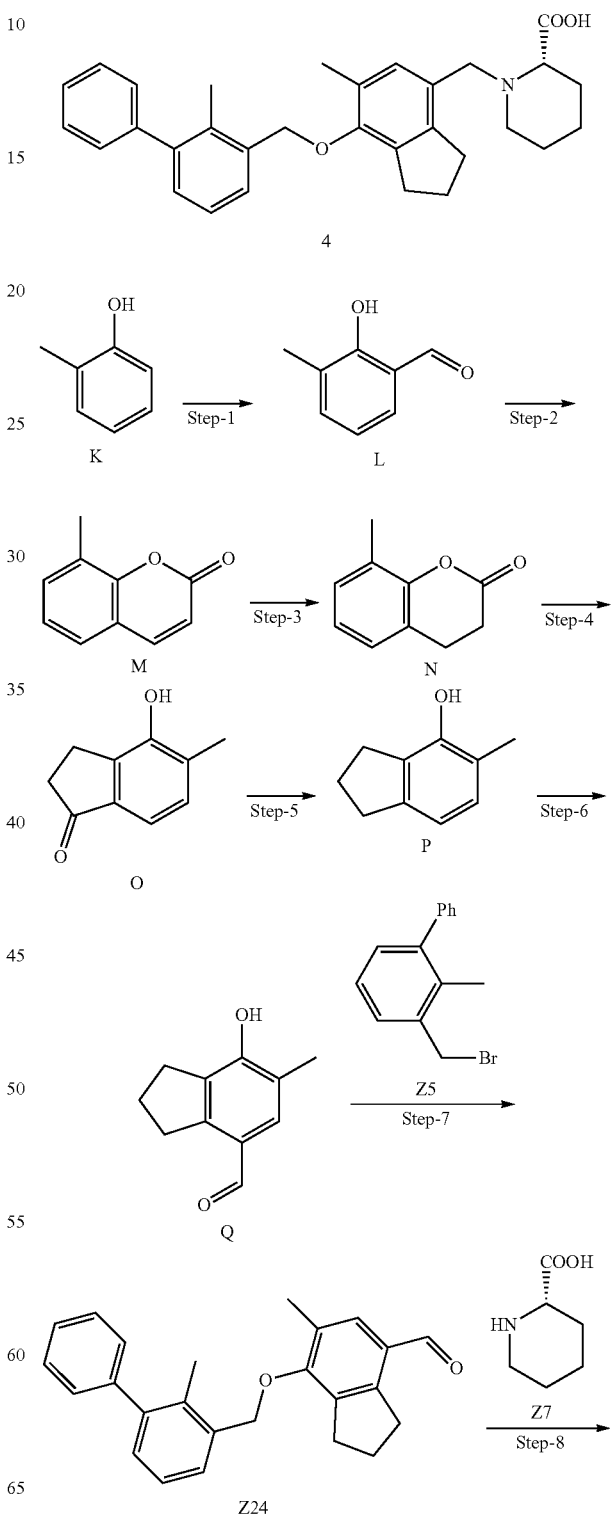

-continued

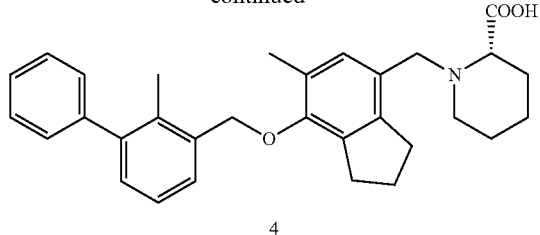

4

Step-1: To a solution of o-cresol (4.0 g, 0.0369 mol) in acetonitrile (100 mL), magnesium chloride (5.2 g, 0.055 mol) and triethylamine (9.35 g, 0.092 mol) were added and the mixture was stirred for 15 minutes. Paraformaldehyde (5.5 g, 0.185 mol) was added and the mixture was heated at 90° C. for 3 h. After completion of the reaction, the reaction mixture was concentrated under reduced pressure and the residue was diluted with aqueous 1N HCl solution (100 mL). The aqueous mixture was extracted with EtOAc (2×100 mL) and the organic layer was washed with brine (50 mL), dried over sodium sulfate and concentrated. The resulting crude was purified by flash chromatography (silica gel, 12 g) using 4% EtOAc in hexane as eluent to afford 2-hydroxy-3-methylbenzaldehyde (Yield: 1.7 g, 34%) as light greenish solid. $^1$H NMR (400 MHz, CDCl$_3$) δ ppm: 2.28 (s, 3H), 6.93 (t, J=7.6 Hz, 1H), 7.39 (d, J=7.6 Hz, 2H), 9.88 (s, 1H), 11.27 (s, 1H).

Step-2: To a solution of 2-hydroxy-3-methylbenzaldehyde (10 g, 70 mmol) in acetic anhydride (15 g, 146 mmol), sodium acetate (15 g, 183 mmol) was added. The mixture was heated at 180° C. for 10 h. After completion of reaction, the mixture was cooled and diluted with water (300 mL). The mixture was extracted with EtOAc (3×500 mL) and the combined extracts were washed with saturated sodium bicarbonate solution (250 mL), water (100 mL), brine (100 mL), dried over sodium sulfate and concentrated under reduced pressure. The resulting crude mixture was purified by flash chromatography (silica gel, 40 g) using 15% EtOAc in hexane as eluent to give 8-methyl-2H-chromen-2-one (Yield: 4.1 g, 35%) as off-white solid. $^1$H NMR (400 MHz, CDCl$_3$) δ ppm: 2.46 (s, 3H), 6.41 (t, J=9.6 Hz, 1H), 7.18 (t, J=7.6 Hz, 1H), 7.32 (d, J=7.6 Hz, 1H), 7.38 (d, J=7.2 Hz, 1H), 7.70 (d, J=9.6 Hz, 1H).

Step-3: To a solution of 8-methyl-2H-chromen-2-one (8.0 g, 50 mmol) in AcOH (60 mL), 10% palladium on carbon (50% wet, 4.0 g) was added under nitrogen and the resulting mixture was hydrogenated using a hydrogen balloon for 4 h at room temperature. After completion of reaction, the reaction mixture was filtered over celite bed and the bed was washed with EtOAc (20 mL). The filtrate was washed with saturated sodium bicarbonate solution (10 mL), water (10 mL), brine (10 mL), dried over sodium sulfate and concentrated under vacuum to obtain 8-methylchroman-2-one (3.40 g, crude). $^1$H NMR (400 MHz, CDCl$_3$) δ ppm: 2.30 (s, 3H), 2.77 (m, 2H), 2.98 (m, 2H), 6.97-7.02 (m, 2H), 7.10 (d, J=6.0 Hz, 1H).

Step-4: A mixture of 8-methylchroman-2-one (2.0 g, 13.5 mmol) and anhydrous AlCl$_3$ (5.4 g, 40.5 mmol) was heated at 180° C. for 2 h. After completion of the reaction, it was cooled and quenched with ice cold water (100 mL). The aqueous mixture was extracted with EtOAc (3×100 mL) and the EtOAc extract was dried over sodium sulfate and concentrated. The resulting residue was triturated with pentane and filtered to obtain 4-hydroxy-5-methyl-2,3-dihydro-1H-inden-1-one (Yield: 1.7 g, 67%) as brown solid. $^1$H NMR (400 MHz, DMSO-d$_6$) δ ppm: 2.24 (s, 3H), 2.59 (m, 2H), 2.95 (m, 2H), 7.04 (d, J=7.6 Hz, 1H), 7.15 (d, J=7.6 Hz, 1H), 9.19 (s, 1H).

Step-5: To a solution of 4-hydroxy-5-methyl-2,3-dihydro-1H-inden-1-one (0.70 g, 4.3 mmol) in 1,2-dichloroethane (20 mL) at room temperature under nitrogen atmosphere, sodium cyanoborohydride (0.8 g, 12.9 mmol) and ZnI$_2$ (5.5 g, 17 mmol) were added slowly and the resulting mixture was heated at 80° C. for 16 h. After completion, the reaction mixture was quenched with water (50 mL) and filtered through celite bed. The bed was washed with EtOAc (200 mL) and the filtrate was dried over sodium sulfate and concentrated under vacuum. The resulting crude was purified by column chromatography (silica gel, 100-200 mesh) using 20% EtOAc in hexane to afford 5-methyl-2,3-dihydro-1H-inden-4-ol (Yield: 0.50 g, 72%) as white solid. $^1$H NMR (400 MHz, CDCl$_3$) δ ppm: 2.10 (m, 2H), 2.23 (s, 3H), 2.82 (m, 2H), 2.90 (m, 2H), 6.73 (d, J=7.2 Hz, 1H), 6.92 (d, J=7.2 Hz, 1H).

Step-6: To a solution of 5-methyl-2,3-dihydro-1H-inden-4-ol (0.50 g, 3.3 mmol) in TFA (12.5 mL), hexamine (0.56 g, 4.0 mmol) was added and the mixture was stirred at 120° C. for 3 h. After cooling the mixture to 0° C., a 10% aqueous H$_2$SO$_4$ solution (12.5 mL) was added and the mixture was heated at 100° C. for 2 h. The reaction mixture was cooled to room temperature and quenched with solid sodium bicarbonate until the effervescence stopped. After diluting the mixture with water (50 mL), it was extracted with DCM (3×50 mL) and the organic extract was dried over sodium sulfate and concentrated. The resulting crude was purified by flash chromatography (silica gel, 4 g) using 20% EtOAc in hexane to obtain 7-hydroxy-6-methyl-2,3-dihydro-1H-indene-4-carbaldehyde (Yield: 220 mg, 38%) as yellow solid. LCMS (ES) m/z=177.24 [M+H]$^+$; $^1$H NMR (400 MHz, DMSO-d$_6$) δ ppm: 2.18 (m, 2H), 2.29 (s, 3H), 2.82 (t, J=7.2 Hz, 2H), 3.29 (t, J=7.2 Hz, 2H), 5.05 (m, 1H), 7.46 (s, 1H), 9.97 (s, 1H).

Step-7: To a solution of 7-hydroxy-6-methyl-2,3-dihydro-1H-indene-4-carbaldehyde (0.22 g, 1.25 mmol) in acetonitrile (5 mL), potassium carbonate (0.25 g, 1.86 mmol) was added and the reaction mixture was stirred for 30 min. 3-(bromomethyl)-2-methyl-1,1'-biphenyl (0.32 g, 1.25 mmol) was added and the reaction mixture was stirred for 5 h. After completion, the reaction mixture was diluted with water (10 mL) and extracted with EtOAc (3×10 mL). The combined organic layer was dried over sodium sulfate and concentrated. The resulting crude was purified by flash chromatography (silica gel, 4 g) using 0-20% EtOAc in hexane as eluent to obtain 6-methyl-7-((2-methyl-[1,1'-biphenyl]-3-yl)methoxy)-2,3-dihydro-1H-indene-4-carbaldehyde (Yield: 0.35 g, 79%) as white solid. LCMS (ES) m/z=357.19 [M+H]$^+$; $^1$H NMR (400 MHz, DMSO-d6) δ ppm: 2.07 (m, 2H), 2.24 (s, 6H), 2.99 (m, 2H), 3.19 (m, 2H), 5.14 (s, 2H), 7.19 (d, J=7.2 Hz, 1H), 7.27-7.32 (m, 3H), 7.38 (m, 1H), 7.44-7.49 (m, 3H), 7.56 (s, 1H), 10.01 (s, 1H).

Step-8: A solution of 6-methyl-7-((2-methyl-[1,1'-biphenyl]-3-yl)methoxy)-2,3-dihydro-1H-indene-4-carbaldehyde (100 mg, 0.28 mmol), (S)-piperidine-2-carboxylic acid (50 mg, 0.42 mmol) and acetic acid (1 drop) in DMF (2 mL) and MeOH (2 mL) was stirred at room temperature for 2 h. Sodium cyanoborohydride (50 mg, 0.84 mmol) was added and the mixture was stirred for 16 h. After completion, the reaction mixture was concentrated and the residue was diluted with water (10 mL). The aqueous mixture was extracted with 10% MeOH in DCM (3×10 mL). The combined organic layer was dried over sodium sulfate and concentrated. The resulting crude was purified by flash chromatography (silica gel, 4 g) using 0-20% MeOH in DCM as eluent to obtain (S)-1-((6-methyl-7-((2-methyl-[1,1'-biphenyl]-3-yl)methoxy)-2,3-dihydro-1H-inden-4-yl)methyl)piperidine-2-carboxylic acid (Yield: 62 mg, 46%) as white solid.

LCMS (ES) m/z=470.20 [M+H]$^+$; $^1$H NMR (400 MHz, DMSO-d$_6$) δ ppm: 1.22-1.34 (m, 2H), 1.48 (m, 3H), 1.78 (m, 2H), 1.99 (m, 2H), 2.19 (s, 3H), 2.23 (s, 3H), 2.83 (m, 1H), 2.88 (m, 4H), 3.09 (m, 1H), 3.41 (d, J=12.8 Hz, 1H), 3.81 (d, J=12.8 Hz, 1H), 4.94 (s, 2H), 6.97 (s, 1H), 7.19 (d, J=7.2 Hz, 1H), 7.27-7.32 (m, 3H), 7.37 (m, 1H), 7.44-7.49 (m, 3H).

Example 5

(S)-1-((6-chloro-7-((2-methyl-[1,1'-biphenyl]-3-yl)methoxy)-2,3-dihydro-1H-inden-4-yl)methyl)piperidine-2-carboxylic acid (5)

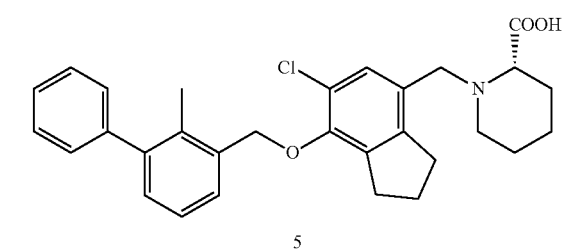

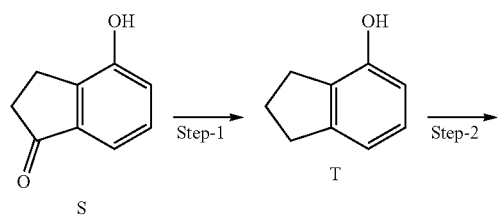

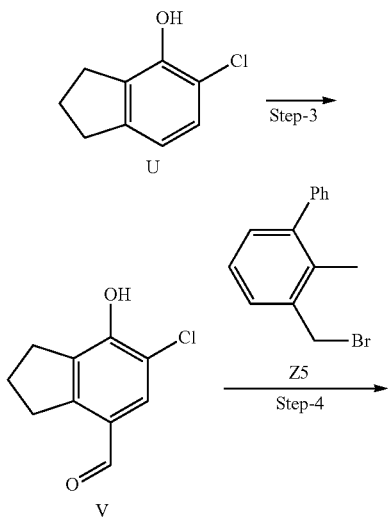

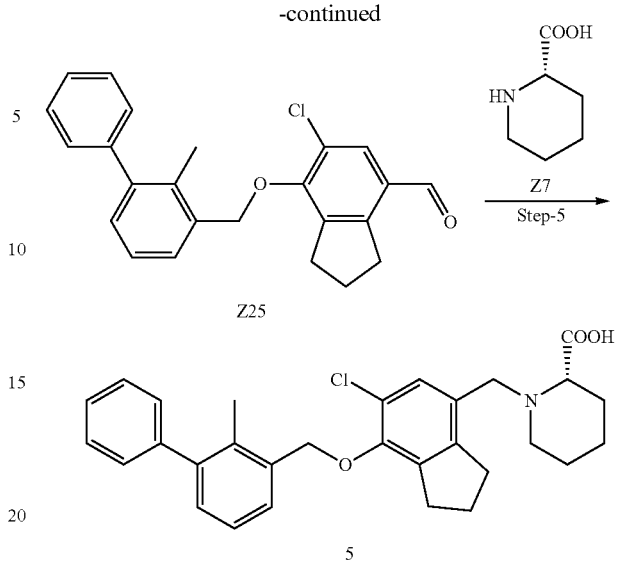

Step-1: To a solution of 4-hydroxy-2,3-dihydro-1H-inden-1-one (5.0 g, 33.7 mmol) in 1,2-dichloroethane (500 mL) at room temperature under nitrogen atmosphere, sodium cyanoborohydride (8.48 g, 135 mmol) and ZnI$_2$ (43 g, 135 mmol) were added slowly and the resulting mixture was heated at 80° C. for 5 h. After completion of reaction, the reaction mixture was filtered through silica gel bed in warm condition and washed with warm DCM (500 mL). The filtrate was concentrated under vacuum to get 2,3-dihydro-1H-inden-4-ol (Yield: 3.3 g, 75%) as brown viscous solid which was used in next step without further purification. $^1$H NMR (400 MHz, CDCl$_3$) δ ppm: 1.99 (m, 2H), 2.67 (m, 2H), 2.82 (m, 2H), 6.54 (d, J=7.6 Hz, 1H), 6.65 (d, J=7.6 Hz, 1H), 6.91 (t, J=7.6 Hz, 1H), 9.15 (s, 1H).

Step-2: To a solution of 2,3-dihydro-1H-inden-4-ol (3.3 g, 24.6 mmol) in chloroform (150 mL) at 60° C., N-chlorosuccinimide (3.2 g, 24.6 mmol) was added. After stirring at room temperature for 1 h, conc.HCl (1 mL) was added and the mixture was refluxed for 10 h. After completion, the reaction mixture was cooled and diluted with water (100 mL). The aqueous mixture was extracted with DCM (2×100 mL) and the combined organic layer was dried over sodium sulfate and concentrated. The crude was purified by flash chromatography (silica gel, 12 g) using 0 to 40% EtOAc in hexane as eluent to afford 5-chloro-2,3-dihydro-1H-inden-4-ol (Yield: 1.3 g, 32%) as yellow liquid. $^1$H NMR (400 MHz, DMSO-d$_6$) δ ppm: 1.99 (m, 2H), 2.82 (m, 4H), 6.69 (d, J=8.0 Hz, 1H), 7.07 (d, J=8.0 Hz, 1H), 9.24 (s, 1H).

Step-3: To a solution of 5-chloro-2,3-dihydro-1H-inden-4-ol (1.3 g, 7.7 mmol) in TFA (50 mL), hexamine (940 mg, 9.25 mmol) was added and the mixture was heated at 120° C. for 2 h. After completion, the reaction mixture was quenched with solid sodium bicarbonate (5 g). After diluting with water (30 mL), the mixture was extracted with EtOAc (2×50 mL) and the organic layer was dried over anhydrous sodium sulfate and concentrated. The crude was purified by flash chromatography (silica gel) using 0 to 40% EtOAc in hexane as eluent to afford 6-chloro-7-hydroxy-2,3-dihydro-1H-indene-4-carbaldehyde (Yield: 0.6 g, 40%) as yellow liquid. $^1$H NMR (400 MHz, DMSO-d$_6$) δ ppm: 2.06 (m, 2H), 2.83 (t, J=7.6 Hz, 2H), 3.16 (t, J=7.6 Hz, 2H), 7.69 (s, 1H), 9.87 (s, 1H), 10.52 (bs, 1H).

Step-4: To a solution of 6-chloro-7-hydroxy-2,3-dihydro-1H-indene-4-carbaldehyde (0.60 g, 3.06 mmol) in acetonitrile (10 mL), potassium carbonate (0.63 g, 4.6 mmol) was added and the reaction mixture was stirred for 30 minutes. To this mixture, 3-(bromomethyl)-2-methyl-1,1'-biphenyl (0.79 g, 3.06 mmol) was added and was continued for 16 h. After completion of reaction, the reaction mixture was diluted with water (10 mL) and extracted with EtOAc (3×10 mL). The combined organic layer was dried over sodium sulfate and concentrated. The resulting crude product was purified by flash chromatography (silica gel, 4 g) using 0-40% EtOAc in hexane as eluent to obtain 6-chloro-7-((2-methyl-[1,1'-biphenyl]-3-yl)methoxy)-2,3-dihydro-1H-indene-4-carbaldehyde (Yield: 0.70 g, 64%) as yellow solid. LCMS (ES) m/z=377.41 [M+H]$^+$; H NMR (400 MHz, DMSO-d$_6$) δ ppm: 2.08 (m, 2H), 2.27 (s, 3H), 2.99 (t, J=7.6 Hz, 2H), 3.19 (t, J=7.6 Hz, 2H), 5.14 (s, 2H), 7.21 (d, J=7.2 Hz, 1H), 7.27-7.30 (m, 3H), 7.36 (m, 1H), 7.44-7.48 (m, 3H), 7.82 (s, 1H), 10.00 (s, 1H).

Step-5: A solution of 6-methyl-7-((2-methyl-[1,1'-biphenyl]-3-yl)methoxy)-2,3-dihydro-1H-indene-4-carbaldehyde (120 mg, 0.30 mmol), (S)-piperidine-2-carboxylic acid (60 mg, 0.40 mmol) and acetic acid (1 drop) in DMF (2 mL) and MeOH (2 mL) was stirred at room temperature for 2 h. Sodium cyanoborohydride (54 mg, 0.90 mmol) was added and the reaction mixture was stirred further for 16 h. After completion of the reaction, the reaction mixture was concentrated and the residue was diluted with water (10 mL) and saturated sodium bicarbonate solution (2 mL). The aqueous mixture was extracted with EtOAc (3×10 mL). The combined organic layer was dried over sodium sulphate and concentrated. The resulting crude was purified by flash chromatography (silica gel, 4 g) using 0-20% MeOH in DCM as eluent to obtain (S)-1-((6-chloro-7-((2-methyl-[1,1'-biphenyl]-3-yl)methoxy)-2,3-dihydro-1H-inden-4-yl)methyl)piperidine-2-carboxylic acid (Yield: 80 mg, 57%) as white solid. LCMS (ES) m/z=490.14 [M+H]$^+$; $^1$H NMR (400 MHz, DMSO-d$_6$) δ ppm: 1.22-1.34 (m, 2H), 1.48 (m, 3H), 1.75 (m, 2H), 2.01 (m, 2H), 2.26 (s, 3H), 2.82-2.88 (m, 5H), 3.08 (m, 1H), 3.36 (d, J=13.6 Hz, 1H), 3.74 (d, J=13.6 Hz, 1H), 5.04 (s, 2H), 7.20 (d, J=7.6 Hz, 1H), 7.25 (d, J=8.0 Hz, 1H), 7.27-7.32 (m, 3H), 7.37 (m, 1H), 7.44-7.49 (m, 3H).

Example 6

Methyl 7-(((2-acetamidoethyl)amino)methyl)-4-((2-methyl-[1,1'-biphenyl]-3-yl)methoxy)-2,3-dihydro-1H-indene-5-carboxylate (6)

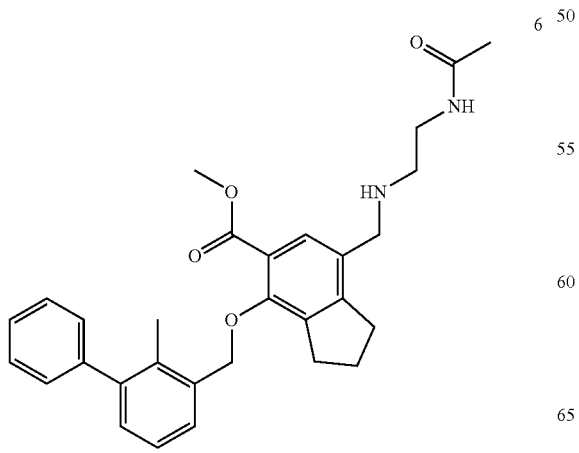

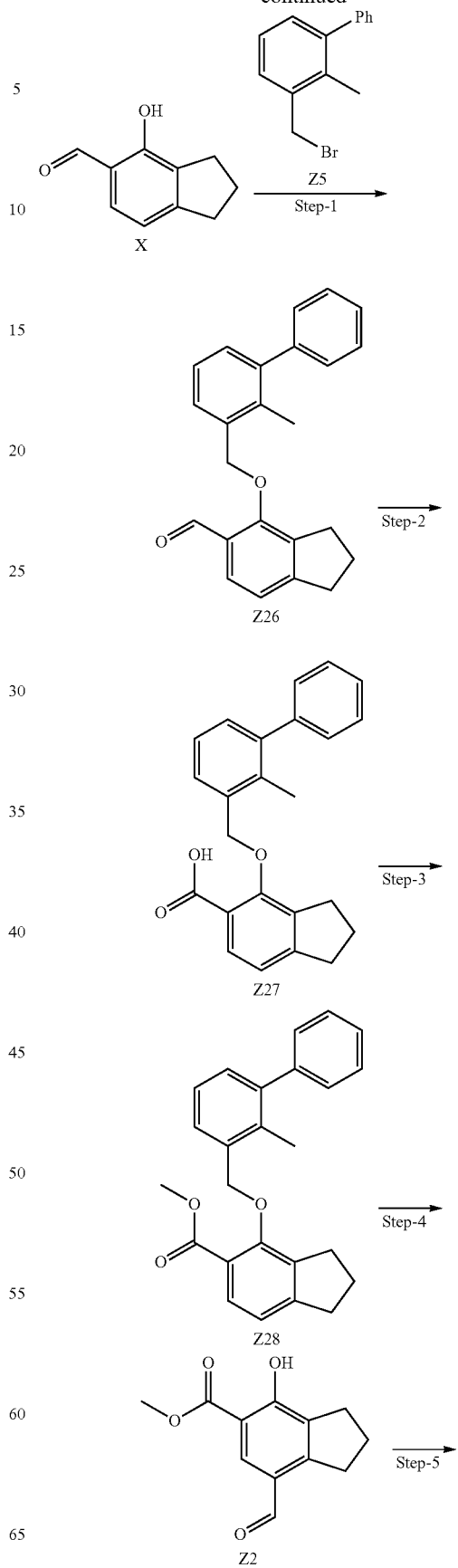

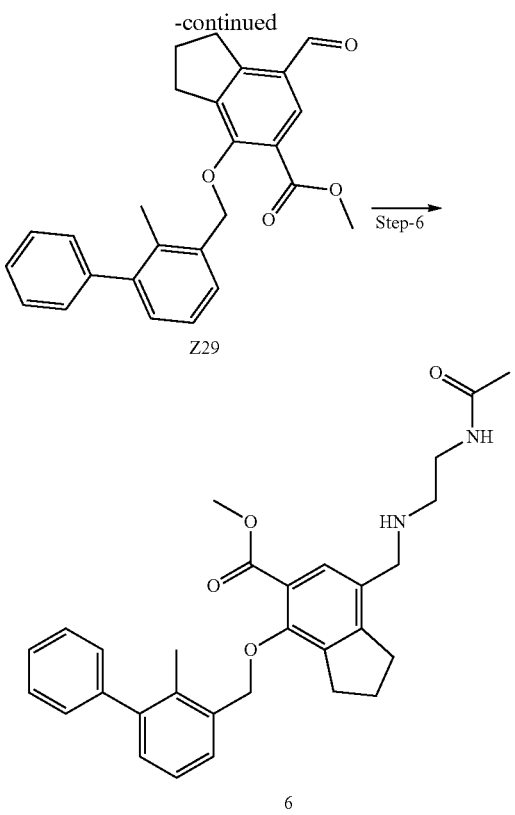

Step-1: To a solution of 4-hydroxy-2,3-dihydro-1H-indene-5-carbaldehyde (0.50 g, 3.08 mmol) in acetonitrile (20 mL), potassium carbonate (0.64 g, 4.6 mmol) was added and the reaction mixture was stirred for 30 minutes at room temperature. After stirring, 3-(bromomethyl)-2-methyl-1,1'-biphenyl (0.79 g, 3.08 mmol) was added and the reaction mixture was allowed to stir at room temperature for 6 h. After completion of reaction, the reaction mixture was diluted with water (25 mL) and extracted with EtOAc (3×25 mL). The combined organic layer was dried over sodium sulfate and concentrated. The resulting crude was purified by flash chromatography (silica gel, 4 g) using 0-20% EtOAc in hexane as eluent to obtain 4-((2-methyl-[1,1'-biphenyl]-3-yl)methoxy)-2,3-dihydro-1H-indene-5-carbaldehyde (Yield: 1.05 g, 99.5%) as sticky solid. LCMS (ES) m/z=343.44 [M+H]$^+$; $^1$H NMR (400 MHz, CDCl$_3$) δ ppm: 2.13 (m, 2H), 2.28 (s, 3H), 2.98 (t, J=7.2 Hz, 2H), 3.03 (t, J=7.2 Hz, 2H), 5.16 (s, 2H), 7.17 (d, J=7.2 Hz, 1H), 7.31 (m, 2H), 7.35-7.38 (m, 2H), 7.38-7.44 (m, 4H), 7.70 (d, J=7.6 Hz, 1H), 10.29 (s, 1H).

Step-2: To a solution of 4-((2-methyl-[1,1'-biphenyl]-3-yl)methoxy)-2,3-dihydro-1H-indene-5-carbaldehyde (0.80 g, 2.3 mmol) in acetonitrile (30 mL) and water (2 mL) at 0° C., NaH$_2$PO$_4$ (112 mg, 0.9 mmol), 30% hydrogen peroxide solution (4 mL) and sodium chlorite (0.63 g, 7.0 mmol) were added successively. After stirring at 0° C. for 3 h, the reaction mixture was diluted with water (50 mL) and extracted with DCM (3×50 mL). The organic layer was washed with brine (30 mL), dried over sodium sulfate and concentrated under vacuum to obtain 4-((2-methyl-[1,1'-biphenyl]-3-yl)methoxy)-2,3-dihydro-1H-indene-5-carboxylic acid (Yield: 0.80 g, 95%) as white solid. LCMS (ES) m/z=357.43 [M−H]$^-$; $^1$H NMR (400 MHz, DMSO-d$_6$) δ ppm: 2.02 (m, 2H), 2.22 (s, 3H), 2.87 (m, 4H), 5.06 (s, 2H), 7.04 (d, J=7.2 Hz, 1H), 7.17 (d, J=7.2 Hz, 1H), 7.24-7.31 (m, 3H), 7.38 (m, 1H), 7.43-7.47 (m, 2H), 7.49-7.52 (m, 2H), 12.77 (bs, 1H).

Step-3: To a solution of 4-((2-methyl-[1,1'-biphenyl]-3-yl)methoxy)-2,3-dihydro-1H-indene-5-carboxylic acid (0.30 g, 0.837 mmol) in acetone (10 mL), potassium carbonate (0.29 g, 2.09 mmol) and methyl iodide (0.18 g, 1.26 mmol) were added. The reaction mixture was heated to reflux for 4 h. After completion of the reaction, the reaction mixture was cooled and filtered. The filtrate was concentrated and the resulting crude was purified by flash chromatography (silica gel) using 5% EtOAc in hexane as eluent to obtain methyl 4-((2-methyl-[1,1'-biphenyl]-3-yl)methoxy)-2,3-dihydro-1H-indene-5-carboxylate (Yield: 0.30 g, 96%) as white solid. LCMS (ES) m/z=373.18 [M+H]$^+$; $^1$H NMR (400 MHz, DMSO-d$_6$) δ ppm: 2.04 (m, 2H), 2.23 (s, 3H), 2.92 (m, 4H), 3.74 (s, 3H), 5.03 (s, 2H), 7.10 (d, J=7.6 Hz, 1H) 7.18 (d, J=7.6 Hz, 1H), 7.27 (m, 1H), 7.31 (d, J=7.6 Hz, 2H) 7.38 (m, 1H), 7.44-7.48 (m, 3H), 7.54 (d, J=7.6 Hz, 1H).

Step-4: To a solution of methyl 4-((2-methyl-[1,1'-biphenyl]-3-yl)methoxy)-2,3-dihydro-1H-indene-5-carboxylate (0.20 g, 0.537 mmol) in TFA (5 mL), hexamine (0.112 g, 0.805 mmol) was added. The mixture was stirred at 120° C. for 3 h. After cooling the mixture to 0° C., a 10% aqueous H$_2$SO$_4$ solution (5 mL) was added and heated at 100° C. for 2 h. The reaction mixture was cooled to room temperature and quenched with solid sodium bicarbonate until the effervescence stopped. After diluting the mixture with water (25 mL), it was extracted with DCM (3×50 mL) and the organic extract was dried over sodium sulfate and concentrated. The resulting crude was purified by flash chromatography (silica gel, 4 g) using 10% EtOAc in hexane to obtain methyl 7-formyl-4-hydroxy-2,3-dihydro-1H-indene-5-carboxylate (Yield: 80 mg, 67.6%) as white solid. LCMS (ES) m/z=221.32 [M+H]$^+$; $^1$H NMR (400 MHz, DMSO-d$_6$) δ ppm: 2.10 (m, 2H), 2.83 (t, J=7.6 Hz, 2H), 3.25 (t, J=7.6 Hz, 2H), 3.94 (s, 3H), 8.22 (s, 1H), 9.96 (s, 1H), 11.13 (bs, 1H).

Step-5: To a solution of methyl 7-formyl-4-hydroxy-2,3-dihydro-1H-indene-5-carboxylate (0.12 g, 0.54 mmol) in acetonitrile (5 mL), potassium carbonate (0.11 g, 0.82 mmol) was added. The reaction mixture was stirred for 30 minutes. To this mixture, 3-(bromomethyl)-2-methyl-1,1'-biphenyl (0.14 g, 0.54 mmol) was added. The reaction mixture was stirred for 6 h. After completion of reaction, the reaction mixture was diluted with water (10 mL) and extracted with EtOAc (3×25 mL). The combined organic layer was dried over sodium sulfate and concentrated. The resulting crude was purified by flash chromatography (silica gel, 4 g) using 0-10% EtOAc in hexane as eluent to obtain methyl 7-formyl-4-((2-methyl-[1,1'-biphenyl]-3-yl)methoxy)-2,3-dihydro-1H-indene-5-carboxylate (Yield: 70 mg, 58%) as off-white solid. LCMS (ES) m/z=401.14 [M+H]$^+$.

Step-6: A solution of methyl 7-formyl-4-((2-methyl-[1,1'-biphenyl]-3-yl)methoxy)-2,3-dihydro-1H-indene-5-carboxylate (70 mg, 0.175 mmol), N-(2-aminoethyl)acetamide (30 mg, 0.26 mmol) and acetic acid (1 drop) in DMF (2.5 mL) and MeOH (2.5 mL) was stirred at room temperature for 8 h. To this reaction mixture, sodium cyanoborohydride (33 mg, 0.525 mmol) was added and the reaction mixture was stirred further for 8 h. After completion of reaction, the reaction mixture was concentrated and the residue was diluted with water (10 mL) and extracted with DCM (3×10 mL). The combined organic layer was dried over sodium sulfate and concentrated. The resulting crude was purified by flash chromatography (silica gel, 4 g) using 0-20% MeOH in DCM as eluent to obtain methyl 7-(((2-acetamidoethyl)

amino)methyl)-4-((2-methyl-[1,1'-biphenyl]-3-yl)methoxy)-2,3-dihydro-1H-indene-5-carboxylate (Yield: 33 mg, 41%) as sticky solid. LCMS (ES) m/z=487.21 [M+H]$^+$; $^1$H NMR (400 MHz, DMSO-d$_6$) δ ppm: 1.88 (s, 3H), 2.03 (m, 2H), 2.23 (s, 3H), 2.56 (m, 2H), 2.91 (m, 4H), 3.14 (m, 2H), 3.64 (s, 2H), 3.76 (s, 3H), 5.01 (s, 2H), 7.18 (d, J=7.2 Hz, 1H), 7.26-7.32 (m, 3H), 7.38 (m, 1H), 7.44-7.48 (m, 3H), 7.55 (s, 1H), 7.77 (m, 1H).
Example 7
(S)-1-((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)piperidine-2-carboxylic acid (7
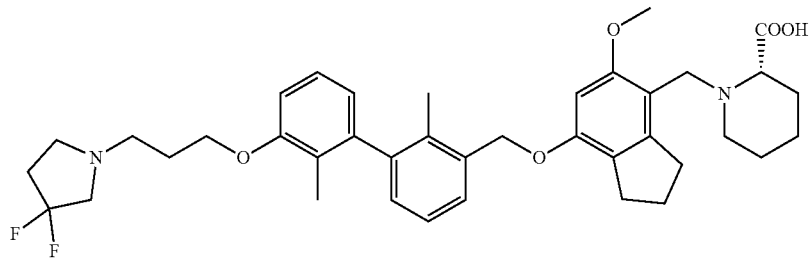
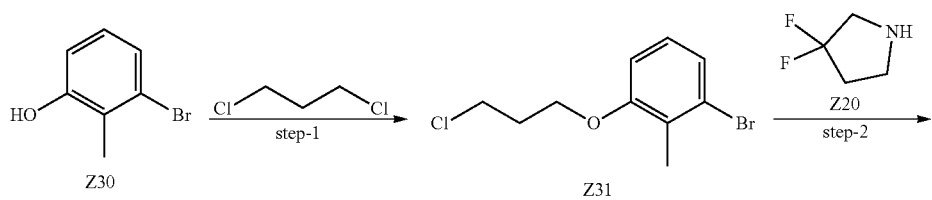
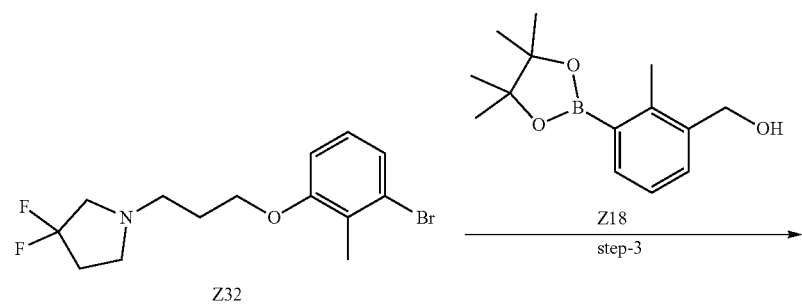
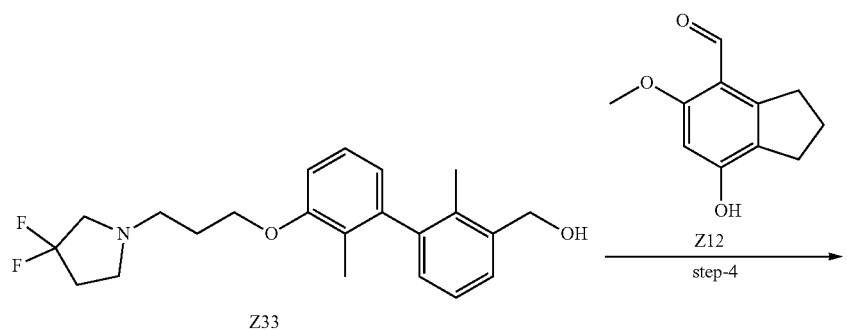

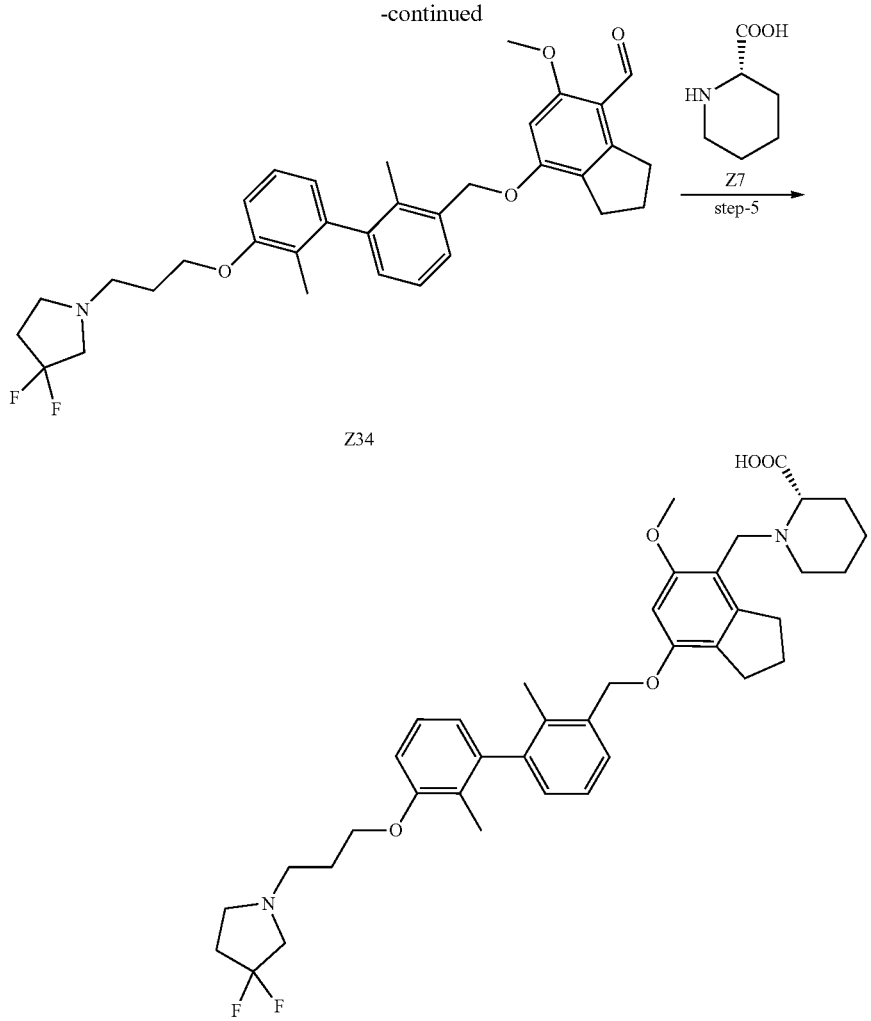

Step-1: To a solution of 3-bromo-2-methylphenol (9.8 g, 52 mmol) in DMF (80 mL), 1,3-dichloropropane (11.73 g, 10 mmol) and potassium carbonate (21.5 g, 156 mmol) were added. The reaction mixture was stirred at 80° C. for 12 h under nitrogen atmosphere. After completion of the reaction, the mixture was cooled to room temperature and diluted with EtOAc (100 mL), washed with ice cold water (50 mL) and brine (30 mL). The organic phase was dried over sodium sulphate and concentrated under vacuum to give a crude product. The resulting crude was purified by column chromatography (silica gel, 100-200 mesh) using 10% EtOAc in hexanes to afford 1-(3-(3-bromo-2-methylphenoxy)propyl)-3,3-difluoropyrrolidine (Yield: 10.1 g, 73.7%) as yellow liquid. $^1$H NMR (400 MHz, CDCl$_3$) δ ppm: 2.25-2.31 (m, 5H), 3.77 (m, 2H), 4.12 (m, 2H), 6.80 (d, J=8.2 Hz, 1H), 6.98-7.02 (m, 1H), 7.17 (d, J=8 Hz, 1H).

Step-2: To a stirred solution of 1-bromo-3-(3-chloropropoxy)-2-methylbenzene (10.1 g, 38 mmol) in DMF (60 mL), 3,3-difluoropyrrolidine (11 g, 76 mmol), potassium carbonate (22.5 g, 163 mmol) and sodium iodide (8.5 g, 57 mmol) were added and the reaction mixture was heated at 80° C. for 12 h under nitrogen atmosphere. After completion of the reaction, the reaction mixture was cooled to room temperature and diluted with EtOAc (100 mL), washed with ice cold water (50 mL), brine (50 mL) and the organic phase was dried over sodium sulphate and concentrated under vacuum to give a crude product. The resulting crude was purified by column chromatography (silica gel, 100-200 mesh) using 15% EtOAc in hexane to afford 1-(3-(3-bromo-2-methylphenoxy)propyl)-3,3-difluoropyrrolidine (7.1 g, 56.3%) as yellow liquid. $^1$H NMR (400 MHz, CDCl$_3$) δ ppm: 1.96 (m, 2H), 2.22-2.33 (m, 5H), 2.66 (m, 2H), 2.75 (m, 2H), 2.94 (m, 2H), 4.01 (m, 2H), 6.78 (d, J=8.0 Hz, 1H), 6.96-7.00 (m, 1H), 7.15 (d, J=8.0 Hz, 1H).

Step-3: To a solution of 1-(3-(3-bromo-2-methylphenoxy)propyl)-3,3-difluoropyrrolidine (2 g, 0.059 mol) and (2-methyl-3-(4,4,5,5-tetramethyl-1,3,2-dioxaborolan-2-yl)phenyl)methanol (1.78 g, 71 mmol) in toluene:ethanol:water (1:1:1) (30 mL) at room temperature, potassium carbonate (2.47 g, 17 mmol) was added and the reaction mixture was purged with nitrogen for 15 minutes. To this mixture, Pd(dppf)Cl$_2$-DCM (0.24 g, 0.29 mmol) was added and reaction mixture was again purged with nitrogen for 10 min and heated at 95° C. for 12 h. After completion of the reaction, the reaction mixture was cooled to room temperature and filtered through celite pad. The filtrate was diluted with water (100 mL) and the mixture was extracted with EtOAc (2×500 mL). The organic layer was washed with brine (500 mL), dried over sodium sulfate and concentrated to get crude compound. The resulting crude was purified by column chromatography (silica gel, 100-200 mesh) using 10% EtOAc in hexane as eluent to afford (3'-(3-(3,3-difluoropyrrolidin-1-yl)propoxy)-2,2'-dimethyl-[1,1'-biphenyl]-3-yl)methanol (Yield: 2 g, 90%) as off white solid. $^1$H NMR (400 MHz, DMSO-$d_6$) δ ppm: 1.77 (s, 3H), 1.94 (s, 3H), 2.20-2.32 (m, 4H), 2.62-2.68 (m, 4H), 2.92 (m, 2H), 4.06 (m, 2H), 4.54 (m, 2H), 5.09 (m, 1H), 6.64 (d, J=7.44 Hz, 1H), 6.94 (d, J=7.84 Hz, 2H), 7.15-7.22 (m, 2H), 7.39 (d, J=7.44 Hz, 1H).

Step-4: To a stirred solution of (3'-(3-(3,3-difluoropyrrolidin-1-yl)propoxy)-2,2'-dimethyl-[1,1'-biphenyl]-3-yl)methanol (0.55 g, 14 mmol) and 7-hydroxy-5-methoxy-2,3-dihydro-1H-indene-4-carbaldehyde (0.28 g, 14 mmol) in dry THF (20 mL) under nitrogen atmosphere at 0° C., triphenylphosphine (0.96 g, 35 mmol), and DEAD (1.15 g, 66 mmol) were added and the reaction mixture was stirred at room temperature for 24 h. After completion of the reaction, the mixture was diluted with EtOAc (50 mL) and washed with ice cold water (20 mL) and brine (20 mL). The organic phase was dried over sodium sulphate, concentrated under vacuum to give crude product which was purified by column chromatography (silica gel, 100-200 mesh) using 30% EtOAc in hexane to afford 7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-indene-4-carbaldehyde (Yield: 0.110 g, 13%) as white solid. LCMS (ES) m/z=550.25 [M+H]$^+$.

Step-5: A solution of 7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-indene-4-carbaldehyde (100 mg, 0.185 mmol), (S)-piperidine-2-carboxylic acid (36 mg, 0.27 mmol) and acetic acid (1 drop) in DMF (2 mL) and MeOH (2 mL) was stirred at room temperature for 2 h. To this mixture, sodium cyanoborohydride (34 mg, 0.55 mmol) was added and the reaction mixture was stirred for 16 h. After completion of the reaction, the reaction mixture was diluted with ice cold water (10 mL) and the aqueous mixture was extracted with 10% MeOH in DCM (3×100 mL). The combined organic layer was dried over sodium sulfate and concentrated. The resulting crude was purified by Prep-TLC using 10% MeOH in DCM as solvent system to obtain(S)-1-((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)piperidine-2-carboxylic acid (36, Yield: 50 mg, 44%) as white solid. LCMS: (ES) m/z=663.31 [M+H]$^+$; $^1$H NMR (400 MHz, DMSO-$d_6$) δ ppm: 1.76 (m, 2H), 1.82 (s, 3H), 1.90-2.00 (m, 9H), 2.19 (m, 4H), 2.50-2.72 (m, 7H), 2.75-2.89 (m, 5H), 2.98-3.11 (m, 2H), 3.73 (m, 1H), 3.80 (s, 3H), 3.89 (m, 1H), 4.05 (m, 2H), 5.18 (s, 2H), 6.63 (s, 1H), 6.86 (d, J=7.48 Hz, 1H), 6.96 (d, J=8.16 Hz, 1H), 7.06 (d, J=7.36 Hz, 1H), 7.17-7.28 (m, 2H), 7.47 (d, J=7.52 Hz, 1H).

Example 8

(S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxylicacid (8

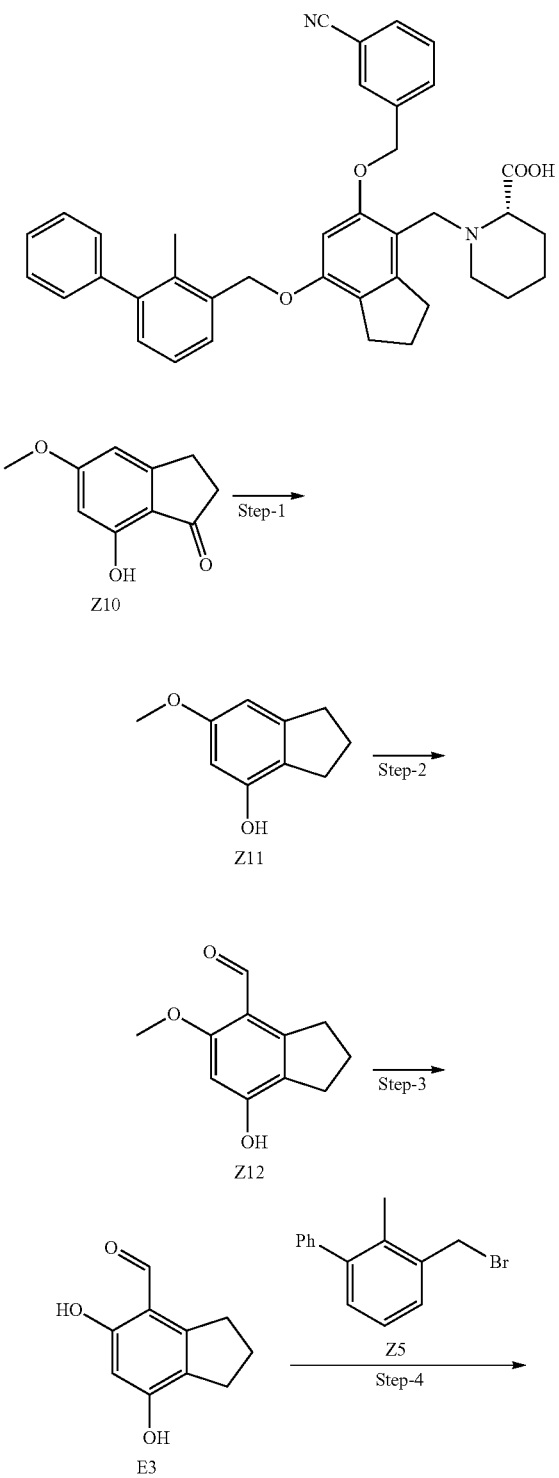

-continued

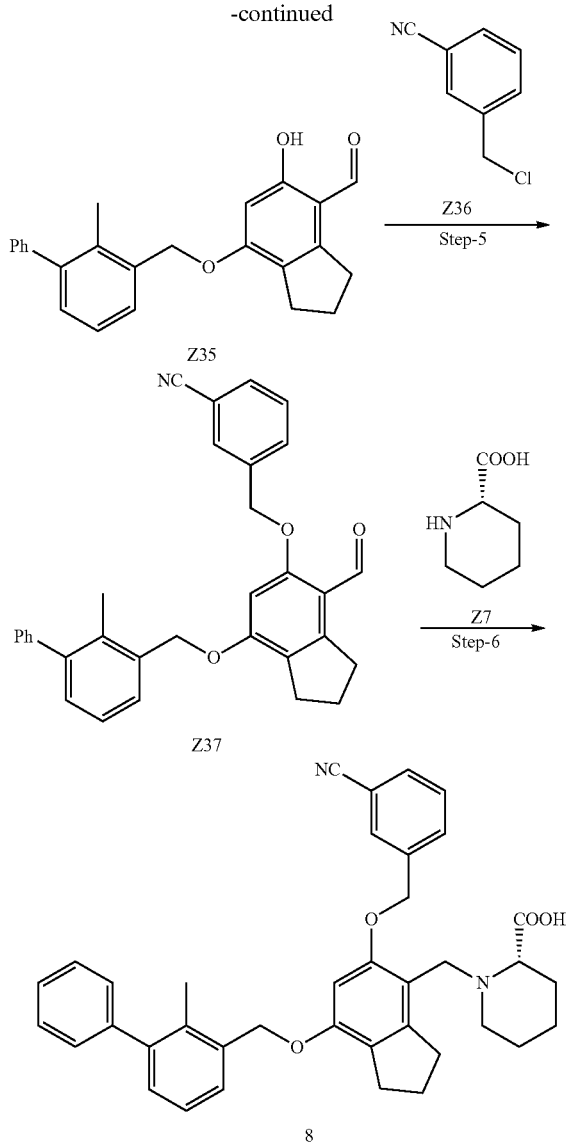

Step-1: A mixture of 7-hydroxy-5-methoxy-2,3-dihydro-1H-inden-1-one (20 g, 0.1122 mol) in DCE (200 mL), zinc iodide (107.48 g, 0.337 mol) and sodium cyanoborohydride (28.21 g, 0.448 mol) were heated at 75° C. for 8 h. The reaction mixture was filtered and the residue was washed with DCM (200 mL). The filtrate was washed with water (100 mL), brine (100 mL) and dried over anhydrous sodium sulfate and concentrated under vacuum. The resulting crude was purified by column chromatography (silica gel, 100-200 mesh) using 30% EtOAc in hexane as eluent to obtain 6-methoxy-2,3-dihydro-1H-inden-4-ol (Yield: 17 g, 92%) as white solid. LCMS (ES) m/z=165.04 [M+H]$^+$; $^1$H NMR (400 MHz, DMSO-d$_6$) δ ppm: 1.95 (m, 2H), 2.65 (t, J=7.2 Hz, 2H), 2.76 (t, J=7.6 Hz, 2H), 3.64 (s, 3H), 6.14 (s, 1H), 6.27 (s, 1H), 9.11 (s, 1H).

Step-2: To a solution of 6-methoxy-2,3-dihydro-1H-inden-4-ol (1 g, 0.006 mol) in 10% aqueous NaOH solution (45 mL), O-cyclodextrin (8 g, 0.007 mol) was added and the mixture was heated to 60° C. To this mixture, chloroform (6 mL, 0.125 mol) was added slowly for 3 h. After consumption of starting material, reaction mixture was cooled to room temperature and acidified with 1N HCl solution to pH=2. The aqueous layer was extracted with EtOAc (3×200 mL) and the combined organic layer was dried over sodium sulfate and concentrated. The crude was purified by flash chromatography (silica gel) using 30% EtOAc in hexane as eluent to obtain 7-hydroxy-5-methoxy-2,3-dihydro-1H-indene-4-carbaldehyde (Yield: 200 mg, 17%) as off-white solid. LCMS (ES) m/z=193.03 [M+H]$^+$; $^1$H NMR (400 MHz, DMSO-d$_6$) δ ppm: 1.99 (m, 2H), 2.64 (t, J=7.2 Hz, 2H), 3.08 (t, J=7.6 Hz, 2H), 3.80 (s, 3H), 6.36 (s, 1H), 10.24 (s, 1H), 10.45 (s, 1H).

Step-3: To a solution of 7-hydroxy-5-methoxy-2,3-dihydro-1H-indene-4-carbaldehyde (600 mg, 3.12 mmol) in DCM (100 mL) at 0° C., 1M BBr$_3$ solution in DCM (4.7 mL, 4.68 mmol) was added slowly and the solution was allowed to stir at room temperature for 6 h. After completion, the reaction mixture was quenched with water (100 mL) and extracted with DCM (2×100 mL). The organic layer was dried over anhydrous sodium sulfate and concentrated. The resulting crude product was purified by flash chromatography using 30% EtOAc in hexane as eluent to obtain 5,7-dihydroxy-2,3-dihydro-1H-indene-4-carbaldehyde (Yield: 405 mg, 71%) as white solid. LCMS (ES) m/z=177.28 [M−H]$^+$; $^1$H NMR (400 MHz, DMSO-d$_6$) δ ppm: 2.00 (m, 2H), 2.63 (t, J=7.2 Hz, 2H), 3.08 (t, J=7.6 Hz, 2H), 6.177 (s, 1H), 9.97 (s, 1H), 10.59 (s, 1H), 11.10 (s, 1H).

Step-4: To a solution of 5,7-dihydroxy-2,3-dihydro-1H-indene-4-carbaldehyde (0.40 g, 2.247 mmol) in acetonitrile (20 mL), potassium carbonate (0.37 g, 2.69 mmol) and 3-(bromomethyl)-2-methyl-1,1'-biphenyl (0.59 g, 2.25 mmol) were added. The reaction mixture was stirred at room temperature for 16 h. After completion, the reaction mixture was diluted with water (20 mL) and extracted with EtOAc (3×20 mL). The combined organic layer was dried over sodium sulfate and concentrated. The resulting crude was purified by flash chromatography (silica gel, 4 g) using 0-20% EtOAc in hexane as eluent to obtain 5-hydroxy-7-((2-methyl-[1,1'-biphenyl]-3-yl)methoxy)-2,3-dihydro-1H-indene-4-carbaldehyde (Yield: 0.70 g, 87%) as white solid. LCMS (ES) m/z=359.35 [M+H]$^+$; $^1$H NMR (400 MHz, DMSO-d$_6$) δ ppm: 2.05 (m, 2H), 2.19 (s, 3H), 2.71 (t, J=7.2 Hz, 2H), 3.14 (t, J=7.2 Hz, 2H), 5.24 (s, 2H), 6.55 (s, 1H), 7.21 (d, J=7.6 Hz, 1H), 7.28-7.33 (m, 3H), 7.38 (m, 1H), 7.44-7.48 (m, 3H), 10.05 (s, 1H), 11.31 (s, 1H).

Step-5: To a solution of 5-hydroxy-7-((2-methyl-[1,1'-biphenyl]-3-yl)methoxy)-2,3-dihydro-1H-indene-4-carbaldehyde (0.50 g, 1.39 mmol) in acetonitrile (20 mL), potassium carbonate (0.35 g, 2.5 mmol) and 3-(chloromethyl)benzonitrile (0.41 g, 2.0 mmol) were added. The reaction mixture was stirred at room temperature for 16 h. After completion, the reaction mixture was diluted with water (20 mL) and extracted with EtOAc (3×30 mL). The combined organic layer was dried over sodium sulfate and concentrated. The resulting crude was purified by flash chromatography (silica gel, 4 g cartridge) using 0-30% EtOAc in hexane as eluent to obtain 3-(((4-formyl-7-((2-methyl-[1,1'-biphenyl]-3-yl)methoxy)-2,3-dihydro-1H-inden-5-yl)oxy)methyl)benzonitrile (Yield: 0.505 g, 75%) as white solid. LCMS (ES) m/z=474.41 [M+H]$^+$; $^1$H NMR (400 MHz, DMSO-d$_6$) δ ppm: 2.00 (m, 2H), 2.21 (s, 3H), 2.70 (t, J=7.2 Hz, 2H), 3.13 (t, J=7.2 Hz, 2H), 5.30 (s, 2H), 5.38 (s, 2H), 6.92 (s, 1H), 7.22 (d, J=7.6 Hz, 1H), 7.27-7.33 (m, 3H), 7.38 (m, 1H), 7.44-7.48 (m, 3H), 7.63 (t, J=7.6 Hz, 1H), 7.85 (m, 2H), 8.01 (s, 1H), 10.39 (s, 1H).

Step-6: A solution of 3-(((4-formyl-7-((2-methyl-[1,1'-biphenyl]-3-yl)methoxy)-2,3-dihydro-1H-inden-5-yl)oxy)methyl)benzonitrile (100 mg, 0.21 mmol), (S)-piperidine-2- carboxylic acid (40.8 mg, 0.32 mmol), sodium cyanoborohydride (66.4 mg, 1.06 mmol) and acetic acid (2 drops) in DMF (5 mL) was stirred at 70° C. for 4 h. After completion, the reaction mixture was poured on to ice-cold water (10 mL). The solid was filtered and dissolved in DCM. The organic solvent was dried over sodium sulfate and concentrated. The resulting crude was purified by flash chromatography (silica gel, 4 g cartridge) using 0-10% MeOH in DCM as eluent to obtain (S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxylic acid (Yield: 26 mg, 46%) as white solid. LCMS (ES) m/z=587.15 [M+H]$^+$; $^1$H NMR (400 MHz, DMSO-d$_6$) δ ppm: 1.32-1.45 (m, 4H), 1.78 (m, 2H), 1.97 (m, 2H), 2.20 (s, 3H), 2.32 (m, 1H), 2.73 (m, 2H), 2.81 (m, 1H), 2.94-3.03 (m, 2H), 3.14 (m, 1H), 3.71 (d, J=12.4 Hz, 1H), 3.88 (d, J=12.4 Hz, 1H), 5.14 (s, 2H), 5.23 (s, 2H), 6.73 (s, 1H), 7.19 (d, J=7.6 Hz, 1H), 7.25-7.33 (m, 3H), 7.37 (m, 1H), 7.44-7.49 (m, 3H), 7.61 (t, J=7.6 Hz, 1H), 7.80 (d, J=7.2 Hz, 1H), 7.86 (d, J=7.2 Hz, 1H), 7.98 (s, 1H).

Example 9

Synthesis of(S)-1-((5-((5-fluoropyridin-3-yl)methoxy)-7-((2-methyl-[1,1'-biphenyl]-3-yl)methoxy)-2,3-dihydro-1H-inden-4-yl)methyl)piperidine-2-carboxylicacid

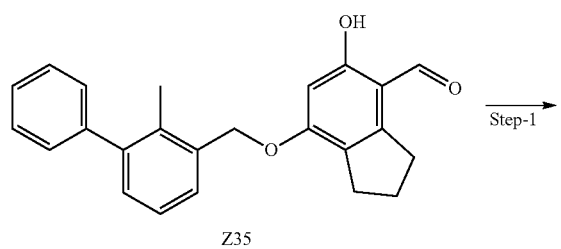

Z35

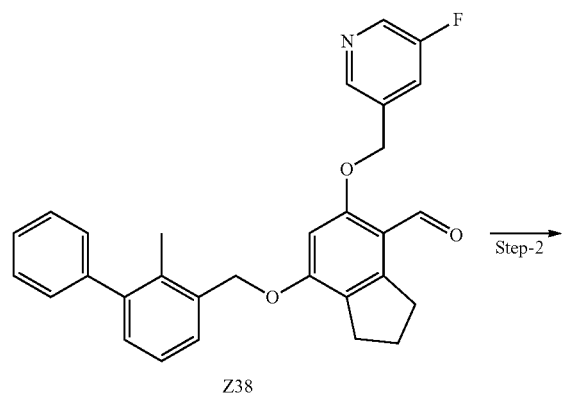

Z38

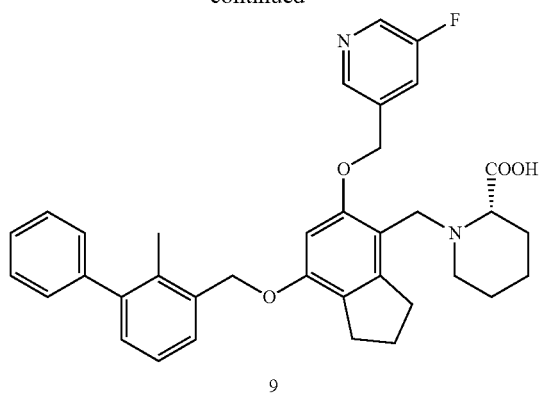

9

Step-1: To a solution of 5-hydroxy-7-((2-methyl-[1,1'-biphenyl]-3-yl)methoxy)-2,3-dihydro-1H-indene-4-carbaldehyde (0.40 g, 1.117 mmol) in DMF (20 mL), potassium carbonate (0.46 g, 3.38 mmol) and 3-(chloromethyl)-5-fluoropyridine (0.325 g, 2.25 mmol) was added and stirred at room temperature for 16 h. After completion, the reaction mixture was diluted with water (20 mL) and extracted with EtOAc (3×30 mL). The combined organic layer was dried over sodium sulfate and concentrated. The resulting crude was purified by flash chromatography (silica gel, 4 g cartridge using DCM as eluent to obtain 5-((5-fluoropyridin-3-yl)methoxy)-7-((2-methyl-[1,1'-biphenyl]-3-yl)methoxy)-2,3-dihydro-1H-indene-4-carbaldehyde (Yield: 0.201 g, 38%) as white solid. LCMS (ES) m/z=468.16 [M+H]$^+$; $^1$H NMR (400 MHz, DMSO-d$_6$) δ ppm: 1.99-2.00 (m, 2H), 2.22 (s, 3H), 2.71 (m, 2H), 3.13 (m, 2H), 5.32 (s, 2H), 5.40 (s, 2H), 6.95 (s, 1H), 7.22 (d, J=7.6 Hz, 1H), 7.27-7.40 (m, 4H), 7.44-7.48 (m, 3H), 7.92 (d, J=9.2 Hz, 1H), 8.58 (s, 1H), 8.62 (s, 1H), 10.35 (s, 1H).

Step-2: To a solution of 5-((5-fluoropyridin-3-yl)methoxy)-7-((2-methyl-[1,1'-biphenyl]-3-yl)methoxy)-2,3-dihydro-1H-indene-4-carbaldehyde (50 mg, 0.11 mmol), (S)-piperidine-2-carboxylic acid (52 mg, 0.32 mmol) in MeOH (3 mL) and DMF (3 mL), sodium cyanoborohydride (19 mg, 0.32 mmol) and acetic acid (2 drops) were added and the mixture was stirred at room temperature for 8 h. After completion, the reaction mixture was diluted with water (10 mL) and extracted with DCM (3×30 mL). The organic layer was dried over anhydrous sodium sulphate and concentrated. The resulting crude was purified by flash chromatography (silica gel, 4 g cartridge) using 0-10% MeOH in DCM as eluent to obtain (S)-1-((5-((5-fluoropyridin-3-yl)methoxy)-7-((2-methyl-[1,1'-biphenyl]-3-yl)methoxy)-2,3-dihydro-1H-inden-4-yl)methyl)piperidine-2-carboxylic acid (Yield: 30 mg, 48%) as white solid. LCMS (ES) m/z=581.47 [M+H]$^+$; $^1$H NMR (400 MHz, DMSO-d$_6$) δ ppm: 1.32-1.45 (m, 4H), 1.75 (m, 2H), 1.97 (m, 2H), 2.32 (m, 3H), 2.49 (m, 1H), 2.74 (m, 2H), 2.81-3.05 (m, 3H), 3.14 (m, 1H), 3.68 (d, J=12.8 Hz, 1H), 3.88 (d, J=12.4 Hz, 1H), 5.16 (s, 2H), 5.26 (m, 2H), 6.78 (s, 1H), 7.19 (d, J=7.6 Hz, 1H), 7.25-7.33 (m, 3H), 7.39 (m, 1H), 7.44-7.47 (m, 3H), 7.92 (d, J=9.6 Hz, 1H), 8.54 (s, 1H), 8.61 (s, 1H).

Example 10

N-(2-(((5-((5-fluoropyridin-3-yl)methoxy)-7-((2-methyl-[1,1'-biphenyl]-3-yl)methoxy)-2,3-dihydro-1H-inden-4-yl)methyl)amino)ethyl)acetamide was prepared by following procedure similar to Example 9

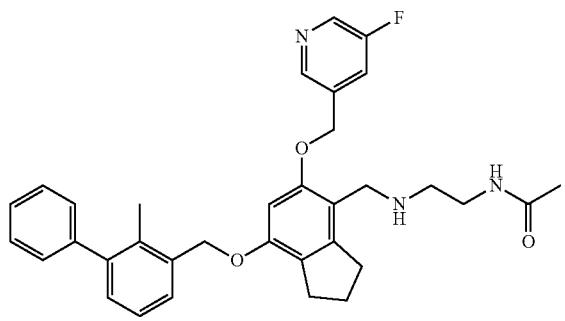

LCMS (ES) m/z=554.44 [M+H]$^+$; $^1$H NMR (400 MHz, DMSO-d$_6$) δ ppm: 1.75 (s, 3H), 1.97-2.01 (m, 2H), 2.20 (m, 3H), 2.61 (m, 2H), 2.76 (m, 2H), 2.89 (m, 2H), 3.13 (m, 2H), 3.71 (s, 2H), 5.16 (s, 2H), 5.26 (m, 2H), 6.77 (s, 1H), 7.19 (d, J=7.6 Hz, 1H), 7.25-7.33 (m, 3H), 7.39 (m, 1H), 7.44-7.47 (m, 3H), 7.80 (bs, 1H), 7.86 (d, J=9.2 Hz, 1H), 8.55 (s, 1H), 8.59 (s, 1H).

Example 11

Synthesis of (S)-5-((5-methoxy-7-((2-methyl-[1,1'-biphenyl]-3-yl)methoxy)-2,3-dihydro-1H-inden-4-yl)methyl)-5-azaspiro[2.4]heptane-6-carboxylic acid Step-1: To a solution of (S)-5-(tert-butoxycarbonyl)-5-azaspiro[2.4]heptane-6-carboxylic acid (1.0 g, 3.6 mmol) in 1,4-dioxane (10 mL) at 0° C., 4M HCl in 1,4-dioxane (15 mL) was added drop wise and allowed the mixture to stir at room temperature for 3 h. After completion, the reaction mixture was concentrated under vacuum to obtain (S)-5-azaspiro[2.4]heptane-6-carboxylic acid hydrochloride (700 mg, crude) as off-white solid. LCMS (ES) m/z=142.28 [M+H]$^+$; $^1$H NMR (400 MHz, DMSO-d$_6$) δ ppm: 0.64 (m, 4H), 1.97-2.02 (m, 1H), 2.22 (m, 1H), 3.12 (m, 2H), 4.44 (m, 1H), 8.91 (bs, 1H), 10.24 (bs, 1H).

Step-2: A solution of 5-methoxy-7-((2-methyl-[1,1'-biphenyl]-3-yl)methoxy)-2,3-dihydro-1H-indene-4-carbaldehyde (200 mg, 0.42 mmol), (S)-5-azaspiro[2.4]heptane-6-carboxylic acid hydrochloride (89 mg, 0.50 mmol) and acetic acid (2 drops) in MeOH (2.5 mL) and DMF (2.5 mL) was stirred at room temperature for 30 minutes. To this mixture, sodium cyanoborohydride (39 mg, 0.63 mmol) was added and continued stirring at room temperature for 16 h. After completion, the reaction mixture was diluted with water (10 mL) and extracted with 10% MeOH in DCM (3×15 mL). The organic layer was dried over anhydrous sodium sulfate and concentrated. The resulting crude was purified by flash chromatography (silica gel, 4 g cartridge) using 0-10% MeOH in DCM as eluent, to obtain (S)-5-((5-methoxy-7-((2-methyl-[1,1'-biphenyl]-3-yl)methoxy)-2,3-dihydro-1H-inden-4-yl)methyl)-5-azaspiro[2.4]heptane-6-carboxylic acid (Yield: 90 mg, 45%) as white solid. LCMS (ES) m/z=498.43 [M+H]$^+$; $^1$H NMR (400 MHz, DMSO-d$_6$) δ ppm: 0.46 (m, 1H), 0.58-0.64 (m 3H), 1.81-1.99 (m, 1H), 1.99-2.04 (m, 2H), 2.22 (s, 3H), 2.36 (m, 1H), 2.75 (m, 2H), 2.86-3.06 (m, 4H), 3.85 (m, 1H), 3.86 (s, 3H), 4.15 (m, 2H), 5.21 (s, 2H), 6.72 (s, 1H), 7.20 (d, J=7.6 Hz, 1H), 7.28-7.33 (m, 3H), 7.39 (m, 1H), 7.44-7.50 (m, 3H).

Example 12

Synthesis of (S)-1-((7-((2-methyl-[1,1'-biphenyl]-3-yl)methoxy)-5-(2,2,2-trifluoroethoxy)-2,3-dihydro-1H-inden-4-yl)methyl)piperidine-2-carboxylic acid

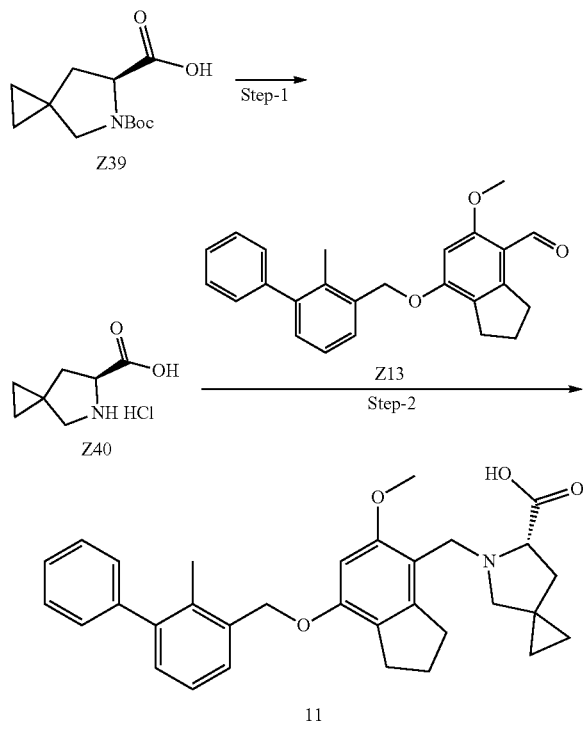

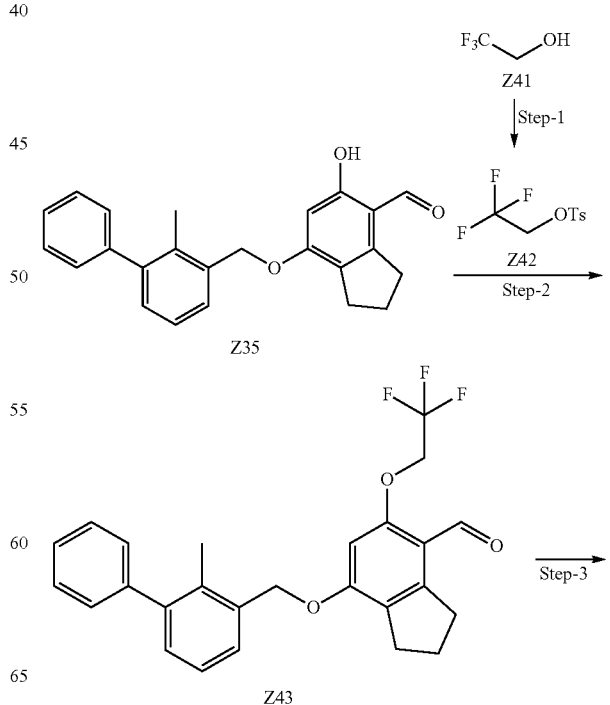

119

-continued

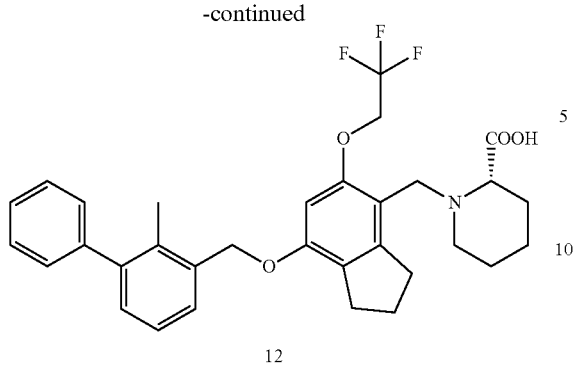

12

Step-1: To a solution of trifluoroethanol (500 mg, 5.0 mmol) in DCM (10 mL), triethylamine (1.5 g, 15 mmol) was added and cooled to 0° C. To this mixture, p-toluene sulfonyl chloride (1.2 g, 6.0 mmol) was added and allowed the reaction mixture to stir at room temperature for 6 h. After completion, the reaction mixture was diluted with water (10 mL) and separated the layers. The aqueous layer was further extracted with EtOAc (2×10 mL) and the combined organic layer was dried over anhydrous sodium sulfate and concentrated. The crude was purified by flash chromatography (silica gel, 12 g cartridge) using 20% EtOAc in hexanes as eluent to obtain 2,2,2-trifluoroethyl 4-methylbenzenesulfonate (Yield: 405 mg, 31%) as oil. $^1$H NMR (400 MHz, DMSO-d$_6$) δ ppm: 2.44 (s, 3H), 4.86 (m, 2H), 7.52 (d, J=8.0 Hz, 2H), 7.86 (d, J=8.0 Hz, 2H).

Step-2: To a solution of 5-hydroxy-7-((2-methyl-[1,1'-biphenyl]-3-yl)methoxy)-2,3-dihydro-1H-indene-4-carbaldehyde (0.40 g, 1.12 mmol) and 2,2,2-trifluoroethyl 4-methylbenzenesulfonate (0.34 g, 1.34 mmol) in DMF (8 mL), potassium carbonate (0.28 g, 2.0 mmol) was added and stirred the mixture at room temperature for 16 h. After completion, the mixture was diluted with water (20 mL) and extracted with EtOAc (3×25 mL). The organic layer was dried over sodium sulfate and concentrated. The crude was purified by flash chromatography (silica gel, 12 g cartridge) using 20% EtOAc in hexanes as eluent to obtain 7-((2-methyl-[1,1'-biphenyl]-3-yl)methoxy)-5-(2,2,2-trifluoroethoxy)-2,3-dihydro-1H-indene-4-carbaldehyde (Yield: 102 mg, 21%) as white solid. LCMS (ES) m/z=441.57 [M+H]$^+$.

Step-3: A solution of 7-((2-methyl-[1,1'-biphenyl]-3-yl)methoxy)-5-(2,2,2-trifluoroethoxy)-2,3-dihydro-1H-indene-4-carbaldehyde (100 mg, 0.23 mmol), (S)-piperidine-2-carboxylic acid (87 mg, 0.68 mmol), sodium cyanoborohydride (42.2 mg, 0.68 mmol) and acetic acid (2 drops) in MeOH (2 mL) and DMF (3 mL) was stirred at room temperature for 16 h. After completion, the reaction mixture was diluted with water (10 mL) and extracted with 10% MeOH in DCM (3×25 mL). The organic layer was dried over anhydrous sodium sulfate and concentrated. The residue was diluted with DCM (10 mL) and washed with DM water (4 mL). The organic layer was concentrated and purified by reverse phase HPLC using method-A to obtain (S)-1-((7-((2-methyl-[1,1'-biphenyl]-3-yl)methoxy)-5-(2,2,2-trifluoroethoxy)-2,3-dihydro-1H-inden-4-yl)methyl)piperidine-2-carboxylic acid (Yield: 20 mg, 16%) as white solid. LCMS (ES) m/z=554.47 [M+H]$^+$; $^1$H NMR (400 MHz, DMSO-d$_6$) δ ppm: 1.47 (m, 1H), 1.60 (m, 3H), 1.73 (m, 1H), 2.03 (m, 3H), 2.21 (s, 3H), 2.79 (m, 2H), 2.83 (bs, 1H), 3.11 (m, 3H), 3.85 (bs, 1H), 3.95-4.02 (m, 2H), 4.84 (m, 2H), 5.20 (s, 2H), 6.86 (s, 1H), 7.21 (d, J=7.6 Hz, 1H), 7.28-7.33 (m, 3H), 7.39 (m, 1H), 7.44-7.47 (m, 3H).

120

Example 13

Synthesis of N-(2-(((5-((3-cyanobenzyl)oxy)-7-((2-methyl-[1,1'-biphenyl]-3-yl)methoxy)-2,3-dihydro-1H-inden-4-yl)methyl)amino)ethyl)-N-methylacetamide

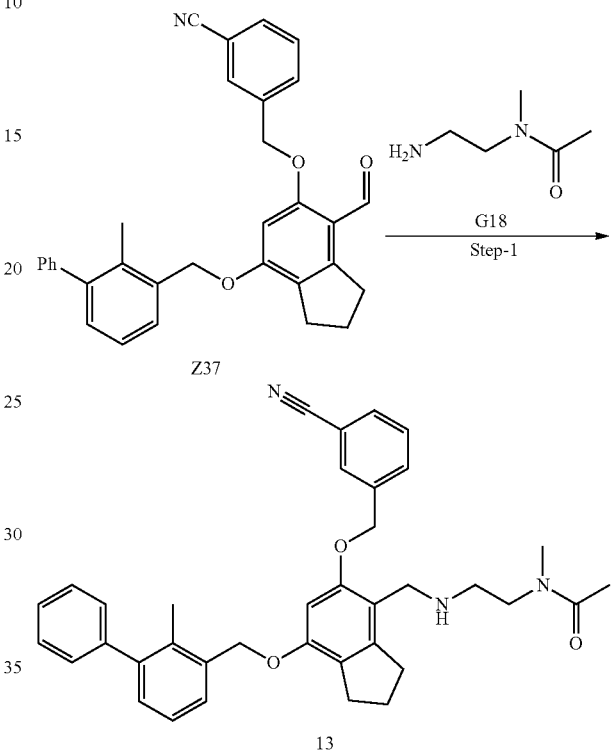

13

Step-5: To a solution of 3-(((4-formyl-7-((2-methyl-[1,1'-biphenyl]-3-yl)methoxy)-2,3-dihydro-1H-inden-5-yl)oxy)methyl)benzonitrile (135 mg, 0.29 mmol), N-(2-aminoethyl)-N-methylacetamide (100 mg, 0.86 mmol) in 1:1 mixture of MeOH and DMF (5 mL), acetic acid (2 drops) was added and stirred for 15 minutes. To this mixture, sodium cyanoborohydride (53 mg, 0.86 mmol) was added and continued stirring the reaction mixture at room temperature for 16 h. After completion, the reaction mixture was diluted with water (10 mL) and extracted with 10% MeOH in DCM (3×25 mL). The organic layer was dried over sodium sulfate and concentrated. The resulting crude was purified by flash chromatography (silica gel, 4 g cartridge) using 0-10% MeOH in DCM as eluent to obtain N-(2-(((5-((3-cyanobenzyl)oxy)-7-((2-methyl-[1,1'-biphenyl]-3-yl)methoxy)-2,3-dihydro-1H-inden-4-yl)methyl)amino)ethyl)-N-methylacetamide (Yield: 46 mg, 28%) as white solid. LCMS (ES) m/z=574.54 [M+H]$^+$; $^1$H NMR (400 MHz, DMSO-d$_6$) δ ppm: 1.72 (s, 3H), 1.97 (m, 2H), 2.09 (s, 3H), 2.20 (s, 3H), 2.36 (m, 2H), 2.74 (m, 2H), 2.88 (m, 2H), 3.13 (m, 2H), 3.40 (s, 2H), 5.13 (s, 2H), 5.20 (s, 2H), 6.72 (s, 1H), 7.19 (d, J=7.6 Hz, 1H), 7.25 (m, 1H), 7.33 (m, 2H), 7.37 (m, 1H), 7.44-7.49 (m, 3H), 7.59-7.61 (m, 2H), 7.81 (t, J=8.8 Hz, 2H), 7.95 (s, 1H).

Example 14

Synthesis of N-(2-(((5-(1-(3-cyanophenyl)ethoxy)-7-((2-methyl-[1,1'-biphenyl]-3-yl)methoxy)-2,3-dihydro-1H-inden-4-yl)methyl)amino)ethyl)acetamide

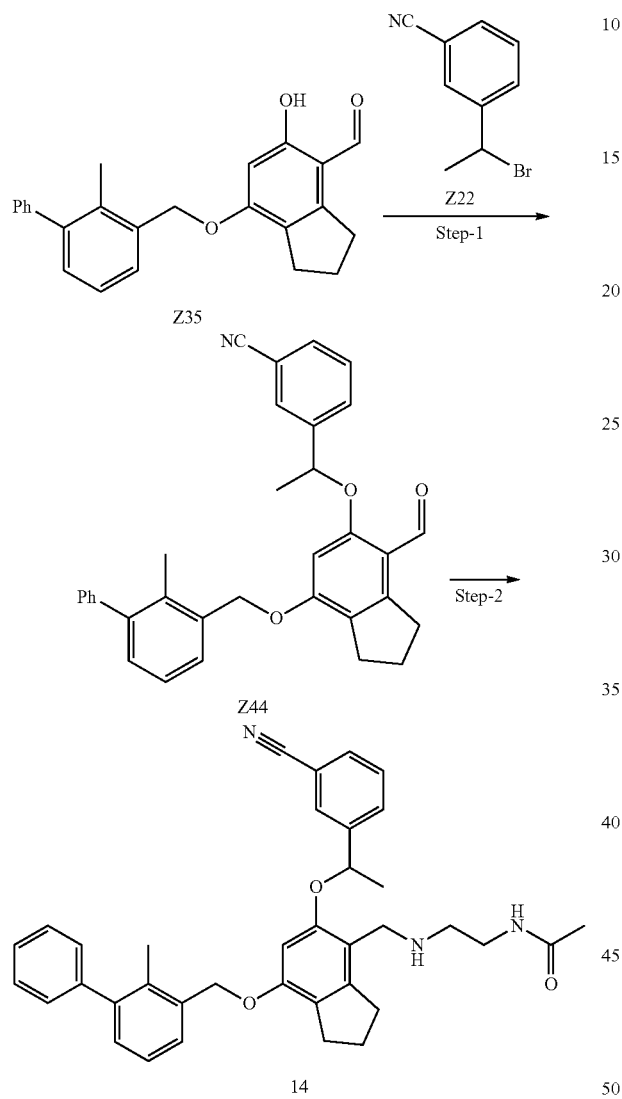

Step-1: To a solution of 5-hydroxy-7-((2-methyl-[1,1'-biphenyl]-3-yl)methoxy)-2,3-dihydro-1H-indene-4-carbaldehyde (0.250 g, 0.68 mmol) in DMF (10 mL), potassium carbonate (0.192 g, 1.39 mmol) and 3-(1-bromoethyl)benzonitrile (0.22 g, 1.04 mmol) were added and stirred the reaction mixture at room temperature for 10 minutes. After completion, the reaction mixture was diluted with water (20 mL) and extracted with EtOAc (3×30 mL). The combined organic layer was dried over sodium sulfate and concentrated. The resulting crude was purified by flash chromatography (silica gel, 4 g cartridge) using 0-20% EtOAc in hexane as eluent to obtain 3-(1-((4-formyl-7-((2-methyl-[1,1'-biphenyl]-3-yl)methoxy)-2,3-dihydro-1H-inden-5-yl)oxy)ethyl)benzonitrile (Yield: 0.275 g, 80%) as white solid. LCMS (ES) m/z=488.34 [M+H]$^+$; $^1$H NMR (400 MHz, DMSO-d$_6$) δ ppm: 1.63 (d, J=6.4 Hz, 3H), 1.97 (m, 2H), 2.18 (s, 3H), 2.65 (m, 2H), 3.08 (m, 2H), 5.10 (d, J=12.4 Hz, 1H), 5.26 (d, J=12.4 Hz, 1H), 5.86 (m, 1H), 6.73 (s, 1H), 7.27 (m, 2H), 7.30-7.40 (m, 4H), 7.44-7.48 (m, 2H), 7.55 (t, J=7.6 Hz, 1H), 7.74 (d, J=7.6 Hz, 1H), 7.83 (d, J=7.6 Hz, 1H), 8.01 (s, 1H), 10.45 (s, 1H).

Step-2: A solution of 3-(1-((4-formyl-7-((2-methyl-[1,1'-biphenyl]-3-yl)methoxy)-2,3-dihydro-1H-inden-5-yl)oxy)ethyl)benzonitrile (150 mg, 0.31 mmol), N N-(2-aminoethyl)acetamide (47 mg, 0.46 mmol) in 1:1 mixture of MeOH and DMF (5 mL), acetic acid (5 drops) was added and stirred for 15 minutes. To this mixture, sodium cyanoborohydride (38 mg, 0.62 mmol) was added and continued stirring the reaction mixture at room temperature for 16 h. After completion, the reaction mixture was diluted with water (10 mL) and extracted with 10% MeOH in DCM (3×25 mL). The organic layer was dried over sodium sulfate and concentrated. The resulting crude was purified by flash chromatography (silica gel, 4 g cartridge) using 0-10% MeOH in DCM as eluent to obtain N-(2-(((5-(1-(3-cyanophenyl)ethoxy)-7-((2-methyl-[1,1'-biphenyl]-3-yl)methoxy)-2,3-dihydro-1H-inden-4-yl)methyl)amino)ethyl)acetamide (Yield: 55 mg, 31%) as white solid. LCMS (ES) m/z=574.51 [M+H]$^+$; $^1$H NMR (400 MHz, DMSO-d$_6$) δ ppm: 1.57 (d, J=6.4 Hz, 3H), 1.78 (s, 3H), 1.94-1.97 (m, 2H), 2.15 (s, 3H), 2.61 (m, 2H), 2.67-2.75 (m, 2H), 2.86 (m, 2H), 3.16 (m, 2H), 3.69 (bs, 2H), 4.89 (d, J=12.0 Hz, 1H), 5.07 (d, J=12.4 Hz, 1H), 5.60 (m, 1H), 6.46 (s, 1H), 7.15-7.22 (m, 2H), 7.25-7.31 (m, 3H), 7.37 (m, 1H), 7.44-7.48 (m, 2H), 7.54 (t, J=7.6 Hz, 1H), 7.73 (d, J=7.6 Hz, 1H), 7.78 (d, J=7.6 Hz, 1H), 7.82 (bs, 1H), 7.94 (s, 1H).

Example 15

Synthesis of N-(1-((5-((3-cyanobenzyl)oxy)-7-((2-methyl-[1,1'-biphenyl]-3-yl)methoxy)-2,3-dihydro-1H-inden-4-yl)methyl)piperidin-3-yl)acetamide

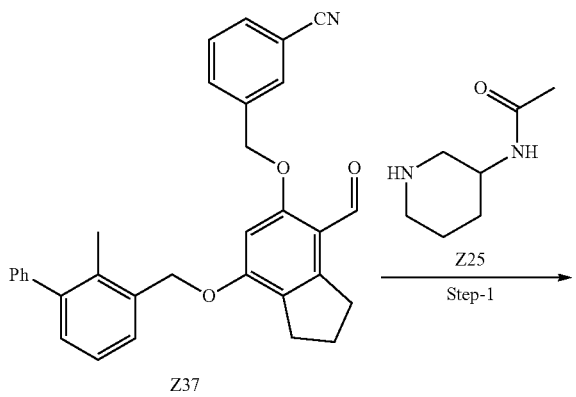

123
-continued

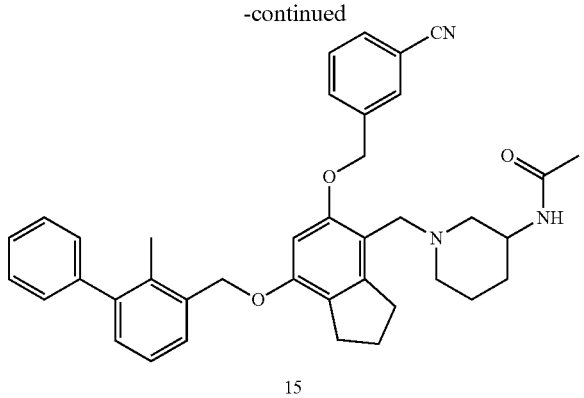
15

Step-1: A solution of 3-(((4-formyl-7-((2-methyl-[1,1'-biphenyl]-3-yl)methoxy)-2,3-dihydro-1H-inden-5-yl)oxy)methyl)benzonitrile (150 mg, 0.40 mmol), N-(piperidin-3-yl)acetamide (170 mg, 1.20 mmol) in triethylamine (82 mg) and acetic acid (5 drops) was stirred for 1 h. To this mixture, sodium cyanoborohydride (74.6 mg, 1.20 mmol) was added and continued stirring the reaction mixture at room temperature for 16 h. After completion, the reaction mixture was diluted with water (10 mL) and extracted with EtOAc (3×25 mL). The organic layer was dried over sodium sulfate and concentrated. The resulting crude was purified by flash chromatography (silica gel, 4 g cartridge) using 0-10% MeOH in DCM as eluent to obtain N-(1-((5-((3-cyanobenzyl)oxy)-7-((2-methyl-[1,1'-biphenyl]-3-yl)methoxy)-2,3-dihydro-1H-inden-4-yl)methyl)piperidin-3-yl)acetamide (Yield: 23 mg, 9.5%) as white solid. LCMS (ES) m/z=600.55 [M+H]$^+$; $^1$H NMR (400 MHz, DMSO-d$_6$) δ ppm: 1.10 (m, 1H), 1.39 (m, 1H), 1.58-1.74 (m, 6H), 1.83-1.99 (m, 3H), 2.21 (s, 3H), 2.61.2.76 (m, 4H), 2.88 (m, 2H), 3.39 (m, 2H), 3.60 (m, 1H), 5.13 (s, 2H), 5.20 (s, 2H), 6.72 (s, 1H), 7.20 (d, J=7.52 Hz, 1H), 7.25-7.33 (m, 3H), 7.37 (m, 1H), 7.43-7.47 (m, 3H), 7.63 (m, 2H), 7.80 (d, J=7.36 Hz, 1H), 7.86 (d, J=7.52 Hz, 1H), 7.97 (s, 1H).

The following compounds were prepared following procedures described above

TABLE 2

| S. No. | Structure | LCMS m/z [M + H]$^+$ | $^1$H NMR (400 MHz, DMSO-d$_6$) δ ppm |
|---|---|---|---|
| 16 | N-(2-(((7-((2-methyl-[1,1'-biphenyl]-3-yl)methoxy)-2,3-dihydro-1H-inden-4-yl)methyl)amino)ethyl)acetamide | 429.3 | 1.78 (s, 3H), 1.98-2.02 (m, 2H), 2.18 (s, 3H), 2.64-2.66 (m, 2H), 2.81 (t, J = 7.2 Hz, 2H), 2.88 (t, J = 7.4 Hz, 2H), 3.16-3.18 (m, 2H), 3.70 (s, 2H), 5.13 (s, 2H), 6.89 (d, J = 8.4 Hz, 1H), 7.11 (d, J = 8.4 Hz, 1H), 7.17 (d, J = 7.6 Hz, 1H), 7.23-7.31 (m, 3H), 7.34-7.46 (m, 4H), 7.81 (s, 1H) |
| 17 | 6-((7-((2-methyl-[1,1'-biphenyl]-3-yl)methoxy)-2,3-dihydro-1H-inden-4-yl)methyl)-2-oxa-6-azaspiro[3.3]heptane | 426.3 | 1.96-1.99 (m, 2H), 2.18 (s, 3H), 2.79-2.81 (m, 4H), 3.26-3.31 (m, 6H), 4.58 (s, 4H), 5.11 (s, 2H), 6.85 (bs, 1H), 6.99 (bs, 1H), 7.16-7.18 (m, 1H), 7.24-7.38 (m, 4H), 7.42-7.44 (m, 3H) |
| 18 | 2-(hydroxymethyl)-2-(((7-((2-methyl-[1,1'-biphenyl]-3-yl)methoxy)-2,3-dihydro-1H-inden-4-yl)methyl)amino)propane-1,3-diol | 448.0 | 1.99-2.01 (m, 2H), 2.18 (s, 3H), 2.81-2.89 (m, 4H), 3.30 (s, 6H), 3.65 (bs, 2H), 4.32 (bs, 3H), 5.12 (s, 2H), 6.81-6.89 (m, 1H), 7.04-7.20 (m, 2H), 7.22-7.39 (m, 4H), 7.42-7.44 (m, 3H) |

TABLE 2-continued

| S. No. | Structure | LCMS m/z [M + H]+ | 1H NMR (400 MHz, DMSO-d6) δ ppm |
|---|---|---|---|
| 19 | 1-(((7-((2-methyl-[1,1'-biphenyl]-3-yl)methoxy)-2,3-dihydro-1H-inden-4-yl)methyl)amino)cyclopropane-1-carboxylic acid | 428.2 | 0.86-0.87 (m, 2H), 1.08-1.09 (m, 2H), 1.94-2.02 (m, 2H), 2.17 (s, 3H), 2.77-2.88 (m, 4H), 3.73 (s, 2H), 5.11 (s, 2H), 6.83 (d, J = 7.6 Hz, 1H), 7.03 (d, J = 8.4 Hz, 1H), 7.16 (d, J = 7.6 Hz, 1H), 7.23-7.37 (m, 4H), 7.42-7.45 (m, 3H) |
| 20 | ((7-((2-methyl-[1,1'-biphenyl]-3-yl)methoxy)-2,3-dihydro-1H-inden-4-yl)methyl)glycine | 402.1 | 1.98-2.02 (m, 2H), 2.18 (s, 3H), 2.80-2.94 (m, 4H), 3.08 (s, 2H), 3.86 (s, 2H), 5.15 (s, 2H), 6.94 (d, J = 8.0 Hz, 1H), 7.16-7.21(m, 2H), 7.23-7.31 (m, 3H), 7.36-7.37 (m, 1H), 7.42-7.44 (m, 3H) |
| 21 | 3-(((7-((2-methyl-[1,1'-biphenyl]-3-yl)methoxy)-2,3-dihydro-1H-inden-4-yl)methyl)amino)propanoic acid | 417.2 | 1.98-2.02 (m, 2H), 2.18 (s, 3H), 2.25-2.28 (m, 2H), 2.80-2.91 (m, 6H), 3.74 (s, 2H), 5.13 (s, 2H), 6.90 (d, J = 8.0 Hz, 1H), 7.09-7.17 (m, 2H), 7.23-7.37 (m, 4H), 7.42-7.44 (m, 3H), 8.01-9.91 (bs, 2H) |
| 22 | N-methyl-N-((7-((2-methyl-[1,1'-biphenyl]-3-yl)methoxy)-2,3-dihydro-1H-inden-4-yl)methyl)glycine | 417.2 | 1.94-1.99 (m, 2H), 2.17 (s, 3H), 2.22 (s, 3H), 2.79 (t, J = 7.6 Hz, 2H), 2.84-2.91 (m, 4H), 3.53 (s, 2H), 5.10 (s, 2H), 6.84 (d, J = 8.4 Hz, 1H), 7.04 (d, J = 8.4 Hz, 1H), 7.45 (d, J = 7.6 Hz, 1H), 7.22-7.30 (m, 3H), 7.33-7.44 (m, 4H) |
| 23 | 3-(((7-((2-methyl-[1,1'-biphenyl]-3-yl)methoxy)-2,3-dihydro-1H-inden-4-yl)methyl)amino)butanoic acid | 430.2 | 1.15-1.16 (m, 3H), 2.00-2.05 (m, 2H), 2.10-2.25 (m, 5H), 2.81-2.95 (m, 4H), 3.09-3.11 (m, 1H), 3.73 (d, J = 12.8 Hz, 1H), 3.87 (d, J = 12.8 Hz, 1H), 5.15 (s, 2H), 6.93 (d, J = 8.0 Hz, 1H), 7.12-7.18 (m, 2H), 7.24-7.37 (m, 4H), 7.42-7.44 (m, 2H), 9.98 (bs, 1H) |

TABLE 2-continued

| S. No. | Structure | LCMS m/z [M + H]+ | 1H NMR (400 MHz, DMSO-d6) δ ppm |
|---|---|---|---|
| 24 | 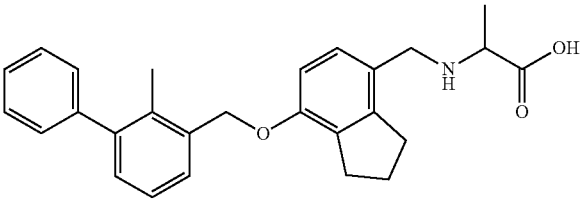 [SMILES: Cc1c(COc2ccc(CNC(C)C(=O)O)c3c2CCC3)cccc1-c1ccccc1]<br>((7-((2-methyl-[1,1'-biphenyl]-3-yl)methoxy)-2,3-dihydro-1H-inden-4-yl)methyl)alanine | 415.2 | 1.25-1.26 (m, 3H), 1.98-2.02 (m, 2H), 2.18 (s, 3H), 2.80-2.97 (m, 4H), 3.16-3.18 (m, 1H), 3.78-3.90 (m, 2H), 5.15 (s, 2H), 6.94 (d, J = 8.0 Hz, 1H), 7.16-7.37 (m, 6H), 7.42-7.44 (m, 2H), 7.56-8.34 (bs, 1H) |
| 25 | 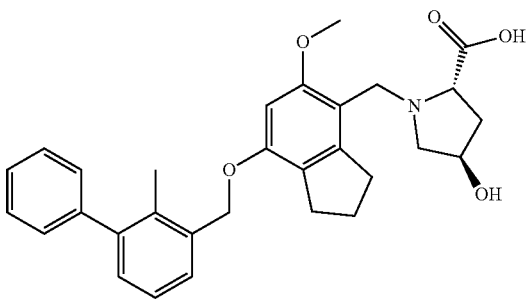 [SMILES: COc1cc(OCc2cccc(-c3ccccc3)c2C)c2c(c1CN1C[C@H](O)C[C@H]1C(=O)O)CCC2]<br>(2S,4R)-4-hydroxy-1-((5-methoxy-7-((2-methyl-[1,1'-biphenyl]-3-yl)methoxy)-2,3-dihydro-1H-inden-4-yl)methyl)pyrrolidine-2-carboxylic acid | 488.5 | 1.13-1.19 (m, 1H), 1-98-2.0 (m, 3H), 2.15-2.23 (m, 1H), 2.21 (s, 3H), 2.74 (t, J = 7.6 Hz, 3H), 2.89-2.97 (m, 2H), 3.19 (bs, 1H), 3.74 (bs, 1H), 3.83 (s, 3H), 4.07-4.08 (m, 2H), 4.23 (bs, 1H), 4.19 (s, 2H), 4.21 (bs, 1H), 6.69 (s, 1H), 7.19-7.21 (m, 1H), 7.26-7.31 (m, 3H), 7.34-7.38 (m, 1H), 7.42-7.49 (m, 3H) |
| 26 | 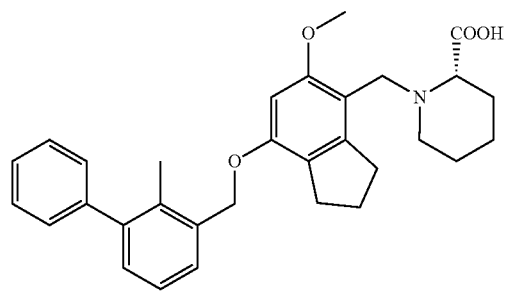 [SMILES: COc1cc(OCc2cccc(-c3ccccc3)c2C)c2c(c1CN1CCCC[C@H]1C(=O)O)CCC2]<br>(S)-1-((5-methoxy-7-((2-methyl-[1,1'-biphenyl]-3-yl)methoxy)-2,3-dihydro-1H-inden-4-yl)methyl)piperidine-2-carboxylic acid | 486.5 | 1.35-1.51 (m, 4H), 1.75 (bs, 2H), 1.96 (t, J = 7.2 Hz, 3H), 2.20 (s, 3H), 2.52 (s, 2H), 2.73 (t, J = 7.6 Hz, 2H), 2.68-2.78 (m, 1H), 2.79-2.93 (m, 1H), 3.10-3.11 (m, 1H), 3.71-3.74 (m, 1H), 3.78 (s, 3H), 3.82-3.84 (m, 1H), 5.17 (s, 2H), 6.64 (s, 1H), 7.18 (d, J = 7.6 Hz, 1H), 7.25-7.31 (m, 3H), 7.34-7.38 (m, 1H), 7.42-7.48 (m, 3H) |
| 27 | 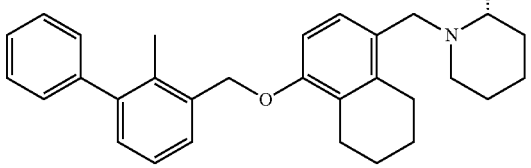<br>1-((4-((2-methyl-[1,1'-biphenyl]-3-yl)methoxy)-5,6,7,8-tetrahydronaphthalen-1-yl)methyl)piperidine-2-carboxylic acid | 468.2 | 1.47(bs, 2H), 1.63-1.70 (m, 8H), 2.03 (bs, 2H), 2.18 (s, 3H), 2.65 (bs, 2H), 2.80-2.89 (m, 1H), 3.07 (bs, 1H), 3.86 (bs, 2H), 4.21 (bs, 1H), 5.13 (s, 2H), 6.86-7.14 (m, 1H), 7.19-7.26 (m, 2H), 7.27-7.38 (m, 4H), 7.42-.47 (m, 3H) 1.47 (bs, 2H), 1.63-1.70 (m, 8H), 2.03 (bs, 2H), 2.18 (s, 3H), 2.65 (bs, 3H), 2.80-2.89 (m, 2H), 3.07 (bs, 1H), 3.86 (bs, 2H), 4.21 (bs, 1H), 5.13 (s, 1H), 6.86-7.14 (m, 1H), 7.19-7.26 (m, 2H), 7.27-7.38 (m, 4H), 7.42-.47 (m, 3H) |

TABLE 2-continued

| S. No. | Structure | LCMS m/z [M + H]+ | 1H NMR (400 MHz, DMSO-d6) δ ppm |
|---|---|---|---|
| 28 | N-(2-(((6-methyl-7-((2-methyl-[1,1'-biphenyl]-3-yl)methoxy)-2,3-dihydro-1H-inden-4-yl)methyl)amino)ethyl)acetamide | 443.20 | 1.96-1.99 (m, 2H), 2.18 (s, 3H), 2.79-2.81 (m, 4H), 3.26-3.31 (m, 6H), 4.58 (s, 4H), 5.11 (s, 2H), 6.85 (bs, 1H), 6.99 (bs, 1H), 7.16-7.18 (m, 1H), 7.24-7.38 (m, 4H), 7.42-7.44 (m, 3H) |
| 29 | (2S,4R)-4-hydroxy-1-((6-methyl-7-((2-methyl-[1,1'-biphenyl]-3-yl)methoxy)-2,3-dihydro-1H-inden-4-yl)methyl)pyrrolidine-2-carboxylic acid | 472.18 | 1.99 (m, 4H), 2.19 (s, 3H), 2.23 (s, 3H), 2.43 (m, 1H), 2.83-2.93 (m, 5H), 3.16 (m, 1H), 3.50 (m, 1H), 3.60 (d, J = 12.8 Hz, 1H), 3.99 (d, J = 12.8 Hz, 1H), 4.21 (bs, 1H), 4.95 (s, 2H), 5.01 (bs, 1H), 6.99 (s, 1H), 7.19 (d, J = 7.2 Hz, 1H), 7.27-7.32 (m, 3H), 7.37 (m, 1H), 7.44-7.49 (m, 3H). |
| 30 | N-(2-(((6-chloro-7-((2-methyl-[1,1'-biphenyl]-3-yl)methoxy)-2,3-dihydro-1H-inden-4-yl)methyl)amino)ethyl)acetamide | 463.17 | 1.79 (s, 3H), 2.01 (m, 2H), 2.27 (s, 3H), 2.54 (m, 2H), 2.83 (m, 2H), 2.89 (m, 2H), 3.14 (m, 2H), 3.60 (s, 2H), 5.03 (s, 2H), 7.19 (d, J = 7.2 Hz, 1H), 7.26-7.32 (m, 4H), 7.38 (m, 1H), 7.44-7.48 (m, 3H), 7.80 (bs, 1H). |
| 31 | (2S,4R)-1-((6-chloro-7-((2-methyl-[1,1'-biphenyl]-3-yl)methoxy)-2,3-dihydro-1H-inden-4-yl)methyl)-4-hydroxypyrrolidine-2-carboxylic acid | 492.09 | 1.99 (m, 4H), 2.27 (s, 3H), 2.23 (m, 1H), 2.83-2.93 (m, 4H), 3.16 (m, 1H), 3.50 (m, 1H), 3.60 (d, J = 12.8 Hz, 1H), 3.99 (d, J = 12.8 Hz, 1H), 4.21 (bs, 1H), 4.9 (bs, 1H), 5.05 (s, 2H), 7.21 (d, J = 7.2 Hz, 1H), 7.28 (s, 2H), 7.29-7.32 (m, 2H), 7.37 (m, 1H), 7.44-7.49 (m, 3H), 11.0-13.0 (bs, 1H). |

TABLE 2-continued

| S. No. | Structure | LCMS m/z [M + H]+ | 1H NMR (400 MHz, DMSO-d6) δ ppm |
|---|---|---|---|
| 32 | N-(2-(((7-(((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)amino)ethyl)acetamide | 636.92 | 1.76 (s, 3H), 1.82 (s, 3H) 1.87-2.00 (m, 5H), 2.01 (s 3H), 2.20-2.28 (m, 4H), 2.75-2.59 (m, 6H), 2.83-2.92 (m, 4H), 3.06 (m, 2H), 3.55 (s, 2H), 3.76 (s, 3H), 4.05 (m, 2H), 5.16 (s, 2H), 6.59 (s, 1H), 6.68 (d, J = 7.48 Hz, 1H), 6.96 (d, J = 8.16 Hz, 1H), 7.06 (d, J = 7.36 Hz, 1H), 7.17-7.28 (m, 2H), 7.47 (bs, 1H). |
| 33 | (2S,4R)-1-((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)-4-hydroxypyrrolidine-2-carboxylic acid | 665.241 | 1.82 (s, 2H), 1.90-2.09 (m, 8H), 2.10-2.30 (m, 4H), 2.55-3.00 (m, 11H), 3.10-3.49 (bs, 2H), 3.60 (m, 1H), 3.83 (s, 3H), 4.00-4.09 (m, 4H), 4.11 (m, 1H), 5.20 (m, 3H), 6.86 (m, 2H), 6.96 (d, J = 8.16 Hz, 1H), 7.06 (d, J = 7.36 Hz, 1H), 7.17-7.28 (m, 2H), 7.47 (d, J = 7.52 Hz, 1H). |

TABLE 2-continued

| S. No. | Structure | LCMS m/z [M + H]+ | ¹H NMR (400 MHz, DMSO-d₆) δ ppm |
|---|---|---|---|
| 34 | 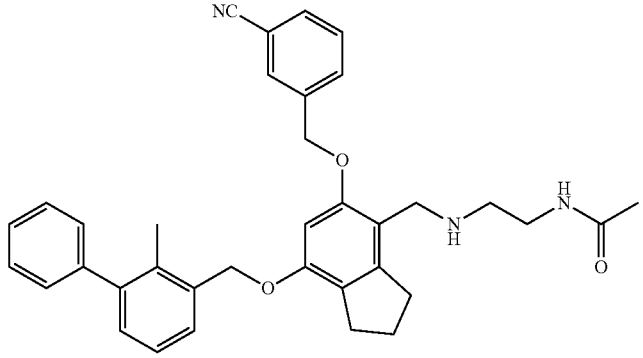 [SMILES: CC(=O)NCCNCc1c(OCc2cccc(C#N)c2)cc(OCc2cccc(-c3ccccc3)c2C)c2c1CCC2]<br>N-(2-(((5-((3-cyanobenzyl)oxy)-7-((2-methyl-[1,1'-biphenyl]-3-yl)methoxy)-2,3-dihydro-1H-inden-4-yl)methyl)amino)ethyl)acetamide | 560.30 | 1.76 (s, 3H), 1.99 (m, 2H), 2.20 (s, 3H), 2.66 (m, 2H), 2.76 (m, 2H), 2.90 (m, 2H), 3.16 (m, 2H), 3.77 (s, 2H), 5.14 (s, 2H), 5.24 (s, 2H), 6.74 (s, 1H), 7.18 (d, J = 7.6 Hz, 1H), 7.26 (t, J = 7.6 Hz, 1H), 7.31 (d, J = 7.2 Hz, 2H), 7.36-7.48 (m, 4H), 7.61 (t, J = 7.2 Hz, 1H), 7.82 (d, J = 7.2 Hz, 2H), 7.84 (bs, 1H) 7.97 (s, 1H) |
| 35 | 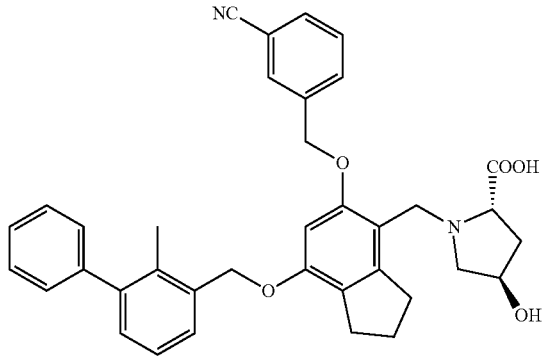 [SMILES: Cc1c(COc2cc(OCc3cccc(C#N)c3)c(CN3C[C@H](O)C[C@H]3C(=O)O)c3c2CCC3)cccc1-c1ccccc1]<br>(2S,4R)-1-((5-((3-cyanobenzyl)oxy)-7-((2-methyl-[1,1'-biphenyl]-3-yl)methoxy)-2,3-dihydro-1H-inden-4-yl)methyl)-4-hydroxypyrrolidine-2-carboxylic acid | 589.28 | 1.99-2.10 (m, 4H), 2.20 (s, 3H), 2.73 (m, 2H), 2.83-3.02 (m, 3H), 3.30 (m, 2H), 3.73 (m, 1H), 4.12-4.20 (m, 2H), 4.26 (bs, 1H), 5.16 (s, 2H), 5.31 (s, 2H), 6.78 (s, 1H), 7.19 (d, J = 7.2 Hz, 1H), 7.26 (d, J = 7.6 Hz, 1H), 7.32 (d, J = 7.2 Hz, 2H), 7.36-7.49 (m, 4H), 7.61 (t, J = 7.6 Hz, 1H), 7.80 (d, J = 7.6 Hz, 1H), 7.90 (d, J = 7.6 Hz, 1H), 8.03 (s, 1H). |
| 36 | 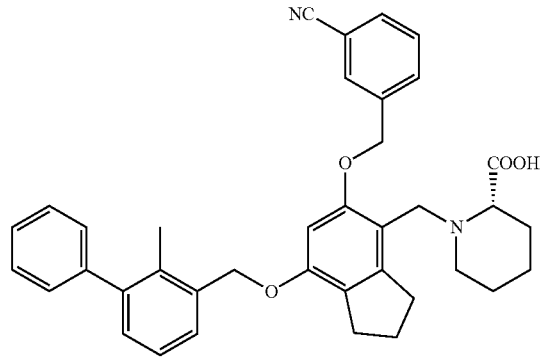 [SMILES: Cc1c(COc2cc(OCc3cccc(C#N)c3)c(CN3CCCC[C@H]3C(=O)O)c3c2CCC3)cccc1-c1ccccc1]<br>(S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxylic acid | 587.15 | 1.45 (m, 4H), 1.76 (m, 2H), 1.97 (m, 2H), 2.20 (s, 3H), 2.32 (m, 2H), 2.66-3.14 (m, 4H), 3.32 (m, 1H), 3.73 (m, 1H), 3.90 (m, 1H), 5.13 (s, 2H), 5.23 (s, 2H), 6.73 (s, 1H), 7.20 (d, J = 7.44 Hz, 1H), 7.24-7.32 (m, 3H), 7.37-7.45 (m, 4H), 7.60 (m, 1H), 7.80 (d, J = 7.26 Hz, 1H), 7.87 (d, J = 7.32 Hz, 1H), 7.98 (s, 1H). |

TABLE 2-continued

| S. No. | Structure | LCMS m/z [M + H]+ | 1H NMR (400 MHz, DMSO-d6) δ ppm |
|---|---|---|---|
| 37 | 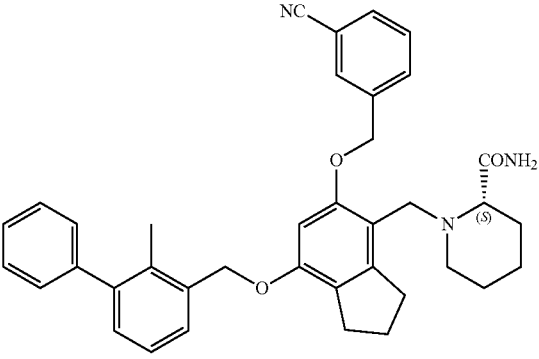<br>(S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxamide | 586.55 | 1.49-1.58 (m, 4H), 1.73 (m, 1H), 1.91-1.97 (m, 4H), 2.19 (s, 3H), 2.59-2.74 (m, 4H), 2.82 (m, 1H), 2.98 (m, 1H), 3.19 (d, J = 12.5 Hz, 1H), 3.69 (d, J = 12 Hz, 1H), 5.10 (s, 2H), 5.24 (s, 2H), 6.69 (s, 1H), 6.95 (bs, 1H), 7.06 (bs, 1H), 7.19 (m, 1H), 7.25 (m, 1H), 7.32 (m, 2H), 7.36-7.47 (m, 4H), 7.59 (m, 1H), 7.78-7.82 (m, 2H), 7.93 (s, 1H). |
| 38 | 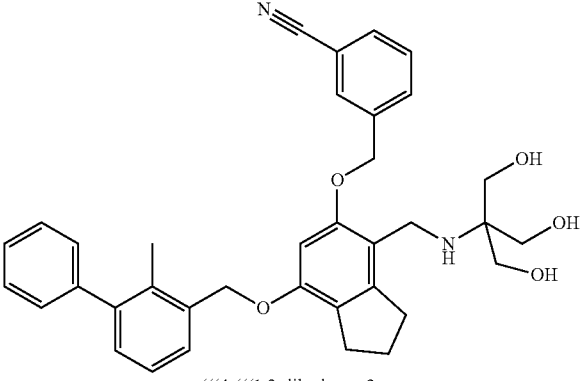<br>(((4-(((1,3-dihydroxy-2-(hydroxymethyl)propan-2-yl)amino)methyl)-7-((2-methyl-[1,1'-biphenyl]-3-yl)methoxy)-2,3-dihydro-1H-inden-5-yl)oxy)methyl)benzonitrile | 579.39 | 1.97 (m, 2H), 2.19 (s, 3H), 2.74 (m, 2H), 2.90 (m, 2H), 3.41 (s, 6H), 3.69 (bs, 2H), 4.22 (bs, 3H), 5.13 (s, 2H), 5.21 (s, 2H), 6.72 (s, 1H), 7.19 (m, 1H), 7.25 (m, 1H), 7.32 (m, 2H), 7.36-7.47 (m, 4H), 7.59 (m, 1H), 7.78 (d, J = 7.96 Hz, 1H), 7.90 (d, J = 7.88 Hz, 1H), 7.97 (s, 1H). |
| 39 | 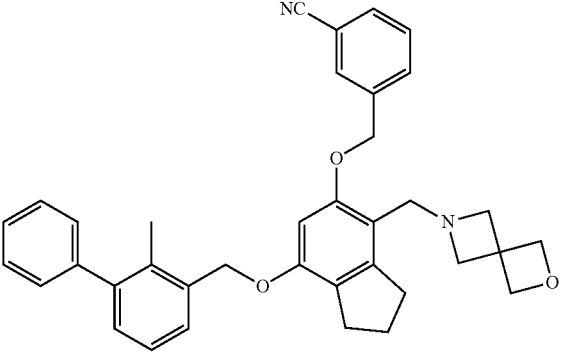 [SMILES: Cc1c(COc2cc(OCc3cccc(C#N)c3)c(CN3CC4(COC4)C3)c3c2CCC3)cccc1-c1ccccc1]<br>3-(((4-((2-oxa-6-azaspiro[3.3]heptan-6-yl)methyl)-7-((2-methyl-[1,1'-biphenyl]-3-yl)methoxy)-2,3-dihydro-1H-inden-5-yl)oxy)methyl)benzonitrile | 557.41 | 1.97 (m, 2H), 2.19 (s, 3H), 2.74 (m, 2H), 2.86 (m, 2H), 3.23 (m, 2H), 3.31 (m, 2H), 3.45 (m, 2H), 4.55 (s, 4H), 5.13 (s, 2H), 5.22 (s, 2H), 6.72 (s, 1H), 7.19 (m, 1H), 7.25 (m, 1H), 7.32 (m, 2H), 7.39-7.47 (m, 4H), 7.62 (m, 1H), 7.84 (m, 2H), 7.98 (s, 1H). |

TABLE 2-continued

| S. No. | Structure | LCMS m/z [M + H]+ | 1H NMR (400 MHz, DMSO-d6) δ ppm |
|---|---|---|---|
| 40 | 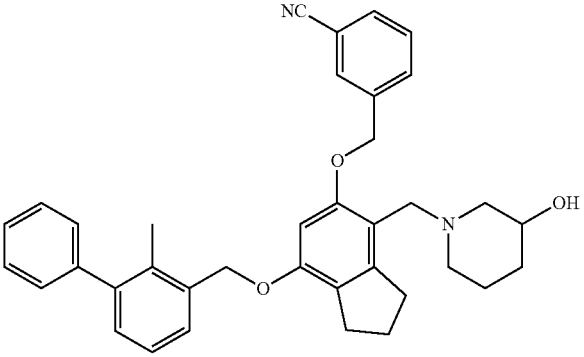 [SMILES: Cc1c(COc2cc(OCc3cccc(C#N)c3)c(CN3CCCC(O)C3)c3c2CCC3)cccc1-c1ccccc1]<br>(((4-((3-hydroxypiperidin-1-yl)methyl)-7-((2-methyl-[1,1'-biphenyl]-3-yl)methoxy)-2,3-dihydro-1H-inden-5-yl)oxy)methyl)benzonitrile | 559.41 | 1.23-1.33 (m, 4H), 1.35 (m, 1H), 1.56 (m, 1H), 1.69-1.84 (m, 3H), 1.98 (m, 2H), 2.21 (s, 3H), 2.74-2.76 (m, 3H), 2.87 (m, 2H), 3.45 (m, 1H), 4.49 (bs, 1H), 5.13 (s, 2H), 5.21 (s, 2H), 6.72 (s, 1H), 7.20 (d, J = 7.32 Hz, 1H), 7.25-7.32 (m, 3H), 7.39 (m, 1H), 7.44-7.47 (m, 3H), 7.63 (m, 1H), 7.80 (d, J = 7.68 Hz, 1H), 7.85 (d, J = 7.85 Hz, 1H), 7.94 (s, 1H). |
| 41 | 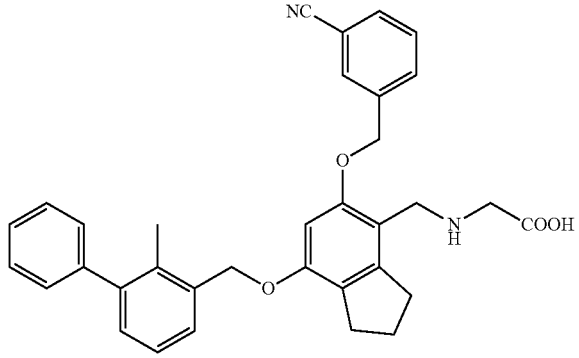 [SMILES: Cc1c(COc2cc(OCc3cccc(C#N)c3)c(CNCC(=O)O)c3c2CCC3)cccc1-c1ccccc1]<br>((5-((3-cyanobenzyl)oxy)-7-((2-methyl-[1,1'-biphenyl]-3-yl)methoxy)-2,3-dihydro-1H-inden-4-yl)methyl)glycine | 533.49 | 2.00 (m, 2H), 2.19 (s, 3H), 2.76 (m, 2H), 2.92 (m, 2H), 3.07 (s, 2H), 3.99 (s, 2H), 5.16 (s, 2H), 5.27 (s, 2H), 6.76 (s, 1H), 7.19 (d, J = 7.44 Hz, 1H), 7.27 (m, 1H), 7.32 (d, J = 7.24 Hz, 1H), 7.36-7.47 (m, 4H), 7.60 (m, 1H), 7.81 (d, J = 7.52 Hz, 1H), 7.91 (d, J = 7.76 Hz, 1H), 8.02 (s, 1H). |
| 42 | 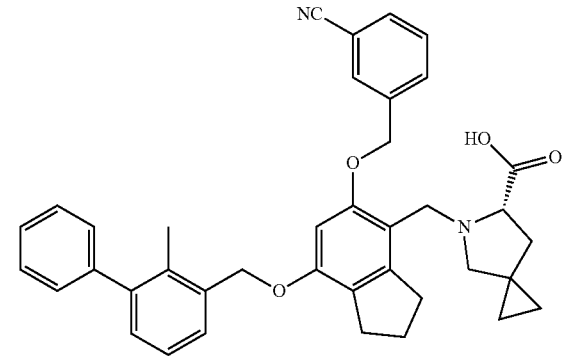 [SMILES: Cc1c(COc2cc(OCc3cccc(C#N)c3)c(CN3CC4(CC4)C[C@H]3C(=O)O)c3c2CCC3)cccc1-c1ccccc1]<br>(S)-5-((5-((3-cyanobenzyl)oxy)-7-((2-methyl-[1,1'-biphenyl]-3-yl)methoxy)-2,3-dihydro-1H-inden-4-yl)methyl)-5-azaspiro[2.4]heptane-6-carboxylic acid | 599.49 | 0.43-0.54 (m, 4H), 1.77 (m, 1H), 2.00 (m, 2H), 2.20 (s, 3H), 2.31 (m, 1H), 2.75 (m, 2H), 2.88-2.92 (m, 4H), 3.60 (m, 1H), 4.12 (m, 2H), 5.16 (m, 2H), 5.31 (m, 2H), 6.79 (s, 1H), 7.20 (d, J = 7.32 Hz, 1H), 7.27 (m, 1H), 7.32 (d, J = 7.12 Hz, 2H), 7.39 (m, 1H), 7.44-7.47 (m, 3H), 7.67 (m, 1H), 7.83 (d, J = 7.62 Hz, 1H), 7.91 (d, J =7.8 Hz, 1H), 8.02 (s, 1H). |

| S. No. | Structure | LCMS m/z [M + H]+ | 1H NMR (400 MHz, DMSO-d6) δ ppm |
|---|---|---|---|
| 43 | rac-(1R,6S)-2-((5-((3-cyanobenzyl)oxy)-7-((2-methyl-[1,1'-biphenyl]-3-yl)methoxy)-2,3-dihydro-1H-inden-4-yl)methyl)-2-azabicyclo[4.1.0]heptane-1-carboxylic acid (cis, racemic) | 599.55 | 1.20-1.40 (m, 4H), 1.58 (m, 1H), 1.71-1.79 (m, 2H), 1.95 (m, 2H), 2.19 (s, 3H), 2.32 (m, 2H), 2.72-2.79 (m, 3H), 3.00 (m, 1H), 3.60 (d, J = 12.48 Hz, 1H), 3.67 (d, J = 12.52 Hz, 1H), 5.11 (m, 2H), 5.31 (m, 2H), 6.72 (s, 1H), 7.19 (d, J = 7.12 Hz, 1H), 7.27 (m, 1H), 7.32 (d, J = 7 Hz, 2H), 7.39 (m, 2H), 7.44-7.47 (m, 2H), 7.61 (m, 1H), 7.80 (m, 2H), 7.92 (s, 1H), 11.90 (bs, 1H). |
| 44 | (((5-((3-cyanobenzyl)oxy)-7-((2-methyl-[1,1'-biphenyl]-3-yl) methoxy)-2,3-dihydro-1H-inden-4-yl)methyl)amino)butanoic acid | 561.46 | 1.66 (m, 2H), 2.00 (m, 2H), 2.23 (m, 6H), 2.76 (m, 4H), 2.93 (m, 2H), 3.81 (s, 2H), 5.16 (s, 2H), 5.24 (s, 2H), 6.76 (s, 1H), 7.26-7.45 (m, 9H), 7.61 (m, 1H), 7.80-7.85 (m, 2H), 7.99 (s, 1H). |
| 45 | (1R,6S)-2-((5-methoxy-7-((2-methyl-[1,1'-biphenyl]-3-yl) methoxy)-2,3-dihydro-1H-inden-4-yl) methyl)-2-azabicyclo[4.1.0]heptane-1-carboxylic acid (cis, racemic) | 498.49 | 1.15-1.33 (m, 2H), 1.37 (m, 2H), 1.62 (m, 1H), 1.78 (m, 1H), 2.01 (m, 2H), 2.18 (m, 3H), 2.32 (m, 1H), 2.76 (m, 2H), 2.95 (m, 1H), 3.09 (s, 1H), 3.49 (m, 2H), 3.59 (m, 2H), 3.84 (s, 3H), 5.20 (s, 2H), 6.71 (s, 1H), 7.21 (d, J = 7.44 Hz, 1H), 7.27-7.31 (m, 3H), 7.37 (m, 1H), 7.44-7.50 (m, 3H) |

Example 46

Synthesis of (S)-1-((5-((5-cyanopyridin-3-yl)methoxy)-7-((2-methyl-[1,1'-biphenyl]-3-yl)methoxy)-2,3-dihydro-1H-inden-4-yl)methyl)piperidine-2-carboxylic acid

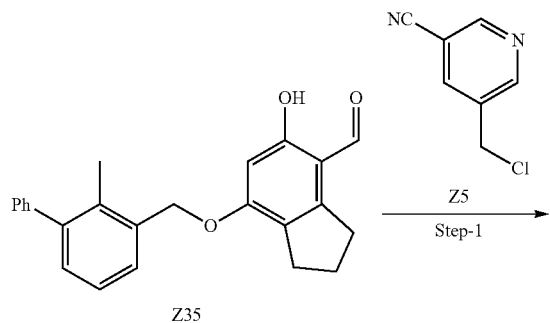

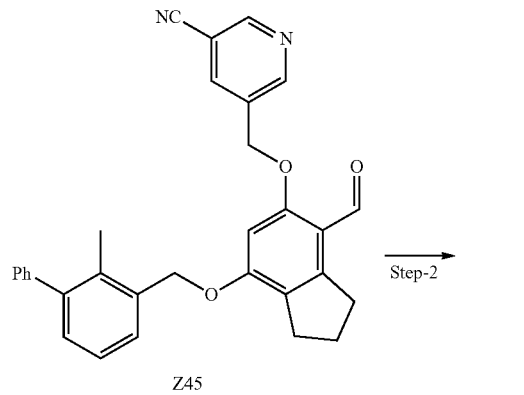

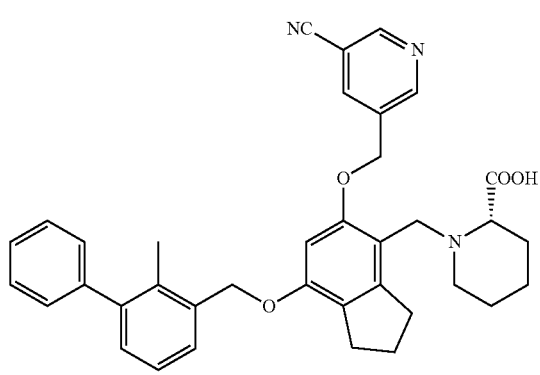

46

Step-1: To a solution of 5-hydroxy-7-((2-methyl-[1,1'-biphenyl]-3-yl)methoxy)-2,3-dihydro-1H-indene-4-carbaldehyde (0.20 g, 0.55 mmol) in acetonitrile (20 mL), potassium carbonate (0.30 g, 2.23 mmol) and 5-(chloromethyl)nicotinonitrile (5, 0.25 g, 1.67 mmol) was added and stirred the reaction mixture at RT for 16 h. After completion, the reaction mixture was diluted with water (20 mL) and extracted with EtOAc (3×30 mL). The combined organic layer was dried over sodium sulfate and concentrated. The resulting crude was purified by flash chromatography (silica gel, 4 g cartridge) using 0-30% EtOAc in hexane as eluent to obtain 5-(((4-formyl-7-((2-methyl-[1,1'-biphenyl]-3-yl)methoxy)-2,3-dihydro-1H-inden-5-yl)oxy)methyl)nicotinonitrile (Yield: 0.07 g, 26%) as white solid. LCMS (ES) m/z=475.47 [M+H]$^+$; $^1$H NMR (400 MHz, DMSO-d$_6$) δ ppm: 1.97-2.00 (m, 2H), 2.21 (s, 3H), 2.71 (m, 2H), 3.13 (m, 2H), 5.32 (s, 2H), 5.42 (s, 2H), 6.92 (s, 1H), 7.22 (d, J=7.6 Hz, 1H), 7.29-7.40 (m, 3H), 7.44-7.48 (m, 3H), 8.52 (s, 1H), 9.01 (s, 2H), 10.37 (s, 1H).

Step-6: A solution of 5-(((4-formyl-7-((2-methyl-[1,1'-biphenyl]-3-yl)methoxy)-2,3-dihydro-1H-inden-5-yl)oxy)methyl)nicotinonitrile (100 mg, 0.21 mmol), (S)-piperidine-2-carboxylic acid (40.8 mg, 0.32 mmol), sodium cyanoborohydride (66.4 mg, 1.06 mmol) and acetic acid (2 drops) in DMF (5 mL), the reaction mixture was stirred at 70° C. for 4 h. After completion, the reaction mixture was poured on ice cold water (10 mL) and collected the white solid by filtration. A solution of white solid in DCM (20 mL) was dried over sodium sulfate and concentrated. The resulting crude was purified by flash chromatography (silica gel, 4 g cartridge) using 0-10% MeOH in DCM as eluent. The product was further purified by reverse phase HPLC using method-B to obtain (S)-1-((5-((5-cyanopyridin-3-yl)methoxy)-7-((2-methyl-[1,1'-biphenyl]-3-yl)methoxy)-2,3-dihydro-1H-inden-4-yl)methyl)piperidine-2-carboxylic acid (Yield: 26 mg, 46%) as white solid. LCMS (ES) m/z=588.38 [M+H]$^+$; $^1$H NMR (400 MHz, DMSO-d$_6$) δ ppm: 1.32-1.45 (m, 4H), 1.75 (m, 2H), 1.97 (m, 2H), 2.21 (s, 3H), 2.32 (m, 1H), 2.76 (m, 2H), 2.81-3.03 (m, 3H), 3.11 (m, 1H), 3.68 (d, J=12.28 Hz, 1H), 3.88 (d, J=12.4 Hz, 1H), 5.14 (s, 2H), 5.28 (m, 2H), 6.77 (s, 1H), 7.19 (d, J=7.6 Hz, 1H), 7.25-7.33 (m, 3H), 7.39 (m, 1H), 7.44-7.47 (m, 3H), 8.48 (s, 1H), 9.01 (m, 1H).

Following compounds were prepared by following similar to above procedures

TABLE 3

| S. No. | Structure | LCMS m/z [M + H]+ | 1H NMR (400 MHz, DMSO-d6) δ ppm |
|---|---|---|---|
| 47 | 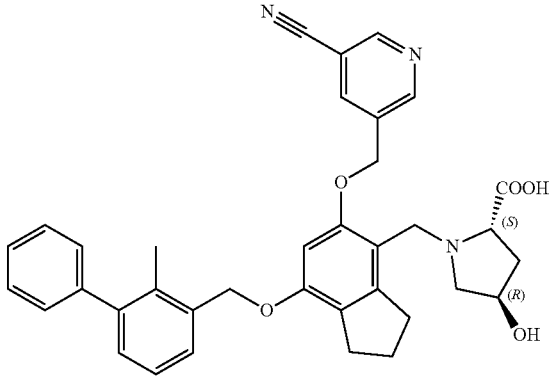<br>(2S,4R)-1-((5-((5-cyanopyridin-3-yl)methoxy)-7-((2-methyl-[1,1'-biphenyl]-3-yl)methoxy)-2,3-dihydro-1H-inden-4-yl)methyl)-4-hydroxypyrrolidine-2-carboxylic acid | 590.35 | 1.96-2.10 (m, 5H), 2.20 (s, 3H), 2.73 (m, 2H), 2.83-3.02 (m, 2H), 3.27 (bs, 1H), 3.66 (m, 1H), 4.16 (m, 2H), 4.23 (m, 1H), 5.18 (m, 3H), 5.36 (m, 2H), 6.81 (s, 1H), 7.20 (m, 1H), 7.29 (m, 1H), 7.33 (m, 2H), 7.36-7.47 (m, 4H), 8.53 (s, 1H), 9.03 (m, 2H) |
| 48 | 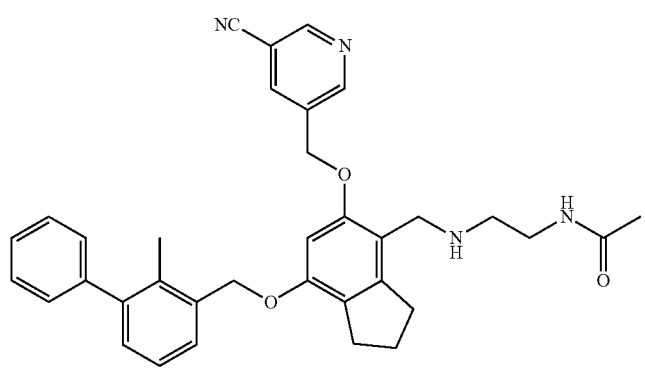 [SMILES: CC(=O)NCCNCc1c(OCc2cncc(C#N)c2)cc(OCc2cccc(-c3ccccc3)c2C)c2c1CCC2]<br>N-(2-(((5-((5-cyanopyridin-3-yl)methoxy)-7-((2-methyl-[1,1'-biphenyl]-3-yl)methoxy)-2,3-dihydro-1H-inden-4-yl)methyl)amino)ethyl)acetamide | 561.39 | 1.76 (s, 3H), 1.99 (m, 2H), 2.20 (s, 3H), 2.62 (m, 2H), 2.78 (m, 2H), 2.90 (m, 2H), 3.11-3.16 (m, 2H), 3.73 (s, 2H), 5.15 (s, 2H), 5.28 (s, 2H), 6.76 (s, 1H), 7.18 (d, J = 7.6 Hz, 1H), 7.24 (t, J = 7.6 Hz, 1H), 7.31 (d, J = 7.2 Hz, 2H), 7.36-7.48 (m, 4H), 7.80 (bs, 1H), 8.43 (s, 1H), 8.99 (s, 2H). |
| 49 | 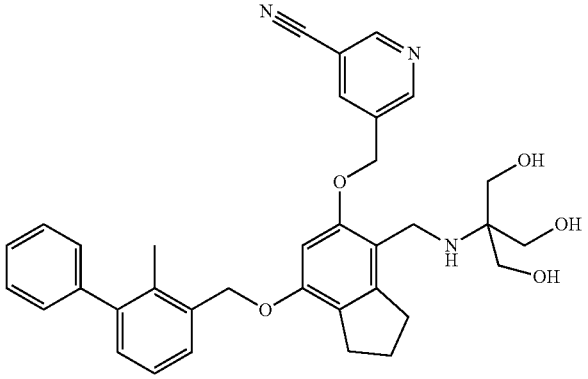 [SMILES: Cc1c(COc2cc(OCc3cncc(C#N)c3)c(CNC(CO)(CO)CO)c3c2CCC3)cccc1-c1ccccc1]<br>(((4-(((1,3-dihydroxy-2-(hydroxymethyl)propan-2-yl)amino)methyl)-7-((2-methyl-[1,1'-biphenyl]-3-yl)methoxy)-2,3-dihydro-1H-inden-5-yl)oxy)methyl)nicotinonitrile | 579.39 | 1.97 (m, 2H), 2.20 (s, 3H), 2.77 (m, 2H), 2.91 (m, 2H), 3.39 (s, 6H), 3.66 (bs, 2H), 4.00-4.50 (bs, 3H), 5.14 (s, 2H), 5.26 (s, 2H), 6.75 (s, 1H), 7.17 (m, 1H), 7.28 (m, 1H), 7.36 (m, 2H), 7.39 (m, 1H), 7.43-7.47 (m, 3H), 8.45 (s, 1H), 9.00 (s, 2H). |

TABLE 3-continued

| S. No. | Structure | LCMS m/z [M + H]+ | 1H NMR (400 MHz, DMSO-d6) δ ppm |
|---|---|---|---|
| 50 | (S)-4-((5-((5-cyanopyridin-3-yl)methoxy)-7-((2-methyl-[1,1'-biphenyl]-3-yl)methoxy)-2,3-dihydro-1H-inden-4-yl)methyl)morpholine-3-carboxylic acid | 588.42 | 1.98 (m, 2H), 2.21 (s, 3H), 2.87 (m, 2H), 2.92-2.94 (m, 1H), 2.96-3.00 (m, 2H), 3.09 (bs, 1H), 3.43 (m, 1H), 3.50-3.64 (m, 4H), 3.80 (m, 2H), 5.14 (s, 2H), 5.26 (m, 2H), 6.75 (s, 1H), 7.20 (d, J = 7.28 Hz, 1H), 7.28 (m, 1H), 7.33 (d, J = 7.04 Hz, 2H), 7.37 (m 1H), 7.39-7.47 (m, 3H), 8.44 (s, 1H), 9.01 (d, J = 10.5 Hz, 2H), 12.32 (bs, 1H). |
| 51 | rac-(1R,6S)-2-((5-((5-cyanopyridin-3-yl)methoxy)-7-((2-methyl-[1,1'-biphenyl]-3-yl)methoxy)-2,3-dihydro-1H-inden-4-yl)methyl)-2-azabicyclo[4.1.0]heptane-1-carboxylic acid (cis, racemic) | 600.57 | 1.09-1.40 (m, 4H), 1.56 (m, 1H), 1.70 (m, 1H), 1.78 (m, 1H), 1.96-1.99 (m, 2H), 2.20 (s, 3H), 2.32-2.40 (m, 2H), 2.73-2.82 (m, 3H), 2.99-3.05 (m, 1H), 3.63 (m, 2H), 5.15 (s, 2H), 5.32 (s, 2H), 6.78 (s, 1H), 7.19 (d, J = 7.28 Hz, 1H), 7.27 (m, 1H), 7.33 (d, J = 7.04 Hz, 2H), 7.37-7.47 (m, 4H), 8.41 (s, 1H), 8.96 (m, 1H), 8.99 (m, 2H), 11.73 (bs, 1H). |
| 52 | (S)-5-((5-((5-cyanopyridin-3-yl)methoxy)-7-((2-methyl-[1,1'-biphenyl]-3- | 600.52 | 0.41 (m, 1H), 0.53 (m, 3H), 1.75-1.79 (m, 1H), 1.99-2.01 (m, 2H), 2.21 (s, 3H), 2.31 (m, 1H), 2.76 (m, 2H), 2.89-3.31 (m, 4H), 3.60 (m, 1H), 4.13 (m, 2H), 5.18 (m, 2H), 5.33 (m, 2H), 6.83 (s, 1H), 7.19 (m, 1H), 7.29 (m, 1H), 7.33 (m, 2H), 7.38 (m, 1H), 7.40-7.48 (m, 3H), 8.55 (s, 1H), 9.02 (m, 1H), 9.05 (m, 1H) | yl)methoxy)-2,3-dihydro-
1H-inden-4-yl)methyl)-5-
azaspiro[2.4]heptane-6-
carboxylic acid Synthesis of N-(2-(((5-((3-cyanobenzyl)oxy)-7-((2-methyl-[1,1'-biphenyl]-3-yl)methoxy)-2,3-dihydro-1H-inden-4-yl)methyl)(methyl)amino)ethyl)acetamide

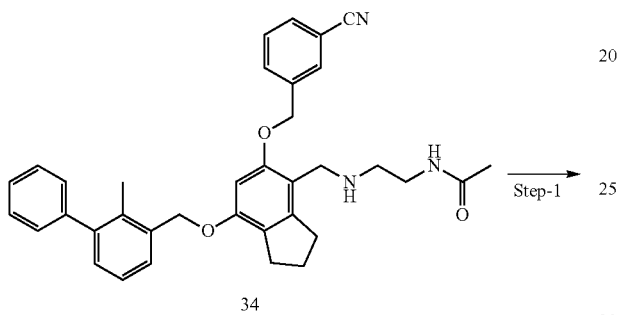

34

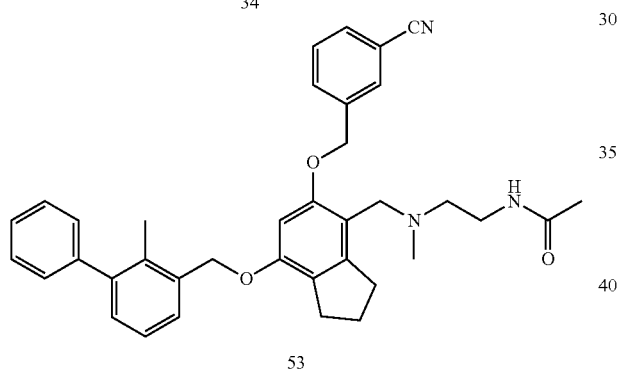

53

Step-1: To a stirred solution of N-(2-(((5-((3-cyanobenzyl)oxy)-7-((2-methyl-[1,1'-biphenyl]-3-yl)methoxy)-2,3-dihydro-1H-inden-4-yl)methyl)amino)ethyl)acetamide (1, 0.3 g, 0.523 mmol) in DMF (8 mL), formaldehyde (64.4 mg, 2.14 mmol) and formic acid (98 mg, 2.14 mmol) were added and stirred for 15 minutes. To this mixture, sodium cyanoborohydride (133 mg, 2.14 mmol) was added and stirred the reaction mixture for 4 h at room temperature. After completion, the reaction mixture was diluted with water (10 mL) and extracted with 10% DCM in MeOH (3×25 mL). The combined organic layer was dried over anhydrous sodium sulfate and concentrated. The crude residue was purified by flash chromatography (silica gel, 4 g cartridge) using 0-10% MeOH in DCM as eluent followed by recrystallized from THF and pentane to obtain N-(2-(((5-((3-cyanobenzyl)oxy)-7-((2-methyl-[1,1'-biphenyl]-3-yl)methoxy)-2,3-dihydro-1H-inden-4-yl)methyl)(methyl)amino)ethyl)acetamide (Yield: 68 mg, 21%) as white solid. LCMS (ES) m/z=574.60 [M+H]$^+$; $^1$H NMR (400 MHz, DMSO-d$_6$) δ ppm: 1.72 (s, 3H), 1.95-1.99 (m, 2H), 2.09 (s, 3H), 2.21 (s, 3H), 2.36 (m, 2H), 2.74 (t, J=7.2 Hz, 2H), 2.88 (t, J=7.4 Hz, 2H), 3.12 (m, 2H), 3.40 (s, 2H), 5.13 (s, 2H), 5.21 (s, 2H), 6.73 (s, 1H), 7.19 (d, J=7.6 Hz, 1H), 7.23-7.31 (m, 3H), 7.37 (m, 1H), 7.44-7.48 (m, 3H), 7.59-7.63 (m, 2H), 7.81 (t, J=8.4 Hz, 2H), 7.95 (s, 1H).

Example 54

Synthesis of N-(2-(((5-((4-cyanobenzyl)oxy)-7-((2-methyl-[1,1'-biphenyl]-3-yl)methoxy)-2,3-dihydro-1H-inden-4-yl)methyl)amino)ethyl)acetamide

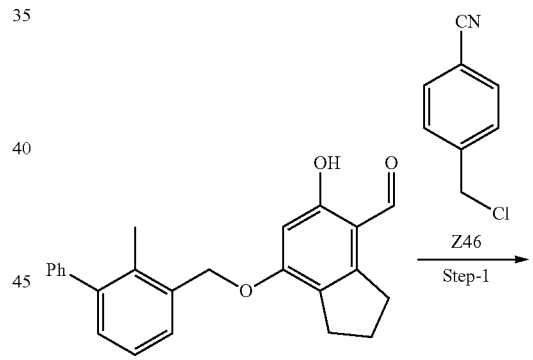

Z35

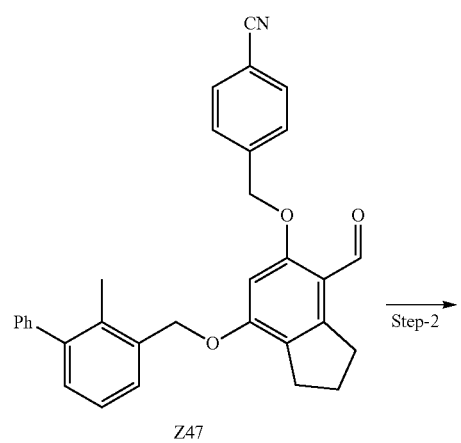

Z47

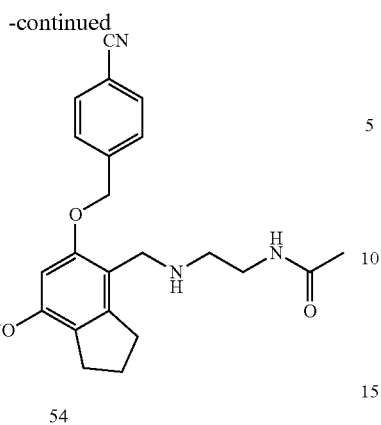

54

Step-1: Preparation of 4-(((4-formyl-7-((2-methyl-[1,1'-biphenyl]-3-yl)methoxy)-2,3-dihydro-1H-inden-5-yl)oxy)methyl)benzonitrile To a solution of 5-hydroxy-7-((2-methyl-[1,1'-biphenyl]-3-yl)methoxy)-2,3-dihydro-1H-indene-4-carbaldehyde (1, 0.30 g, 0.83 mmol) in DMF (10 mL), potassium carbonate (0.34 g, 2.4 mmol) and 4-(chloromethyl)benzonitrile (0.16 g, 0.83 mmol) was added and stirred the reaction mixture at RT for 16 h. After completion, the reaction mixture was diluted with water (20 mL) and extracted with EtOAc (3×30 mL). The combined organic layer was dried over sodium sulfate and concentrated. The resulting crude was purified by flash chromatography (silica gel, 4 g cartridge) using 0-30% EtOAc in hexane as eluent to obtain 3-(((4-formyl-7-((2-methyl-[1,1'-biphenyl]-3-yl)methoxy)-2,3-dihydro-1H-inden-5-yl)oxy)methyl)benzonitrile (Yield: 0.35 g, 89.27%) as white solid.

LCMS (ES) m/z=474.41 [M+H]+; 1H NMR (400 MHz, DMSO-d6) δ ppm: 2.00 (m, 2H), 2.21 (s, 3H), 2.70 (t, J=7.2 Hz, 2H), 3.13 (t, J=7.2 Hz, 2H), 5.30 (s, 2H), 5.38 (s, 2H), 6.92 (s, 1H), 7.22 (d, J=7.6 Hz, 1H), 7.27-7.33 (m, 3H), 7.38 (m, 1H), 7.44-7.48 (m, 3H), 7.63 (t, J=7.6 Hz, 1H), 7.85 (m, 2H), 8.01 (s, 1H), 10.39 (s, 1H).

Step-2: N-(2-(((5-((4-cyanobenzyl)oxy)-7-((2-methyl-[1,1'-biphenyl]-3-yl)methoxy)-2,3-dihydro-1H-inden-4-yl)methyl)amino)ethyl)acetamide A solution of 4-(((4-formyl-7-((2-methyl-[1,1'-biphenyl]-3-yl)methoxy)-2,3-dihydro-1H-inden-5-yl) oxy)methyl) benzonitrile (150 mg, 0.31 mmol), N-(2-aminoethyl)acetamide (32 mg, 0.31 mmol), and acetic acid (2 drops) in DMF (3 mL) and MeOH (3 mL) was stirred at RT for 2 h. To this mixture, sodium cyanoborohydride (60 mg, 0.93 mmol) was added and stirred the reaction mixture for 16 h. After completion, the reaction mixture was poured on ice cold water (10 mL) and collected the white solid by filtration. A solution of white solid in DCM (20 mL) was dried over sodium sulfate and concentrated. The resulting crude was purified by flash chromatography (silica gel, 4 g cartridge) using 0-10% MeOH in DCM as eluent to obtain N-(2-(((5-((4-cyanobenzyl)oxy)-7-((2-methyl-[1,1'-biphenyl]-3-yl) methoxy)-2,3-dihydro-1H-inden-4-yl)methyl)amino)ethyl) acetamide (Yield: 90 mg, 52%) as white solid. LCMS (ES) m/z=560.49 [M+H]+; 1H NMR (400 MHz, DMSO-d6) δ ppm: 1.77 (m, 3H), 1.99 (m, 2H), 2.20 (s, 3H), 2.74-2.78 (m, 4H), 2.90 (m, 2H), 3.21 (m, 2H), 3.85 (bs, 2H), 5.14 (m, 2H), 5.29 (s, 2H), 6.74 (s, 1H), 7.20 (d, J=7.48 Hz, 1H), 7.25 (t, J=7.6 Hz, 1H), 7.31 (d, J=7.08 Hz, 2H), 7.36-7.48 (m, 4H), 7.70 (d, J=5.92 Hz, 2H), 7.87 (d, J=8.16 Hz, 2H), 7.92 (bs, 1H).

Example 55

Synthesis of (S)-1-((7-((2-cyano-[1,1'-biphenyl]-3-yl)methoxy)-5-methoxy-2,3-dihydro-1H-inden-4-yl) methyl)piperidine-2-carboxylicacid

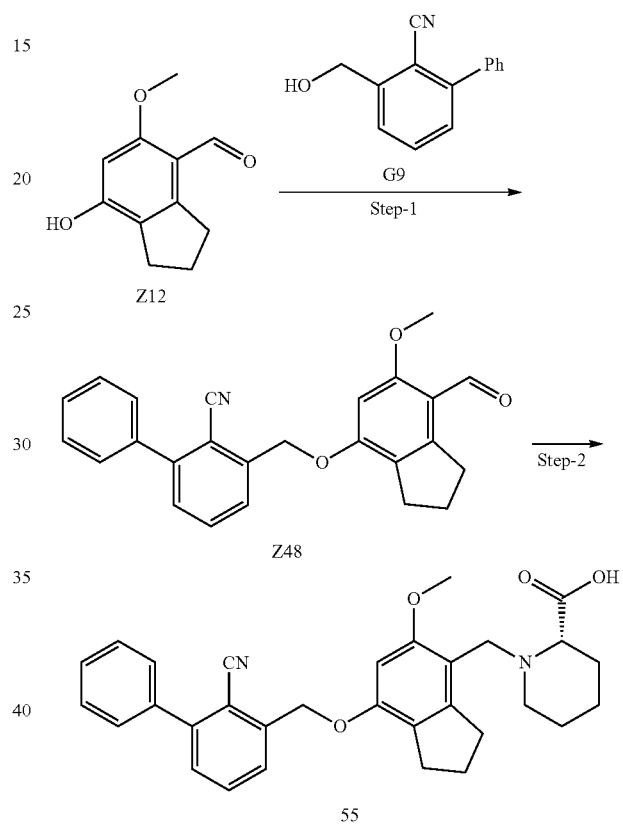

55

Step-1: To a solution of 7-hydroxy-5-methoxy-2,3-dihydro-1H-indene-4-carbaldehyde (918 mg, 4.7 mmol) and 3-(hydroxymethyl)-[1,1'-biphenyl]-2-carbonitrile (1.0 g, 4.7 mmol) in dry THF (30 mL), triphenyl phosphine (3 g, 0.035 mol) was added and cooled the mixture to 0° C. To this mixture, DEAD (266 mg, 0.014 mol) and stirred the mixture for 2 h. After completion, the reaction mixture was diluted with water (50 mL) and extracted with EtOAc (3×100 mL). The organic layer was dried over sodium sulphate and concentrated. The resulting crude was purified by flash chromatography (silica gel, 12 g cartridge) using 0-20% EtOAc in hexanes as eluent to obtain 3-(((7-formyl-6-methoxy-2,3-dihydro-1H-inden-4-yl)oxy)methyl)-[1,1'-biphenyl]-2-carbonitrile (Yield: 450 mg, 24.5%) as white solid. LCMS (ES) m/z=384.44 [M+H]+; 1H NMR (400 MHz, DMSO-d6) δ ppm: 1.95-2.01 (m, 2H), 2.71 (m, 2H), 3.11 (m, 2H), 4.04 (s, 3H), 5.50 (s, 2H), 6.79 (s, 1H), 7.48-7.65 (m, 6H), 7.78-7.84 (m, 2H), 10.30 (s, 1H).

Step-2: To a solution of 3-(((7-formyl-6-methoxy-2,3-dihydro-1H-inden-4-yl)oxy)methyl)-[1,1'-biphenyl]-2-carbonitrile (60 mg, 0.156 mmol) and (S)-piperidine-2-carboxylic acid (26 mg, 0.20 mmol) in DMF (3 mL), acetic acid (3 drops) was added and stirred the reaction mixture for 10 minutes. To this mixture, sodium cyanoborohydride (29 mg, 0.47 mmol) was added and stirred at 70° C. for 3 h. After completion, the reaction mixture was diluted with ice cold water (10 mL) and collected the resulting solid by filtration. The solid was further dissolved in DCM (30 mL) and dried over sodium sulphate and concentrated. The residue was purified by flash chromatography (silica gel, 4 g cartridge) using 0-10% MeOH in DCM as eluent to obtain (S)-1-((7-((2-cyano-[1,1'-biphenyl]-3-yl)methoxy)-5-methoxy-2,3-dihydro-1H-inden-4-yl)methyl)piperidine-2-carboxylic acid (Yield: 15 mg, 19%) as white solid. LCMS (ES) m/z=497.25 [M+H]$^+$; $^1$H NMR (400 MHz, DMSO-d$_6$) δ ppm: 1.48 (m, 4H), 1.77 (m, 2H), 1.95-2.01 (m, 2H), 2.73 (m, 2H), 2.83 (m, 1H), 2.92 (m, 1H), 3.07 (m, 2H), 3.14 (m, 1H), 3.74 (m, 1H), 3.79 (s, 3H), 3.88 (m 1H), 5.36 (s, 2H), 6.65 (s, 1H), 7.48-7.62 (m, 6H), 7.77 (t, J=7.2 Hz, 1H), 7.82 (t, J=7.6 Hz, 1H).

Following compounds were prepared by following similar to above procedures

| S. No | Structure | LCMS m/z [M + H]$^+$ | $^1$H NMR (400 MHz, DMSO-d$_6$) δ ppm |
|---|---|---|---|
| 56 | N-(2-(((7-((2-cyano-[1,1'-biphenyl]-3-yl)methoxy)-5-methoxy-2,3-dihydro-1H-inden-4-yl)methyl)amino)ethyl)acetamide | 470.32 | 1.78 (s, 3H), 1.95-1.99 (m, 2H), 2.57 (m, 2H), 2.77 (m, 2H), 2.87 (m, 2H), 3.14 (m, 2H), 3.64 (bs, 2H), 3.79 (s, 3H), 5.35 (s, 2H), 6.63 (s, 1H), 7.50-7.61 (m, 6H), 7.75-7.84 (m, 3H). |
| 57 | (2S,4R)-1-((7-((2-cyano-[1,1'-biphenyl]-3-yl)methoxy)-5-methoxy-2,3-dihydro-1H-inden-4-yl)methyl)-4-hydroxypyrrolidine-2-carboxylic acid | 499.31 | 1.95-1.99 (m, 3H), 2.09 (m, 1H), 2.77 (m, 3H), 2.87-2.99 (m, 2H), 3.26 (m, 1H), 3.65 (m, 1H), 3.84 (s, 3H), 4.08 (m, 2H), 4.23 (bs, 1H), 5.26 (bs, 1H), 5.38 (s, 2H), 6.69 (s, 1H), 7.50-7.61 (m, 6H), 7.75-7.84 (m, 2H). |
| 58 | 3-(((7-(((1,3-dihydroxy-2-(hydroxymethyl)propan-2-yl)amino)methyl)-6-methoxy-2,3-dihydro-1H-inden-4-yl)oxy)methyl)-[1,1'-biphenyl]-2-carbonitrile | 489.32 | 1.96-1.99 (m, 2H), 2.78 (m, 2H), 2.89 (m, 2H), 3.52 (bs, 7H), 3.80 (s, 3H), 4.03 (m, 2H), 4.71 (bs, 2H), 5.36 (s, 2H), 6.65 (s, 1H), 7.50-7.61 (m, 6H), 7.75-7.84 (m, 2H). |

-continued

| S. No | Structure | LCMS m/z [M + H]+ | 1H NMR (400 MHz, DMSO-d6) δ ppm |
|---|---|---|---|
| 59 | (S)-4-((7-((2-cyano[1,1'-biphenyl]-3-yl)methoxy)-5-methoxy-2,3-dihydro-1H-inden-4-yl)methyl)morpholine-3-carboxylic acid | 499.34 | 1.94-1.98 (m, 2H), 2.27 (m, 1H), 2.76 (m, 2H), 2.86 (m, 1H), 2.98 (m, 2H), 3.10 (m, 1H), 3.46 (m, 1H), 3.55 (m, 1H), 3.61-3.68 (m, 3H), 3.74 (m, 1H), 3.76 (s, 3H), 5.34 (s, 2H), 6.60 (s, 1H), 7.48-7.62 (m, 6H), 7.77 (t, J = 7.2 Hz, 1H), 7.82 (t, J = 7.6 Hz, 1H). |
| 60 | ((7-((2-cyano-[1,1'-biphenyl]-3-yl)methoxy)-5-methoxy-2,3-dihydro-1H-inden-4-yl)methyl)glycine | 443.44 | 1.95-1.99 (m, 2H), 2.78 (m, 2H), 2.92 (m, 2H), 3.09 (bs, 2H), 3.84 (s, 3H), 3.93 (s, 2H), 5.39 (s, 2H), 6.69 (s, 1H), 7.50-7.62 (m, 6H), 7.75-7.84 (m, 2H). |
| 61 | (S)-5-((7-((2-cyano-[1,1'-biphenyl]-3-yl)methoxy)-5-methoxy-2,3-dihydro-1H-inden-4-yl)methyl)-5-azaspiro[2.4]heptane-6-carboxylic acid | 509.45 | 0.48 (m, 1H), 0.61 (m, 3H), 1.87 (m, 1H), 1.97-2.01 (m, 2H), 2.36 (m, 1H), 2.78 (m, 2H), 2.87-3.03 (m, 5H), 3.85 (s, 3H), 4.18 (m, 2H), 5.38 (s, 2H), 6.71 (s, 1H), 7.50-7.61 (m, 6H), 7.75-7.84 (m, 2H). |
| 62 | rac-(1R,6S)-2-((7-((2-cyano-[1,1'-biphenyl]-3-yl)methoxy)-5-methoxy-2,3-dihydro-1H-inden-4-yl)methyl)-2-azabicyclo[4.1.0]heptane-1-carboxylic acid (cis, racemic) | 509.39 | 1.19 (m, 1H), 1.25 (m, 2H), 1.37 (m, 1H), 1.62 (m, 1H), 1.78 (m, 2H), 1.97-2.01 (m, 2H), 2.21 (m, 1H), 2.30 (m, 1H), 2.66-2.78 (m, 3H), 2.93-3.03 (m, 1H), 3.48 (d, J = 12.4 Hz, 1H), 3.58 (d, J = 12.4 Hz, 1H), 3.84 (s, 3H), 5.37 (s, 2H), 6.70 (s, 1H), 7.50-7.61 (m, 6H), 7.75-7.84 (m, 2H). |

| S. No | Structure | LCMS m/z [M + H]+ | $^1$H NMR (400 MHz, DMSO-$d_6$) δ ppm |
|---|---|---|---|
| 63 | 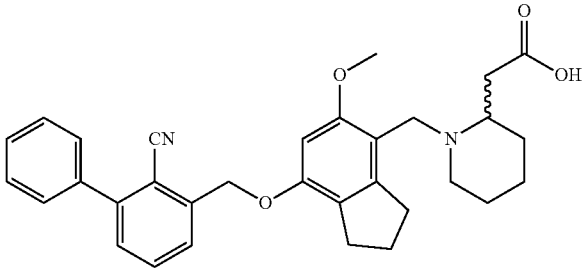 [SMILES: COc1cc(OCc2cccc(-c3ccccc3)c2C#N)c2c(c1CN1CCCCC1CC(=O)O)CCC2]  2-(1-((7-((2-cyano-[1,1'-biphenyl]-3-yl)methoxy)-5-methoxy-2,3-dihydro-1H-inden-4-yl)methyl)piperidin-2-yl)acetic acid | 511.48 | 1.37 (m, 3H), 1.59 (m, 2H), 1.84 (m, 1H), 1.97-2.01 (m, 2H), 2.13-2.19 (m, 1H), 2.39 (m, 1H), 2.66 (m, 1H), 2.78 (m, 3H), 2.84-2.99 (m, 3H), 3.66 (d, J = 12.8 Hz, 1H), 3.78 (s, 3H), 3.85 (m, 1H), 5.36 (s, 2H), 6.64 (s, 1H), 7.50-7.61 (m, 6H), 7.75-7.84 (m, 2H). |

Example-64

Synthesis of N-(2-(((7-((2-cyano-[1,1'-biphenyl]-3-yl)methoxy)-5-methoxy-2,3-dihydro-1H-inden-4-yl)methyl)(methyl)amino)ethyl)-N-methylacetamide

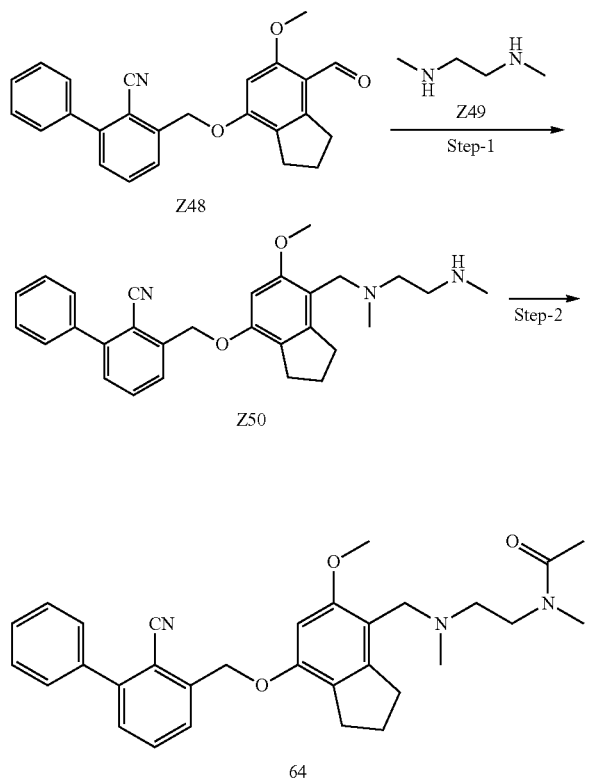

Step-1: To a solution of 3-(((7-formyl-6-methoxy-2,3-dihydro-1H-inden-4-yl)oxy)methyl)-[1,1'-biphenyl]-2-carbonitrile (250 mg, 0.65 mmol), N$^1$,N$^2$-dimethylethane-1,2-diamine (115 mg, 1.30 mmol), and acetic acid (2 drops) in DMF (3 mL)) and MeOH (3 mL), the reaction mixture was stirred at rt for 30 minutes. To this mixture, sodium cyanoborohydride (40 mg, 0.130 mmol) was added and stirred for 16 h. After completion, the reaction mixture was poured on ice cold water (10 mL) and extracted with DCM (3×50 mL) and the organic layer was dried over sodium sulfate and concentrated. The resulting crude was purified by flash chromatography (silica gel, 4 g cartridge) using 0-20% MeOH in DCM as eluent to obtain 3-(((6-methoxy-7-((methyl(2-(methylamino)ethyl)amino)methyl)-2,3-dihydro-1H-inden-4-yl)oxy)methyl)-[1,1'-biphenyl]-2-carbonitrile (Yield: 100 mg, 33%) as white solid. LCMS (ES) m/z=456.30 [M+H]+.

Step-2: To a stirred solution of 3-(((6-methoxy-7-((methyl(2-(methylamino)ethyl)amino)methyl)-2,3-dihydro-1H-inden-4-yl)oxy)methyl)-[1,1'-biphenyl]-2-carbonitrile (80 mg, 0.176 mmol), AcOH (5 drops) in DMF (5 mL), HOBt (35 mg, 0.26 mmol), EDC.HCl (50 mg, 0.26 mmol), N,N-diisopropylethylamine (68 mg, 0.53 mmol) were added and stirred the mixture for 12 h at room temperature. After completion, diluted the mixture with water (10 mL) and extracted with 10% MeOH in DCM (3×20 mL). The organic layer was dried and concentrated. The crude was purified by flash chromatography (silica gel, 4 g cartridge) using 0-10% MeOH in DCM as eluent to obtain N-(2-(((7-((2-cyano-[1,1'-biphenyl]-3-yl)methoxy)-5-methoxy-2,3-dihydro-1H-inden-4-yl)methyl)(methyl)amino)ethyl)-N-methylacetamide (Yield: 12 mg) as white solid. LCMS (ES) m/z=498.25 [M+H]+; $^1$H NMR (400 MHz, DMSO-$d_6$) δ ppm: 1.90-2.14 (m, 8H), 2.48 (m, 2H), 2.58 (m, 1H), 2.77-2.86 (m, 6H), 3.32-3.37 (bs, 3H), 3.76 (s, 3H), 3.78 (m, 1H), 5.35 (s, 2H), 6.68 (s, 1H), 7.50-7.61 (m, 6H), 7.75-7.84 (m, 3H).

Example-65

Synthesis of 5-((4-(((2-acetamidoethyl)amino)methyl)-7-((2-methyl-[1,1'-biphenyl]-3-yl)methoxy)-2,3-dihydro-1H-inden-5-yl)oxy)pentanoic acid

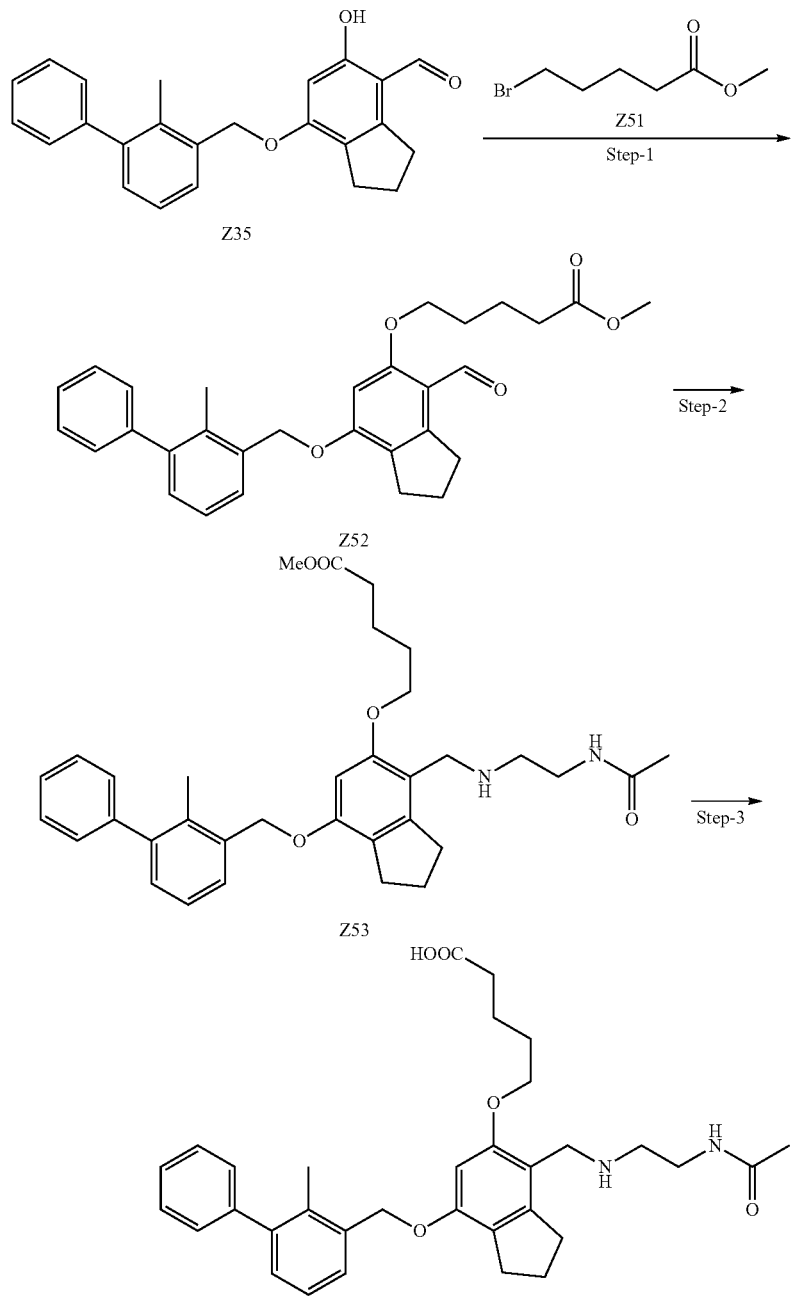

Step-1: To a solution of 5-hydroxy-7-((2-methyl-[1,1'-biphenyl]-3-yl)methoxy)-2,3-dihydro-1H-indene-4-carbaldehyde (0.40 g, 1.12 mmol) in DMF (10 mL), potassium carbonate (0.46 g, 3.38 mmol) and methyl 5-bromopentanoate (0.217 g, 1.22 mmol) was added and the reaction mixture was stirred at 60° C. for 6 h. After completion, the reaction mixture was diluted with water (20 mL) and extracted with EtOAc (3×30 mL). The combined organic layer was dried over sodium sulfate and concentrated. The resulting crude was purified by flash chromatography (silica gel, 12 g cartridge) using 20% EtOAc in hexanes as eluent to obtain methyl 5-((4-formyl-7-((2-methyl-[1,1'-biphenyl]-3-yl)methoxy)-2,3-dihydro-1H-inden-5-yl)oxy)pentanoate (Yield: 0.310 g, 58%) as white solid. LCMS (ES) m/z=473.50 [M+H]$^+$; $^1$H NMR (400 MHz, DMSO-d$_6$) δ ppm: 1.71-1.81 (m, 4H), 1.99-2.00 (m, 2H), 2.22 (s, 3H), 2.41 (m, 2H), 2.69 (m, 2H), 3.13 (m, 2H), 3.58 (s, 3H), 4.16 (m, 2H), 5.32 (s, 2H), 6.78 (s, 1H), 7.22 (d, J=8.0 Hz, 1H), 7.28-7.40 (m, 4H), 7.44-7.50 (m, 3H), 10.35 (s, 1H).

Step-2: To a solution of methyl 5-((4-formyl-7-((2-methyl-[1,1'-biphenyl]-3-yl)methoxy)-2,3-dihydro-1H-inden-5-yl)oxy)pentanoate (150 mg, 0.32 mmol), in MeOH (3 mL) and DMF (3 mL), N-(2-aminoethyl)acetamide (32.7 mg, 0.48 mmol) and acetic acid (3 drops) were added and stirred the reaction mixture for 10 minutes. To this mixture, sodium cyanoborohydride (57 mg, 0.935 mmol) was added and the mixture was stirred at room temperature for 16 h. After completion, the reaction mixture was diluted with water (10 mL) and extracted with 10% MeOH in DCM (3×30 mL). The organic layer was dried over anhydrous sodium sulphate and concentrated. The resulting crude was purified by flash chromatography (silica gel, 4 g cartridge) using 0-10% MeOH in DCM as eluent to obtain methyl 5-((4-(((2-acetamidoethyl)amino)methyl)-7-((2-methyl-[1,1'-biphenyl]-3-yl)methoxy)-2,3-dihydro-1H-inden-5-yl)oxy)pentanoate (Yield: 80 mg, 45%) as white solid. LCMS (ES) m/z=559.55 [M+H]$^+$; $^1$H NMR (400 MHz, DMSO-d$_6$) δ ppm: 1.70-1.76 (m, 4H), 1.78 (s, 3H), 1.99-2.00 (m, 2H), 2.33 (s, 3H), 2.39 (m, 2H), 2.57 (m, 2H), 2.75 (m, 2H), 2.88 (m, 2H), 3.18 (m, 2H), 3.59 (s, 3H), 3.72 (m, 2H), 4.01 (m, 2H), 5.18 (s, 2H), 6.70 (s, 1H), 7.22 (d, J=8.0 Hz, 1H), 7.28-7.40 (m, 4H), 7.44-7.48 (m, 3H), 7.86 (bs, 1H).

Step-3: To a stirred solution of methyl 5-((4-(((2-acetamidoethyl)amino)methyl)-7-((2-methyl-[1,1'-biphenyl]-3-yl)methoxy)-2,3-dihydro-1H-inden-5-yl)oxy)pentanoate (70 mg, 0.125 mmol) in THF (3 mL) and water (1.5 mL), lithium hydroxide (10.5 mg, 0.25 mmol) was added and stirred the mixture at room temperature for 16 h. After completion, the reaction mixture was diluted with water (5 mL) and acidified with 1N HCl. The aqueous mixture was extracted with EtOAc (3×20 mL) and combined organic extract was dried over sodium sulphate and concentrated. The crude was purified by flash chromatography (silica gel, 4 g cartridge) using ammoniated solution of 10% MeOH in DCM as eluent to obtain 5-((4-(((2-acetamidoethyl)amino)methyl)-7-((2-methyl-[1,1'-biphenyl]-3-yl)methoxy)-2,3-dihydro-1H-inden-5-yl)oxy)pentanoic acid (Yield: 20 mg, 29%) as white solid. LCMS (ES) m/z=545.46 [M+H]$^+$; $^1$H NMR (400 MHz, DMSO-d$_6$) δ ppm: 1.67-1.74 (m, 4H), 1.76 (s, 3H), 1.95-1.98 (m, 2H), 2.21 (s, 3H), 2.28 (m, 2H), 2.55 (m, 2H), 2.74 (m, 2H), 2.85 (m, 2H), 3.12 (m, 2H), 3.60 (s, 2H), 3.98 (m, 2H), 5.15 (s, 2H), 6.61 (s, 1H), 7.18 (d, J=7.6 Hz, 1H), 7.26-7.39 (m, 4H), 7.44-7.48 (m, 3H), 7.83 (bs, 1H).

Example-66

Synthesis of 5-((4-(((2-acetamidoethyl)amino)methyl)-7-((2-methyl-[1,1'-biphenyl]-3-yl)methoxy)-2,3-dihydro-1H-inden-5-yl)oxy)pentanamide

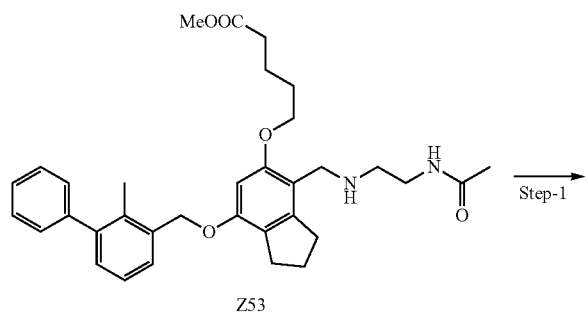

Z53

-continued

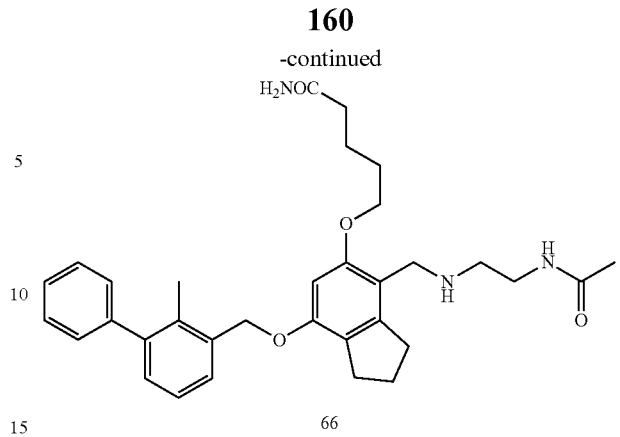

66

Step-1: To a stirred solution of methyl 5-((4-(((2-acetamidoethyl)amino)methyl)-7-((2-methyl-[1,1'-biphenyl]-3-yl)methoxy)-2,3-dihydro-1H-inden-5-yl)oxy)pentanoate (60 mg, 0.107 mmol) in MeOH (10 mL) at −60° C. in a steel bomb, ammonia gas was purged for 10 minutes, after sealing the steel bomb the mixture was heated at 60° C. and stirred for 16 h. After completion, excess ammonia was removed by flushing nitrogen gas and concentrated the reaction mixture. The crude was purified by flash chromatography (silica gel, 4 g cartridge) using 10% MeOH in DCM as eluent to obtain 5-((4-(((2-acetamidoethyl)amino)methyl)-7-((2-methyl-[1,1'-biphenyl]-3-yl)methoxy)-2,3-dihydro-1H-inden-5-yl)oxy)pentanamide (Yield: 30 mg, 51%) as white solid. LCMS (ES) m/z=544.42 [M+H]$^+$; $^1$H NMR (400 MHz, DMSO-d$_6$) δ ppm: 1.67-1.74 (m, 4H), 1.76 (s, 3H), 1.95-1.98 (m, 2H), 2.21 (s, 3H), 2.45 (m, 2H), 2.56 (m, 2H), 2.75 (m, 2H), 2.86 (m, 2H), 3.12 (m, 2H), 3.63 (s, 2H), 3.98 (m, 2H), 5.16 (s, 2H), 6.62 (s, 1H), 6.74 (bs, 1H), 7.19 (d, J=7.6 Hz, 1H), 7.26-7.39 (m, 5H), 7.44-7.48 (m, 3H), 7.80 (bs, 1H).

Example-67

Synthesis of (S)-1-((5-(4-carboxybutoxy)-7-((2-methyl-[1,1'-biphenyl]-3-yl)methoxy)-2,3-dihydro-1H-inden-4-yl)methyl)piperidine-2-carboxylic acid

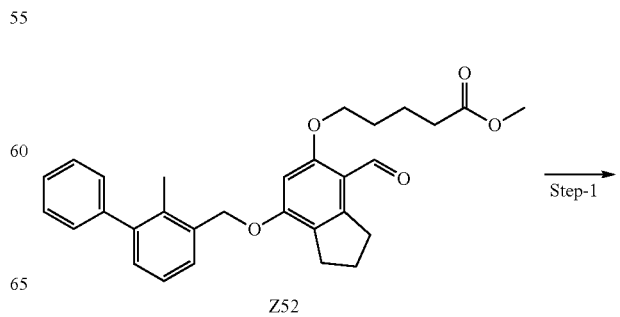

Z52

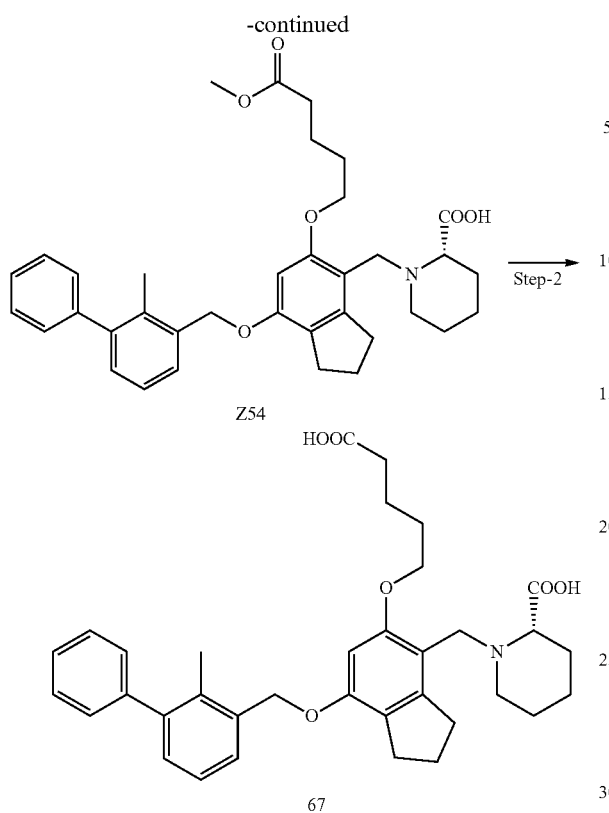

Z54

67

Step-1: To a solution of methyl 5-((4-formyl-7-((2-methyl-[1,1'-biphenyl]-3-yl)methoxy)-2,3-dihydro-1H-inden-5-yl)oxy)pentanoate (340 mg, 0.71 mmol), in MeOH (4 mL) and DMF (4 mL), (S)-piperidine-2-carboxylic acid (102 mg, 0.79 mmol) and acetic acid (3 drops) were added and stirred for 2 h. To this mixture, sodium cyanoborohydride (134 mg, 2.1 mmol) was added and the mixture was stirred at room temperature for 16 h. After completion, the reaction mixture was diluted with water (10 mL) and extracted with 10% MeOH in DCM (3×30 mL). The organic layer was dried over anhydrous sodium sulphate and concentrated. The resulting crude was purified by flash chromatography (silica gel, 4 g cartridge) using 0-10% MeOH in DCM as eluent to obtain (S)-1-((5-((5-methoxy-5-oxopentyl)oxy)-7-((2-methyl-[1,1'-biphenyl]-3-yl)methoxy)-2,3-dihydro-1H-inden-4-yl)methyl)piperidine-2-carboxylic acid (Yield: 245 mg, 59%) as light yellow solid. LCMS (ES) m/z=584.63 [M−H]$^+$; $^1$H NMR (400 MHz, DMSO-d$_6$) δ ppm: 1.45 (m, 4H), 1.74 (m, 7H), 1.96-2.00 (m, 2H), 2.21 (s, 3H), 2.39 (m, 2H), 2.75 (m, 2H), 2.80 (m, 1H), 2.95 (m, 1H), 3.05 (m, 1H), 3.11 (m, 1H), 3.59 (s, 3H), 3.75 (d, J=12.0 Hz, 1H), 3.88 (d, J=12.0 Hz, 1H), 4.00 (m, 2H), 5.20 (s, 2H), 6.64 (s, 1H), 7.19 (d, J=7.6 Hz, 1H), 7.27-7.40 (m, 4H), 7.44-7.49 (m, 3H).

Step-2: To a stirred solution of (S)-1-((5-((5-methoxy-5-oxopentyl)oxy)-7-((2-methyl-[1,1'-biphenyl]-3-yl)methoxy)-2,3-dihydro-1H-inden-4-yl)methyl)piperidine-2-carboxylic acid (70 mg, 0.11 mmol) in THF (3 mL) and water (1.5 mL), lithium hydroxide (10.5 mg, 0.23 mmol) was added and stirred the mixture at room temperature for 16 h. After completion, the reaction mixture was diluted with water (10 mL) and acidified with 1N HCl. The aqueous mixture was extracted with EtOAc (3×20 mL) and combined organic extract was dried over sodium sulphate and concentrated. The crude was purified by flash chromatography (silica gel, 4 g cartridge) using ammoniated solution of 10% MeOH in DCM as eluent to obtain (S)-1-((5-(4-carboxybutoxy)-7-((2-methyl-[1,1'-biphenyl]-3-yl)methoxy)-2,3-dihydro-1H-inden-4-yl)methyl)piperidine-2-carboxylic acid (Yield: 38 mg, 61%) as white solid. LCMS (ES) m/z=572.39 [M+H]$^+$; $^1$H NMR (400 MHz, DMSO-d$_6$) δ ppm: 1.38-1.49 (m, 4H), 1.74 (m, 6H), 1.95-1.98 (m, 2H), 2.21 (s, 3H), 2.26 (m, 2H), 2.73 (m, 2H), 2.81 (m, 1H), 3.03 (m, 2H), 3.12 (m, 2H), 3.84 (s, 2H), 3.98 (m, 2H), 5.16 (s, 2H), 6.63 (s, 1H), 7.18 (d, J=7.6 Hz, 1H), 7.26-7.39 (m, 4H), 7.44-7.49 (m, 3H).

Example-68

Synthesis of (S)-1-((5-((5-amino-5-oxopentyl)oxy)-7-((2-methyl-[1,1'-biphenyl]-3-yl)methoxy)-2,3-dihydro-1H-inden-4-yl)methyl)piperidine-2-carboxylic acid

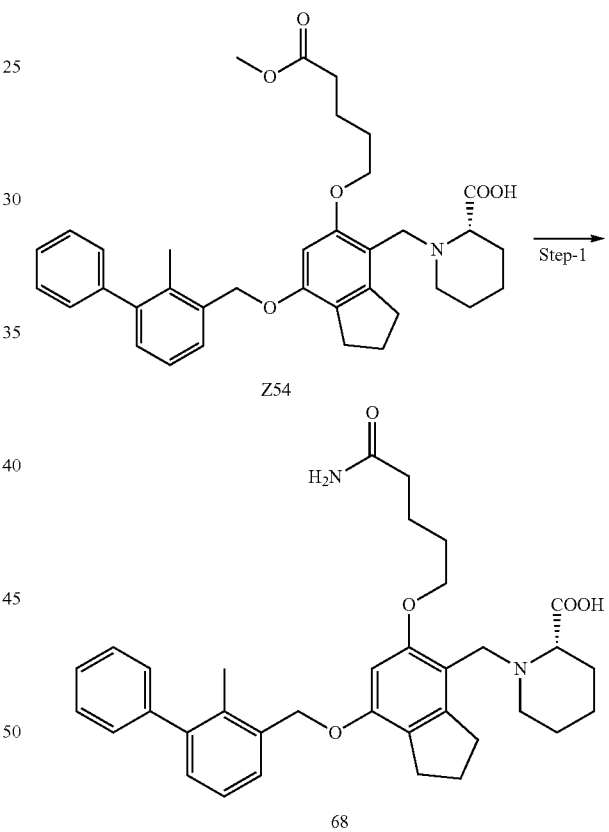

Z54

68

Step-1: To a stirred solution of (S)-1-((5-((5-methoxy-5-oxopentyl)oxy)-7-((2-methyl-[1,1'-biphenyl]-3-yl)methoxy)-2,3-dihydro-1H-inden-4-yl)methyl)piperidine-2-carboxylic acid (103 mg, 0.18 mmol) in MeOH (10 mL) at −35° C. in a steel bomb, ammonia gas was purged for 5 minutes. After sealing the steel bomb, the mixture was heated at 55° C. and stirred for 36 h. After completion, excess ammonia was removed by flushing nitrogen gas and concentrated the reaction mixture. The crude was purified by flash chromatography (silica gel, 4 g cartridge) using 8% MeOH in DCM as eluent to obtain (S)-1-((5-((5-amino-5-oxopentyl)oxy)-7-((2-methyl-[1,1'-biphenyl]-3-yl)

methoxy)-2,3-dihydro-1H-inden-4-yl)methyl)piperidine-2-carboxylic acid (Yield: 60 mg, 60%) as off-white solid. LCMS (ES) m/z=571.45 [M+H]$^+$; $^1$H NMR (400 MHz, DMSO-d$_6$) δ ppm: 1.43-1.74 (m, 5H), 1.74 (m, 4H), 1.95-1.98 (m, 3H), 2.11-2.13 (m, 2H), 2.21 (s, 3H), 2.73 (m, 2H), 2.83 (m, 1H), 3.05 (m, 2H), 3.50 (m, 2H), 3.96-4.03 (m, 4H), 5.19 (s, 2H), 6.67 (s, 1H), 6.75 (bs, 1H), 7.20 (d, J=7.6 Hz, 1H), 7.26-7.39 (m, 5H), 7.44-7.49 (m, 3H).

Example-69

Synthesis of (S)-1-((5-((5-cyanopyridin-3-yl)methoxy)-7-((2-methyl-[1,1'-biphenyl]-3-yl)methoxy)-2,3-dihydro-1H-inden-4-yl)methyl)piperidine-2-carboxylic acid

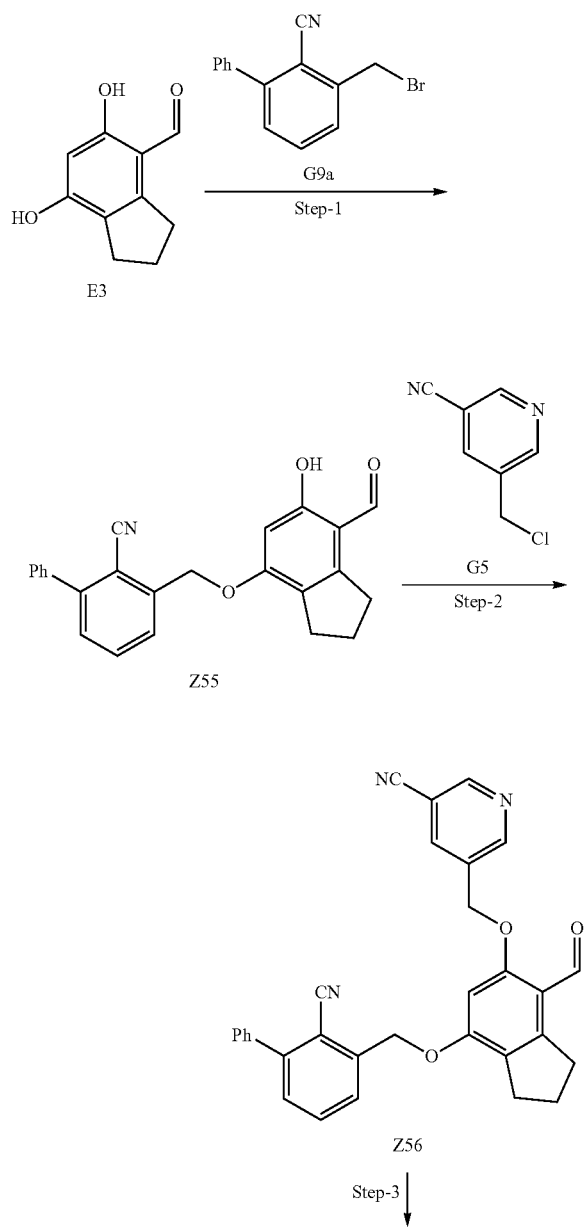

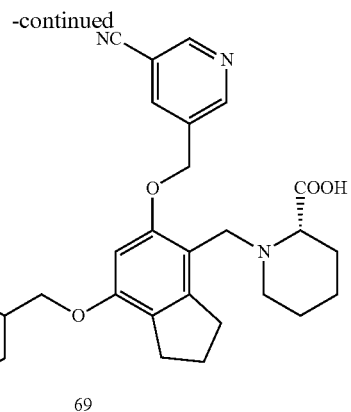

Step-1: To a solution of 5,7-dihydroxy-2,3-dihydro-1H-indene-4-carbaldehyde (0.34 g, 1.92 mmol) in acetonitrile (20 mL), potassium carbonate (0.31 g, 2.30 mmol) and 3-(bromomethyl)-[1,1'-biphenyl]-2-carbonitrile (0.50 g, 1.92 mmol) were added. The reaction mixture was stirred at room temperature for 16 h. After completion, the reaction mixture was diluted with water (20 mL) and extracted with EtOAc (3×20 mL). The combined organic layer was dried over sodium sulfate and concentrated. The resulting crude was purified by flash chromatography (silica gel, 4 g cartridge) using 0-20% EtOAc in hexane as eluent to obtain 3-(((7-formyl-6-hydroxy-2,3-dihydro-1H-inden-4-yl)oxy)methyl)-[1,1'-biphenyl]-2-carbonitrile (Yield: 0.50 g, 71%) as yellow solid. LCMS (ES) m/z=370.45 [M+H]$^+$; $^1$H NMR (400 MHz, DMSO-d$_6$) δ ppm: 2.04 (m, 2H), 2.73 (t, J=7.2 Hz, 2H), 3.14 (t, J=7.6 Hz, 2H), 5.41 (s, 2H), 6.53 (s, 1H), 7.51-7.63 (m, 6H), 7.75 (m, 1H), 7.83 (m, 1H), 10.08 (s, 1H), 11.22 (s, 1H).

Step-2: To a solution of 3-(((7-formyl-6-hydroxy-2,3-dihydro-1H-inden-4-yl)oxy)methyl)-[1,1'-biphenyl]-2-carbonitrile (0.75 g, 2.03 mmol) in DMF (15 mL), potassium carbonate (0.82 g, 6.09 mmol) and 5-(chloromethyl)nicotinonitrile (0.92 g, 6.09 mmol) was added and stirred the mixture at room temperature for 16 h. After completion, the reaction mixture was diluted with ice cold water (30 mL) and extracted with EtOAc (3×50 mL). The combined organic layer was dried over sodium sulfate and concentrated. The resulting crude was purified by column chromatography (silica gel, 100-200 mesh) using 0-50% EtOAc in hexane as eluent to obtain 5-(((7-((2-cyano-[1,1'-biphenyl]-3-yl)methoxy)-4-formyl-2,3-dihydro-1H-inden-5-yl)oxy)methyl)nicotinonitrile (Yield: 0.55 g, 57%) as off-white solid. LCMS (ES) m/z=486.50 [M+H]$^+$; $^1$H NMR (400 MHz, DMSO-d$_6$) δ ppm: 1.99-2.02 (m, 2H), 2.73 (m, 2H), 3.14 (m, 2H), 5.42 (s, 2H), 5.49 (s, 2H), 6.94 (s, 1H), 7.51-7.64 (m, 6H), 7.74 (m, 1H), 7.82 (m, 1H), 8.51 (s, 1H), 9.01 (d, J=5.2 Hz, 2H), 10.38 (s, 1H).

Step-3: To a solution of 5-(((7-((2-cyano-[1,1'-biphenyl]-3-yl)methoxy)-4-formyl-2,3-dihydro-1H-inden-5-yl)oxy)methyl)nicotinonitrile (180 mg, 0.37 mmol), (S)-piperidine-2-carboxylic acid (40 mg, 0.33 mmol) in DMF (2 mL) and MeOH (2 mL), acetic acid (2 drops) was added and stirred the mixture for 2 h. To this mixture, sodium cyanoborohydride (68 mg, 1.11 mmol) and) was added and continued stirring at room temperature for 16 h. After completion, the reaction mixture was poured on ice cold water (10 mL) and extracted with 5% MeOH in DCM (3×10 mL). The combined organic layer was dried over sodium sulfate and concentrated. The resulting crude was purified by column chromatography (silica gel, 100-200 mesh) using 0-20% MeOH in DCM as eluent to obtain (S)-1-((7-((2-cyano-[1,1'-biphenyl]-3-yl)methoxy)-5-((5-cyanopyridin-3-yl)methoxy)-2,3-dihydro-1H-inden-4-yl)methyl)piperidine-2-carboxylic acid (Yield: 30 mg, 14%) as white solid. LCMS (ES) m/z=599.55 [M+H]$^+$; $^1$H NMR (400 MHz, DMSO-d$_6$) δ ppm: 1.33-1.46 (m, 4H), 1.74 (m, 2H), 1.93-2.00 (m, 2H), 2.30 (m, 1H), 2.81 (m, 2H), 2.82-3.08 (m, 4H), 3.62 (d, J=12.4 Hz, 1H), 3.86 (d, J=12.4 Hz, 1H), 5.28 (s, 2H), 5.33 (m, 2H), 6.76 (s, 11H), 7.50-7.61 (m, 6H), 7.72 (d, J=7.2 Hz, 11H), 7.79 (t, J=7.6 Hz, 11H), 8.47 (s, 11H), 8.98 (s, 11H), 9.00 (s, 11H).

Following compounds were prepared by following similar to above procedures

TABLE 4

| S. No | Structure | LCMS m/z [M + H]$^+$ | $^1$H NMR (400 MHz, DMSO-d$_6$) δ ppm |
|---|---|---|---|
| 70 | 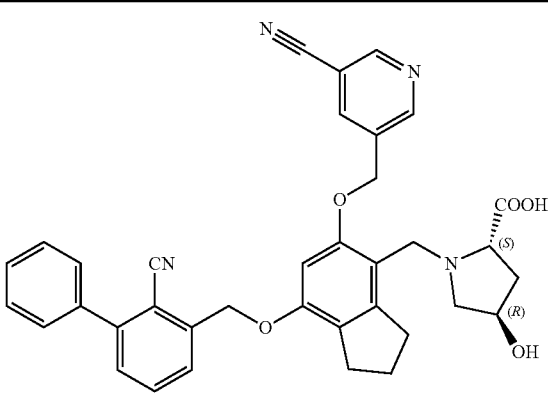 (2S,4R)-1-((7-((2-cyano-[1,1'-biphenyl]-3-yl)methoxy)-5-((5-cyanopyridin-3-yl)methoxy)-2,3-dihydro-1H-inden-4-yl)methyl)-4-hydroxypyrrolidine-2-carboxylic acid | 601.50. | 1.96-2.09 (m, 4H), 2.73-2.78 (m, 3H), 2.87-3.05 (m, 2H), 3.27 (bs, 1H), 3.66 (m, 1H), 4.16 (m, 2H), 4.23 (m, 1H), 5.19 (s, 1H), 5.29 (s, 2H), 5.35 (m, 2H), 6.81 (s, 1H), 7.51-7.62 (m, 6H), 7.72 (d, J = 7.2 Hz, 1H), 7.79 (t, J = 7.6 Hz, 1H), 8.51 (s, 1H), 8.99 (s, 1H), 9.01 (s, 1H). |
| 71 | 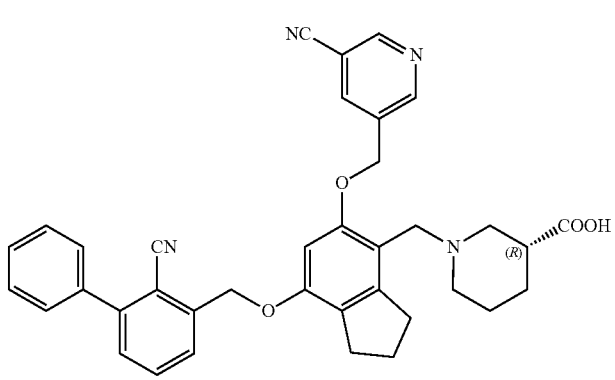 (R)-1-((7-((2-cyano-[1,1'-biphenyl]-3-yl)methoxy)-5((5-cyanopyridin-3-yl)methoxy)-2,3-dihydro-1H-inden-4-yl)methyl)piperidine-3-carboxylic acid | 599.45. | 1.33-1.42 (m, 2H), 1.58 (m, 1H), 1.76 (m, 1H), 1.96-2.01 (m, 2H), 2.10 (m, 1H), 2.20 (m, 1H), 2.33 (m, 1H), 2.56 (m, 1H), 2.78 (m, 3H), 2.88 (m, 2H), 3.42 (s, 2H), 5.26 (s, 2H), 5.33 (m, 2H), 6.76 (s, 1H), 7.49-7.61 (m, 6H), 7.72 (d, J = 7.2 Hz, 1H), 7.80 (t, J = 7.6 Hz, 1H), 8.38 (s, 1H), 8.98 (s, 1H), 8.99 (s, 1H). |

TABLE 4-continued

| S. No | Structure | LCMS m/z [M + H]+ | 1H NMR (400 MHz, DMSO-d6) δ ppm |
|---|---|---|---|
| 72 | 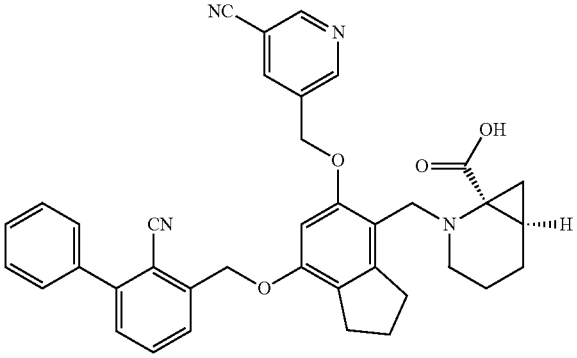<br>rac-(1R,6S)-2-((7-((2-cyano-[1,1'-biphenyl]-3-yl)methoxy)-5-((5-cyanopyridin-3-yl)methoxy)-2,3-dihydro-1H-inden-4-yl)methyl)-2-azabicyclo[4.1.0]heptane-1-carboxylic acid (cis; racemic) | 611.48 [M + H]+; | 1.13-1.33 (m, 4H), 1.56 (m, 1H), 1.66 (m, 1H), 1.76 (m, 1H), 1.96-1.99 (m, 2H), 2.32-2.38 (m, 2H), 2.75-2.82 (m, 3H), 2.99-3.03 (m, 1H), 3.66 (m, 2H), 5.31 (s, 2H), 5.33 (m, 2H), 6.77 (s, 1H), 7.50-7.61 (m, 6H), 7.69 (d, J = 7.2 Hz, 1H), 7.79 (t, J = 7.6 Hz, 1H), 8.39 (s, 1H), 8.94 (s, 1H), 8.99 (s, 1H). |
| 73 | 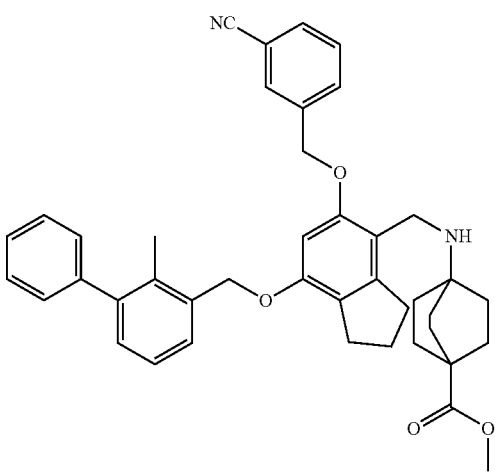 [SMILES: COC(=O)C12CCC(NCc3c(OCc4cccc(C#N)c4)cc(OCc4cccc(-c5ccccc5)c4C)c4c3CCC4)(CC1)CC2]<br>methyl 4-(((5-((3-cyanobenzyl)oxy)-7-((2-methyl-[1,1'-biphenyl]-3-yl)methoxy)-2,3-dihydro-1H-inden-4-yl)methyl)amino)bicyclo[2.2.2]octane-1-carboxylate | 641.39. | 0.95 (m, 1H), 1.52 (m, 6H), 1.75 (m, 6H), 1.97 (m, 2H), 2.20 (s, 3H), 2.74 (m, 2H), 2.85 (m, 2H), 3.50-3.56 (m, 5H), 5.14-5.18 (m, 4H), 6.72 (s, 1H), 7.19 (d, J = 7.2 Hz, 1H), 7.24-7.32 (m, 3H), 7.39 (m, 1H), 7.43-7.47 (m, 3H), 7.61 (t, J = 8.56 Hz, 1H), 7.81 (m, 2H), 8.02 (s, 1H). |

Example-74

Synthesis of 4-(((5-((3-cyanobenzyl)oxy)-7-((2-methyl-[1,1'-biphenyl]-3-yl)methoxy)-2,3-dihydro-1H-inden-4-yl)methyl)amino)bicyclo[2.2.2]octane-1-carboxylic acid

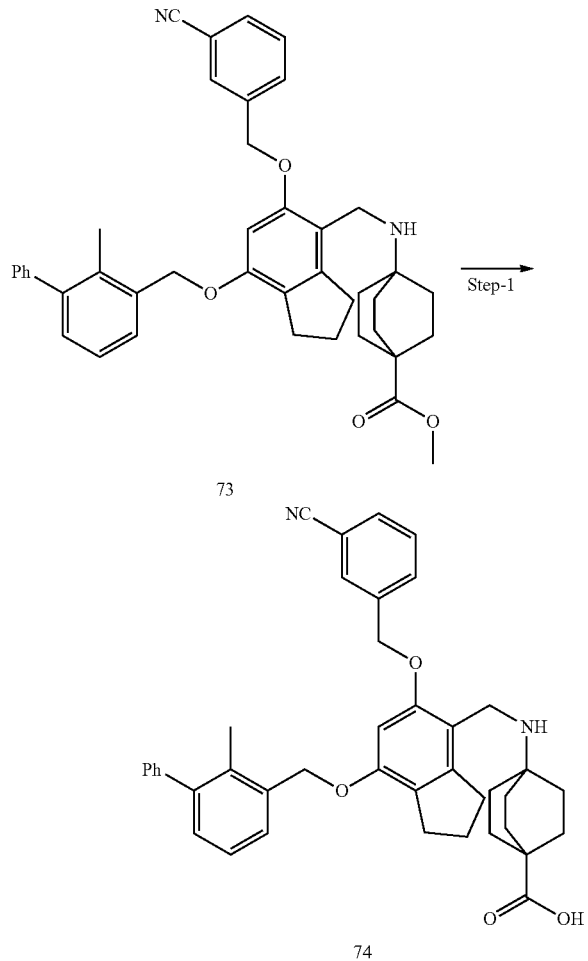

Step-1: To a solution of methyl 4-(((5-((3-cyanobenzyl)oxy)-7-((2-methyl-[1,1'-biphenyl]-3-yl)methoxy)-2,3-dihydro-1H-inden-4-yl)methyl)amino) bicyclo[2.2.2]octane-1-carboxylate (160 mg, 0.24 mmol) in THF (6 mL) and water (4 mL), lithium hydroxide (83 mg, 1.99 mmol) was added and stirred the mixture at room temperature for 12 h. After completion, the reaction mixture was diluted with water (20 mL) and extracted with EtOAc (30 mL). The aqueous layer was acidified to pH 4 using 3N HCl solution and the reaction mixture was extracted with 10% MeOH in DCM (2×100 mL). The combined organic layer was dried over sodium sulfate and concentrated. The resulting crude was purified by flash chromatography (silica gel, 4 g cartridge) using 0-10% MeOH in DCM as eluent to obtain 4-(((5-((3-cyanobenzyl)oxy)-7-((2-methyl-[1,1'-biphenyl]-3-yl)methoxy)-2,3-dihydro-1H-inden-4-yl)methyl)amino)bicyclo[2.2.2]octane-1-carboxylic acid (Yield: 50 mg, 32%) as white solid. LCMS (ES) m/z=627.37 [M+H]$^+$; $^1$H NMR (400 MHz, DMSO-d$_6$) δ ppm: 1.73 (m, 12H), 2.00 (m, 2H), 2.20 (s, 3H), 2.77 (m, 2H), 3.02 (m, 2H), 3.86 (m, 2H), 5.20-5.22 (m, 4H), 6.82 (s, 1H), 7.19 (d, J=7.2 Hz, 1H), 7.24-7.32 (m, 3H), 7.39 (m, 1H), 7.43-7.47 (m, 3H), 7.66 (t, J=8.56 Hz, 1H), 7.87 (m, 2H), 8.02 (s, 1H), 8.43 (bs, 1H), 12.14 (bs, 1H).

Example-75

Synthesis of (S)-1-((5-methoxy-7-((2-(trifluoromethyl)-[1,1'-biphenyl]-3-yl)methoxy)-2,3-dihydro-1H-inden-4-yl)methyl)piperidine-2-carboxylic acid

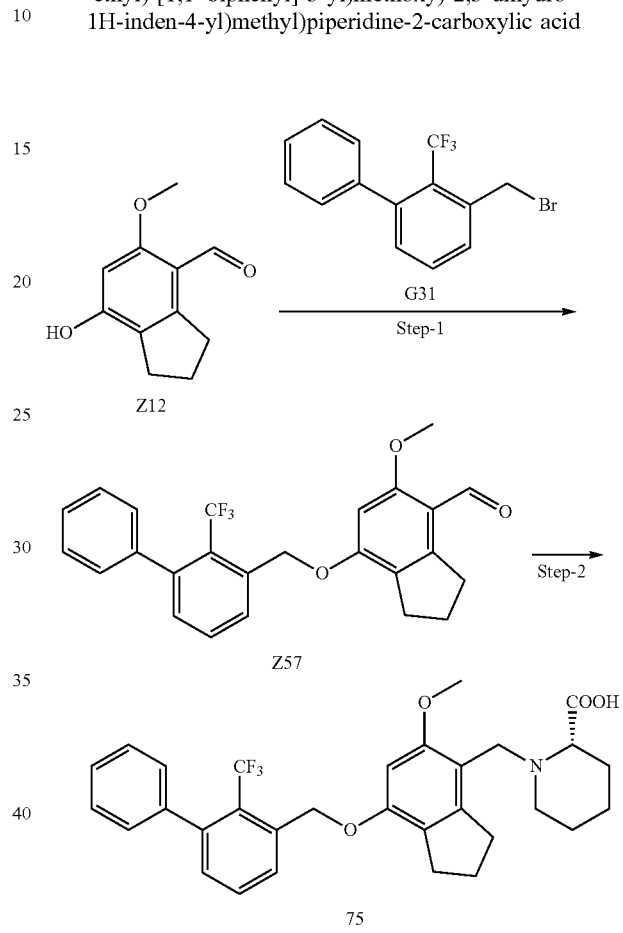

Step-1: To a solution of 7-hydroxy-5-methoxy-2,3-dihydro-1H-indene-4-carbaldehyde (0.50 g, 1.5 mmol) and 3-(bromomethyl)-2-(trifluoromethyl)-1,1'-biphenyl (0.29 g, 1.5 mmol) in ACN (10 mL), potassium carbonate (0.31 g, 2.25 mmol) was added and stirred the mixture at room temperature for 16 h. After completion, the reaction mixture was diluted with water (20 mL) and extracted with EtOAc (3×40 mL). The organic layer was dried over sodium sulphate and concentrated. The crude was purified by flash chromatography (silica gel, 12 g cartridge) using 0-30% EtOAc in hexanes as eluent to obtain 5-methoxy-7-((2-(trifluoromethyl)-[1,1'-biphenyl]-3-yl)methoxy)-2,3-dihydro-1H-indene-4-carbaldehyde (Yield: 0.3 g, 47%) as off-white solid. LCMS (ES) m/z=427.45 [M+H]$^+$; $^1$H NMR (400 MHz, DMSO-d$_6$) δ ppm: 1.98-2.04 (m, 2H), 2.70 (m, 2H), 3.12 (m, 2H), 3.91 (s, 3H), 5.47 (s, 2H), 6.69 (s, 1H), 7.30 (d, J=6.0 Hz, 2H), 7.37-7.46 (m, 4H), 7.73 (t, J=7.6 Hz, 1H), 7.79 (d, J=7.6 Hz, 1H), 10.31 (s, 1H).

Step-2: To a stirred solution of 5-methoxy-7-((2-(trifluoromethyl)-[1,1'-biphenyl]-3-yl)methoxy)-2,3-dihydro-1H-indene-4-carbaldehyde (0.10 g, 0.23 mmol), (S)-piperidine- 2-carboxylic acid (27 mg, 0.21 mmol) in DMF (1 mL) and MeOH (1 mL), acetic acid (2 drops) was added and continued stirring of the mixture for 1 h. To this mixture, sodium cyanoborohydride (40 mg, 0.69 mmol) and) was added and continued stirring at room temperature for 16 h and the mixture was heated at 50° C. for 5 h. After completion, the reaction mixture was poured on ice cold water (10 mL) and extracted with 10% MeOH in DCM (3×10 mL). The combined organic layer was dried over sodium sulfate and concentrated. The resulting crude was purified by flash chromatography (silica gel, 4 g cartridge) using 0-10% MeOH in DCM as eluent to obtain (S)-1-((5-methoxy-7-((2-(trifluoromethyl)-[1,1'-biphenyl]-3-yl)methoxy)-2,3-dihydro-1H-inden-4-yl)methyl)piperidine-2-carboxylic acid (Yield: 30 mg, 25%) as white solid. LCMS (ES) m/z=540.36 [M+H]⁺; ¹H NMR (400 MHz, DMSO-d₆) δ ppm: 1.33-1.46 (m, 4H), 1.77 (m, 2H), 1.97-2.00 (m, 2H), 2.42 (m, 1H), 2.76 (m, 2H), 2.84 (m, 1H), 2.91 (m, 1H), 3.02-3.09 (m, 1H), 3.14 (m, 1H), 3.73-3.76 (m, 4H), 3.88 (d, J=12.4 Hz, 1H), 5.34 (s, 2H), 6.54 (s, 1H), 7.30 (d, J=6.4 Hz, 2H), 7.35 (d, J=7.6 Hz, 1H), 7.41-7.46 (m, 3H), 7.71 (t, J=7.6 Hz, 1H), 7.79 (d, J=7.6 Hz, 1H).

Following compounds were prepared by following similar to above procedures

Example 76

(2S,4R)-4-hydroxy-1-((5-methoxy-7-((2-(trifluoromethyl)-[1,1'-biphenyl]-3-yl)methoxy)-2,3-dihydro-1H-inden-4-ylmethyl)pyrrolidine-2-carboxylic acid

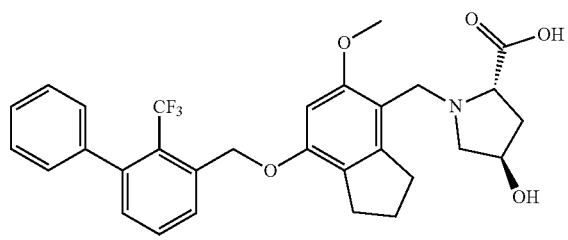 [SMILES: COc1cc(OCc2cccc(-c3ccccc3)c2C(F)(F)F)c2c(c1CN1C[C@H](O)C[C@H]1C(=O)O)CCC2]

LCMS (ES) m/z=542.41 [M+H]⁺; ¹H NMR (400 MHz, DMSO-d₆) δ ppm: 1.95-1.99 (m, 3H), 2.09 (m, 1H), 2.26-2.79 (m, 3H), 2.86-3.02 (m, 2H), 3.25 (m, 1H), 3.66 (m, 1H), 3.81 (s, 3H), 4.05-4.12 (m, 2H), 4.23 (bs, 1H), 5.26 (bs, 1H), 5.36 (s, 2H), 6.59 (s, 1H), 7.30 (d, J=6.4 Hz, 2H), 7.35 (d, J=7.6 Hz, 1H), 7.41-7.46 (m, 3H), 7.71 (t, J=7.6 Hz, 1H), 7.79 (d, J=7.6 Hz, 1H).

Example-77

Synthesis of (2S)-1-((7-((2-methyl-[1,1'-biphenyl]-3-yl)methoxy)-5-((1-methylpiperidin-3-yl)methoxy)-2,3-dihydro-1H-inden-4-yl)methyl)piperidine-2-carboxylic acid

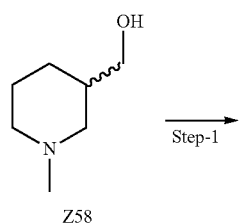

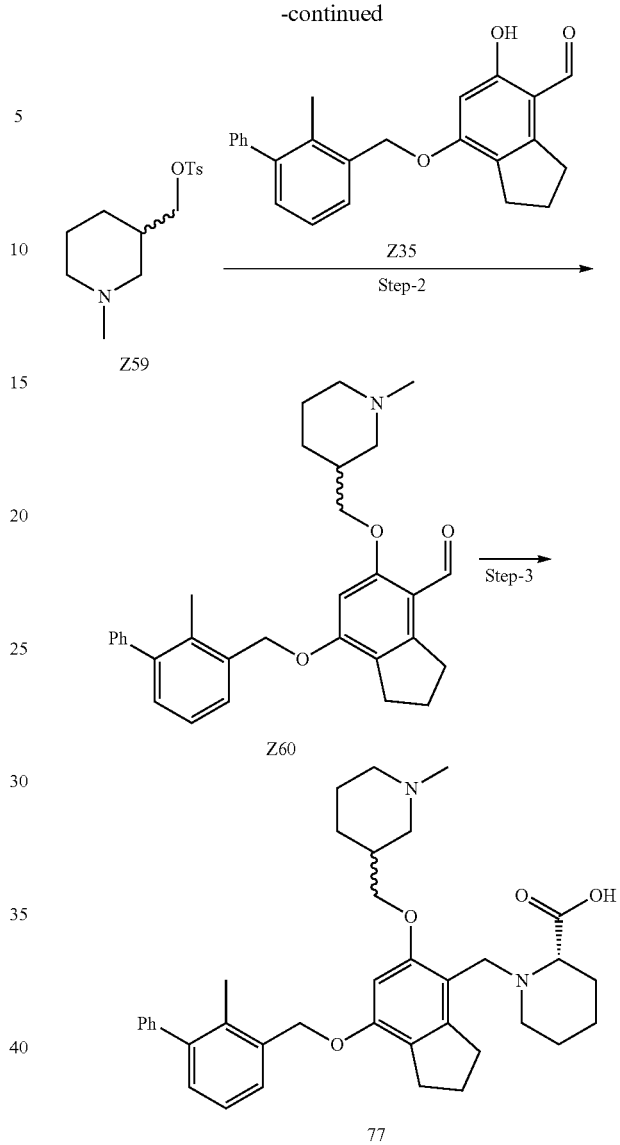

Step-1: To a stirred solution of 1-methyl-3-hydroxymethylpiperidine (2 g, 15.5 mmol) in DCM (30 mL) at 0° C., triethylamine (4.9 g, 46 mmol) and tosyl chloride (4.41 g, 23.2 mmol) were added and allowed the mixture to stir at room temperature for 6 h. After completion, the reaction mixture was diluted with water (30 mL) and extracted with DCM (3×30 mL). The combined organic layer was dried over sodium sulfate and concentrated. The resulting crude was purified by flash chromatography (silica gel, 12 g cartridge) using 0-20% EtOAc in hexanes as eluent to obtain (1-methylpiperidin-3-yl)methyl 4-methylbenzenesulfonate (Yield: 2.50 g, 58%) as white solid. LCMS (ES) m/z=284.36 [M+H]⁺; ¹H NMR (400 MHz, DMSO-d₆) δ ppm: 0.87-0.95 (m, 1H), 1.33-1.50 (m, 4H), 1.63 (m, 1H), 1.80-1.85 (m, 2H), 2.06 (s, 3H), 2.42 (s, 3H), 2.46-2.52 (m, 1H), 3.90 (m, 2H), 7.48 (d, J=8.0 Hz, 2H), 7.78 (d, J=8.0 Hz, 2H).

Step-2: To a solution of 5-hydroxy-7-((2-methyl-[1,1'-biphenyl]-3-yl)methoxy)-2,3-dihydro-1H-indene-4-carbaldehyde (200 mg, 0.558 mmol) in DMF (5 mL), potassium carbonate (231 mg, 1.67 mmol) and (1-methylpiperidin-3-yl)methyl 4-methylbenzenesulfonate (238 mg, 0.84 mmol) were added and stirred the reaction mixture at room temperature for 16 h. After completion, the reaction mixture was diluted with ice cold water (15 mL) and extracted with 5% MeOH in DCM (3×20 mL). The combined organic layer was dried over sodium sulfate and concentrated. The resulting crude was purified by column chromatography (silica gel, 100-200 mesh) using 0-10% MeOH in DCM as eluent to obtain 7-((2-methyl-[1,1'-biphenyl]-3-yl)methoxy)-5-((1-methylpiperidin-3-yl)methoxy)-2,3-dihydro-1H-indene-4-carbaldehyde (Yield: 0.15 g, 57%) as white solid. LCMS (ES) m/z=470.54 [M+H]+;

Step-3: A solution of 7-((2-methyl-[1,1'-biphenyl]-3-yl)methoxy)-5-((1-methylpiperidin-3-yl)methoxy)-2,3-dihydro-1H-indene-4-carbaldehyde (150 mg, 0.319 mmol), (S)-piperidine-2-carboxylic acid (123 mg, 0.96 mmol) in DMF (2.5 mL) and MeOH (2.5 mL), acetic acid (3 drops) were added and stirred the mixture for 1 h. To this mixture, sodium cyanoborohydride (60 mg, 0.96 mmol) and) was added and continued stirring at room temperature for 16 h. After completion, the reaction mixture was poured on ice cold water (10 mL) and extracted with 10% MeOH in DCM (3×20 mL). The combined organic layer was dried over sodium sulfate and concentrated. The resulting crude was purified by column chromatography (silica gel, 100-200 mesh) using 0-10% MeOH in DCM as eluent to obtain (2S)-1-((7-((2-methyl-[1,1'-biphenyl]-3-yl)methoxy)-5-((1-methylpiperidin-3-yl)methoxy)-2,3-dihydro-1H-inden-4-yl)methyl)piperidine-2-carboxylic acid (Yield: 18 mg, 9.6%) as white solid. LCMS (ES) m/z=583.57 [M+H]+; 1H NMR (400 MHz, DMSO-$d_6$) δ ppm: 1.47 (m, 5H), 1.64 (m, 4H), 1.74 (m, 2H), 1.98-2.04 (m, 4H), 2.21 (s, 6H), 2.74 (m, 2H), 2.82 (m, 3H), 2.98-3.04 (m, 3H), 3.15 (m, 1H), 3.72 (d, J=12.4 Hz, 1H), 3.89 (m, 3H), 5.17 (s, 2H), 6.61 (s, 1H), 7.19 (d, J=7.2 Hz, 1H), 7.26-7.32 (m, 3H), 7.38 (t, J=7.2 Hz, 1H), 7.44-7.48 (m, 3H).

Example-78

Synthesis of (S)-1-((5-(4-carboxybutoxy)-7-((2-cyano-[1,1'-biphenyl]-3-yl)methoxy)-2,3-dihydro-1H-inden-4-yl)methyl)piperidine-2-carboxylic acid

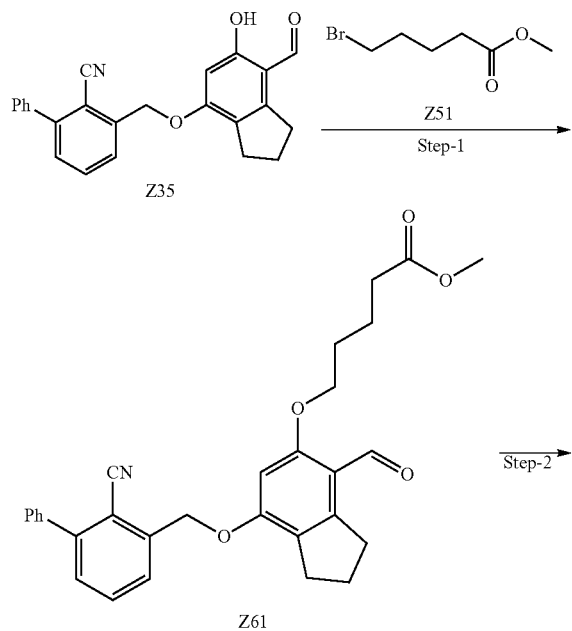

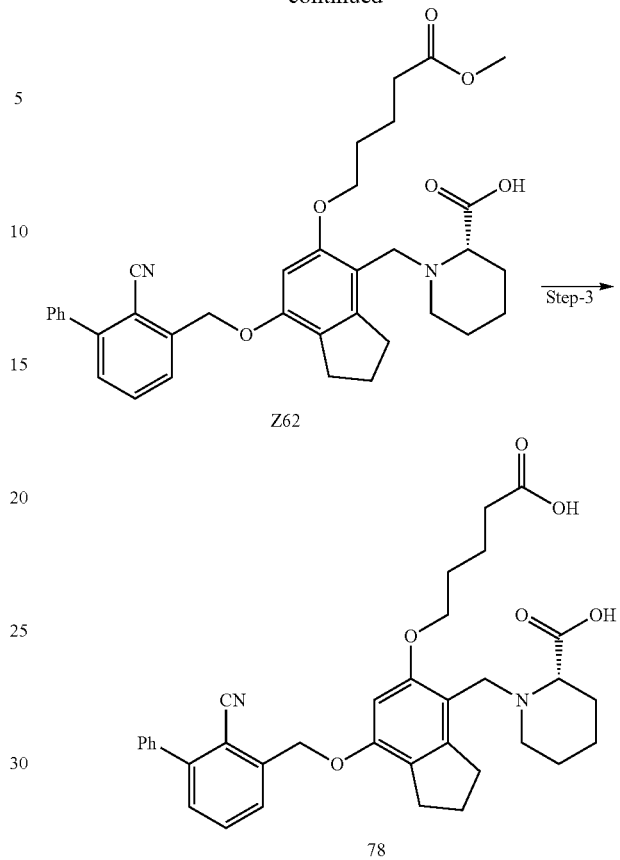

Step-1: To a solution of 3-(((7-formyl-6-hydroxy-2,3-dihydro-1H-inden-4-yl)oxy)methyl)-[1,1'-biphenyl]-2-carbonitrile (0.25 g, 0.697 mmol) in ACN (10 mL), potassium carbonate (0.280 g, 2.03 mmol) and methyl 5-bromopentanoate (0.396 g, 2.03 mmol) were added and stirred the mixture at room temperature for 16 h. After completion, the reaction mixture was diluted with water (20 mL) and extracted with EtOAc (3×30 mL). The combined organic layer was dried over sodium sulfate and concentrated. The resulting crude was purified by flash chromatography (silica gel, 12 g cartridge) using 30% EtOAc in hexanes as eluent to obtain methyl 5-((7-((2-cyano-[1,1'-biphenyl]-3-yl)methoxy)-4-formyl-2,3-dihydro-1H-inden-5-yl)oxy)pentanoate (Yield: 0.150 g, 45%) as white solid. LCMS (ES) m/z=484.26 [M+H]+; 1H NMR (400 MHz, DMSO-$d_6$) δ ppm: 1.69-1.80 (m, 4H), 1.95-2.02 (m, 2H), 2.40 (m, 2H), 2.69 (m, 2H), 3.13 (m, 2H), 3.58 (s, 3H), 4.16 (m, 2H), 5.48 (s, 2H), 6.78 (s, 1H), 7.49-7.58 (m, 6H), 7.75 (m, 1H), 7.83 (m, 1H), 10.33 (s, 1H).

Step-2: A solution of methyl 5-((7-((2-cyano-[1,1'-biphenyl]-3-yl)methoxy)-4-formyl-2,3-dihydro-1H-inden-5-yl)oxy)pentanoate (220 mg, 0.46 mmol), (S)-piperidine-2-carboxylic acid (176 mg, 1.366 mmol) in DMF (2 mL) and MeOH (2 mL), acetic acid (6 drops) was stirred for 30 minutes. To this mixture, sodium cyanoborohydride (86 mg, 1.366 mmol) and) were added and continued stirring at room temperature for 16 h. After completion, the reaction mixture was poured on ice cold water (10 mL) and extracted with DCM (3×15 mL). The combined organic layer was dried over sodium sulfate and concentrated. The resulting crude was purified by column chromatography (silica gel, 100-200 mesh) using 0-10% MeOH in DCM as eluent to obtain (S)-1-((7-((2-cyano-[1,1'-biphenyl]-3-yl)methoxy)-5-((5-methoxy-5-oxopentyl)oxy)-2,3-dihydro-1H-inden-4-yl)methyl)piperidine-2-carboxylic acid (Yield: 80 mg, 29%) as white solid. LCMS (ES) m/z=597.68 [M+H]⁺; ¹H NMR (400 MHz, DMSO-d₆) δ ppm: 1.33-1.46 (m, 4H), 1.69-1.80 (m, 5H), 1.95-2.02 (m, 2H), 2.45 (m, 2H), 2.78 (m, 2H), 2.82-3.08 (m, 4H), 3.12 (m, 2H), 3.58 (s, 3H), 3.71 (d, J=12.4 Hz, 1H), 3.86 (d, J=12.8 Hz, 1H), 3.98 (m, 2H), 5.34 (m, 2H), 6.62 (s, 1H), 7.50-7.62 (m, 6H), 7.75 (m, 1H), 7.83 (m, 1H).

Step-3: To a stirred solution of (S)-1-((7-((2-cyano-[1,1'-biphenyl]-3-yl)methoxy)-5-((5-methoxy-5-oxopentyl)oxy)-2,3-dihydro-1H-inden-4-yl)methyl)piperidine-2-carboxylic acid (70 mg, 0.117 mmol) in THF (3 mL) and water (1.5 mL), lithium hydroxide (9.8 mg, 0.23 mmol) was added and stirred the mixture at room temperature for 16 h. After completion, the reaction mixture was diluted with water (10 mL) and acidified with 1N HCl. The aqueous mixture was extracted with EtOAc (3×20 mL) and combined organic extract was dried over sodium sulphate and concentrated. The crude was purified by flash chromatography (silica gel, 4 g cartridge) using 0-15% MeOH in DCM as eluent to obtain (S)-1-((5-(4-carboxybutoxy)-7-((2-cyano-[1,1'-biphenyl]-3-yl)methoxy)-2,3-dihydro-1H-inden-4-yl)methyl)piperidine-2-carboxylic acid (Yield: 15 mg, 22%) as white solid. LCMS (ES) m/z=583.48 [M+H]⁺; ¹H NMR (400 MHz, DMSO-d₆) δ ppm: 1.38-1.49 (m, 4H), 1.76 (m, 6H), 1.95-1.98 (m, 2H), 2.29 (m, 2H), 2.73 (m, 2H), 2.81 (m, 1H), 3.03 (m, 3H), 3.15 (m, 1H), 3.78 (d, J=12.4 Hz, 1H), 3.90 (d, J=12.8 Hz, 1H), 3.99 (m, 2H), 5.35 (s, 2H), 6.63 (s, 1H), 7.50-7.62 (m, 6H), 7.75 (m, 1H), 7.83 (m, 1H).

Example-79

Synthesis of N-(2-(((5-(4-cyanobutoxy)-7-((2-methyl-[1,1'-biphenyl]-3-yl)methoxy)-2,3-dihydro-1H-inden-4-yl)methyl)amino)ethyl)acetamide

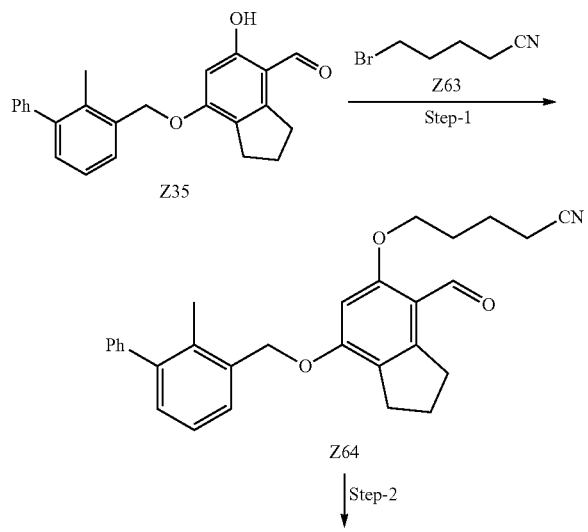

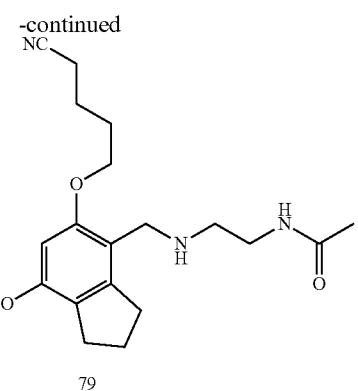

Step-1: To a solution of 5-hydroxy-7-((2-methyl-[1,1'-biphenyl]-3-yl)methoxy)-2,3-dihydro-1H-indene-4-carbaldehyde (0.50 g, 1.39 mmol) in DMF (10 mL), potassium carbonate (0.288 g, 2.08 mmol) and 5-bromopentanenitrile (0.25 g, 1.53 mmol) were added and stirred the mixture at room temperature for 5 h. After completion, the reaction mixture was diluted with water (20 mL) and extracted with EtOAc (3×30 mL). The combined organic layer was dried over sodium sulfate and concentrated. The resulting crude was purified by flash chromatography (silica gel, 12 g cartridge) using 20% EtOAc in hexanes as eluent to obtain 5-((4-formyl-7-((2-methyl-[1,1'-biphenyl]-3-yl)methoxy)-2,3-dihydro-1H-inden-5-yl)oxy)pentanenitrile (Yield: 0.425 g, 69%) as white solid. LCMS (ES) m/z=440.51 [M+H]⁺; ¹H NMR (400 MHz, DMSO-d₆) δ ppm: 1.74-1.80 (m, 2H), 1.86-1.90 (m, 2H), 1.97-2.01 (m, 2H), 2.21 (s, 3H), 2.59 (m, 2H), 2.69 (m, 2H), 3.11 (m, 2H), 4.20 (m, 2H), 5.31 (s, 2H), 6.79 (s, 1H), 7.22 (d, J=7.6 Hz, 1H), 7.28-7.40 (m, 4H), 7.44-7.48 (m, 3H), 10.34 (s, 1H).

Step-2: To a solution of 5-((4-formyl-7-((2-methyl-[1,1'-biphenyl]-3-yl)methoxy)-2,3-dihydro-1H-inden-5-yl)oxy)pentanenitrile (150 mg, 0.35 mmol) in DMF (10 mL), N-(2-aminoethyl)acetamide (45 mg, 0.44 mmol) and acetic acid (2 drops) were added and stirred the mixture for 10 minutes. To this mixture, sodium cyanoborohydride (32 mg, 0.52 mmol) was added and the mixture was stirred at room temperature for 6 h. After completion, the reaction mixture was diluted with water (15 mL) and extracted with 10% MeOH in DCM (3×30 mL). The organic layer was dried over anhydrous sodium sulphate and concentrated. The resulting crude was purified by flash chromatography (silica gel, 4 g cartridge) using 0-10% MeOH in DCM as eluent. The resulting product was further purified by reverse phase HPLC using Method-E to obtain N-(2-(((5-(4-cyanobutoxy)-7-((2-methyl-[1,1'-biphenyl]-3-yl)methoxy)-2,3-dihydro-1H-inden-4-yl)methyl)amino)ethyl)acetamide (Yield: 40 mg) as sticky liquid. LCMS (ES) m/z=526.50 [M+H]⁺; ¹H NMR (400 MHz, DMSO-d₆) δ ppm: 1.78-1.82 (m, 5H), 1.84 (m, 2H), 1.97-1.99 (m, 2H), 2.21 (s, 3H), 2.50 (m, 2H), 2.59 (m, 2H), 2.73 (m, 2H), 2.86 (m, 2H), 3.11 (m, 2H), 3.60 (m, 2H), 4.02 (m, 2H), 5.15 (s, 2H), 6.63 (s, 1H), 7.19 (d, J=7.6 Hz, 1H), 7.26-7.40 (m, 4H), 7.44-7.48 (m, 3H), 7.76 (bs, 1H).

The following compounds were prepared following procedures described above

Example 80

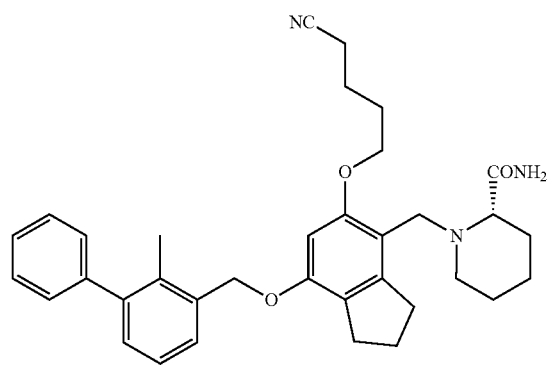 [SMILES: Cc1c(COc2cc(OCCCCC#N)c(CN3CCCC[C@H]3C(N)=O)c3c2CCC3)cccc1-c1ccccc1]

(S)-1-((5-(4-cyanobutoxy)-7-((2-methyl-[1,1'-biphenyl]-3-yl)methoxy)-2,3-dihydro-1H-inden-4-yl)methyl)piperidine-2-carboxamide, LCMS (ES) m/z=552.52 [M+H]+; 1H NMR (400 MHz, DMSO-d6) δ ppm: 1.47 (m, 1H), 1.58 (m, 2H), 1.72-1.79 (m, 6H), 1.93-1.97 (m, 3H), 2.21 (s, 3H), 2.59 (m, 3H), 2.66-2.83 (m, 5H), 2.94-3.02 (m, 1H), 3.15 (d, J=12.0 Hz, 1H), 3.63 (d, J=12.0 Hz, 1H), 4.02 (m, 2H), 5.15 (s, 2H), 6.62 (s, 1H), 7.06 (bd, 2H), 7.19 (d, J=7.6 Hz, 1H), 7.27-7.40 (m, 4H), 7.44-7.49 (m, 3H).

Example 81

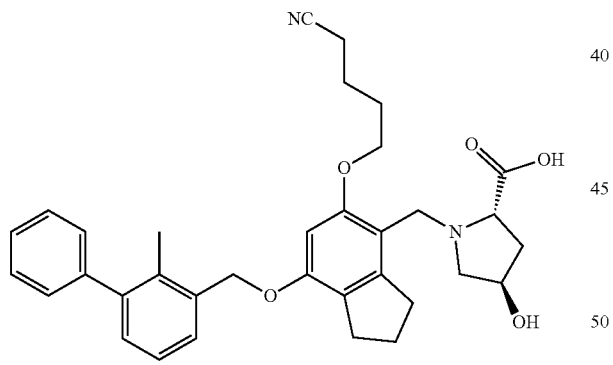

(2S,4R)-1-((5-(4-cyanobutoxy)-7-((2-methyl-[1,1'-biphenyl]-3-yl)methoxy-2,3-dihydro-1H-inden-4-yl)methyl)-4-hydroxypyrrolidine-2-carboxylic acid, LCMS (ES) m/z=551.51 [M+H]+; 1H NMR (400 MHz, DMSO-d6) δ ppm: 1.78-1.81 (m, 2H), 1.84-1.90 (m, 2H), 1.96-2.05 (m, 3H), 2.13 (m, 1H), 2.22 (s, 3H), 2.59 (t, J=7.2 Hz, 2H), 2.74-2.81 (m, 3H), 2.88-2.98 (m, 2H), 3.27 (m, 1H), 3.70 (t, J=8.0 Hz, 1H), 4.03-4.18 (m, 4H), 4.25 (m, 1H), 5.19 (s, 2H), 5.29 (bs, 1H), 6.70 (s, 1H), 7.19 (d, J=7.6 Hz, 1H), 7.27-7.40 (m, 4H), 7.44-7.49 (m, 3H).

Example-82

Synthesis of (S)-1-((5-(((1S,2R)-2-carboxycyclopropyl)methoxy)-7-((2-methyl-[1,1'-biphenyl]-3-yl)methoxy)-2,3-dihydro-1H-inden-4-yl)methyl)piperidine-2-carboxylic acid Step-1: To a solution of 5-hydroxy-7-((2-methyl-[1,1'-biphenyl]-3-yl)methoxy)-2,3-dihydro-1H-indene-4-carbaldehyde (0.20 g, 0.55 mmol) in DMF (4 mL), potassium carbonate (0.227 g, 1.6 mmol) and methyl (1R,2S)-2-((tosyloxy)methyl)cyclopropane-1-carboxylate (0.321 g, 1.39 mmol) was added and stirred the mixture at room temperature for 12 h. After completion, the reaction mixture was diluted with water (6 mL) and extracted with EtOAc (3×10 mL). The combined organic layer was dried over sodium sulfate and concentrated. The resulting crude was purified by flash chromatography (silica gel, 4 g cartridge) using 20% EtOAc in hexanes as eluent to obtain methyl (1R,2S)-2-(((4-formyl-7-((2-methyl-[1,1'-biphenyl]-3-yl)methoxy)-2,3-dihydro-1H-inden-5-yl)oxy)methyl)cyclopropane-1-carboxylate (Yield: 0.330 g, crude) as yellow solid. $^1$H NMR (400 MHz, DMSO-$d_6$) δ ppm: 0.85 (m, 1H), 1.07 (m, 1H), 1.66 (m, 1H), 1.74-1.80 (m, 2H), 1.86-1.90 (m, 2H), 1.97-2.01 (m, 2H), 2.21 (s, 3H), 2.71 (m, 2H), 3.10 (m, 1H), 3.53 (s, 3H), 5.31 (s, 2H), 6.78 (s, 1H), 7.22 (d, J=7.6 Hz, 1H), 7.28-7.40 (m, 4H), 7.44-7.48 (m, 3H), 10.24 (s, 1H).

Step-2: To a solution of methyl (1R,2S)-2-(((4-formyl-7-((2-methyl-[1,1'-biphenyl]-3-yl)methoxy)-2,3-dihydro-1H-inden-5-yl)oxy)methyl)cyclopropane-1-carboxylate (150 mg, 0.32 mmol) in DMF (2 mL) and MeOH (2 mL), (S)-piperidine-2-carboxylic acid (61 mg, 0.48 mmol) and acetic acid (2 drops) were added and stirred the mixture for 30 minutes. To this mixture, sodium cyanoborohydride (60 mg, 0.95 mmol) was added and the mixture was stirred at 60° C. for 4 h. After completion, the reaction mixture was diluted with water (15 mL) and extracted with 10% MeOH in DCM (3×30 mL). The organic layer was dried over anhydrous sodium sulphate and concentrated. The resulting crude was purified by flash chromatography (silica gel, 4 g cartridge) using 0-12% MeOH in DCM as eluent to obtain (S)-1-((5-(((1S,2R)-2-(methoxycarbonyl)cyclopropyl)methoxy)-7-((2-methyl-[1,1'-biphenyl]-3-yl)methoxy)-2,3-dihydro-1H-inden-4-yl)methyl)piperidine-2-carboxylic acid (Yield: 180 mg) as off-white solid. LCMS (ES) m/z=584.59 [M+H]$^+$; $^1$H NMR (400 MHz, DMSO-$d_6$) δ ppm: 0.95 (m, 1H), 1.03 (m, 1H), 1.39 (m, 1H), 1.43-1.54 (m, 5H), 1.78-1.90 (m, 4H), 1.97-1.99 (m, 2H), 2.21 (s, 3H), 2.72 (m, 2H), 2.84 (m, 2H), 3.03 (m, 2H), 3.51 (s, 3H), 3.79 (m, 1H), 3.92 (m, 1H), 4.34 (m, 1H), 5.16 (s, 2H), 6.59 (s, 1H), 7.19 (d, J=7.6 Hz, 1H), 7.26-7.40 (m, 4H), 7.44-7.48 (m, 3H).

Step-3: To a stirred solution of (S)-1-((5-(((1S,2R)-2-(methoxycarbonyl)cyclopropyl)methoxy)-7-((2-methyl-[1,1'-biphenyl]-3-yl)methoxy)-2,3-dihydro-1H-inden-4-yl)methyl)piperidine-2-carboxylic acid (100 mg, 0.17 mmol) in THF (3 mL) and water (1.5 mL), lithium hydroxide (14 mg, 0.35 mmol) was added and stirred the mixture at room temperature for 6 h. After completion, the reaction mixture was diluted with water (5 mL) and acidified with 1N HCl (pH 5-6). The aqueous mixture was extracted with 10% MeOH in DCM (3×10 mL) and combined organic extract was dried over sodium sulphate and concentrated. The crude was purified by column chromatography (silica gel, 100-200 mesh) using 0-30% MeOH in DCM as eluent. The resulting product was further purified by reverse phase column chromatography to obtain (S)-1-((5-(((1S,2R)-2-carboxycyclopropyl)methoxy)-7-((2-methyl-[1,1'-biphenyl]-3-yl)methoxy)-2,3-dihydro-1H-inden-4-yl)methyl)piperidine-2-carboxylic acid (Yield: 45 mg, 46%) as off-white solid. LCMS (ES) m/z=570.57 [M+H]$^+$; $^1$H NMR (400 MHz, DMSO-$d_6$) δ ppm: 0.95 (m, 1H), 1.07 (m, 1H), 1.39 (m, 1H), 1.43-1.54 (m, 3H), 1.78-1.90 (m, 4H), 1.97-1.99 (m, 2H), 2.21 (s, 3H), 2.72 (m, 2H), 2.84 (m, 2H), 3.03 (m, 2H), 3.79 (m, 1H), 3.97 (m, 2H), 4.39 (s, 1H), 5.17 (s, 2H), 6.65 (s, 1H), 7.19 (d, J=7.6 Hz, 1H), 7.26-7.40 (m, 4H), 7.44-7.48 (m, 3H).

The following compounds were prepared following procedures described above

Example 83

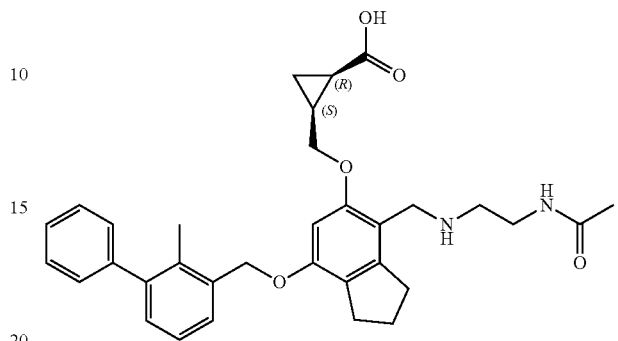

(1R,2S)-2-(((4-(((2-acetamidoethyl)amino)methyl)-7-((2-methyl-[1,1'-biphenyl]-3-yl)methoxy)-2,3-dihydro-1H-inden-5-yl)oxy)methyl)cyclopropane-1-carboxylic acid, LCMS (ES) m/z=543.54 [M+H]$^+$; $^1$H NMR (400 MHz, DMSO-$d_6$) δ ppm: 0.95 (m, 2H), 1.67 (m, 2H), 1.78 (s, 3H), 1.97-2.00 (m, 2H), 2.20 (s, 3H), 2.73 (m, 2H), 2.88 (m, 4H), 3.26-3.32 (m, 2H), 3.73 (m, 1H), 3.89 (m, 1H), 3.95 (d, J=12.8 Hz, 1H), 4.56 (m, 1H), 5.18 (s, 2H), 6.69 (s, 1H), 7.19 (d, J=7.6 Hz, 1H), 7.27-7.39 (m, 4H), 7.44-7.49 (m, 3H), 8.64 (bs, 1H).

Example-84

Synthesis of (S)-1-((7-((3-(2,3-dihydrobenzo[b][1,4]dioxin-6-yl)-2-methylbenzyl)oxy)-5-methoxy-2,3-dihydro-1H-inden-4-yl)methyl)piperidine-2-carboxylic acid

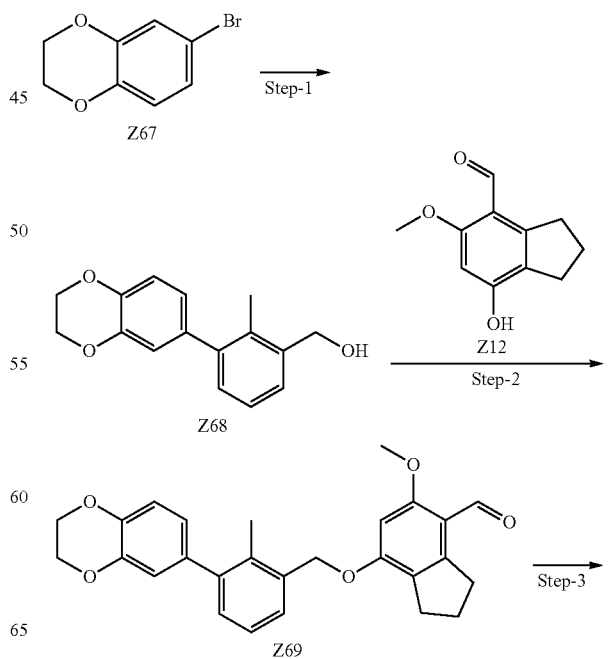

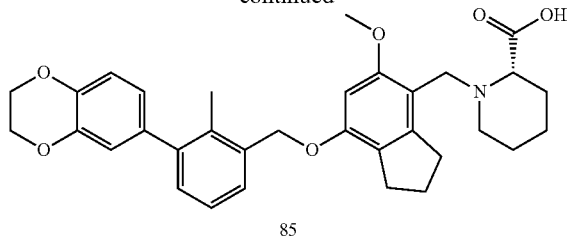

85

Step-1: A mixture of 6-bromo-2,3-dihydrobenzo[b][1,4] dioxine (5 g, 0.023 mol), (2-methyl-3-(4,4,5,5-tetramethyl-1,3,2-dioxaborolan-2-yl)phenyl)methanol (8.6 g, 0.034 mol), potassium carbonate (9.5 g. 0.069 mol), toluene (50 mL), water (50 mL) and EtOH (50 mL) was degassed with nitrogen gas for 15 minutes. To this mixture, PdCl$_2$(dppf) DCM (0.93 g, 1.15 mmol) was added and degassed for another 5 minutes with nitrogen. After sealing the vessel, the mixture was heated at 90° C. for 8 h. After completion, the reaction was diluted with water (300 mL) and extracted with EtOAc (3×300 mL). The organic layer was dried over sodium sulphate and concentrated. The crude was purified by column chromatography (silica gel, 100-200 mesh) using 0-30% EtOAc in hexanes to obtain (3-(2,3-dihydrobenzo[b][1,4]dioxin-6-yl)-2-methylphenyl)methanol (Yield: 5.8 g, 97%) as yellow sticky liquid. $^1$H NMR (400 MHz, DMSO-d$_6$) δ ppm: 2.11 (s, 3H), 4.27 (s, 4H), 4.51 (m, 2H), 5.10 (m, 1H), 6.69-6.74 (m, 2H), 6.89 (d, J=7.6 Hz, 1H), 7.04 (d, J=7.6 Hz, 1H), 7.18 (t, J=7.6 Hz, 1H), 7.35 (d, J=7.2 Hz, 1H).

Step-2: To a solution of 7-hydroxy-5-methoxy-2,3-dihydro-1H-indene-4-carbaldehyde (500 mg, 2.6 mmol) and (3-(2,3-dihydrobenzo[b][1,4]dioxin-6-yl)-2-methylphenyl) methanol (866 mg, 3.3 mmol) in dry THF (15 mL) at 0° C., triphenyl phosphine (1.7 g, 6.5 mmol) was added and stirred the mixture for 10 minutes at 0° C. To this mixture, DEAD (1.355 g, 7.8 mmol) was added and stirred the mixture for 30 minutes. After completion, the reaction mixture was diluted with water (20 mL) and extracted with EtOAc (3×25 mL). The organic layer was dried over sodium sulphate and concentrated. The resulting crude was purified by flash chromatography (silica gel, 12 g cartridge) using 0-30% EtOAc in hexanes as eluent to obtain 7-((3-(2,3-dihydrobenzo[b][1,4]dioxin-6-yl)-2-methylbenzyl)oxy)-5-methoxy-2,3-dihydro-1H-indene-4-carbaldehyde (Yield: 350 mg, 27%) as white solid. LCMS (ES) m/z=431.43 [M+H]$^+$; $^1$H NMR (400 MHz, DMSO-d$_6$) δ ppm: 1.95-2.01 (m, 2H), 2.23 (s, 3H), 2.71 (m, 2H), 3.11 (m, 2H), 3.94 (s, 3H), 4.28 (s, 4H), 5.31 (s, 2H), 6.73-6.79 (m, 3H), 6.92 (d, J=8.0 Hz, 1H), 7.18 (d, J=7.6 Hz, 1H), 7.26 (t, J=7.6 Hz, 1H), 7.47 (d, J=7.2 Hz, 1H), 10.30 (s, 1H).

Step-3: To a solution of 7-((3-(2,3-dihydrobenzo[b][1,4] dioxin-6-yl)-2-methylbenzyl)oxy)-5-methoxy-2,3-dihydro-1H-indene-4-carbaldehyde (100 mg, 0.23 mmol) and (S)-piperidine-2-carboxylic acid (36 mg, 0.27 mmol) in DMF (3 mL), acetic acid (3 drops) was added and stirred for 10 minutes. To this mixture, sodium cyanoborohydride (43 mg, 0.69 mmol) was added and stirred the mixture at 80° C. for 3 h. After completion, the reaction mixture was diluted with ice cold water (10 mL) and extracted with 10% MeOH in DCM (3× The solid was further dissolved in DCM (30 mL) and dried over sodium sulphate and concentrated. The residue was purified by flash chromatography (silica gel, 4 g cartridge) using 0-10% MeOH in DCM as eluent. The product was further purified by reverse phase prep-HPLC using Method-B to obtain (S)-1-((7-((3-(2,3-dihydrobenzo[b][1,4]dioxin-6-yl)-2-methylbenzyl)oxy)-5-methoxy-2,3-dihydro-1H-inden-4-yl)methyl)piperidine-2-carboxylic acid (Yield: 35 mg, 28%) as white solid. LCMS (ES) m/z=544.39 [M+H]$^+$; $^1$H NMR (400 MHz, DMSO-d$_6$) δ ppm: 1.38 (m, 1H), 1.48 (m, 3H), 1.76 (m, 2H), 1.95-1.98 (m, 2H), 2.22 (s, 3H), 2.42 (m, 1H), 2.73 (m, 2H), 2.82-2.90 (m, 2H), 3.00-3.08 (m, 2H), 3.70 (d, J=12.0 Hz, 1H), 3.79 (s, 3H), 3.87 (d, J=12.4 Hz, 1H), 4.28 (s, 4H), 5.16 (s, 2H), 6.64 (s, 1H), 6.74-6.78 (m, 2H), 6.91 (d, J=8.0 Hz, 1H), 7.16 (d, J=7.2 Hz, 1H), 7.24 (t, J=7.6 Hz, 1H), 7.44 (d, J=7.2 Hz, 1H).

The following compounds were prepared following procedures described above

Example 85

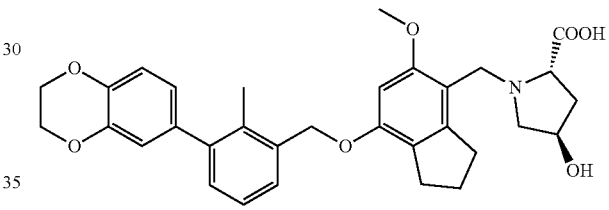

(2S,4R)-1-((7-((3-(2,3-dihydrobenzo[b][1,4]dioxin-6-yl)-2-methylbenzyl)oxy)-5-methoxy-2,3-dihydro-1H-inden-4-yl)methyl)-4-hydroxypyrrolidine-2-carboxylic acid, LCMS (ES) m/z=546.31 [M+H]$^+$; $^1$H NMR (400 MHz, DMSO-d$_6$) δ ppm: 1.95-1.99 (m, 3H), 2.09 (m, 1H), 2.23 (s, 3H), 2.73-2.77 (m, 3H), 2.86-2.96 (m, 2H), 3.27 (m, 1H), 3.67 (m, 1H), 3.85 (s, 3H), 4.09 (m, 2H), 4.24 (m, 1H), 4.28 (s, 4H), 5.18 (s, 2H), 5.27 (bs, 1H), 6.70 (s, 1H), 6.74-6.78 (m, 2H), 6.91 (d, J=8.0 Hz, 1H), 7.16 (d, J=7.2 Hz, 1H), 7.25 (t, J=7.6 Hz, 1H), 7.45 (d, J=7.2 Hz, 1H).

Example-86

Synthesis of N-(2-(((5-((3-cyanobenzyl)oxy)-7-((2,2'-dimethyl-[1,1'-biphenyl]-3-yl)methoxy)-2,3-dihydro-1H-inden-4-yl)methyl)amino)ethyl)acetamide

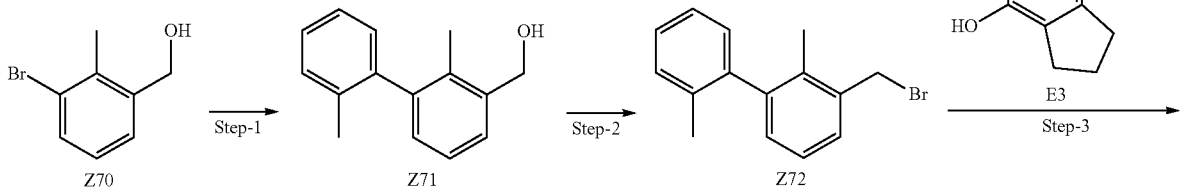

-continued

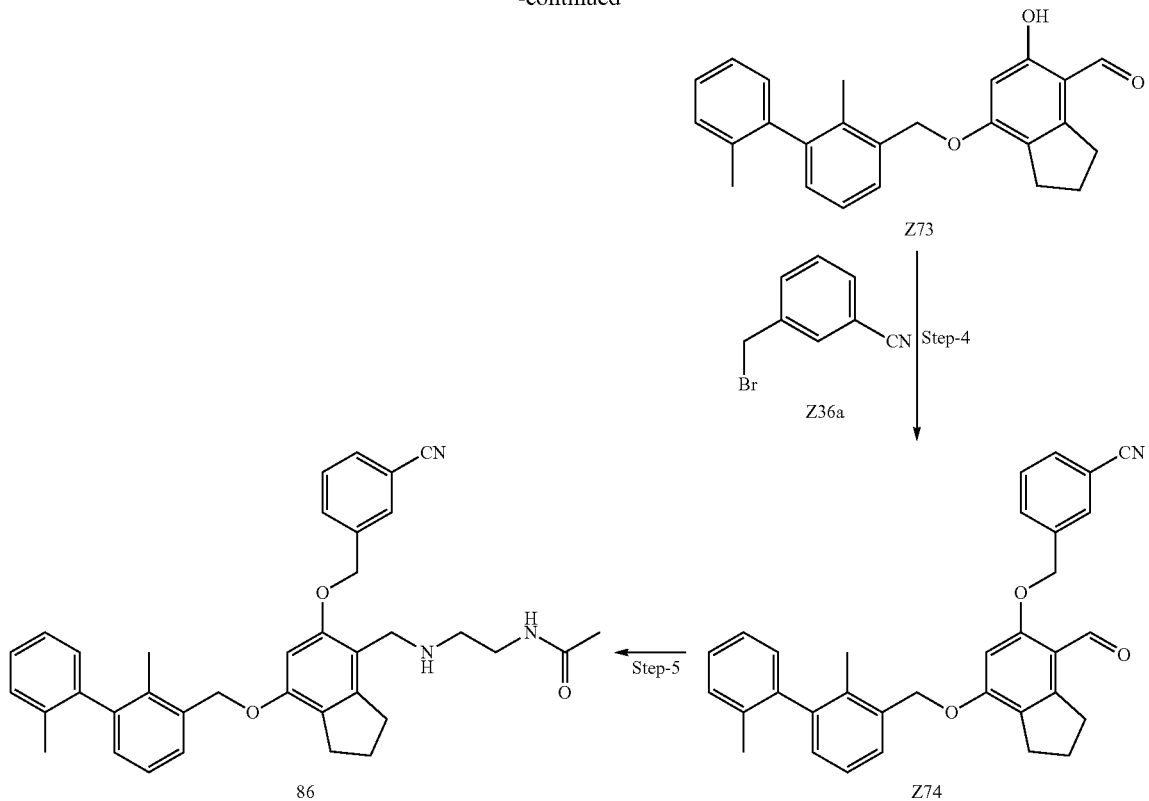

Step-1: A mixture of (3-bromo-2-methylphenyl)methanol (2 g, 9.95 mmol), o-tolylboronic acid (4.06 g, 29.84 mmol), sodium carbonate (12.4 g. 0.117 mol), toluene (27 mL), water (9 mL) and MeOH (9 mL) was degassed with nitrogen gas for 15 minutes. To this mixture, Pd(PPh$_3$)$_4$ (1.1 g, 0.99 mmol) was added and degassed for another 5 minutes with nitrogen. After sealing the vessel, the mixture was heated at 90° C. for 16 h. After completion, the reaction was diluted with water (50 mL) and extracted with EtOAc (3×50 mL). The organic layer was dried over sodium sulphate and concentrated. The crude was purified by column chromatography (silica gel, 100-200 mesh) using 0-20% EtOAc in hexane to obtain (2,2'-dimethyl-[1,1'-biphenyl]-3-yl)methanol (Yield: 2.05 g, 97%) as colourless liquid. $^1$H NMR (400 MHz, DMSO-d$_6$) δ ppm: 1.90 (s, 3H), 1.97 (s, 3H), 4.54 (m, 2H), 5.12 (m, 1H), 6.95 (d, J=7.6 Hz, 1H), 7.03 (d, J=6.8 Hz, 1H), 7.19-7.28 (m, 4H), 7.39 (d, J=7.2 Hz, 1H).

Step-2: To a solution of (2,2'-dimethyl-[1,1'-biphenyl]-3-yl)methanol (1.7 g, 8.01 mmol) in DCM (5 mL) at 0° C., PBr$_3$ (2.38 g, 8.8 mmol) was added and stirred the mixture at room temperature for 16 h. After completion, the reaction mixture was concentrated under vacuum and the crude was purified by flash chromatography (silica gel, 12 g cartridge) using 0-10% EtOAc in hexane as eluent to obtain 3-(bromomethyl)-2,2'-dimethyl-1,1'-biphenyl (Yield: 1.7 g, 77%) as colourless sticky liquid. $^1$H NMR (400 MHz, DMSO-d$_6$) δ ppm: 1.97 (s, 3H), 2.04 (s, 3H), 4.79 (s, 2H), 7.05 (d, J=7.2 Hz, 2H), 7.18-7.33 (m, 4H), 7.43 (d, J=8.8 Hz, 1H).

Step-3: To a solution of 5,7-dihydroxy-2,3-dihydro-1H-indene-4-carbaldehyde (0.31 g, 1.7 mmol) in acetonitrile (10 mL), potassium carbonate (0.28 g, 2.01 mmol) and 3-(bromomethyl)-2,2'-dimethyl-1,1'-biphenyl (0.47 g, 1.7 mmol) were added. The reaction mixture was stirred at room temperature for 12 h. After completion, the reaction mixture was diluted with water (20 mL) and extracted with EtOAc (3×20 mL). The combined organic layer was dried over sodium sulfate and concentrated. The resulting crude was purified by flash chromatography (silica gel, 4 g cartridge) using 0-30% EtOAc in hexane as eluent to obtain 7-((2,2'-dimethyl-[1,1'-biphenyl]-3-yl)methoxy)-5-hydroxy-2,3-dihydro-1H-indene-4-carbaldehyde (Yield: 0.61 g, 94%) as light yellow solid. LCMS (ES) m/z=373.16 [M+H]$^+$; $^1$H NMR (400 MHz, DMSO-d$_6$) δ ppm: 1.97 (s, 3H), 2.02 (m, 2H), 2.04 (s, 3H), 2.71 (t, J=7.2 Hz, 2H), 3.14 (t, J=7.2 Hz, 2H), 5.24 (s, 2H), 6.55 (s, 1H), 7.05 (d, J=7.2 Hz, 2H), 7.18-7.33 (m, 4H), 7.43 (d, J=8.8 Hz, 1H), 10.35 (s, 1H), 11.31 (s, 1H).

Step-4: To a solution of 7-((2,2'-dimethyl-[1,1'-biphenyl]-3-yl)methoxy)-5-hydroxy-2,3-dihydro-1H-indene-4-carbaldehyde (0.56 g, 1.5 mmol) in DMF (10 mL), potassium carbonate (0.416 g, 3.0 mmol) and 3-(chloromethyl)benzonitrile (0.29 g, 1.5 mmol) were added. The reaction mixture was stirred at room temperature for 16 h. After completion, the reaction mixture was diluted with water (20 mL) and extracted with EtOAc (3×20 mL). The combined organic layer was dried over sodium sulfate and concentrated. The resulting crude was purified by flash chromatography (silica gel, 4 g cartridge) using 0-50% EtOAc in hexane as eluent to obtain 3-(((7-((2,2'-dimethyl-[1,1'-biphenyl]-3-yl)methoxy)-4-formyl-2,3-dihydro-1H-inden-5-yl)oxy)methyl)benzonitrile (Yield: 0.705 g, 96%) as light yellow solid. LCMS (ES) m/z=488.41 [M+H]$^+$; $^1$H NMR (400 MHz, DMSO-d$_6$) δ ppm: 2.00 (m, 2H), 2.02 (s, 3H), 2.21 (s, 3H), 2.70 (t, J=7.2 Hz, 2H), 3.13 (m, 2H), 5.12 (s, 2H), 5.20 (s, 2H), 6.72 (s, 1H), 7.05-7.07 (m, 2H), 7.23-7.32 (m, 4H), 7.42 (d, J=7.2 Hz, 1H), 7.63 (t, J=7.6 Hz, 1H), 7.85 (m, 2H), 7.96 (s, 1H), 10.37 (s, 1H).

Step-5: To a solution of 3-(((7-((2,2'-dimethyl-[1,1'-biphenyl]-3-yl)methoxy)-4-formyl-2,3-dihydro-1H-inden-5-yl)oxy)methyl)benzonitrile (150 mg, 0.30 mmol) in DMF (4 mL) and MeOH (4 mL), N-(2-aminoethyl)acetamide (31 mg, 0.30 mmol) and acetic acid (2 drops) were added and stirred the mixture for 10 minutes. To this mixture, sodium cyanoborohydride (56 mg, 0.90 mmol) was added and the mixture was stirred at room temperature for 16 h. After completion, the reaction mixture was diluted with water (15 mL) and extracted with 10% MeOH in DCM (3×30 mL). The organic layer was dried over anhydrous sodium sulphate and concentrated. The resulting crude was purified by flash chromatography (silica gel, 4 g cartridge) using 0-10% MeOH in DCM as eluent. The resulting product was further purified by reverse phase HPLC using method-A to obtain N-(2-(((5-((3-cyanobenzyl)oxy)-7-((2,2'-dimethyl-[1,1'-biphenyl]-3-yl)methoxy)-2,3-dihydro-1H-inden-4-yl)methyl)amino)ethyl)acetamide (Yield: 100 mg, 21%) as white solid. LCMS (ES) m/z=574.52 [M+H]$^+$; $^1$H NMR (400 MHz, DMSO-$d_6$) δ ppm: 1.74 (s, 3H), 1.96-2.00 (m, 8H), 2.53 (m, 2H), 2.73 (t, J=7.2 Hz, 2H), 2.88 (t, J=7.2 Hz, 2H), 3.13 (m, 2H), 3.64 (s, 2H), 5.12 (s, 2H), 5.20 (s, 2H), 6.71 (s, 1H), 7.05-7.07 (m, 2H), 7.23-7.32 (m, 4H), 7.42 (d, J=7.2 Hz, 1H), 7.61 (t, J=7.6 Hz, 1H), 7.75 (m, 1H), 7.80-7.82 (m, 2H), 7.94 (s, 1H), The following compounds were prepared following procedures described above Example 87

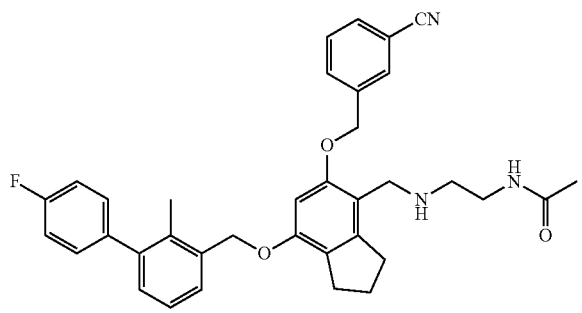 [SMILES: CC(=O)NCCNCc1c(OCc2cccc(C#N)c2)cc(OCc2cccc(-c3ccc(F)cc3)c2C)c2c1CCC2]

N-(2-(((5-((3-cyanobenzyl)oxy)-7-((4'-fluoro-2-methyl-[1,1'-biphenyl]-3-yl)methoxy)-2,3-dihydro-1H-inden-4-yl)methyl)amino)ethyl)acetamide, LCMS (ES) m/z=578.44 [M+H]$^+$; $^1$H NMR (400 MHz, DMSO-$d_6$) δ ppm: 1.79 (s, 3H), 1.96-2.01 (m, 2H), 2.18 (s, 3H), 2.77 (t, J=7.2 Hz, 2H), 2.90-2.97 (m, 4H), 3.27 (m, 2H), 4.00 (s, 2H), 5.17 (s, 2H), 5.28 (s, 2H), 6.79 (s, 1H), 7.19 (d, J=7.2 Hz, 1H), 7.23-7.37 (m, 5H), 7.41 (d, J 7.2 Hz, 1H), 7.62 (t, J=7.6 Hz, 1H), 7.81-7.87 (m, 2H), 8.00 (bs, 1H), 8.07 (bs, 1H), Example-88

Synthesis of (S)-1-((5-((3-carbamoylbenzyl)oxy)-7-((2-methyl-[1,1'-biphenyl]-3-yl)methoxy)-2,3-dihydro-1H-inden-4-yl)methyl)piperidine-2-carboxylic acid

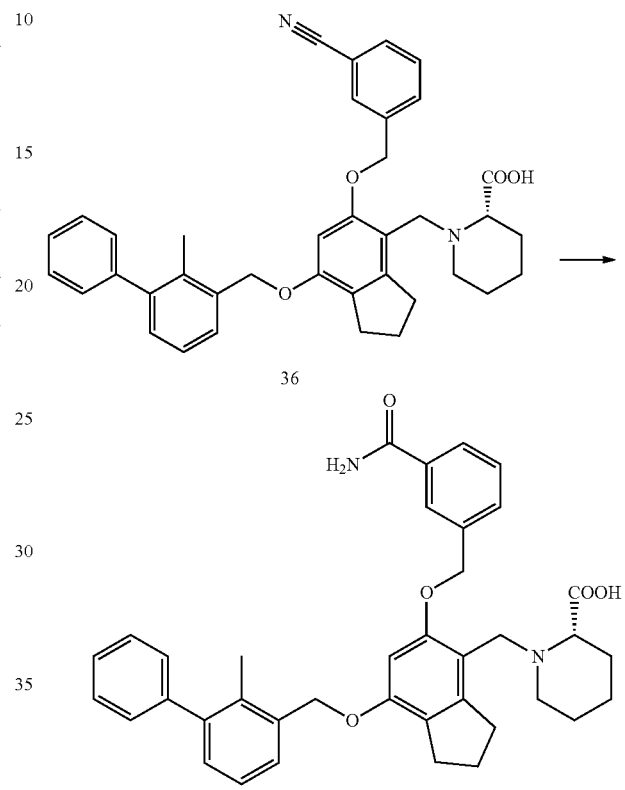

To a solution of (S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxylic acid (90 mg, 0.15 mmol) in MeOH (5 mL), water (5 mL), 1,4-dioxane (3 mL), and sodium hydroxide (10 mg) were added and stirred the mixture at 90° C. for 3 h. After completion, the reaction mixture was diluted with water (10 mL) and extracted with 10% MeOH in DCM (3×20 mL). The organic layer was concentrated and the crude was purified by flash chromatography (silica gel, 4 g cartridge) using 0-15% MeOH in DCM to obtain (S)-1-((5-((3-carbamoylbenzyl)oxy)-7-((2-methyl-[1,1'-biphenyl]-3-yl)methoxy)-2,3-dihydro-1H-inden-4-yl)methyl)piperidine-2-carboxylic acid (Yield: 40 mg, 44%) as white solid. LCMS (ES) m/z=605.37 [M+H]$^+$; $^1$H NMR (400 MHz, DMSO-$d_6$) δ ppm: 1.33-1.48 (m, 4H), 1.79 (m, 2H), 1.95-1.99 (m, 2H), 2.21 (s, 3H), 2.74 (m, 2H), 2.83 (m, 1H), 2.96-3.02 (m, 3H), 3.17 (m, 1H), 3.82 (d, J=12.0 Hz, 1H), 4.04 (d, J=12.8 Hz, 1H), 5.15 (s, 2H), 5.23 (s, 2H), 6.79 (bs, 1H), 7.19 (m, 1H), 7.25-7.33 (m, 4H), 7.39 (m, 1H), 7.44-7.48 (m, 4H), 7.65 (d, J=8.0 Hz, 1H), 7.83 (d, J=7.6 Hz, 1H), 8.12 (s, 1H), 8.31 (bs, 1H).

Example-89

Synthesis of 3-(((4-(aminomethyl)-7-((2-methyl-[1,1'-biphenyl]-3-yl)methoxy)-2,3-dihydro-1H-inden-5-yl)oxy)methyl)benzonitrile

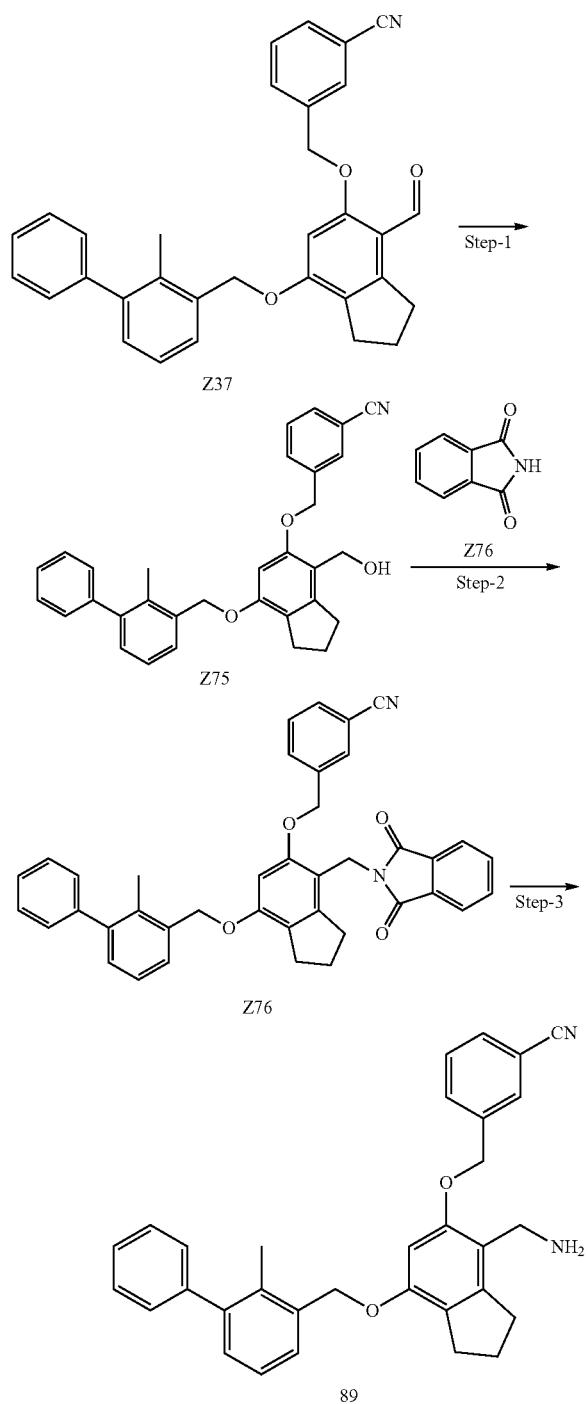

Step-1: To a solution of 3-(((4-formyl-7-((2-methyl-[1,1'-biphenyl]-3-yl)methoxy)-2,3-dihydro-1H-inden-5-yl)oxy) methyl)benzonitrile (60 mg, 0.126 mmol) in MeOH (2 mL), THF (2 mL) at 0° C., sodium borohydride (12 mg, 0.40 mmol) was added slowly and allowed the mixture to stir at RT for 3 h. After completion, the reaction was quenched with water (10 mL) and extracted with DCM (2×100 mL). The organic layer was dried over anhydrous sodium sulfate and concentrated. The resulting crude was purified by flash chromatography using 30% EtOAc in hexanes as eluent to obtain 3-(((4-(hydroxymethyl)-7-((2-methyl-[1,1'-biphenyl]-3-yl) methoxy)-2,3-dihydro-1H-inden-5-yl) oxy) methyl) benzonitrile (Yield: 50 mg, 83%) as white solid. LCMS (ES) m/z=476 [M−H]$^+$; $^1$H NMR (400 MHz, DMSO-$d_6$) δ ppm: 1.94-2.02 (m, 2H), 2.19 (s, 3H), 2.74 (m, 2H), 2.91 (m, 2H), 4.45 (m, 2H), 4.54 (m, 1H), 5.13 (s, 2H), 5.20 (s, 2H), 6.69 (s, 1H), 7.32 (d, J=7.28 Hz, 1H) 7.35-7.47 (m, 4H), 7.60 (m, 1H), 7.81 (m, 2H), 7.95 (s, 1H).

Step-2: To a solution of 3-(((4-(hydroxymethyl)-7-((2-methyl-[1,1'-biphenyl]-3-yl) methoxy)-2,3-dihydro-1H-inden-5-yl) oxy) methyl) benzonitrile (250 mg, 0.526 mmol) and pthalimide (229 mg, 1.31 mmol) in dry THF (5 mL), triphenyl phosphine (345 mg, 1.31 mmol) was added and cooled the mixture to 0° C. To this mixture, DIAD (266 mg, 1.31 mmol) was added and allowed the mixture to stir at room temperature for 6 h. After completion, the reaction mixture was diluted with water (20 mL) and extracted with EtOAc (3×40 mL). The combined organic layer was dried over sodium sulphate and concentrated. The crude was purified by flash chromatography using 20% EtOAc in hexane as eluent to obtain 3-(((4-((1,3-dioxoisoindolin-2-yl) methyl)-7-((2-methyl-[1,1'-biphenyl]-3-yl)methoxy)-2,3-dihydro-1H-inden-5-yl)oxy)methyl)benzonitrile (Yield: 300 mg, 94%) as white solid. LCMS (ES) m/z=605.31 [M+H]$^+$ Step-3: To a solution of 3-(((4-((1,3-dioxoisoindolin-2-yl) methyl)-7-((2-methyl-[1,1'-biphenyl]-3-yl)methoxy)-2,3-dihydro-1H-inden-5-yl)oxy)methyl)benzonitrile (300 mg, 0.495 mmol) in EtOH (15 mL), at room temperature, hydrazine hydrate solution (2 mL) was added slowly and allowed to stir the mixture at RT for 3 h. After completion, the reaction was quenched with water (10 mL) and extracted with DCM (2×100 mL). The organic layer was dried over anhydrous sodium sulfate and concentrated. The resulting crude was purified by flash chromatography using 30% EtOAc in hexanes as eluent to obtain 3-(((4-(aminomethyl)-7-((2-methyl-[1,1'-biphenyl]-3-yl)methoxy)-2,3-dihydro-1H-inden-5-yl)oxy)methyl)benzonitrile (Yield: 35 mg, 15%) as white solid. LCMS (ES) m/z=475.6 [M+H]$^+$; $^1$H NMR (400 MHz, DMSO-$d_6$) δ ppm: 1.98 (m, 2H), 2.19 (s, 3H), 2.74 (m, 2H), 2.89 (m, 2H), 3.62 (s, 2H), 5.12 (s, 2H), 5.21 (s, 2H), 6.69 (s, 1H), 7.17 (d, J=7.24 Hz, 1H), 7.25 (m, 1H), 7.32 (d, J=7.04 Hz, 1H), 7.37-7.47 (m, 4H), 7.59 (m, 1H), 7.78-7.86 (m, 2H), 7.91 (m, 1H).

Example-90

Synthesis of N-((5-((3-cyanobenzyl)oxy)-7-((2-methyl-[1,1'-biphenyl]-3-yl) methoxy)-2,3-dihydro-1H-inden-4-yl)methyl)acetamide

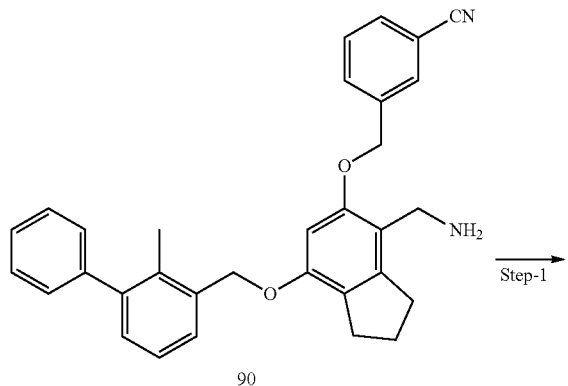

Step-1: A solution of 3-(((4-(aminomethyl)-7-((2-methyl-[1,1'-biphenyl]-3-yl)methoxy)-2,3-dihydro-1H-inden-5-yl)oxy)methyl)benzonitrile (40 mg, 0.084 mmol), triethylamine (12.7 mg, 0.21 mmol) in DCM (5 mL) was cooled to 0° C. To this mixture, acetyl chloride (16 mg, 0.021 mmol) was added and the reaction mixture was stirred at room temperature for 6 h. After completion of the reaction, the reaction mixture was diluted with ice cold water (10 mL) and the aqueous mixture was extracted with EtOAc (3×100 mL). The combined organic layer was dried over sodium sulfate and concentrated. The resulting crude was purified by flash chromatography (silica gel, 4 g cartridge) using 0-30% EtOAc in hexanes as eluent to obtain N-((5-((3-cyanobenzyl) oxy)-7-((2-methyl-[1,1'-biphenyl]-3-yl)methoxy)-2,3-dihydro-1H-inden-4-yl) methyl) acetamide (Yield: 32 mg, 73%) as white solid. LCMS (ES) m/z=517.34 [M−H]$^+$; $^1$H NMR (400 MHz, DMSO-$d_6$) δ ppm: 1.79 (s, 3H), 1.98 (m, 2H), 2.19 (s, 3H), 2.74 (m, 2H), 2.87 (m, 2H), 4.21 (m, 2H), 5.12 (s, 2H), 5.21 (s, 2H), 6.72 (s, 1H), 7.19 (d, J=7.08 Hz, 1H), 7.25 (m, 1H), 7.32 (d, J=7.04 Hz, 2H), 7.40-7.47 (m, 4H), 7.59 (m, 1H), 7.78-7.82 (m, 3H), 7.91 (s, 1H).

Example-91

Synthesis of 6-acetamido-N-((5-((3-cyanobenzyl)oxy)-7-((2-methyl-[1,1'-biphenyl]-3-yl)methoxy)-2,3-dihydro-1H-inden-4-yl)methyl)hexanamide

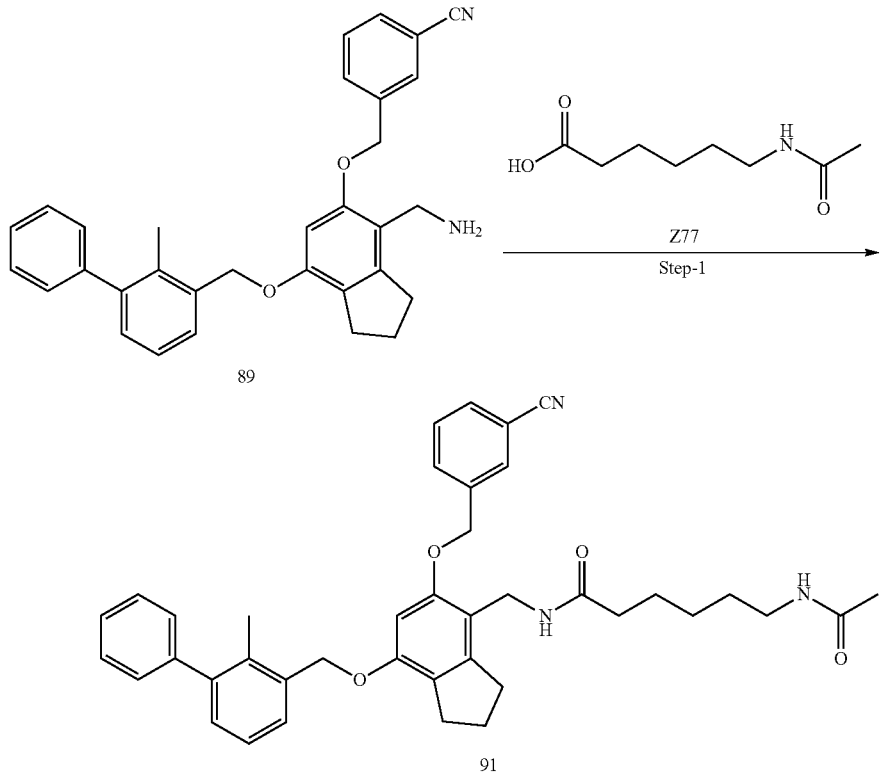

Step-1: A solution of 3-(((4-(aminomethyl)-7-((2-methyl-[1,1'-biphenyl]-3-yl)methoxy)-2,3-dihydro-1H-inden-5-yl)oxy)methyl)benzonitrile (150 mg, 0.31 mmol), 6-acetamidohexanoic acid (82 mg, 0.47 mmol), HOBt (64 mg, 0.47 mmol), EDC.HCl (90 mg, 0.47 mmol) and DIPEA (244 mg, 1.89 mmol) in DMF (10 mL) was stirred for 12 h at room temperature. After completion of the reaction, the reaction mixture was diluted with ice cold water (20 mL) and extracted with 10% MeOH in DCM (2×50 mL). The combined organic layer was washed with brine solution (20 mL), dried over sodium sulfate and concentrated. The resulting crude was purified by flash chromatography (silica gel, 4 g cartridge) using 0-10% MeOH in DCM as eluent to obtain 6-acetamido-N-((5-((3-cyanobenzyl)oxy)-7-((2-methyl-[1,1'-biphenyl]-3-yl)methoxy)-2,3-dihydro-1H-inden-4-yl)methyl)hexanamide (Yield: 80 mg, 40%) as white solid. LCMS (ES) m/z=630.68 [M−H]$^+$; $^1$H NMR (400 MHz, DMSO-d$_6$) δ ppm: 1.16-1.21 (m, 2H), 1.29-1.36 (m, 2H), 1.41-1.49 (m, 2H), 1.75 (s, 3H), 1.93-2.06 (m, 4H), 2.19 (s, 3H), 2.66-2.74 (m, 2H), 2.87 (m, 2H), 2.96 (m, 2H), 4.21 (m, 2H), 5.13 (s, 2H), 5.21 (s, 2H), 6.72 (s, 1H), 7.19 (d, J=7.36 Hz, 1H), 7.25 (m, 1H), 7.32 (d, J=7.04 Hz, 1H), 7.37-7.47 (m, 4H), 7.59 (t, J=7.76 Hz, 1H), 7.78-7.82 (m, 4H), 7.93 (s, 1H).

Example-92

Synthesis of 3-(((4-((dimethylamino)methyl)-7-((2-methyl-[1,1'-biphenyl]-3-yl)methoxy)-2,3-dihydro-1H-inden-5-yl)oxy)methyl)benzonitrile

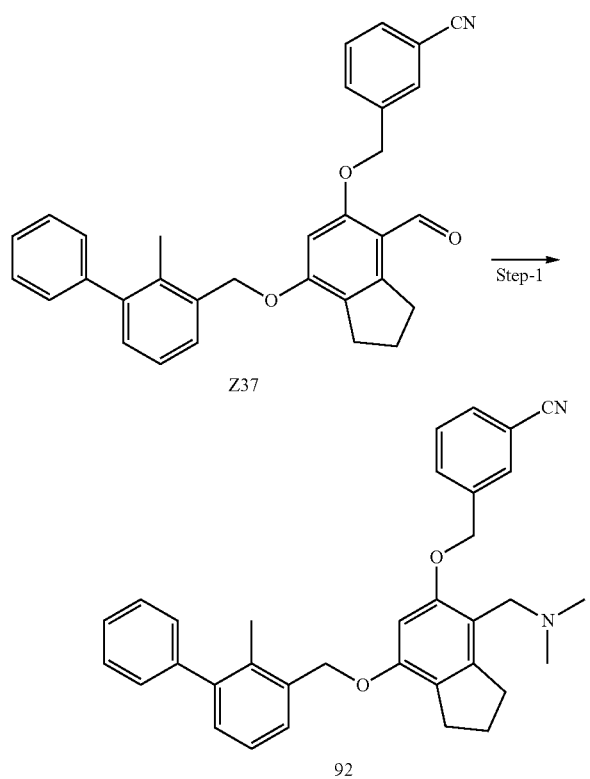

Step-1: A solution of 3-(((4-formyl-7-((2-methyl-[1,1'-biphenyl]-3-yl)methoxy)-2,3-dihydro-1H-inden-5-yl)oxy)methyl)benzonitrile (120 mg, 0.25 mmol), dimethylamine solution in methanol (4 mL), and acetic acid (1 drop) in DMF (4 mL) was stirred at room temperature for 2 h. To this mixture, sodium cyanoborohydride (47 mg, 0.76 mmol) was added and stirred for 12 h. After completion, the reaction mixture was poured on ice cold water (10 mL) and collected the white solid by filtration. A solution of white solid in DCM (20 mL) was dried over sodium sulfate and concentrated. The resulting crude was purified by flash chromatography (silica gel, 4 g cartridge) using 0-10% MeOH in DCM as eluent to obtain 3-(((4-((dimethylamino)methyl)-7-((2-methyl-[1,1'-biphenyl]-3-yl) methoxy)-2,3-dihydro-1H-inden-5-yl)oxy)methyl)benzonitrile (Yield: 12 mg, 9.6%) as white solid. LCMS (ES) m/z=503.5 [M−H]$^+$; $^1$H NMR (400 MHz, DMSO-d$_6$) δ ppm: 2.01 (m, 2H), 2.20 (s, 3H), 2.62-2.79 (m, 8H), 2.97 (m, 2H), 4.20 (m, 2H), 5.19 (s, 2H), 5.30 (s, 2H), 6.84 (s, 1H), 7.19 (d, J=7.08 Hz, 1H), 7.25-7.32 (m, 3H), 7.38-7.48 (m, 4H), 7.62 (t, J=7.04 Hz, 1H), 7.82-7.88 (m, 2H), 8.03 (s, 1H).

Example-93

Synthesis of 5-(((4-(((2-acetamidoethyl)amino) methyl)-7-((2-methyl-[1,1'-biphenyl]-3-yl)methoxy)-2,3-dihydro-1H-inden-5-yl)oxy)methyl)nicotinic acid

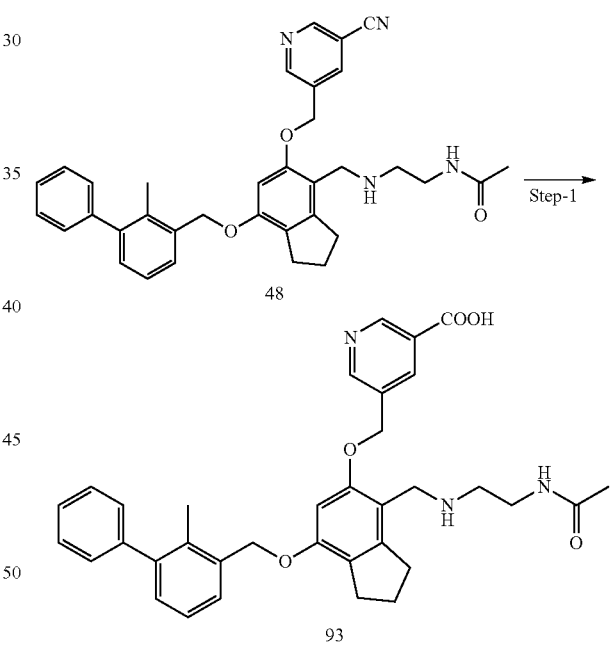

To a solution of N-(2-(((5-((5-cyanopyridin-3-yl)methoxy)-7-((2-methyl-[1,1'-biphenyl]-3-yl)methoxy)-2,3-dihydro-1H-inden-4-yl)methyl)amino)ethyl)acetamide (0.12 g, 0.21 mmol) in ethanol (8 mL) and water (8 mL), potassium hydroxide (60 mg, 1.07 mmol) was added and refluxed for 20 h. After completion, the reaction mixture was diluted with water (20 mL) and washed with EtOAc (30 mL). The aqueous layer was acidified to pH 4 using 6N HCl solution and then the mixture was extracted with 10% MeOH in DCM (2×100 mL). The combined organic layer was dried over sodium sulfate and concentrated. The resulting crude was purified by flash chromatography (silica gel, 4 g cartridge) using 0-10% MeOH in DCM as eluent. The compound was further purified by reverse phase HPLC using method-B to obtain 5-(((4-(((2-acetamidoethyl) amino)methyl)-7-((2-methyl-[1,1'-biphenyl]-3-yl) methoxy)-2,3-dihydro-1H-inden-5-yl)oxy)methyl)nicotinic acid (Yield: 20 mg, 16%) as white solid. LCMS (ES) m/z=580.58 [M+H]$^+$; $^1$H NMR (400 MHz, DMSO-d$_6$) δ ppm: 1.76 (s, 3H), 2.00 (m, 2H), 2.20 (s, 3H), 2.74-2.83 (m, 4H), 2.94 (m, 2H), 3.25 (m, 2H), 3.87 (s, 2H), 5.18 (s, 2H), 5.27 (s, 2H), 6.85 (s, 1H), 7.18 (d, J=7.6 Hz, 1H), 7.24-7.32 (m, 3H), 7.39 (m, 1H), 7.43-7.48 (m, 3H), 8.32 (s, 1H), 8.40 (br, 1H), 8.74 (s, 1H), 8.96 (s, 1H).

Example-94

Synthesis of 5-(((4-(((2-acetamidoethyl)amino) methyl)-7-((2-methyl-[1,1'-biphenyl]-3-yl)methoxy)- 2,3-dihydro-1H-inden-5-yl)oxy)methyl)nicotinamide

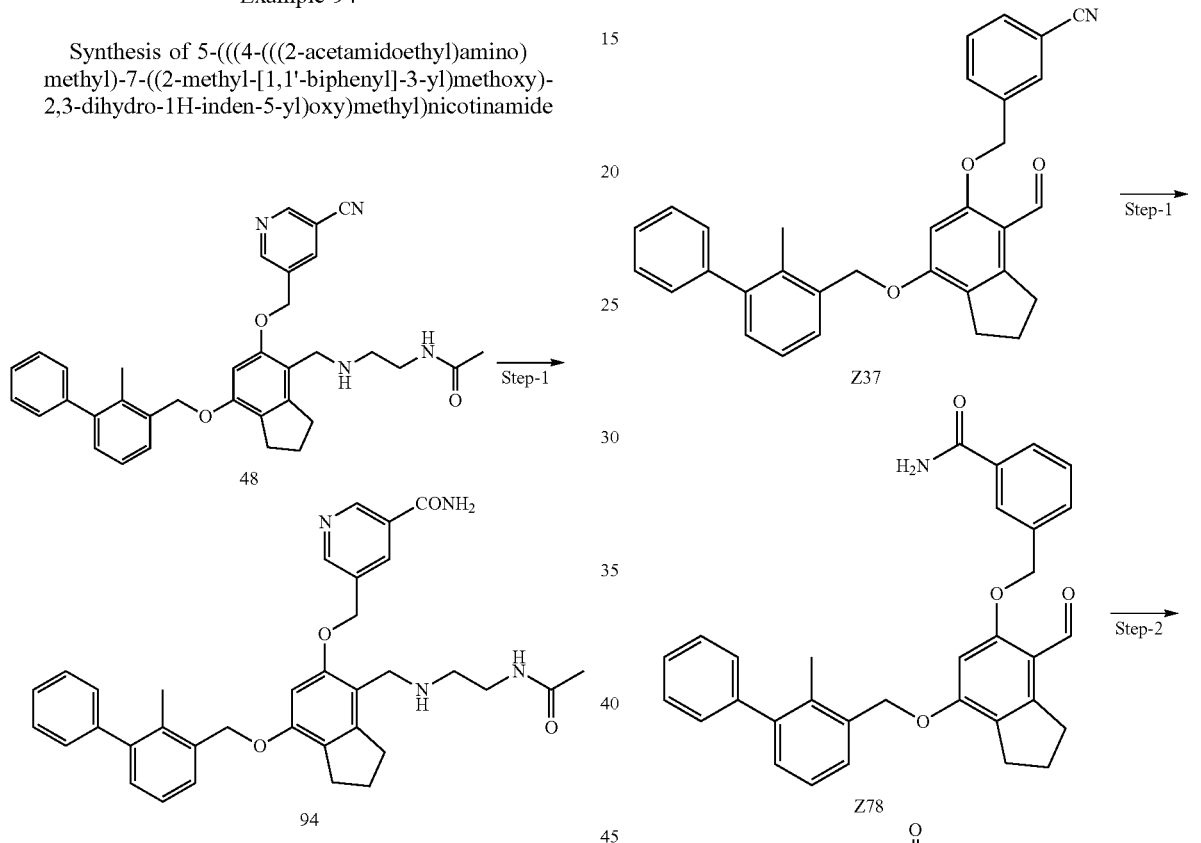

Step-1: To a solution of N-(2-(((5-((5-cyanopyridin-3-yl) methoxy)-7-((2-methyl-[1,1'-biphenyl]-3-yl)methoxy)-2,3- dihydro-1H-inden-4-yl)methyl)amino)ethyl)acetamide (1, 0.15 g, 0.25 mmol) in Ethanol (8 mL) and water (8 mL), potassium hydroxide (60 mg, 1.07 mmol) was added and refluxed for 6 h. After completion, the reaction mixture was diluted with water (20 mL) and washed with EtOAc (30 mL). The aqueous layer was acidified to pH 4 using 6N HCl solution and the reaction mixture was extracted with 10% MeOH in DCM (2×100 mL). The combined organic layer was dried over sodium sulfate and concentrated. The resulting crude was purified by flash chromatography (silica gel, 4 g cartridge) using 0-10% MeOH in DCM as eluent. The compound was further purified by reverse phase HPLC using method-B to obtain 5-(((4-(((2-acetamidoethyl) amino)methyl)-7-((2-methyl-[1,1'-biphenyl]-3-yl) methoxy)-2,3-dihydro-1H-inden-5-yl)oxy)methyl)nicotinamide (Yield: 30 mg, 20%) as white solid. LCMS (ES) m/z=579.6 [M+H]$^+$; $^1$H NMR (400 MHz, DMSO-d$_6$) δ ppm: 1.74 (s, 3H), 1.84 (m, 2H), 1.97 (m, 2H), 2.20 (s, 3H), 2.74 (m, 2H), 2.87 (m, 2H), 3.07 (m, 2H), 3.61 (s, 2H), 5.13 (s, 2H), 5.25 (s, 2H), 6.77 (s, 1H), 7.18 (d, J=7.6 Hz, 1H), 7.31-7.33 (m, 2H), 7.39 (m, 1H), 7.43-7.48 (m, 3H), 7.64 (m, 1H), 7.73 (m, 1H), 8.21 (bs, 1H), 8.32 (s, 1H), 8.32 (s, 1H), 8.81 (s, 1H), 8.99 (s, 1H).

Example-95

Synthesis of 3-(((4-(((2-acetamidoethyl)amino) methyl)-7-((2-methyl-[1,1'-biphenyl]-3-yl)methoxy)- 2,3-dihydro-1H-inden-5-yl)oxy)methyl)benzamide

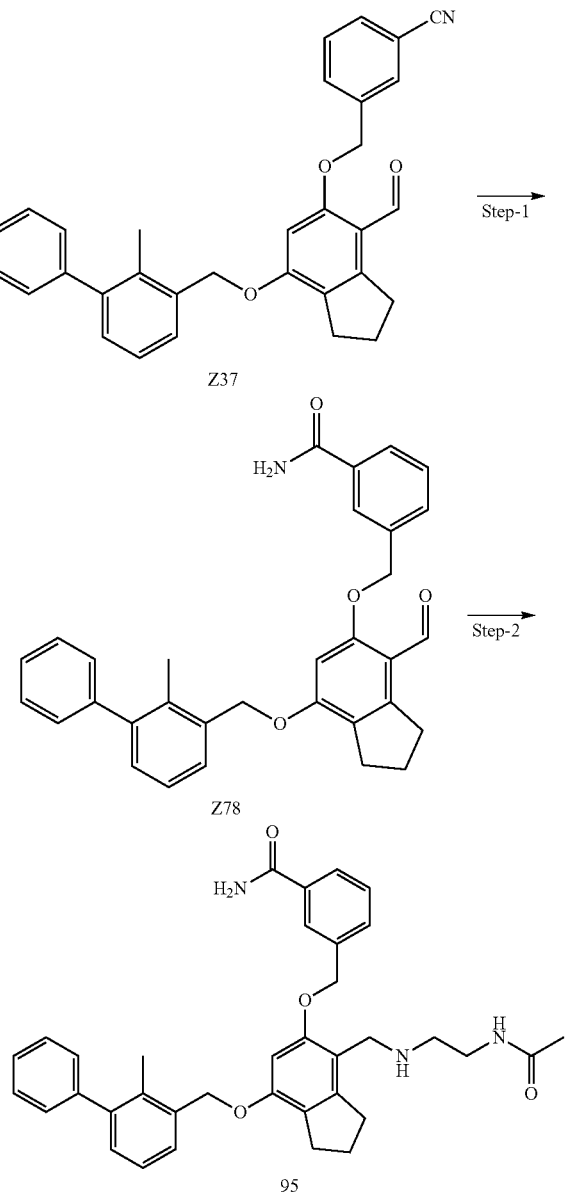

Step-1: To a solution of 3-(((4-formyl-7-((2-methyl-[1,1'- biphenyl]-3-yl)methoxy)-2,3-dihydro-1H-inden-5-yl)oxy) methyl)benzonitrile (0.30 g, 0.63 mmol) in ethanol (10 mL) and water (10 mL), potassium hydroxide (0.15 g, 2.67 mmol) was added and refluxed for 12 h. After completion, the reaction mixture was diluted with water (20 mL) and extracted with EtOAc (30 mL). The aqueous layer was acidified to pH 4 using 6N HCl solution and the reaction mixture was extracted with 10% MeOH in DCM (2×100 mL). The combined organic layer was dried over sodium sulfate and concentrated. The resulting crude provided a mixture of 3-(((4-formyl-7-((2-methyl-[1,1'-biphenyl]-3-yl) methoxy)-2,3-dihydro-1H-inden-5-yl)oxy)methyl)benzamide (240 mg; crude) as yellow viscous liquid which was used in next step without further purification.

Step-2: A solution of 3-(((4-formyl-7-((2-methyl-[1,1'-biphenyl]-3-yl)methoxy)-2,3-dihydro-1H-inden-5-yl)oxy) methyl)benzamide (240 mg, 0.487 mmol), N-(2-aminoethyl)acetamide (50 mg, 0.487 mmol) and acetic acid (1 drop) in DMF (4 mL) and MeOH (4 mL) was stirred at room temperature for 2 h. To this mixture, sodium cyanoborohydride (92 mg, 1.46 mmol) was added and the reaction mixture was stirred for 16 h. After completion of the reaction, the reaction mixture was diluted with ice cold water (10 mL) and the aqueous mixture was extracted with 10% MeOH in DCM (3×100 mL). The combined organic layer was dried over sodium sulfate and concentrated. The resulting crude was purified by flash chromatography (silica gel, 4 g cartridge) using 0-10% MeOH in DCM as eluent to obtain 3-(((4-(((2-acetamidoethyl) amino)methyl)-7-((2-methyl-[1,1'-biphenyl]-3-yl)methoxy)-2,3-dihydro-1H-inden-5-yl)oxy)methyl)benzamide (32 mg) as white solid. LCMS (ES) m/z=578.62 [M+H]$^+$; $^1$H NMR (400 MHz, DMSO-$d_6$) δ ppm: 1.73 (s, 3H), 1.99 (m, 2H), 2.20 (s, 3H), 2.53 (m, 2H), 2.74 (m, 2H), 2.87 (m, 2H), 3.07 (m, 2H), 3.62 (s, 2H), 5.12 (s, 2H), 5.18 (s, 2H), 6.74 (s, 1H), 7.18 (d, J=7.26 Hz, 1H), 7.26 (m, 1H), 7.31 (d, J=8.16 Hz, 2H), 7.36-7.48 (m, 6H), 7.61 (d, J=7.6 Hz, 1H), 7.74 (m, 1H), 7.82 (d, J=7.76 Hz, 1H), 8.01 (m, 2H).

Example-96

Synthesis of (S)-1-((3-methoxy-1-((2-methyl-[1,1'-biphenyl]-3-yl)methoxy)-6,7-dihydro-5H-cyclopenta [c]pyridin-4-yl)methyl)piperidine-2-carboxylic acid

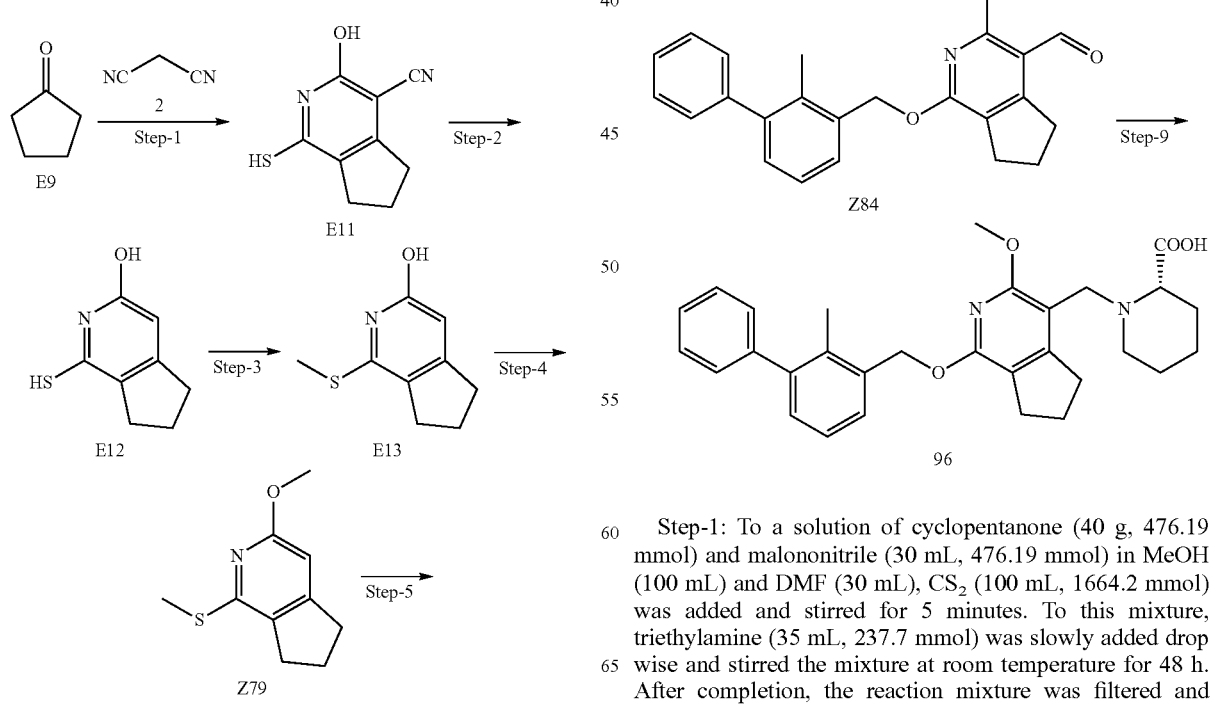

Step-1: To a solution of cyclopentanone (40 g, 476.19 mmol) and malononitrile (30 mL, 476.19 mmol) in MeOH (100 mL) and DMF (30 mL), CS$_2$ (100 mL, 1664.2 mmol) was added and stirred for 5 minutes. To this mixture, triethylamine (35 mL, 237.7 mmol) was slowly added drop wise and stirred the mixture at room temperature for 48 h. After completion, the reaction mixture was filtered and washed with cold MeOH (30 mL) and dried under vacuum to obtain 3-hydroxy-1-mercapto-6,7-dihydro-5H-cyclopenta[c]pyridine-4-carbonitrile (Yield: 13.0 g, crude) as red solid. $^1$H NMR (400 MHz, DMSO-d$_6$) δ ppm: 1.86-1.96 (m, 2H), 2.74 (t, J=8.0 Hz, 2H), 2.93 (t, J=8.0 Hz, 2H), 8.75 (s, 1H), 9.03 (s, 1H).

Step-2: A solution of 3-hydroxy-1-mercapto-6,7-dihydro-5H-cyclopenta[c]pyridine-4-carbonitrile (13 g, 67.56 mmol) in 1N NaOH (250 mL) was stirred at 150° C. for 8 h. After completion, the reaction mixture was acidified with aqueous 6N HCl solution and filtered the solid. The solid was washed with cold water (20 mL) and dried under vacuum to obtain 1-mercapto-6,7-dihydro-5H-cyclopenta[c]pyridin-3-ol (Yield: 6.2 g, crude) as red solid. LCMS (ES) m/z=168.32 [M+H]$^+$; $^1$H NMR (400 MHz, DMSO-d$_6$) δ ppm: 1.90 (t, J=8.0 Hz, 2H), 2.60 (t, J=8.0 Hz, 2H), 2.78 (t, J=8.0 Hz, 2H), 5.94 (s, 1H), 11.50-12.76 (bs, 2H).

Step-3: To a solution of 1-mercapto-6,7-dihydro-5H-cyclopenta[c]pyridin-3-ol (4.0 g, 23.95 mmol) in EtOH (100 mL), potassium carbonate (5.0 g, 36.17 mmol) and MeI (3.39 g, 2.39 mmol) were added and stirred the mixture at room temperature for 6 h. After completion, the reaction was quenched with water (100 mL) and extracted with DCM (2×100 mL). The organic layer was dried over anhydrous sodium sulfate and concentrated. The resulting crude was purified by flash chromatography (silica gel, 12 g cartridge) using 0-30% EtOAc in hexanes as eluent to obtain 1-(methylthio)-6,7-dihydro-5H-cyclopenta[c]pyridin-3-ol (Yield: 1.9 g, 44%) as red solid. LCMS (ES) m/z=182.31 [M+H]$^+$; $^1$H NMR (400 MHz, DMSO-d$_6$) δ ppm: 1.96-2.01 (m, 2H), 2.49 (s, 3H), 2.57 (t, J=8.0 Hz, 2H), 2.75 (t, J=8.0 Hz, 2H), 6.18 (s, 1H), 10.44 (s, 1H).

Step-4: To a solution of 1-(methylthio)-6,7-dihydro-5H-cyclopenta[c]pyridin-3-ol (3.0 g, 16.55 mmol) in benzene (50 mL), Ag$_2$O (2.18 g, 9.40 mmol) and MeI (2.58 g, 18.23 mmol) were added and stirred the mixture at 80° C. for 16 h. After completion, the reaction was quenched with water (100 mL) and extracted with EtOAc (2×100 mL). The organic layer was dried over anhydrous sodium sulfate and concentrated. The resulting crude was purified by flash chromatography (silica gel, 12 g cartridge) using 10% EtOAc in hexanes as eluent to obtain 3-methoxy-1-(methylthio)-6,7-dihydro-5H-cyclopenta[c]pyridine (Yield: 2.3 g, 71%) as white solid. LCMS (ES) m/z=196.35 [M+H]$^+$; $^1$H NMR (400 MHz, DMSO-d$_6$) δ ppm: 2.06-1.99 (m, 2H), 2.49 (s, 3H), 2.60 (t, J=7.2 Hz, 2H), 2.80 (t, J=8.0 Hz, 2H), 3.85 (s, 3H), 6.39 (s, 1H).

Step-5: To a solution of 3-methoxy-1-(methylthio)-6,7-dihydro-5H-cyclopenta[c]pyridine (2.3 g, 11.73 mmol) in DCM (30 mL), Br$_2$ (2.0 g, 11.73 mmol) was added slowly and stirred at room temperature for 4 h. After completion, the reaction was concentrated under vacuum to obtain 4-bromo-3-methoxy-1-(methylthio)-6,7-dihydro-5H-cyclopenta[c]pyridine (Yield: 2.0 g, 62%) as off-white solid. LCMS (ES) m/z=274.31 [M+H]$^+$ & 276.32 [M+2H]$^+$; $^1$H NMR (400 MHz, DMSO-d$_6$) δ ppm: 2.06-2.12 (m, 2H), 2.54 (s, 3H), 2.73 (t, J=8 Hz, 2H), 2.85 (t, J=8.0 Hz, 2H), 3.94 (s, 3H).

Step-6: To a solution of 4-bromo-3-methoxy-1-(methylthio)-6,7-dihydro-5H-cyclopenta[c]pyridine (2.0 g, 10.24 mmol) in DCM (50 mL) at 0° C., mCPBA (4.0 g, 25.60 mmol) was added and stirred the mixture at room temperature for 12 h. After completion, the reaction was quenched with aqueous saturated NaHCO$_3$ solution (100 mL) and extracted with DCM (2×70 mL). The organic layer was dried over anhydrous sodium sulfate and concentrated under vacuum to obtain 4-bromo-3-methoxy-1-(methylsulfonyl)-6,7-dihydro-5H-cyclopenta[c]pyridine (Yield: 1.9 g, 80%) as white solid. LCMS (ES) m/z=306.25 [M+H]$^+$ & 308.21 [M+2H]$^+$; $^1$H NMR (400 MHz, DMSO-d$_6$) δ ppm: 2.10-2.13 (m, 2H), 2.92 (t, J=8 Hz, 2H), 3.23 (t, J=8.0 Hz, 2H), 3.30 (s, 3H), 3.97 (s, 3H).

Step-7: To a solution of (2-methyl-[1,1'-biphenyl]-3-yl)methanol (0.92 g, 4.64 mmol) in DMF (10 mL) at 0° C., NaH (0.25 g, 6.37 mmol) was added and stirred at 0° C. for 30 min. To this mixture, 4-bromo-3-methoxy-1-(methylsulfonyl)-6,7-dihydro-5H-cyclopenta[c]pyridine (1.3 g, 4.24 mmol) was added and stirred the mixture at room temperature for 6 h. After completion, the reaction mixture was quenched with aqueous saturated NaHCO$_3$ solution (100 mL) and extracted with EtOAc (2×80 mL). The organic layer was dried over anhydrous sodium sulfate and concentrated. The resulting crude was purified by flash chromatography (silica gel, 4 g cartridge) using DCM as eluent to obtain 4-bromo-3-methoxy-1-((2-methyl-[1,1'-biphenyl]-3-yl)methoxy)-6,7-dihydro-5H-cyclopenta[c]pyridine (Yield: 700 mg, 39%) as white solid. LCMS (ES) m/z=424.38[M+H]$^+$ and 426.39 [M+2H]$^+$; $^1$H NMR (400 MHz, DMSO-d$_6$) δ ppm: 2.06 (t, J=8.0 Hz, 2H), 2.16 (s, 3H), 2.83 (m, 4H), 3.91 (s, 3H), 5.46 (s, 2H), 7.16-7.18 (m, 1H), 7.24-7.27 (m, 1H), 7.29-7.31 (m, 2H), 7.35-7.39 (m, 1H), 7.43-7.46 (m, 3H).

Step-8: To a solution of 4-bromo-3-methoxy-1-((2-methyl-[1,1'-biphenyl]-3-yl)methoxy)-6,7-dihydro-5H-cyclopenta[c]pyridine (0.7 g, 1.64 mmol) in DMF (20 mL), tributyl(vinyl)tin (1.3 g, 4.10 mmol) was added and degassed with nitrogen gas for 5 min. To this mixture, Pd(PPh$_3$)$_4$ (0.2 g, 0.16 mmol) was added and degassed again with nitrogen gas for 5 min. The mixture was stirred at 90° C. for 16 h. After completion, the reaction was quenched with water (30 mL) and extracted with EtOAc (2×80 mL). The organic layer was dried over anhydrous sodium sulfate and concentrated. The resulting crude was purified by flash chromatography (silica gel, 4 g Cartridge) using hexane as eluent to obtain 3-methoxy-1-((2-methyl-[1,1'-biphenyl]-3-yl)methoxy)-4-vinyl-6,7-dihydro-5H-cyclopenta[c]pyridine (Yield: 550 mg, 89%) as white solid. LCMS (ES) m/z=372.48 [M+H]$^+$; $^1$H NMR (400 MHz, DMSO-d$_6$) δ ppm: 2.03-2.08 (m, 2H), 2.22 (s, 3H), 2.71-2.94 (m, 4H), 3.91 (s, 3H), 5.27 (d, J=11.6 Hz, 1H), 5.48 (s, 2H), 5.67 (d, J=18.8 Hz, 1H), 7.17 (m, 1H), 7.23-7.27 (m, 1H), 7.29-7.31 (m, 2H), 7.35-7.38 (m, 1H), 7.43-7.47 (m, 3H).

Step-9: A solution of 3-methoxy-1-((2-methyl-[1,1'-biphenyl]-3-yl)methoxy)-4-vinyl-6,7-dihydro-5H-cyclopenta[c]pyridine (0.55 g, 1.48 mmol) in THF (3 mL) and water (3 mL) was cooled to 0° C., Osmium tetroxide (0.41 g, 1.62 mmol) was added and stirred at 0° C. for 15 min. To this mixture, NaIO$_4$ (1.1 g, 5.18 mmol) was added and stirred the mixture at room temperature for 16 h. After completion, the reaction was quenched with water (10 mL) and extracted with Et$_2$O (2×20 mL). The organic layer was dried over anhydrous sodium sulfate and concentrated. The resulting crude was purified by flash chromatography (silica gel, 4 g cartridge) using 0-20% EtOAc in hexanes as eluent to obtain 3-methoxy-1-((2-methyl-[1,1'-biphenyl]-3-yl)methoxy)-6,7-dihydro-5H-cyclopenta[c]pyridine-4-carbaldehyde (Yield: 220 mg, 40%) as white solid. LCMS (ES) m/z=374.47 [M+H]$^+$.

Step-10: A solution of 3-methoxy-1-((2-methyl-[1,1'-biphenyl]-3-yl)methoxy)-6,7-dihydro-5H-cyclopenta[c]pyridine-4-carbaldehyde (90 mg, 0.241 mmol), (S)-piperidine-2-carboxylic acid (37 mg, 0.289 mmol), sodium cyanoborohydride (44 mg, 0.71 mmol) and acetic acid (2 drops) in DMF (5 mL) was stirred at 80° C. for 6 h. After completion, the reaction mixture was poured on ice cold water (10 mL) and extracted with 10% MeOH in DCM (2×30 mL). The organic layer was dried over anhydrous sodium sulfate and concentrated. The resulting crude was purified by flash chromatography (silica gel, 4 g cartridge) using 0-10% MeOH in DCM as eluent to obtain (S)-1-((3-methoxy-1-((2-methyl-[1,1'-biphenyl]-3-yl)methoxy)-6,7-dihydro-5H-cyclopenta[c]pyridin-4-yl)methyl)piperidine-2-carboxylic acid (Yield: 35 mg, 30%) as white solid. LCMS (ES) m/z=487.46 [M+H]$^+$; $^1$H NMR (400 MHz, DMSO-d$_6$) δ ppm: 1.39-1.48 (m, 4H), 1.70-1.78 (m, 2H), 2.02 (t, J=8 Hz, 2H), 2.22 (s, 3H), 2.36-2.43 (m, 1H), 2.71 (t, J=8 Hz, 2H), 2.85-3.06 (m, 3H), 3.68-3.77 (m, 1H), 3.78-3.80 (m, 1H), 3.85 (s, 3H), 5.45 (s, 2H), 7.17 (d, J=8 Hz, 1H), 7.25 (t, J=8 Hz, 1H), 7.30 (d, J=8 Hz, 2H), 7.37 (t, J=8.0 Hz, 1H), 7.44 (t, J=8.0 Hz, 3H).

The following compound were prepared following procedures described above

Example 97

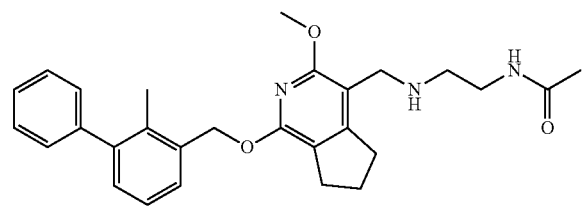 [SMILES: COc1nc(OCc2cccc(-c3ccccc3)c2C)c2c(c1CNCCNC(C)=O)CCC2]

N-(2-(((3-methoxy-1-((2-methyl-[1,1'-biphenyl]-3-yl)methoxy)-6,7-dihydro-5H-cyclopenta[c]pyridin-4-yl)methyl)amino)ethyl)acetamide, LCMS (ES) m/z=460.40 [M+H]$^+$; $^1$H NMR (400 MHz, DMSO-d$_6$) δ ppm: 1.76 (s, 3H), 2.02 (t, J=7.2 Hz, 2H), 2.22 (s, 3H), 2.47 (t, J=7.6 Hz, 2H), 2.72 (t, J=7.2 Hz, 2H), 2.86 (t, J=7.2 Hz, 2H), 3.09 (t, J=6.0 Hz, 2H), 3.54 (s, 2H), 3.85 (s, 3H), 5.44 (s, 2H), 7.16 (t, J=7.6 Hz, 1H), 7.25 (t, J=7.6 Hz, 1H), 7.30 (d, J=7.6 Hz, 2H), 7.37 (t, J=6.8 Hz, 1H), 7.45 (t, J=6.8 Hz, 3H), 7.73 (m, 1H).

Example-98

Synthesis of (S)-4-((5-methoxy-7-((2-methyl-[1,1'-biphenyl]-3-yl)methoxy)-2,3-dihydro-1H-inden-4-yl)methyl)morpholine-3-carboxylicacid

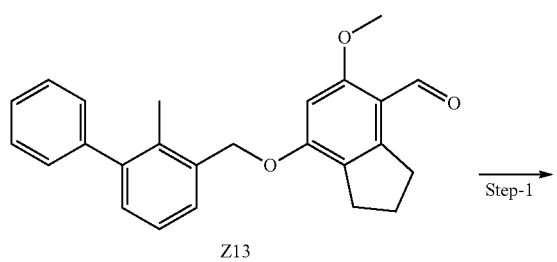

-continued

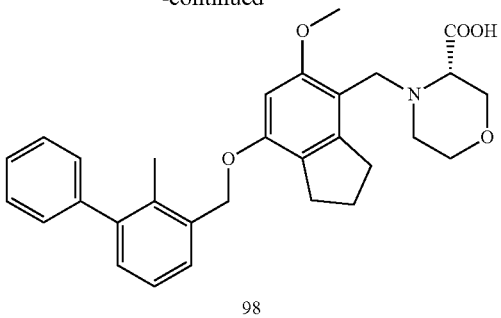

Step-1: A solution of 5-methoxy-7-((2-methyl-[1,1'-biphenyl]-3-yl)methoxy)-2,3-dihydro-1H-indene-4-carbaldehyde (150 mg, 0.403 mmol), (S)-morpholine-3-carboxylic acid (158 mg, 1.209 mmol), in DMF (3 mL) and MeOH (3 mL), AcOH (2 drops) was added and stirred for 2 h at room temperature. To this mixture, sodium cyanoborohydride (74 mg, 1.20 mmol) was added and continued stirring for 16 h. After completion, the reaction mixture was poured on to ice-cold water (10 mL) and extracted with 10% MeOH in DCM (3×20 mL). The organic layer was dried over sodium sulfate and concentrated. The resulting crude was purified by flash chromatography (silica gel, 4 g cartridge) using 0-10% MeOH in DCM as eluent to obtain (S)-4-((5-methoxy-7-((2-methyl-[1,1'-biphenyl]-3-yl)methoxy)-2,3-dihydro-1H-inden-4-yl)methyl)morpholine-3-carboxylic acid (Yield: 12 mg, 6%) as white solid. LCMS (ES) m/z=486.37 [M+H]$^+$; $^1$H NMR (400 MHz, DMSO-d$_6$) δ ppm: 1.95-1.98 (m, 2H), 2.22 (m, 3H), 2.26-2.32 (m, 2H), 2.74 (m, 2H), 2.84 (m, 1H), 2.93-2.99 (m, 2H), 3.11 (m, 1H), 3.46 (m, 1H), 3.55 (m, 1H), 3.68 (m, 2H), 3.75 (s, 4H), 5.17 (s, 2H), 6.62 (s, 1H), 7.19 (d, J=7.6 Hz, 1H), 7.25-7.33 (m, 3H), 7.37 (m, 1H), 7.44-7.49 (m, 3H).

Example-99

5-((5-((3-cyanobenzyl)oxy)-7-((2-methyl-[1,1'-biphenyl]-3-yl)methoxy)-2,3-dihydro-1H-inden-4-yl)methyl)-4,5,6,7-tetrahydro-1H-pyrazolo[4,3-c]pyridine-3-carboxylic acid

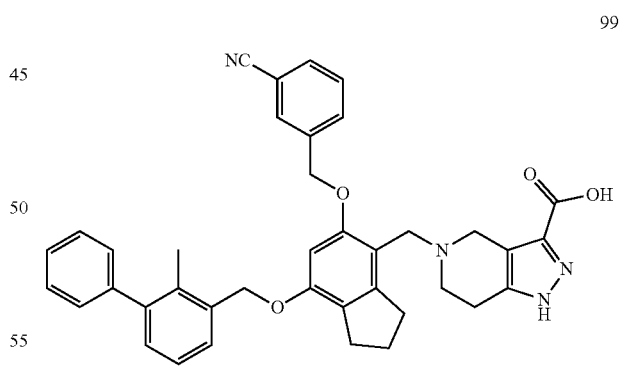

The compound was synthesized according to the procedure out lined in the example 15, LCMS (ES) m/z=625.35 [M+H]$^+$, General Procedure for Biological Evaluation PD-L1 Enzyme Assay: Homogenous Time-Resolved Fluorescence (HTRF) Binding Assay All binding studies were performed using PD-1/PD-L1 Binding Assay Kit from CisBio (Catalog #63ADK000CPAPEG), according to the manufacturer's protocol. The interaction between Tag1-PD-1 and Tag2-PD-1 was detected by anti-Tag1-Eu$^{3+}$ (HTRF donor) and anti-Tag2-XL665 (HTRF acceptor). When the donor and acceptor antibodies were brought to close proximity due to PD-1 and PD-L1 binding, excitation of the donor antibody triggered fluorescent resonance energy transfer (FRET) towards the acceptor antibody, which in turn emitted specifically at 665 nm. This specific signal is positively proportional to PD-1/PD-L1 interaction. The compounds blocking PD-1/PD-L1 interaction will cause a reduction in HTRF signal. The necessary reagents were mixed in the following order: 2 µl compounds (or diluents buffer), 4 µl PD-L1 protein, 4 µl PD-1 protein. After an incubation of 15 minutes, 5 µl of anti-Tag1-Eu$^{3+}$ and 5 µl of anti-Tag2-XL665 were added. The plate was sealed and incubated at room temperature for 1 h. The fluorescence emission was read at two different wavelengths (665 nm and 620 nm) on a BMG PheraStar® multi-plate reader. Results were calculated from the 665 nm and 620 nm fluorescence signal and expressed in HTRF ratio=(665 nm/620 nm)×10$^4$.

Evaluation of Biological Activity:

Table 5, below, shows the biological activity of compounds of the present invention in PD1/PD-L1 inhibition assay. Compounds having IC50<100 nM are designated as "A"; 100-500 nM are designated as "B"; and >500 nM are designated as "C" respectively.

TABLE 5

Biochemical PD1/PD-L1 inhibition data

| Compound | PD1/PD-L1 Activity |
|---|---|
| 1 | B |
| 2 | B |
| 3 | C |
| 4 | B |
| 5 | B |
| 6 | C |
| 7 | C |
| 8 | A |
| 9 | A |
| 10 | A |
| 11 | A |
| 12 | A |
| 13 | A |
| 14 | C |
| 15 | A |
| 16 | C |
| 17 | C |
| 18 | B |
| 19 | B |
| 20 | B |
| 21 | C |
| 22 | B |
| 23 | C |
| 24 | C |
| 25 | A |
| 26 | B |
| 27 | B |
| 28 | C |
| 29 | B |
| 30 | B |
| 31 | B |
| 32 | B |
| 33 | C |
| 34 | A |
| 35 | A |
| 36 | A |
| 37 | A |
| 38 | A |
| 39 | B |
| 40 | A |
| 41 | A |
| 42 | A |
| 43 | A |
| 44 | A |
| 45 | B |
| 46 | A |
| 47 | A |
| 48 | A |
| 49 | A |
| 50 | A |
| 51 | A |
| 52 | A |
| 53 | A |
| 54 | B |
| 55 | A |
| 56 | A |
| 57 | A |
| 58 | A |
| 59 | A |
| 60 | A |
| 61 | A |
| 62 | A |
| 63 | B |
| 64 | B |
| 65 | A |
| 66 | B |
| 67 | A |
| 68 | A |
| 69 | A |
| 70 | A |
| 71 | A |
| 72 | A |
| 73 | B |
| 74 | A |
| 75 | C |
| 76 | C |
| 77 | A |
| 78 | A |
| 79 | A |
| 80 | C |
| 81 | A |
| 82 | B |
| 83 | B |
| 84 | A |
| 85 | B |
| 86 | B |
| 87 | B |
| 88 | B |
| 89 | A |
| 90 | C |
| 91 | C |
| 92 | A |
| 93 | A |
| 94 | A |
| 95 | A |
| 96 | ND |
| 97 | A |
| 98 | A |
| 99 | ND |

ND—not determined

The above-mentioned compounds have potential to be developed as drugs to alleviate the PD1/PD-L1 activity and thus treating cancer, and other diseases or conditions associated with activation of PD1/PD-L1.

What is claimed is:

1. A compound of Formula I

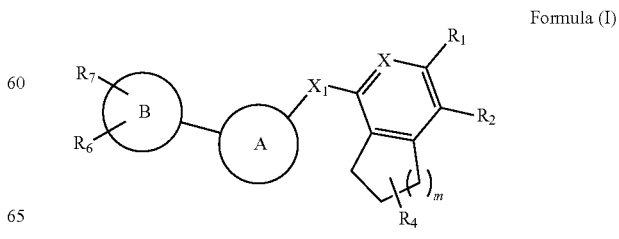

Formula (I)

their stereoisomers and pharmaceutically acceptable salts thereof, wherein, $X_1$ is selected from —CH$_2$O— or —OCH$_2$—;

$R_4$ is hydrogen;

X is selected from CR$_3$ or N;

$R_1$, $R_2$, $R_3$, $R_6$, and $R_7$ are independently selected from hydrogen, halo, $C_{1-6}$ alkyl, (4-10 membered heterocycloalkyl)-$C_{1-4}$ alkyl-, and C(O)OR$^a$, wherein the $C_{1-6}$ alkyl and (4-10 membered heterocycloalkyl)-$C_{1-4}$ alkyl-, are independently optionally substituted with 1, 2, or 3 R$^b$ substituents;

R$^a$ is selected from hydrogen, $C_{1-6}$ alkyl, $C_{1-4}$ haloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein, the $C_{1-6}$ alkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, or 3 R$^d$ substituents;

R$^b$ is selected from hydroxy, amino, $C_{1-4}$ alkyl, 4-10 membered heterocycloalkyl, OR$^c$, C(O)NR$^c$R$^c$, C(O)OR$^c$, NHR$^c$, NR$^c$R$^c$, or NR$^c$C(O)R$^c$; wherein, the $C_{1-4}$ alkyl and 4-10 membered heterocycloalkyl are optionally substituted with 1, 2, or 3 R$^d$ substituents;

R$^c$ is selected from hydrogen, $C_{1-6}$ alkyl, or $C_{3-10}$ cycloalkyl, wherein, the $C_{1-6}$ alkyl and $C_{3-10}$ cycloalkyl are optionally substituted with 1, 2, or 3 R$^f$ substituent;

R$^d$ is selected from cyano, $C_{1-6}$ alkyl, halo, $C_{6-10}$ aryl, 5-10 membered heteroaryl, $C_{3-10}$ cycloalkyl, 4-10 membered heterocycloalkyl, C(O)NR$^c$R$^c$, or C(O)OR$^c$, wherein, the $C_{6-10}$ aryl, 5-10 membered heteroaryl, $C_{3-10}$ cycloalkyl, and 4-10 membered heterocycloalkyl are optionally substituted with 1, 2, or 3 R$^f$ substituents;

R$^f$ is selected from $C_{1-4}$ alkyl, halogen, CN, C(O)NR$^g$R$^g$, C(O)OR$^g$, or NR$^g$C(O)R$^g$;

R$^g$ is selected from hydrogen or $C_{1-6}$ alkyl;

m is 1 or 2;

Ring A is substituted or unsubstituted $C_{6-10}$ aryl, substituted with $C_{1-4}$ alkyl, cyano, or $C_{1-4}$ haloalkyl;

Ring B is selected from $C_{6-10}$ aryl, $C_{3-6}$ cycloalkyl, 5-10 membered monocyclic saturated or unsaturated heterocyclic ring with 1-3 heteroatoms selected from N, S or O.

2. The compound as claimed in claim 1 having the structure of Formula II

Formula II

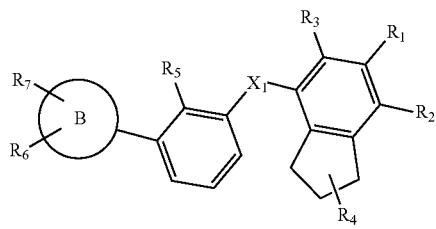

(II)

their stereoisomers and pharmaceutically acceptable salts thereof, wherein, $X_1$ is selected from —CH$_2$O— or —OCH$_2$—;

$R_4$ is hydrogen;

$R_5$ is selected from $C_{1-4}$ alkyl, cyano, or $C_{1-4}$ haloalkyl;

$R_1$, $R_2$, $R_3$, $R_6$, and $R_7$ are independently selected from hydrogen, halo, $C_{1-6}$ alkyl, (4-10 membered heterocycloalkyl)-$C_{1-4}$ alkyl-, C(O)OR$^a$, wherein, the $C_{1-6}$ alkyl and (4-10 membered heterocycloalkyl)-$C_{1-4}$ alkyl-, are independently optionally substituted with 1, 2, or 3 R$^b$ substituents;

R$^a$ is selected from hydrogen, $C_{1-6}$ alkyl, $C_{1-4}$ haloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein, the $C_{1-6}$ alkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, or 3 R$^d$ substituents;

R$^b$ is selected from hydroxy, amino, $C_{1-4}$ alkyl, 4-10 membered heterocycloalkyl, OR$^c$, C(O)NR$^c$R$^c$, C(O)OR$^c$, NHR$^c$, NR$^c$R$^c$, or NR$^c$C(O)R$^c$; wherein, the $C_{1-4}$ alkyl and 4-10 membered heterocycloalkyl are optionally substituted with 1, 2, or 3 R$^d$ substituents;

R$^d$ is selected from cyano, $C_{1-6}$ alkyl, halo, $C_{6-10}$ aryl, 5-10 membered heteroaryl, $C_{3-10}$ cycloalkyl, 4-10 membered heterocycloalkyl, C(O)NR$^c$R$^c$, or C(O)OR$^c$, wherein, the $C_{6-10}$ aryl, 5-10 membered heteroaryl, $C_{3-10}$ cycloalkyl, and 4-10 membered heterocycloalkyl are optionally substituted with 1, 2, or 3 R$^f$ substituents;

R$^c$ is selected from hydrogen, $C_{1-6}$ alkyl, $C_{1-4}$ haloalkyl, or $C_{3-10}$ cycloalkyl, wherein, the $C_{1-6}$ alkyl and $C_{3-10}$ cycloalkyl are optionally substituted with 1, 2, or 3 R$^f$ substituent;

R$^f$ is selected from $C_{1-4}$ alkyl, halogen, CN, OR$^g$, C(O)NR$^g$R$^g$, C(O)OR$^g$, or NR$^g$C(O)R$^g$;

R$^g$ is selected from hydrogen or $C_{1-6}$ alkyl

R$^e$ is selected from hydrogen or $C_{1-4}$ alkyl

Ring B is selected from $C_{6-10}$ aryl, $C_{3-6}$ cycloalkyl, 5-10 membered monocyclic saturated or unsaturated heterocyclic ring with 1-3 heteroatoms selected from N, S or O.

3. The compound as claimed in claim 1 having the structure of Formula III

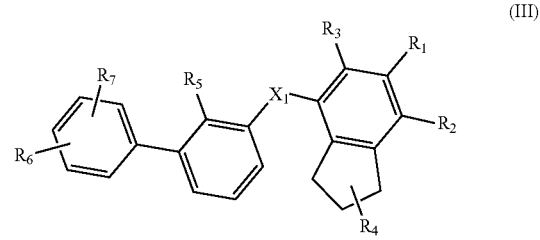

(III)

their stereoisomers and pharmaceutically acceptable salts thereof, wherein $X_1$ is selected from —CH$_2$O— or —OCH$_2$—;

$R_4$ is hydrogen;

$R_5$ is selected from $C_{1-4}$ alkyl, cyano, or $C_{1-4}$ haloalkyl;

$R_1$, $R_2$, $R_3$, $R_6$, and $R_7$ are independently selected from hydrogen, halo, $C_{1-6}$ alkyl, (4-10 membered heterocycloalkyl)-$C_{1-4}$ alkyl-, OR$^a$, and C(O)OR$^a$, wherein, the $C_{1-6}$ alkyl and (4-10 membered heterocycloalkyl)-$C_{1-4}$ alkyl- are independently optionally substituted with 1, 2, or 3 R$^b$ substituents;

R$^a$ is selected from hydrogen, $C_{1-6}$ alkyl, $C_{1-4}$ haloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein, the $C_{1-6}$ alkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, or 3 $R^d$ substituents;

$R^b$ is selected from hydroxy, amino, $C_{1-4}$ alkyl, 4-10 membered heterocycloalkyl, C(O)$NR^cR^c$, C(O)$OR^c$, $NHR^c$, $NR^cR^c$, or $NR^cC(O)R^c$; wherein, the $C_{1-4}$ alkyl and 4-10 membered heterocycloalkyl are optionally substituted with 1, 2, or 3 $R^d$ substituents;

$R^d$ is selected from cyano, $C_{1-6}$ alkyl, halo, $C_{6-10}$ aryl, 5-10 membered heteroaryl, $C_{3-10}$ cycloalkyl, 4-10 membered heterocycloalkyl, C(O)$NR^cR^c$, or C(O)$OR^c$, wherein, the $C_{6-10}$ aryl, 5-10 membered heteroaryl, $C_{3-10}$ cycloalkyl, and 4-10 membered heterocycloalkyl are optionally substituted with 1, 2, or 3 $R^f$ substituents;

$R^c$ is selected from hydrogen, $C_{1-6}$ alkyl, or $C_{3-10}$ cycloalkyl, wherein, the $C_{1-6}$ alkyl and $C_{3-10}$ cycloalkyl are optionally substituted with 1, 2, or 3 $R^f$ substituent;

$R^f$ is selected from $C_{1-4}$ alkyl, halogen, CN, $OR^g$, C(O)$NR^gR^g$, C(O)$OR^g$, or $NR^gC(O)R^g$ $R^g$ is selected from hydrogen or $C_{1-6}$ alkyl $R^e$ is selected from hydrogen or $C_{1-4}$ alkyl.

4. The compound as claimed in claim 1 having the structure of Formula IV

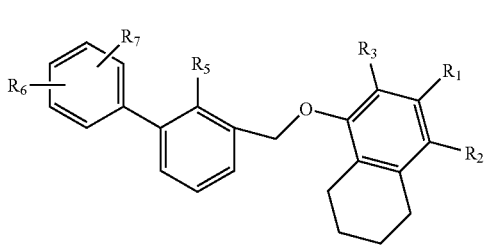

(IV)

their stereoisomers and pharmaceutically acceptable salts thereof, wherein, $R_5$ is selected from $C_{1-4}$ alkyl, cyano, or $C_{1-4}$ haloalkyl;

$R_1$, $R_2$, $R_3$, $R_6$ and $R_7$ are independently selected from hydrogen, halo, $C_{1-6}$ alkyl, (4-10 membered heterocycloalkyl)-$C_{1-4}$ alkyl-, $OR^a$, and C(O)$OR^a$, wherein the $C_{1-6}$ alkyl, and (4-10 membered heterocycloalkyl)-$C_{1-4}$ alkyl-, are independently optionally substituted with 1, 2, or 3 $R^b$ substituents;

$R^a$ is selected from hydrogen, $C_{1-6}$ alkyl, $C_{1-4}$ haloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein, the $C_{1-6}$ alkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, or 3 $R^d$ substituents;

$R^b$ is selected from hydroxy, amino, $C_{1-4}$ alkyl, 4-10 membered heterocycloalkyl, $OR^c$, C(O)$NR^cR^c$, C(O)$OR^c$, $NHR^o$, $NR^cR^c$, or $NR^cC(O)R^c$; wherein, the $C_{1-4}$ alkyl, and 4-10 membered heterocycloalkyl, are optionally substituted with 1, 2, or 3 $R^d$ substituents;

$R^d$ is selected from cyano, $C_{1-6}$ alkyl, halo, $C_{6-10}$ aryl, 5-10 membered heteroaryl, $C_{3-10}$ cycloalkyl, 4-10 membered heterocycloalkyl, C(O)$NR^cR^c$, or C(O)$OR^c$, wherein, the $C_{6-10}$ aryl, 5-10 membered heteroaryl, $C_{3-10}$ cycloalkyl, and 4-10 membered heterocycloalkyl, are optionally substituted with 1, 2, or 3 $R^f$ substituents;

$R^c$ is selected from hydrogen, $C_{1-6}$ alkyl, or $C_{3-10}$ cycloalkyl, wherein, the $C_{1-6}$ alkyl, and $C_{3-10}$ cycloalkyl, are optionally substituted with 1, 2, or 3 $R^f$ substituent;

$R^f$ is selected from $C_{1-4}$ alkyl, halogen, CN, $OR^g$, C(O)$NR^gR^g$, C(O)$OR^g$, or $NR^gC(O)R^g$;

$R^g$ is selected from hydrogen or $C_{1-6}$ alkyl $R^e$ is selected from hydrogen or $C_{1-4}$ alkyl.

5. The compound as claimed in claim 1 having the structure of Formula V

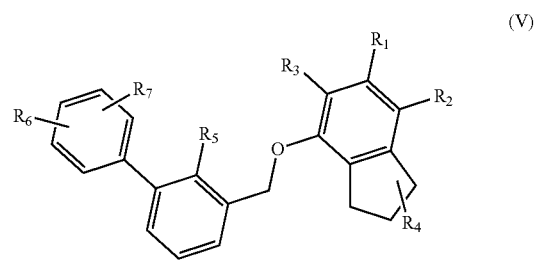

(V)

their stereoisomers and pharmaceutically acceptable salts thereof, wherein, $R_5$ is selected from $C_{1-4}$ alkyl, cyano, or $C_{1-4}$ haloalkyl;

$R_4$ is hydrogen $R_1$, $R_2$, $R_3$, $R_6$, and $R_7$ are independently selected from hydrogen, halo, $C_{1-6}$ alkyl, (4-10 membered heterocycloalkyl)-$C_{1-4}$ alkyl-, $OR^a$, and C(O)$OR^a$, wherein the $C_{1-6}$ alkyl, and (4-10 membered heterocycloalkyl)-$C_{1-4}$ alkyl-, are independently optionally substituted with 1, 2, or 3 $R^b$ substituents;

$R^a$ is selected from hydrogen, $C_{1-6}$ alkyl, $C_{1-4}$ haloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein, the $C_{1-6}$ alkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2, or 3 $R^d$ substituents;

$R^b$ is selected from hydroxy, amino, $C_{1-4}$ alkyl, 4-10 membered heterocycloalkyl, $OR^c$, C(O)$NR^cR^c$, C(O)$OR^c$, $NHR^o$, $NR^cR^c$, or $NR^cC(O)R^c$; wherein, the $C_{1-4}$ alkyl, and 4-10 membered heterocycloalkyl, are optionally substituted with 1, 2, or 3 $R^d$ substituents;

$R^d$ is selected from cyano, $C_{1-6}$ alkyl, halo, $C_{6-10}$ aryl, 5-10 membered heteroaryl, $C_{3-10}$ cycloalkyl, 4-10 membered heterocycloalkyl, C(O)$NR^eR^e$, or C(O)$OR^e$, wherein, the $C_{6-10}$ aryl, 5-10 membered heteroaryl, $C_{3-10}$ cycloalkyl, and 4-10 membered heterocycloalkyl, are optionally substituted with 1, 2, or 3 $R^f$ substituents;

$R^c$ is selected from hydrogen, $C_{1-6}$ alkyl, or $C_{3-10}$ cycloalkyl, wherein, the $C_{1-6}$ alkyl, and $C_{3-10}$ cycloalkyl, are optionally substituted with 1, 2, or 3 $R^f$ substituent;

$R^f$ is selected from $C_{1-4}$ alkyl, halogen, CN, $OR^g$, C(O)$NR^gR^g$, C(O)$OR^g$, or $NR^gC(O)R^g$;

$R^g$ is selected from hydrogen or $C_{1-6}$ alkyl $R^e$ is selected from hydrogen or $C_{1-4}$ alkyl.

6. A compound or its stereoisomers and pharmaceutically acceptable salts thereof, selected from a group consisting of:
(S)-1-((7-((2-methyl-[1,1'-biphenyl]-3-yl)methoxy)-2,3-dihydro-1H-inden-4-yl)methyl) piperidine-2-carboxylic acid (1), N-(2-(((5-methoxy-7-((2-methyl-[1,1'-biphenyl]-3-yl)methoxy)-2,3-dihydro-1H-inden-4-yl) methyl)amino)ethyl)acetamide (2), (S)-1-((7-((3-(1-(3-(3,3-difluoropyrrolidin-1-yl)propyl)-1H-indol-4-yl)-2-methylbenzyl)oxy)-2,3-dihydro-1H-inden-4-yl)methyl)piperidine-2-carboxylic acid (3), (S)-1-((6-methyl-7-((2-methyl-[1,1'-biphenyl]-3-yl)methoxy)-2,3-dihydro-1H-inden-4-yl)methyl)piperidine-2-carboxylic acid (4), (S)-1-((6-chloro-7-((2-methyl-[1,1'-biphenyl]-3-yl)methoxy)-2,3-dihydro-1H-inden-4-yl)methyl)piperidine-2-carboxylic acid (5), Methyl 7-(((2-acetamidoethyl)amino)methyl)-4-((2-methyl-[1,1'-biphenyl]-3-yl)methoxy)-2,3-dihydro-1H-indene-5-carboxylate (6), (S)-1-((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)piperidine-2-carboxylic acid (7), (S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxylic acid (8), (S)-1-((5-((5-fluoropyridin-3-yl)methoxy)-7-((2-methyl-[1,1'-biphenyl]-3-yl)methoxy)-2,3-dihydro-1H-inden-4-yl)methyl)piperidine-2-carboxylic acid (9)

N-(2-(((5-((5-fluoropyridin-3-yl)methoxy)-7-((2-methyl-[1,1'-biphenyl]-3-yl)methoxy)-2,3-dihydro-1H-inden-4-yl)methyl)amino)ethyl)acetamide (10)

(S)-5-((5-methoxy-7-((2-methyl-[1,1'-biphenyl]-3-yl)methoxy)-2,3-dihydro-1H-inden-4-yl)methyl)-5-azaspiro[2.4]heptane-6-carboxylic acid (11)

(S)-1-((7-((2-methyl-[1,1'-biphenyl]-3-yl)methoxy)-5-(2,2,2-trifluoroethoxy)-2,3-dihydro-1H-inden-4-yl)methyl)piperidine-2-carboxylic acid (12)

N-(2-(((5-((3-cyanobenzyl)oxy)-7-((2-methyl-[1,1'-biphenyl]-3-yl)methoxy)-2,3-dihydro-1H-inden-4-yl)methyl)amino)ethyl)-N-methylacetamide (13)

N-(2-(((5-(1-(3-cyanophenyl)ethoxy)-7-((2-methyl-[1,1'-biphenyl]-3-yl)methoxy)-2,3-dihydro-1H-inden-4-yl)methyl)amino)ethyl)acetamide (14)

N-(1-((5-((3-cyanobenzyl)oxy)-7-((2-methyl-[1,1'-biphenyl]-3-yl)methoxy)-2,3-dihydro-1H-inden-4-yl)methyl)piperidin-3-yl)acetamide (15)

N-(2-(((7-((2-methyl-[1,1'-biphenyl]-3-yl)methoxy)-2,3-dihydro-1H-inden-4-yl)methyl)amino)ethyl)acetamide (16)

6-((7-((2-methyl-[1,1'-biphenyl]-3-yl)methoxy)-2,3-dihydro-1H-inden-4-yl)methyl)-2-oxa-6-azaspiro[3.3]heptane (17)

2-(hydroxymethyl)-2-(((7-((2-methyl-[1,1'-biphenyl]-3-yl)methoxy)-2,3-dihydro-1H-inden-4-yl)methyl)amino)propane-1,3-diol (18)

1-(((7-((2-methyl-[1,1'-biphenyl]-3-yl)methoxy)-2,3-dihydro-1H-inden-4-yl)methyl)amino)cyclopropane-1-carboxylic acid (19)

((7-((2-methyl-[1,1'-biphenyl]-3-yl)methoxy)-2,3-dihydro-1H-inden-4-yl)methyl)glycine (20)

3-(((7-((2-methyl-[1,1'-biphenyl]-3-yl)methoxy)-2,3-dihydro-1H-inden-4-yl)methyl)amino)propanoic acid (21)

N-methyl-N-((7-((2-methyl-[1,1'-biphenyl]-3-yl)methoxy)-2,3-dihydro-1H-inden-4-yl)methyl)glycine (22)

3-(((7-((2-methyl-[1,1'-biphenyl]-3-yl)methoxy)-2,3-dihydro-1H-inden-4-yl)methyl)amino)butanoic acid (23)

((7-((2-methyl-[1,1'-biphenyl]-3-yl)methoxy)-2,3-dihydro-1H-inden-4-yl)methyl)alanine (24)

(2S,4R)-4-hydroxy-1-((5-methoxy-7-((2-methyl-[1,1'-biphenyl]-3-yl)methoxy)-2,3-dihydro-1H-inden-4-yl)methyl)pyrrolidine-2-carboxylic acid (25)

(S)-1-((5-methoxy-7-((2-methyl-[1,1'-biphenyl]-3-yl)methoxy)-2,3-dihydro-1H-inden-4-yl)methyl)piperidine-2-carboxylic acid (26)

1-((4-((2-methyl-[1,1'-biphenyl]-3-yl)methoxy)-5,6,7,8-tetrahydronaphthalen-1-yl)methyl)piperidine-2-carboxylic acid (27)

N-(2-(((6-methyl-7-((2-methyl-[1,1'-biphenyl]-3-yl)methoxy)-2,3-dihydro-1H-inden-4-yl)methyl)amino)ethyl)acetamide (28)

(2S,4R)-4-hydroxy-1-((6-methyl-7-((2-methyl-[1,1'-biphenyl]-3-yl)methoxy)-2,3-dihydro-1H-inden-4-yl)methyl)pyrrolidine-2-carboxylic acid (29)

N-(2-(((6-chloro-7-((2-methyl-[1,1'-biphenyl]-3-yl)methoxy)-2,3-dihydro-1H-inden-4-yl)methyl)amino)ethyl)acetamide (30)

(2S,4R)-1-((6-chloro-7-((2-methyl-[1,1'-biphenyl]-3-yl)methoxy)-2,3-dihydro-1H-inden-4-yl)methyl)-4-hydroxypyrrolidine-2-carboxylic acid (31)

N-(2-(((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)amino)ethyl)acetamide (32)

(2S,4R)-1-((7-((3'-(3-(3,3-difluoropyrrolidin-1-yl)propoxy)-2,2'-dimethyl-[1,1'-biphenyl]-3-yl)methoxy)-5-methoxy-2,3-dihydro-1H-inden-4-yl)methyl)-4-hydroxypyrrolidine-2-carboxylic acid (33)

N-(2-(((5-((3-cyanobenzyl)oxy)-7-((2-methyl-[1,1'-biphenyl]-3-yl)methoxy)-2,3-dihydro-1H-inden-4-yl)methyl)amino)ethyl)acetamide (34)

(2S,4R)-1-((5-((3-cyanobenzyl)oxy)-7-((2-methyl-[1,1'-biphenyl]-3-yl)methoxy)-2,3-dihydro-1H-inden-4-yl)methyl)-4-hydroxypyrrolidine-2-carboxylic acid (35)

(S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxylic acid (36)

(S)-1-((5-((3-cyanobenzyl)oxy)-7-((2-methyl-[1,1'-biphenyl]-3-yl)methoxy)-2,3-dihydro-1H-inden-4-yl)methyl)piperidine-2-carboxamide (37)

3-(((4-(((1,3-dihydroxy-2-(hydroxymethyl)propan-2-yl)amino)methyl)-7-((2-methyl-[1,1'-biphenyl]-3-yl)methoxy)-2,3-dihydro-1H-inden-5-yl)oxy)methyl)benzonitrile (38)

3-(((4-((2-oxa-6-azaspiro[3.3]heptan-6-yl)methyl)-7-((2-methyl-[1,1'-biphenyl]-3-yl)methoxy)-2,3-dihydro-1H-inden-5-yl)oxy)methyl)benzonitrile (39)

3-(((4-((3-hydroxypiperidin-1-yl)methyl)-7-((2-methyl-[1,1'-biphenyl]-3-yl)methoxy)-2,3-dihydro-1H-inden-5-yl)oxy)methyl)benzonitrile (40)

((5-((3-cyanobenzyl)oxy)-7-((2-methyl-[1,1'-biphenyl]-3-yl)methoxy)-2,3-dihydro-1H-inden-4-yl)methyl)glycine (41)

(S)-5-((5-((3-cyanobenzyl)oxy)-7-((2-methyl-[1,1'-biphenyl]-3-yl)methoxy)-2,3-dihydro-1H-inden-4-yl)methyl)-5-azaspiro[2.4]heptane-6-carboxylic acid (42)

rac-(1R,6S)-2-((5-((3-cyanobenzyl)oxy)-7-((2-methyl-[1,1'-biphenyl]-3-yl) dihydro-1H-inden-4-yl)methyl)-2-azabicyclo[4.1.0]heptane-1-carboxylic acid (cis, racemic) (43)

4-(((5-((3-cyanobenzyl)oxy)-7-((2-methyl-[1,1'-biphenyl]-3-yl)methoxy)-2,3-dihydro-1H-inden-4-yl)methyl)amino)butanoic acid (44)

(1R,6S)-2-((5-methoxy-7-((2-methyl-[1,1'-biphenyl]-3-yl)methoxy)-2,3-dihydro-1H-inden-4-yl) methyl)-2-azabicyclo [4.1.0]heptane-1-carboxylic acid (cis, racemic) (45)

(S)-1-((5-((5-cyanopyridin-3-yl)methoxy)-7-((2-methyl-[1,1'-biphenyl]-3-yl)methoxy)-2,3-dihydro-1H-inden-4-yl)methyl)piperidine-2-carboxylic acid (46)

(2S,4R)-1-((5-((5-cyanopyridin-3-yl)methoxy)-7-((2-methyl-[1,1'-biphenyl]-3-yl)methoxy)-2,3-dihydro-1H-inden-4-yl)methyl)-4-hydroxypyrrolidine-2-carboxylic acid (47)

N-(2-(((5-((5-cyanopyridin-3-yl)methoxy)-7-((2-methyl-[1,1'-biphenyl]-3-yl)methoxy)-2,3-dihydro-1H-inden-4-yl)methyl)amino)ethyl)acetamide (48)

5-(((4-(((1,3-dihydroxy-2-(hydroxymethyl)propan-2-yl)amino)methyl)-7-((2-methyl-[1,1'-biphenyl]-3-yl)methoxy)-2,3-dihydro-1H-inden-5-yl)oxy)methyl) nicotinonitrile (49)

(S)-4-((5-((5-cyanopyridin-3-yl)methoxy)-7-((2-methyl-[1,1'-biphenyl]-3-yl)methoxy)-2,3-dihydro-1H-inden-4-yl)methyl)morpholine-3-carboxylic acid (50)

rac-(1R,6S)-2-((5-((5-cyanopyridin-3-yl)methoxy)-7-((2-methy 1-[1,1'-biphenyl]-3-yl)methoxy)-2,3-dihydro-1H-inden-4-yl)methyl)-2-azabicyclo[4.1.0]heptane-1-carboxylic acid (cis, racemic) (51)

(S)-5-((5-((5-cyanopyridin-3-yl)methoxy)-7-((2-methyl-[1,1'-biphenyl]-3-yl)methoxy)-2,3-dihydro-1H-inden-4-yl)methyl)-5-azaspiro[2.4]heptane-6-carboxylic acid (52)

N-(2-(((5-((3-cyanobenzyl)oxy)-7-((2-methyl-[1,1'-biphenyl]-3-yl)methoxy)-2,3-dihydro-1H-inden-4-yl)methyl)(methyl)amino)ethyl)acetamide (53)

N-(2-(((5-((4-cyanobenzyl)oxy)-7-((2-methyl-[1,1'-biphenyl]-3-yl)methoxy)-2,3-dihydro-1H-inden-4-yl)methyl)amino)ethyl)acetamide (54)

(S)-1-((7-((2-cyano-[1,1'-biphenyl]-3-yl)methoxy)-5-methoxy-2,3-dihydro-1H-inden-4-yl)methyl)piperidine-2-carboxylic acid (55)

N-(2-(((7-((2-cyano-[1,1'-biphenyl]-3-yl)methoxy)-5-methoxy-2,3-dihydro-1H-inden-4-yl)methyl)amino)ethyl)acetamide (56)

(2S,4R)-1-((7-((2-cyano-[1,1'-biphenyl]-3-yl)methoxy)-5-methoxy-2,3-dihydro-1H-inden-4-yl)methyl)-4-hydroxypyrrolidine-2-carboxylic acid (57)

3-(((7-(((1,3-dihydroxy-2-(hydroxymethyl)propan-2-yl)amino)methyl)-6-methoxy-2,3-dihydro-1H-inden-4-yl)oxy)methyl)-[1,1'-biphenyl]-2-carbonitrile (58)

(S)-4-((7-((2-cyano-[1,1'-biphenyl]-3-yl)methoxy)-5-methoxy-2,3-dihydro-1H-inden-4-yl)methyl)morpholine-3-carboxylic acid (59)

((7-((2-cyano-[1,1'-biphenyl]-3-yl)methoxy)-5-methoxy-2,3-dihydro-1H-inden-4-yl)methyl)glycine (60)

(S)-5-((7-((2-cyano-[1,1'-biphenyl]-3-yl)methoxy)-5-methoxy-2,3-dihydro-1H-inden-4-yl)methyl)-5-azaspiro[2.4]heptane-6-carboxylic acid (61)

rac-(1R,6S)-2-((7-((2-cyano-[1,1'-biphenyl]-3-yl)methoxy)-5-methoxy-2,3-dihydro-1H-inden-4-yl)methyl)-2-azabicyclo[4.1.0]heptane-1-carboxylic acid (cis, racemic) (62)

2-(1-((7-((2-cyano-[1,1'-biphenyl]-3-yl)methoxy)-5-methoxy-2,3-dihydro-1H-inden-4-yl)methyl)piperidin-2-yl)acetic acid (63)

N-(2-(((7-((2-cyano-[1,1'-biphenyl]-3-yl)methoxy)-5-methoxy-2,3-dihydro-1H-inden-4-yl)methyl)(methyl)amino)ethyl)-N-methylacetamide (64)

5-((4-(((2-acetamidoethyl)amino)methyl)-7-((2-methyl-[1,1'-biphenyl]-3-yl)methoxy)-2,3-dihydro-1H-inden-5-yl)oxy)pentanoic acid (65)

5-((4-(((2-acetamidoethyl)amino)methyl)-7-((2-methyl-[1,1'-biphenyl]-3-yl)methoxy)-2,3-dihydro-1H-inden-5-yl)oxy)pentanamide (66)

(S)-1-((5-(4-carboxybutoxy)-7-((2-methyl-[1,1'-biphenyl]-3-yl)methoxy)-2,3-dihydro-1H-inden-4-yl)methyl)piperidine-2-carboxylic acid (67)

(S)-1-((5-((5-amino-5-oxopentyl)oxy)-7-((2-methyl-[1,1'-biphenyl]-3-yl)methoxy)-2,3-dihydro-1H-inden-4-yl)methyl)piperidine-2-carboxylic acid (68)

(S)-1-((5-((5-cyanopyridin-3-yl)methoxy)-7-((2-methyl-[1,1'-biphenyl]-3-yl)methoxy)-2,3-dihydro-1H-inden-4-yl)methyl)piperidine-2-carboxylic acid (69)

(2S,4R)-1-((7-((2-cyano-[1,1'-biphenyl]-3-yl)methoxy)-5-((5-cyanopyridin-3-yl)methoxy)-2,3-dihydro-1H-inden-4-yl)methyl)-4-hydroxypyrrolidine-2-carboxylic acid (70)

(R)-1-((7-((2-cyano-[1,1'-biphenyl]-3-yl)methoxy)-5-((5-cyanopyridin-3-yl)methoxy)-2,3-dihydro-1H-inden-4-yl)methyl)piperidine-3-carboxylic acid (71)

rac-(1R,6S)-2-((7-((2-cyano-[1,1'-biphenyl]-3-yl)methoxy)-5-((5-cyanopyridin-3-yl)methoxy)-2,3-dihydro-1H-inden-4-yl)methyl)-2-azabicyclo[4.1.0]heptane-1-carboxylic acid (cis racemic) (72)

Methyl 4-(((5-((3-cyanobenzyl)oxy)-7-((2-methyl-[1,1'-biphenyl]-3-yl)methoxy)-2,3-dihydro-1H-inden-4-yl)methyl)amino)bicyclo[2.2.2]octane-1-carboxylate (73)

4-(((5-((3-cyanobenzyl)oxy)-7-((2-methyl-[1,1'-biphenyl]-3-yl)methoxy)-2,3-dihydro-1H-inden-4-yl)methyl)amino)bicyclo[2.2.2]octane-1-carboxylic acid (74)

(S)-1-((5-methoxy-7-((2-(trifluoromethyl)-[1,1'-biphenyl]-3-yl)methoxy)-2,3-dihydro-1H-inden-4-yl)methyl)piperidine-2-carboxylic acid (75)

(2S,4R)-4-hydroxy-1-((5-methoxy-7-((2-(trifluoromethyl)-[1,1'-biphenyl]-3-yl)methoxy)-2,3-dihydro-1H-inden-4-yl)methyl)pyrrolidine-2-carboxylic acid (76)

(2S)-1-((7-((2-methyl-[1,1'-biphenyl]-3-yl)methoxy)-5-((1-methylpiperidin-3-yl)methoxy)-2,3-dihydro-1H-inden-4-yl)methyl)piperidine-2-carboxylic acid (77)

(S)-1-((5-(4-carboxybutoxy)-7-((2-cyano-[1,1'-biphenyl]-3-yl)methoxy)-2,3-dihydro-1H-inden-4-yl)methyl)piperidine-2-carboxylic acid (78)

N-(2-(((5-(4-cyanobutoxy)-7-((2-methyl-[1,1'-biphenyl]-3-yl)methoxy)-2,3-dihydro-1H-inden-4-yl)methyl) amino)ethyl)acetamide (79)

(S)-1-((5-(4-cyanobutoxy)-7-((2-methyl-[1,1'-biphenyl]-3-yl)methoxy)-2,3-dihydro-1H-inden-4-yl)methyl)piperidine-2-carboxamide (80)

(2S,4R)-1-((5-(4-cyanobutoxy)-7-((2-methyl-[1,1'-biphenyl]-3-yl)methoxy)-2,3-dihydro-1H-inden-4-yl)methyl)-4-hydroxypyrrolidine-2-carboxylic acid (81)

(S)-1-((5-(((1S,2R)-2-carboxycyclopropyl)methoxy)-7-((2-methyl-[1,1'-biphenyl]-3-yl)methoxy)-2,3-dihydro-1H-inden-4-yl)methyl)piperidine-2-carboxylic acid (82)

(1R,2S)-2-(((4-(((2-acetamidoethyl)amino)methyl)-7-((2-methyl-[1,1'-biphenyl]-3-yl)methoxy)-2,3-dihydro-1H-inden-5-yl)oxy)methyl)cyclopropane-1-carboxylic acid (83)

(S)-1-((7-((3-(2,3-dihydrobenzo[b][1,4]dioxin-6-yl)-2-methylbenzyl)oxy)-5-methoxy-2,3-dihydro-1H-inden-4-yl)methyl)piperidine-2-carboxylic acid (84)

(2S,4R)-1-((7-((3-(2,3-dihydrobenzo[b][1,4]dioxin-6-yl)-2-methylbenzyl)oxy)-5-methoxy-2,3-dihydro-1H-inden-4-yl)methyl)-4-hydroxypyrrolidine-2-carboxylic acid (85)

N-(2-(((5-((3-cyanobenzyl)oxy)-7-((2,2'-dimethyl-[1,1'-biphenyl]-3-yl)methoxy)-2,3-dihydro-1H-inden-4-yl)methyl)amino)ethyl)acetamide (86)

N-(2-(((5-((3-cyanobenzyl)oxy)-7-((4'-fluoro-2-methyl-[1,1'-biphenyl]-3-yl)methoxy)-2,3-dihydro-1H-inden-4-yl)methyl)amino)ethyl)acetamide (87)

(S)-1-((5-((3-carbamoylbenzyl)oxy)-7-((2-methyl-[1,1'-biphenyl]-3-yl)methoxy)-2,3-dihydro-1H-inden-4-yl)methyl)piperidine-2-carboxylic acid (88)

3-(((4-(aminomethyl)-7-((2-methyl-[1,1'-biphenyl]-3-yl)methoxy)-2,3-dihydro-1H-inden-5-yl)oxy)methyl)benzonitrile (89)

N-((5-((3-cyanobenzyl)oxy)-7-((2-methyl-[1,1'-biphenyl]-3-yl)methoxy)-2,3-dihydro-1H-inden-4-yl)methyl)acetamide (90)

6-acetamido-N-((5-((3-cyanobenzyl)oxy)-7-((2-methyl-[1,1'-biphenyl]-3-yl)methoxy)-2,3-dihydro-1H-inden-4-yl)methyl)hexanamide (91)

3-(((4-((dimethylamino)methyl)-7-((2-methyl-[1,1'-biphenyl]-3-yl)methoxy)-2,3-dihydro-1H-inden-5-yl)oxy)methyl)benzonitrile (92)

5-(((4-(((2-acetamidoethyl)amino)methyl)-7-((2-methyl-[1,1'-biphenyl]-3-yl)methoxy)-2,3-dihydro-1H-inden-5-yl)oxy)methyl)nicotinic acid (93)

5-(((4-(((2-acetamidoethyl)amino)methyl)-7-((2-methyl-[1,1'-biphenyl]-3-yl)methoxy)-2,3-dihydro-1H-inden-5-yl)oxy)methyl)nicotinamide (94)

3-(((4-(((2-acetamidoethyl)amino)methyl)-7-((2-methyl-[1,1'-biphenyl]-3-yl)methoxy)-2,3-dihydro-1H-inden-5-yl)oxy)methyl)benzamide (95)

(S)-1-((3-methoxy-1-((2-methyl-[1,1'-biphenyl]-3-yl)methoxy)-6,7-dihydro-5H-cyclopenta[c]pyridin-4-yl)methyl)piperidine-2-carboxylic acid (96)

N-(2-(((3-methoxy-1-((2-methyl-[1,1'-biphenyl]-3-yl)methoxy)-6,7-dihydro-5H-cyclopenta[c]pyridin-4-yl)methyl)amino)ethyl)acetamide (97)

(S)-4-((5-methoxy-7-((2-methyl-[1,1'-biphenyl]-3-yl)methoxy)-2,3-dihydro-1H-inden-4-yl)methyl)morpholine-3-carboxylic acid (98)

5-((5-((3-cyanobenzyl)oxy)-7-((2-methyl-[1,1'-biphenyl]-3-yl)methoxy)-2,3-dihydro-1H-inden-4-yl)methyl)-4,5,6,7-tetrahydro-1H-pyrazolo[4,3-c]pyridine-3-carboxylic acid (99).

7. A process of preparation of compounds of Formula I as claimed in claim 1 or its stereoisomers and pharmaceutically acceptable salts thereof, said process comprising: (a) reacting compounds of Formula I (a) with substituted aliphatic, aromatic, heterocyclic and cyclic amines to obtain compounds of Formula I

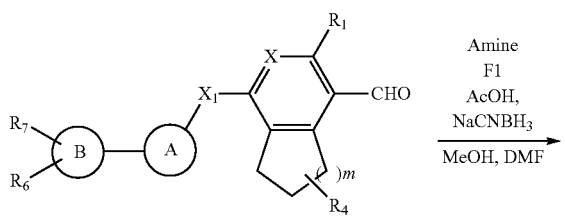

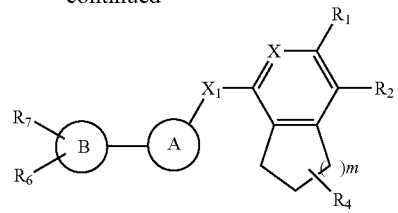

wherein, $X_1$ of Formula I (a) and Formula I is selected from —$CH_2O$— or —$OCH_2$—; $R_4$ of Formula I (a) and Formula I is selected from hydrogen: X of Formula I (a) and Formula I is selected from $CR_3$ or N; $R_1$, $R_2$, $R_3$, $R_6$ and $R_7$ of Formula I (a) and Formula I are independently selected from hydrogen, halo, $C_{1-6}$ alkyl, (4-10 membered heterocycloalkyl)-$C_{1-4}$ alkyl-, $OR^a$, and $C(O)OR^a$, wherein, the $C_{1-6}$ alkyl, and (4-10 membered heterocycloalkyl)-$C_{1-4}$ alkyl-, are independently optionally substituted with 1, 2 or 3 $R^b$ substituents; $R^a$ is selected from hydrogen, $C_{1-6}$ alkyl, $C_{1-4}$ haloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein, the $C_{1-6}$ alkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are independently optionally substituted with 1, 2 or 3 $R^d$ substituents; $R^b$ is selected from hydroxy, amino, $C_{1-4}$ alkyl, 4-10 membered heterocycloalkyl, $OR^c$, $C(O)NR^cR^c$, $C(O)OR^c$, $NHR^c$, $NR^cR^c$, or $NR^cC(O)R^c$; wherein, the $C_{1-4}$ alkyl, and 4-10 membered heterocycloalkyl, are optionally substituted with 1, 2, or 3 $R^d$ substituents; $R^c$ is selected from hydrogen, $C_{1-6}$ alkyl, or $C_{3-10}$ cycloalkyl, wherein, the $C_{1-6}$ alkyl, and $C_{3-10}$ cycloalkyl, are optionally substituted with 1, 2, or 3 $R^f$ substituent;

$R^d$ is selected from cyano, $C_{1-6}$ alkyl, halo, $C_{6-10}$ aryl, 5-10 membered heteroaryl, $C_{3-10}$ cycloalkyl, 4-10 membered heterocycloalkyl, $C(O)NR^cR^c$, or $C(O)OR^c$, wherein, the $C_{6-10}$ aryl, 5-10 membered heteroaryl, $C_{3-10}$ cycloalkyl, and 4-10 membered heterocycloalkyl, are optionally substituted with 1, 2, or 3 $R^f$ substituents; $R^f$ is selected from $C_{1-4}$ alkyl, halogen, CN, $OR^g$, $C(O)NR^gR^g$, $C(O)OR^g$, or $NR^gC(O)R^g$; $R^g$ is selected from hydrogen or $C_{1-6}$ alkyl; $R^e$ is independently selected from hydrogen or $C_{1-4}$ alkyl; m is 1 or 2; Ring A is selected from substituted or unsubstituted $C_{6-10}$ aryl; Ring B is selected from $C_{6-10}$ aryl, $C_{3-6}$ cycloalkyl, 5-10 membered monocyclic saturated or unsaturated heterocyclic ring with 1-3 heteroatoms selected from N, S or O, with substituted amines in the presence of solvents to obtain compounds of Formula 1.

8. A pharmaceutical composition comprising a compound of Formula I or a pharmaceutically acceptable salt thereof as claimed in claim 1, together with a pharmaceutically acceptable carrier, optionally in combination with one or more other pharmaceutical compositions.

9. The pharmaceutical composition as claimed in claim 8, wherein the composition is in the form selected from the group consisting of a tablet, capsule, powder, syrup, solution, aerosol and suspension.

10. A method for the treatment of a proliferative disorder or cancer, comprising administering to a subject suffering from the proliferative disorder or cancer a therapeutically effective amount of the compound of Formula I as claimed in claim 1, with other cytotoxic agents or non-cytotoxic agents or with other immune modulators agents to a subject in need thereof.

11. A method for the treatment of proliferative disorder or cancer, comprising administering to a subject suffering from the proliferative disorder or cancer the pharmaceutical composition as claimed in claim 8, with other cytotoxic agents or non-cytotoxic agents or with other immune modulators agents to a subject in need thereof.

12. A pharmaceutical composition comprising a compound or a pharmaceutically acceptable salt thereof as claimed in claim 6, together with a pharmaceutically acceptable carrier, optionally in combination with one or more other pharmaceutical compositions.

13. The pharmaceutical composition as claimed in claim 12, wherein the composition is in the form selected from the group consisting of a tablet, capsule, powder, syrup, solution, aerosol and suspension.

14. A method for the treatment of a proliferative disorder or cancer, comprising administering to a subject suffering from the proliferative disorder or cancer a therapeutically effective amount of the compound as claimed in claim 6, together with an agent selected from the group consisting of a cytotoxic agent, a non-cytotoxic agents and an immune modulator agent to a subject in need thereof.

15. A method for the treatment of a proliferative disorder or cancer, comprising administering to a subject suffering from the proliferative disorder or cancer the pharmaceutical composition as claimed in claim 12, together with an agent selected from the group consisting of a cytotoxic agent, a non-cytotoxic agent and an immune modulator agent to a subject in need thereof.

\* \* \* \* \*